US008188244B2

(12) United States Patent
La Monica et al.

(10) Patent No.: US 8,188,244 B2
(45) Date of Patent: May 29, 2012

(54) CARCINOEMBRYONIC ANTIGEN FUSIONS AND USES THEREOF

(75) Inventors: Nicola La Monica, Promezia (IT); Andrea Facciabene, Teramo (IT); Luigi Aurisicchio, Albano Laziale (IT); Gennaro Ciliberto, Rome (IT)

(73) Assignee: Istituto di Ricerche di Biologia Molecolare P. Angeletti SpA, Rome (IT)

( * ) Notice: Subject to any disclaimer, the term of this patent is extended or adjusted under 35 U.S.C. 154(b) by 1569 days.

(21) Appl. No.: 10/589,180

(22) PCT Filed: Feb. 3, 2005

(86) PCT No.: PCT/EP2005/001114

§ 371 (c)(1), (2), (4) Date: Aug. 11, 2006

(87) PCT Pub. No.: WO2005/077977

PCT Pub. Date: Aug. 25, 2005

(65) Prior Publication Data

US 2008/0311137 A1 Dec. 18, 2008

Related U.S. Application Data

(60) Provisional application No. 60/543,649, filed on Feb. 11, 2004, provisional application No. 60/635,791, filed on Dec. 14, 2004.

(51) Int. Cl.
*C12N 15/11* (2006.01)
*C12N 15/63* (2006.01)

(52) U.S. Cl. .................................. 536/23.1; 435/320.1

(58) Field of Classification Search ................ 536/23.1; 435/320.1
See application file for complete search history.

(56) References Cited

U.S. PATENT DOCUMENTS

| | | | |
|---|---|---|---|
| 5,274,087 | A | 12/1993 | Barnett et al. |
| 5,571,710 | A | 11/1996 | Barnett et al. |
| 5,698,530 | A | 12/1997 | Schlom et al. |
| 5,843,761 | A | 12/1998 | Barnett et al. |
| 6,384,018 | B1 | 5/2002 | Content et al. |
| 6,482,614 | B1 | 11/2002 | Young |

FOREIGN PATENT DOCUMENTS

| | | | |
|---|---|---|---|
| EP | 0 346 710 | B1 | 11/1993 |
| WO | 00/63253 | A1 | 10/2000 |
| WO | WO 01/14416 | A2 | 3/2001 |
| WO | WO 01/24832 | A2 | 4/2001 |
| WO | WO 01/30382 | A1 | 5/2001 |
| WO | 01/89456 | A2 | 11/2001 |
| WO | WO 02/22080 | A3 | 3/2002 |
| WO | WO 02/38769 | A2 | 5/2002 |
| WO | 02/47727 | A1 | 6/2002 |
| WO | WO 03/059379 | A2 | 7/2002 |
| WO | 03/004055 | A2 | 1/2003 |
| WO | 03/006055 | A2 | 1/2003 |
| WO | WO 2004/072287 | A1 | 8/2004 |
| WO | WO 2004/092216 | A1 | 10/2004 |
| WO | WO 2004/099247 | A2 | 11/2004 |
| WO | WO 2005/019455 | A1 | 3/2005 |

OTHER PUBLICATIONS

Rice et al. "DNA Fusion Vaccine Designed to Induce Cytotoxic T Cell Responses Against Defined Peptide Motifs: Implications for Cancer Vaccines", The Journal of Immunology, 2001, vol. 167, pp. 1558-1565.

Beauchemin, et al., "Isolation and Characterization of Full-Length Functional cDNA Clones for Human Carcinoembryonic Antigen", Mol. and Cell. Biol., vol. 7, No. 9, pp. 3221-3230, Sep. 1987.

Benchimol, et al., "Carcinoembryonic Antigen, a Human Tumor Marker, Functions as an Intercellular Adhesion Molecule", Cell, vol. 57, pp. 327-334, Apr. 21, 1989.

Berinstein, et al., "Carcinoembryonic Antigen as a Target for Therapeutic Anticancer Vaccines: a Review", J. Of Clinical Oncology, vol. 20, No. 8, pp. 2197-2207, Apr. 15, 2002.

Chen, et al., "Enhancement of DNA Vaccine Potency by Linkage of Antigen Gene to an HSP70 Gene", Cancer Research, vol. 60, pp. 1035-1042, Feb. 15, 2000.

Cheng, et al., "Enhancement of Sindbis Virus Self-Replicating RNA Vaccine Potency by Linkage of Mycobacterium tuberculosis Heat Shock Protein 70 Gene to an Antigen Gene", J. of Immunol., vol. 166, pp. 6218-6226, 2001.

Chester, et al., "Recombinant anti-carcinoembryonic antigen antibodies for targeting cancer", Cancer Chemother. Pharmacol., vol. 46 (Suppl) S2-S12, 2000.

Gold, et al., "Demonstration of Tumor-Specific Antigens in Human Colonic Carcinomata by Immunological Tolerance and Absorption Techniques", J. Exp. Med., vol. 121, pp. 439-462 (1965).

Hammarstrom, et al., "Is There a Role for CEA in Innate Immunity in the Colon", Trends in Microbiology, vol. 9, No. 3, pp. 119-125, 2001.

Kantor, et al., "Immunogenicity and Safety of a Recombinant Vaccinia Virus Vaccine Expressing the Carcinoembryonic Antigen Gene in a Nonhuman Primate", Cancer Research, vol. 52, pp. 6917-6925, 1992.

King, et al., "DNA Vaccines With Single-Chain Fv Fused to Fragment C of Tetanus Toxin Induce Protective Immunity Against Lymphoma and Myeloma", Nature Medicine, vol. 4, No. 11, pp. 1281-1286, Nov. 1998.

Lathe, "Synthetic Oligonucleotide Probes Deduced from Amino Acid Sequence Data", J. Mol. Biol., vol. 183, pp. 1-12, 1985.

(Continued)

*Primary Examiner* — Thaian N Ton
*Assistant Examiner* — Magdalene Sgagias
(74) *Attorney, Agent, or Firm* — Alysia A. Finnegan; Sheldon O. Heber

(57) ABSTRACT

Polynucleotides encoding carcinoembryonic antigen (CEA) fusion proteins are provided, the CEA fusion proteins comprising a CEA protein, or functional variant thereof, fused to a substantial portion of an immunoenhancing element. The polynucleotides of the present invention can elicit an immune response in a mammal, which, in preferred embodiments, is stronger than the immune response elicited by a wild-type CEA. The gene encoding CEA is commonly associated with the development of human carcinomas. The present invention provides compositions and methods to elicit or enhance immunity to the protein product expressed by the CEA tumor-associated antigen, wherein aberrant CEA expression is associated with a carcinoma or its development. This invention specifically provides adenoviral vector and plasmid constructs carrying polynucleotides encoding CEA fusion proteins and discloses their use in vaccines and pharmaceutical compositions for preventing and treating cancer.

5 Claims, 62 Drawing Sheets

OTHER PUBLICATIONS

Liu, et al., "Recombinant Adeno-Associated Virus Expressing Human Papillomavirus Type 16 E7 Peptide DNA Fused with Heat Shock Protein DNA as a Potential Vaccine for Cervical Cancer", J. of Virol., vol. 74, No. 6, pp. 2888-2894, Mar. 2000.

Lund, et al., "Signal sequence deletion and fusion to tetanus toxoid epitope augment antitumor immune responses to a human carcinoembryonic antigen (CEA) plasmid DNA vaccine in a murine test system", Cancer Gene Therapy, vol. 10, pp. 365-376, 2003.

Montgomery, et al., "Heterologous and Homologous Protection Against Influenza A by DNA Vaccination: Optimization of DNA Vectors", DNA and Cell Biology, vol. 12, No. 9, pp. 777-783, 1993.

Padua, et al., "PML-RARA-targeted DNA vaccine induces protective immunity in a mouse model of leukemia", Nature Medicine, vol. 9, No. 11, pp. 1413-1417, Nov. 2003.

Paxton, et al., "Sequence Analysis of Carcinoembryonic Antigen:Identification of Glycosylation Sites and Homology With the Immunoglobulin Supergene Family", Proc. Natl. Acad. Sci. USA, vol. 84, pp. 920-924, Feb. 1987.

Renard, et al., "HER-2 DNA and Protein Vaccines Containing Potent Th Cell Epitopes Induce Distinct Protective and Therapeutic Antitumor Responses in HER-2 Transgenic Mice", J. of Immunol., vol. 171, pp. 1588-1595, 2003.

Savalyeva, et al., "Plant viral genes in DNA idiotypic vaccines activate linked CD4+ T-cell mediated immunity against B-cell malignancies", Nature Biotechnology, vol. 19, pp. 760-764, Aug. 2001.

Scholl, et al., "Gene Therapy Applications to Cancer Treatment", J. of Biomed. And Biotech., vol. 1, pp. 35-47, 2003.

Screaton, et al., "Carcinoembryonic Antigen, A Human Tumor Marker, Cooperates with Myc and Bcl-2 in Cellular Transformation", J. of Cell Biology, vol. 137, No. 4, pp. 939-952, May 19, 1997.

Shiver, et al., "Cytotoxic T Lymphocyte and Helper T Cell Responses following HIV Polynucleotide Vaccination", Annals. New York Academy of Sciences, vol. 772, pp. 198-208, 1995.

Su, et al., "Enhanced Induction of Telomerase-specific CD4+ T Cells Using Dendritic Cells Transfected with RNA Encoding a Chimeric Gene Product", Cancer Research, vol. 62, pp. 5041-5048, Sep. 1, 2002.

Thompson, et al., "Molecular cloning of a gene belonging to the carcinoembryonic antigen gene family and discussion of a domain model", Proc. Natl. Acad. Sci. USA, vol. 84, pp. 2965-2969, May 1987.

Arrington, et al. "Plasmid Vectors Encoding Cholera Toxin or the Heat-Labile Enterotoxin from *Escherichia coli* are Strong Adjuvants for DNA Vaccines", Journal of Virology, 2002, vol. 76, pp. 4536-4546.

Holmgren et al. "Mucosal immunisation and adjuvants: a brief overview of recent advances and challenges", Vaccine, 2003, vol. 21, pp. S2/89-S2/95.

Schodel, F. et al, "Synthesis in Vibrio cholerae and secretion of hepatitis B virus antigens fused to *Escherichia coli* heat-labile enterotoxin subunit B", Gene, vol. 99, pp. 255-259, 1991.

LTA
BGH-PolyA
ORI
Kan^r
7766 bp
hCEA
CMVprom/intA
CMVprom/intA
pVIJ/hCEA-LTA
LTB
BGH-PolyA
ORI
Kan^r
7269 bp
hCEA
CMVprom/intA
CMVprom/intA
pVIJ/hCEA-LTB derivatives
ITR
LT
BGH-PolyA
CEAopt
CMVpro
ITR
Ad/hCEAoptLTB
33670 bp hCEA-LTA Nucleotide Sequence

```
   1  ATGGAGTCTC CCTCGGCCCC TCCCCACAGA TGGTGCATCC CCTGGCAGAG
  51  GCTCCTGCTC ACAGCCTCAC TTCTAACCTT CTGGAACCCG CCCACCACTG
 101  CCAAGCTCAC TATTGAATCC ACGCCGTTCA ATGTCGCAGA GGGGAAGGAG
 151  GTGCTTCTAC TTGTCCACAA TCTGCCCCAG CATCTTTTTG GCTACAGCTG
 201  GTACAAAGGT GAAAGAGTGG ATGGCAACCG TCAAATTATA GGATATGTAA
 251  TAGGAACTCA ACAAGCTACC CCAGGGCCCG CATACAGTGG TCGAGAGATA
 301  ATATACCCCA ATGCATCCCT GCTGATCCAG AACATCATCC AGAATGACAC
 351  AGGATTCTAC ACCCTACACG TCATAAAGTC AGATCTTGTG AATGAAGAAG
 401  CAACTGGCCA GTTCCGGGTA TACCCGGAGC TGCCCAAGCC CTCCATCTCC
 451  AGCAACAACT CCAAACCCGT GGAGGACAAG GATGCTGTGG CCTTCACCTG
 501  TGAACCTGAG ACTCAGGACG CAACCTACCT GTGGTGGGTA AACAATCAGA
 551  GCCTCCCGGT CAGTCCCAGG CTGCAGCTGT CCAATGGCAA CAGGACCCTC
 601  ACTCTATTCA ATGTCACAAG AAATGACACA GCAAGCTACA AATGTGAAAC
 651  CCAGAACCCA GTGAGTGCCA GGCGCAGTGA TTCAGTCATC CTGAATGTCC
 701  TCTATGGCCC GGATGCCCCC ACCATTTCCC CTCTAAACAC ATCTTACAGA
 751  TCAGGGGAAA ATCTGAACCT CTCCTGCCAC GCAGCCTCTA ACCCACCTGC
 801  ACAGTACTCT TGGTTTGTCA ATGGGACTTT CCAGCAATCC ACCCAAGAGC
 851  TCTTTATCCC CAACATCACT GTGAATAATA GTGGATCCTA TACGTGCCAA
 901  GCCCATAACT CAGACACTGG CCTCAATAGG ACCACAGTCA CGACGATCAC
 951  AGTCTATGCA GAGCCACCCA AACCCTTCAT CACCAGCAAC AACTCCAACC
1001  CCGTGGAGGA TGAGGATGCT GTAGCCTTAA CCTGTGAACC TGAGATTCAG
1051  AACACAACCT ACCTGTGGTG GGTAAATAAT CAGAGCCTCC CGGTCAGTCC
1101  CAGGCTGCAG CTGTCCAATG ACAACAGGAC CCTCACTCTA CTCAGTGTCA
1151  CAAGGAATGA TGTAGGACCC TATGAGTGTG GAATCCAGAA CGAATTAAGT
1201  GTTGACCACA GCGACCCAGT CATCCTGAAT GTCCTCTATG GCCCAGACGA
1251  CCCCACCATT TCCCCCTCAT ACACCTATTA CCGTCCAGGG GTGAACCTCA
1301  GCCTCTCCTG CCATGCAGCC TCTAACCCAC CTGCACAGTA TTCTTGGCTG
1351  ATTGATGGGA ACATCCAGCA ACACACACAA GAGCTCTTTA TCTCCAACAT
1401  CACTGAGAAG AACAGCGGAC TCTATACCTG CCAGGCCAAT AACTCAGCCA
1451  GTGGCCACAG CAGGACTACA GTCAAGACAA TCACAGTCTC TGCGGAGCTG
1501  CCCAAGCCCT CCATCTCCAG CAACAACTCC AAACCCGTGG AGGACAAGGA
1515  TGCTGTGGCC TTCACCTGTG AACCTGAGGC TCAGAACACA ACCTACCTGT
1601  GGTGGGTAAA TGGTCAGAGC CTCCCAGTCA GTCCCAGGCT GCAGCTGTCC
1651  AATGGCAACA GGACCCTCAC TCTATTCAAT GTCACAAGAA ATGACGCAAG
1701  AGCCTATGTA TGTGGAATCC AGAACTCAGT GAGTGCAAAC CGCAGTGACC
1751  CAGTCACCCT GGATGTCCTC TATGGGCCGG ACACCCCCAT CATTTCCCCC
1801  CCAGACTCGT CTTACCTTTC GGGAGCGAAC CTCAACCTCT CCTGCCACTC
1851  GGCCTCTAAC CCATCCCCGC AGTATTCTTG GCGTATCAAT GGGATACCGC
1901  AGCAACACAC ACAAGTTCTC TTTATCGCCA AAATCACGCC AAATAATAAC
1951  GGGACCTATG CCTGTTTTGT CTCTAACTTG GCTACTGGCC GCAATAATTC
```

FIG.2A-1

```
2001 CATAGTCAAG AGCATCACAG TCTCTGCATC TGGAACTCTA GTTAATGGCG
2051 ACAAATTATA CCGTGCTGAC TCTAGACCCC CAGATGAAAT AAAACGTTCC
2101 GGAGGTCTTA TGCCCAGAGG GCATAATGAG TACTTCGATA GAGGAACTCA
2151 AATGAATATT AATCTTTATG ATCACGCGAG AGGAACACAA ACCGGCTTTG
2201 TCAGATATGA TGACGGATAT GTTTCCACTT CTCTTAGTTT GAGAAGTGCT
2251 CACTTAGCAG GACAGTCTAT ATTATCAGGA TATTCCACTT ACTATATATA
2301 TGTTATAGCG ACAGCACCAA ATATGTTTAA TGTTAATGAT GTATTAGGCG
2351 TATACAGCCC TCACCCATAT GAACAGGAGG TTTCTGCGTT AGGTGGAATA
2401 CCATATTCTC AGATATATGG ATGGTATCGT GTTAATTTTG GTGTAATTGA
2451 TGAACGATTA CATCGTAACA GGGAATATAG AGACCGGTAT TACAGAAATC
2501 TGAATATAGC TCCGGCAGAG GATGGTTACA GATTAGCAGG TTTCCCACCG
2551 GATCACCAAG CTTGGAGAGA AGAACCCTGG ATTCATCATG CACCACAAGG
2601 TTGTGGAAAT TCATCAAGAA CAATTACAGA TGATACTTGT AATGAGGAGA
2651 CCCAGAATCT GAGCACAATA TATCTCAGGA AATATCAATC AAAAGTTAAG
2701 AGGCAGATAT TTTCAGACTA TCAGTCAGAG GTTGACATAT ATAACAGAAT
     TCGGGATGAA TTATGA (SEQ ID NO:7)
```

FIG.2A-2

CEA-LTA Amino Acid Sequence

```
  1  MESPSAPPHR WCIPWQRLLL TASLLTFWNP PTTAKLTIES TPFNVAEGKE
 51  VLLLVHNLPQ HLFGYSWYKG ERVDGNRQII GYVIGTQQAT PGPAYSGREI
101  IYPNASLLIQ NIIQNDTGFY TLHVIKSDLV NEEATGQFRV YPELPKPSIS
151  SNNSKPVEDK DAVAFTCEPE TQDATYLWWV NNQSLPVSPR LQLSNGNRTL
201  TLFNVTRNDT ASYKCETQNP VSARRSDSVI LNVLYGPDAP TISPLNTSYR
251  SGENLNLSCH AASNPPAQYS WFVNGTFQQS TQELFIPNIT VNNSGSYTCQ
301  AHNSDTGLNR TTVTTITVYA EPPKPFITSN NSNPVEDEDA VALTCEPEIQ
351  NTTYLWWVNN QSLPVSPRLQ LSNDNRTLTL LSVTRNDVGP YECGIQNELS
401  VDHSDPVILN VLYGPDDPTI SPSYTYYRPG VNLSLSCHAA SNPPAQYSWL
451  IDGNIQQHTQ ELFISNITEK NSGLYTCQAN NSASGHSRTT VKTITVSAEL
501  PKPSISSNNS KPVEDKDAVA FTCEPEAQNT TYLWWVNGQS LPVSPRLQLS
551  NGNRTLTLFN VTRNDARAYV CGIQNSVSAN RSDPVTLDVL YGPDTPIISP
601  PDSSYLSGAN LNLSCHSASN PSPQYSWRIN GIPQQHTQVL FIAKITPNNN
651  GTYACFVSNL ATGRNNSIVK SITVSASGTL VNGDKLYRAD SRPPDEIKRS
701  GGLMPRGHNE YFDRGTQMNI NLYDHARGTQ TGFVRYDDGY VSTSLSLRSA
751  HLAGQSILSG YSTYYIYVIA TAPNMFNVND VLGVYSPHPY EQEVSALGGI
801  PYSQIYGWYR VNFGVIDERL HRNREYRDRY YRNLNIAPAE DGYRLAGFPP
851  DHQAWREEPW IHHAPQGCGN SSRTITDDTC NEETQNLSTI YLRKYQSKVK
901  RQIFSDYQSE VDIYNRIRDE L (SEQ ID NO:8)
```

FIG.2B hCEA-LTB Coding Sequence

```
   1  ATGGAGTCTC CCTCGGCCCC TCCCCACAGA TGGTGCATCC CCTGGCAGAG
  51  GCTCCTGCTC ACAGCCTCAC TTCTAACCTT CTGGAACCCG CCCACCACTG
 101  CCAAGCTCAC TATTGAATCC ACGCCGTTCA ATGTCGCAGA GGGGAAGGAG
 151  GTGCTTCTAC TTGTCCACAA TCTGCCCCAG CATCTTTTTG GCTACAGCTG
 201  GTACAAAGGT GAAAGAGTGG ATGGCAACCG TCAAATTATA GGATATGTAA
 251  TAGGAACTCA ACAAGCTACC CCAGGGCCCG CATACAGTGG TCGAGAGATA
 301  ATATACCCCA ATGCATCCCT GCTGATCCAG AACATCATCC AGAATGACAC
 351  AGGATTCTAC ACCCTACACG TCATAAAGTC AGATCTTGTG AATGAAGAAG
 401  CAACTGGCCA GTTCCGGGTA TACCCGGAGC TGCCCAAGCC CTCCATCTCC
 451  AGCAACAACT CCAAACCCGT GGAGGACAAG GATGCTGTGG CCTTCACCTG
 501  TGAACCTGAG ACTCAGGACG CAACCTACCT GTGGTGGGTA AACAATCAGA
 551  GCCTCCCGGT CAGTCCCAGG CTGCAGCTGT CCAATGGCAA CAGGACCCTC
 601  ACTCTATTCA ATGTCACAAG AAATGACACA GCAAGCTACA AATGTGAAAC
 651  CCAGAACCCA GTGAGTGCCA GGCGCAGTGA TTCAGTCATC CTGAATGTCC
 701  TCTATGGCCC GGATGCCCCC ACCATTTCCC CTCTAAACAC ATCTTACAGA
 751  TCAGGGGAAA ATCTGAACCT CTCCTGCCAC GCAGCCTCTA ACCCACCTGC
 801  ACAGTACTCT TGGTTTGTCA ATGGGACTTT CCAGCAATCC ACCCAAGAGC
 851  TCTTTATCCC CAACATCACT GTGAATAATA GTGGATCCTA TACGTGCCAA
 901  GCCCATAACT CAGACACTGG CCTCAATAGG ACCACAGTCA CGACGATCAC
 951  AGTCTATGCA GAGCCACCCA AACCCTTCAT CACCAGCAAC AACTCCAACC
1001  CCGTGGAGGA TGAGGATGCT GTAGCCTTAA CCTGTGAACC TGAGATTCAG
1151  AACACAACCT ACCTGTGGTG GGTAAATAAT CAGAGCCTCC CGGTCAGTCC
1101  CAGGCTGCAG CTGTCCAATG ACAACAGGAC CCTCACTCTA CTCAGTGTCA
1151  CAAGGAATGA TGTAGGACCC TATGAGTGTG GAATCCAGAA CGAATTAAGT
1201  GTTGACCACA GCGACCCAGT CATCCTGAAT GTCCTCTATG GCCCAGACGA
1251  CCCCACCATT TCCCCCTCAT ACACCTATTA CCGTCCAGGG GTGAACCTCA
1301  GCCTCTCCTG CCATGCAGCC TCTAACCCAC CTGCACAGTA TTCTTGGCTG
1351  ATTGATGGGA ACATCCAGCA ACACACACAA GAGCTCTTTA TCTCCAACAT
1401  CACTGAGAAG AACAGCGGAC TCTATACCTG CCAGGCCAAT AACTCAGCCA
1451  GTGGCCACAG CAGGACTACA GTCAAGACAA TCACAGTCTC TGCGGAGCTG
1501  CCCAAGCCCT CCATCTCCAG CAACAACTCC AAACCCGTGG AGGACAAGGA
1551  TGCTGTGGCC TTCACCTGTG AACCTGAGGC TCAGAACACA ACCTACCTGT
1601  GGTGGGTAAA TGGTCAGAGC CTCCCAGTCA GTCCCAGGCT GCAGCTGTCC
1651  AATGGCAACA GGACCCTCAC TCTATTCAAT GTCACAAGAA ATGACGCAAG
1701  AGCCTATGTA TGTGGAATCC AGAACTCAGT GAGTGCAAAC CGCAGTGACC
1751  CAGTCACCCT GGATGTCCTC TATGGGCCGG ACACCCCCAT CATTTCCCCC
1801  CCAGACTCGT CTTACCTTTC GGGAGCGAAC CTCAACCTCT CCTGCCACTC
1851  GGCCTCTAAC CCATCCCCGC AGTATTCTTG GCGTATCAAT GGGATACCGC
```

FIG.3A-1

```
1901 AGCAACACAC ACAAGTTCTC TTTATCGCCA AAATCACGCC AAATAATAAC
1951 GGGACCTATG CCTGTTTTGT CTCTAACTTG GCTACTGGCC GCAATAATTC
2001 CATAGTCAAG AGCATCACAG TCTCTGCATC TGGAACTCTA GATGCTCCCC
2051 AGTCTATTAC AGAACTATGT TCGGAATATC GCAACACACA AATATATACG
2101 ATAAATGACA AGATACTATC ATATACGGAA TCGATGGCAG GTAAAAGAGA
2151 AATGGTTATC ATTACATTTA AGAGCGGCGC AACATTTCAG GTCGAAGTCC
2201 CGGGCAGTCA ACATATAGAC TCCCAAAAAA AAGCCATTGA AAGGATGAAG
2251 GACACATTAA GAATCACATA TCTGACCGAG ACCAAAATTG ATAAATTATG
2301 TGTATGGAAT AATAAAACCC CCAATTCAAT TGCGGCAATC AGTATGGAAA
     ACTAG (SEQ ID NO:9)
```

FIG.3A-2

CEA-LTB Amino Acid Sequence

```
  1  MESPSAPPHR WCIPWQRLLL TASLLTFWNP PTTAKLTIES TPFNVAEGKE
 51  VLLLVHNLPQ HLFGYSWYKG ERVDGNRQII GYVIGTQQAT PGPAYSGREI
101  IYPNASLLIQ NIIQNDTGFY TLHVIKSDLV NEEATGQFRV YPELPKPSIS
151  SNNSKPVEDK DAVAFTCEPE TQDATYLWWV NNQSLPVSPR LQLSNGNRTL
201  TLFNVTRNDT ASYKCETQNP VSARRSDSVI LNVLYGPDAP TISPLNTSYR
251  SGENLNLSCH AASNPPAQYS WFVNGTFQQS TQELFIPNIT VNNSGSYTCQ
301  AHNSDTGLNR TTVTTITVYA EPPKPFITSN NSNPVEDEDA VALTCEPEIQ
351  NTTYLWWVNN QSLPVSPRLQ LSNDNRTLTL LSVTRNDVGP YECGIQNELS
401  VDHSDPVILN VLYGPDDPTI SPSYTYYRPG VNLSLSCHAA SNPPAQYSWL
451  IDGNIQQHTQ ELFISNITEK NSGLYTCQAN NSASGHSRTT VKTITVSAEL
501  PKPSISSNNS KPVEDKDAVA FTCEPEAQNT TYLWWVNGQS LPVSPRLQLS
551  NGNRTLTLFN VTRNDARAYV CGIQNSVSAN RSDPVTLDVL YGPDTPIISP
601  PDSSYLSGAN LNLSCHSASN PSPQYSWRIN GIPQQHTQVL FIAKITPNNN
651  GTYACFVSNL ATGRNNSIVK SITVSASGTL DAPQSITELC SEYRNTQIYT
701  INDKILSYTE SMAGKREMVI ITFKSGATFQ VEVPGSQHID SQKKAIERMK
751  DTLRITYLTE TKIDKLCVWN NKTPNSIAAI SMEN (SEQ ID NO:10)
```

FIG.3B

CEAopt-LTB Nucleotide Sequence

```
1     ATGGAGAGCC CCAGCGCCCC CCCCCACCGC TGGTGCATCC CCTGGCAGCG
      CCTGCTGCTG ACCGCCAGCC TGCTGACCTT CTGGAACCCC CCCACCACCG
101   CCAAGCTGAC CATCGAGAGC ACCCCCTTCA ACGTGGCCGA GGGCAAGGAG
      GTGCTGCTGC TGGTGCACAA CCTGCCCCAG CACCTGTTCG GCTACAGCTG
201   GTACAAGGGC GAGCGCGTGG ACGGCAACCG CCAGATCATC GGCTACGTGA
      TCGGCACCCA GCAGGCCACC CCCGGCCCCG CCTACAGCGG CCGCGAGATC
301   ATCTACCCCA ACGCCAGCCT GCTGATCCAG AACATCATCC AGAACGACAC
      CGGCTTCTAC ACCCTGCACG TGATCAAGAG CGACCTGGTG AACGAGGAGG
401   CCACCGGCCA GTTCCGCGTG TACCCCGAGC TGCCCAAGCC CAGCATCAGC
      AGCAACAACA GCAAGCCCGT GGAGGACAAG GACGCCGTGG CCTTCACCTG
501   CGAGCCCGAG ACCCAGGACG CCACCTACCT GTGGTGGGTG AACAACCAGA
      GCCTGCCCGT GAGCCCCCGC CTGCAGCTGA GCAACGGCAA CCGCACCCTG
601   ACCCTGTTCA ACGTGACCCG CAACGACACC GCCAGCTACA AGTGCGAGAC
      CCAGAACCCC GTGAGCGCCC GCCGCAGCGA CAGCGTGATC CTGAACGTGC
701   TGTACGGCCC CGACGCCCCC ACCATCAGCC CCCTGAACAC CAGCTACCGC
      AGCGGCGAGA ACCTGAACCT GAGCTGCCAC GCCGCCAGCA ACCCCCCCGC
801   CCAGTACAGC TGGTTCGTGA ACGGCACCTT CCAGCAGAGC ACCCAGGAGC
      TGTTCATCCC CAACATCACC GTGAACAACA GCGGCAGCTA CACCTGCCAG
901   GCCCACAACA GCGACACCGG CCTGAACCGC ACCACCGTGA CCACCATCAC
      CGTGTACGCC GAGCCCCCCA AGCCCTTCAT CACCAGCAAC AACAGCAACC
1001  CCGTGGAGGA CGAGGACGCC GTGGCCCTGA CCTGCGAGCC CGAGATCCAG
      AACACCACCT ACCTGTGGTG GGTGAACAAC CAGAGCCTGC CCGTGAGCCC
1101  CCGCCTGCAG CTGAGCAACG ACAACCGCAC CCTGACCCTG CTGAGCGTGA
      CCCGCAACGA CGTGGGCCCC TACGAGTGCG GCATCCAGAA CGAGCTGAGC
1201  GTGGACCACA GCGACCCCGT GATCCTGAAC GTGCTGTACG GCCCCGACGA
      CCCCACCATC AGCCCCAGCT ACACCTACTA CCGCCCCGGC GTGAACCTGA
1301  GCCTGAGCTG CCACGCCGCC AGCAACCCCC CCGCCCAGTA CAGCTGGCTG
      ATCGACGGCA ACATCCAGCA GCACACCCAG GAGCTGTTCA TCAGCAACAT
1401  CACCGAGAAG AACAGCGGCC TGTACACCTG CCAGGCCAAC AACAGCGCCA
      GCGGCCACAG CCGCACCACC GTGAAGACCA TCACCGTGAG CGCCGAGCTG
1501  CCCAAGCCCA GCATCAGCAG CAACAACAGC AAGCCCGTGG AGGACAAGGA
      CGCCGTGGCC TTCACCTGCG AGCCCGAGGC CCAGAACACC ACCTACCTGT
1601  GGTGGGTGAA CGGCCAGAGC CTGCCCGTGA GCCCCCGCCT GCAGCTGAGC
      AACGGCAACC GCACCCTGAC CCTGTTCAAC GTGACCCGCA ACGACGCCCG
1701  CGCCTACGTG TGCGGCATCC AGAACAGCGT GAGCGCCAAC CGCAGCGACC
      CCGTGACCCT GGACGTGCTG TACGGCCCCG ACACCCCCAT CATCAGCCCC
1801  CCCGACAGCA GCTACCTGAG CGGCGCCAAC CTGAACCTGA GCTGCCACAG
      CGCCAGCAAC CCCAGCCCCC AGTACAGCTG GCGCATCAAC GGCATCCCCC
```

FIG.4A

1901 AGCAGCACAC CCAGGTGCTG TTCATCGCCA AGATCACCCC CAACAACAAC
GGCACCTACG CCTGCTTCGT GAGCAACCTG GCCACCGGCC GCAACAACAG
2001 CATCGTGAAG AGCATCACCG TGAGCGCCAG CGGCACCTCT AGAGCTCCCC
AGACTATTAC AGAACTATGT TCGGAATATC GCAACACACA AATATATACG
2101 ATAAATGACA AGATACTATC ATATACGGAA TCGATGGCAG GCAAAAGAGA
AATGGTTATC ATTACATTTA AGAGCGGCGA AACATTTCAG GTCGAAGTCC
2201 CGGGCAGTCA ACATATAGAC TCCCAGAAAA AAGCCATTGA AAGGATGAAG
GACACATTAA GAATCACATA TCTGACCGAG ACCAAAATTG ATAAATTATG
2301 TGTATGGAAT AATAAAACCC CCAATTCAAT TGCGGCAATC AGTATGGAAA
ACTAG (SEQ ID NO:11)

FIG.4B hCEA-LTBopt Coding Sequence

```
   1 ATGGAGAGCC CCAGCGCCCC CCCCCACCGC TGGTGCATCC CCTGGCAGCG
     CCTGCTGCTG ACCGCCAGCC TGCTGACCTT CTGGAACCCC CCCACCACCG
 101 CCAAGCTGAC CATCGAGAGC ACCCCCTTCA ACGTGGCCGA GGGCAAGGAG
     GTGCTGCTGC TGGTGCACAA CCTGCCCCAG CACCTGTTCG GCTACAGCTG
 201 GTACAAGGGC GAGCGCGTGG ACGGCAACCG CCAGATCATC GGCTACGTGA
     TCGGCACCCA GCAGGCCACC CCCGGCCCCG CCTACAGCGG CCGCGAGATC
 301 ATCTACCCCA ACGCCAGCCT GCTGATCCAG AACATCATCC AGAACGACAC
     CGGCTTCTAC ACCCTGCACG TGATCAAGAG CGACCTGGTG AACGAGGAGG
 401 CCACCGGCCA GTTCCGCGTG TACCCCGAGC TGCCCAAGCC CAGCATCAGC
     AGCAACAACA GCAAGCCCGT GGAGGACAAG GACGCCGTGG CCTTCACCTG
 501 CGAGCCCGAG ACCCAGGACG CCACCTACCT GTGGTGGGTG AACAACCAGA
     GCCTGCCCGT GAGCCCCCGC CTGCAGCTGA GCAACGGCAA CCGCACCCTG
 601 ACCCTGTTCA ACGTGACCCG CAACGACACC GCCAGCTACA AGTGCGAGAC
     CCAGAACCCC GTGAGCGCCC GCCGCAGCGA CAGCGTGATC CTGAACGTGC
 701 TGTACGGCCC CGACGCCCCC ACCATCAGCC CCCTGAACAC CAGCTACCGC
     AGCGGCGAGA ACCTGAACCT GAGCTGCCAC GCCGCCAGCA ACCCCCCCGC
 801 CCAGTACAGC TGGTTCGTGA ACGGCACCTT CCAGCAGAGC ACCCAGGAGC
     TGTTCATCCC CAACATCACC GTGAACAACA GCGGCAGCTA CACCTGCCAG
 901 GCCCACAACA GCGACACCGG CCTGAACCGC ACCACCGTGA CCACCATCAC
     CGTGTACGCC GAGCCCCCCA AGCCCTTCAT CACCAGCAAC AACAGCAACC
1001 CCGTGGAGGA CGAGGACGCC GTGGCCCTGA CCTGCGAGCC CGAGATCCAG
     AACACCACCT ACCTGTGGTG GGTGAACAAC CAGAGCCTGC CCGTGAGCCC
1101 CCGCCTGCAG CTGAGCAACG ACAACCGCAC CCTGACCCTG CTGAGCGTGA
     CCCGCAACGA CGTGGGCCCC TACGAGTGCG GCATCCAGAA CGAGCTGAGC
1201 GTGGACCACA GCGACCCCGT GATCCTGAAC GTGCTGTACG GCCCCGACGA
     CCCCACCATC AGCCCCAGCT ACACCTACTA CCGCCCCGGC GTGAACCTGA
1301 GCCTGAGCTG CCACGCCGCC AGCAACCCCC CCGCCCAGTA CAGCTGGCTG
     ATCGACGGCA ACATCCAGCA GCACACCCAG GAGCTGTTCA TCAGCAACAT
1401 CACCGAGAAG AACAGCGGCC TGTACACCTG CCAGGCCAAC AACAGCGCCA
     GCGGCCACAG CCGCACCACC GTGAAGACCA TCACCGTGAG CGCCGAGCTG
1501 CCCAAGCCCA GCATCAGCAG CAACAACAGC AAGCCCGTGG AGGACAAGGA
     CGCCGTGGCC TTCACCTGCG AGCCCGAGGC CCAGAACACC ACCTACCTGT
1601 GGTGGGTGAA CGGCCAGAGC CTGCCCGTGA GCCCCCGCCT GCAGCTGAGC
     AACGGCAACC GCACCCTGAC CCTGTTCAAC GTGACCCGCA ACGACGCCCG
1701 CGCCTACGTG TGCGGCATCC AGAACAGCGT GAGCGCCAAC CGCAGCGACC
     CCGTGACCCT GGACGTGCTG TACGGCCCCG ACACCCCCAT CATCAGCCCC
1801 CCCGACAGCA GCTACCTGAG CGGCGCCAAC CTGAACCTGA GCTGCCACAG
     CGCCAGCAAC CCCAGCCCCC AGTACAGCTG GCGCATCAAC GGCATCCCCC
```

FIG.5A-1

```
1901  AGCAGCACAC CCAGGTGCTG TTCATCGCCA AGATCACCCC CAACAACAAC
      GGCACCTACG CCTGCTTCGT GAGCAACCTG GCCACCGGCC GCAACAACAG
2001  CATCGTGAAG AGCATCACCG TGAGCGCCAG CGGCACCTCT AGAGCCCCCC
      AGAGCATCAC CGAGCTGTGC AGCGAGTACC GGAACACCCA GATCTACACC
2101  ATCAACGACA AGATCCTGAG CTACACCGAG AGCATGGCCG GCAAGAGGGA
      GATGGTGATC ATCACCTTCA AGAGCGGCGC CACCTTCCAG GTGGAGGTGC
2201  CCGGCAGCCA GCACATCGAC AGCCAGAAGA AGGCCATCGA GCGGATGAAG
      GACACCCTGC GGATCACCTA CCTCACCGAG ACCAAGATCG ACAAGCTGTG
2301  CGTGTGGAAC AACAAGACCC CCAACAGCAT CGCCGCCATC AGCATGGAGA
      ATTGATAA (SEQ ID NO:12)
```

FIG.5A-2 hCEA-LTB Amino Acid Sequence

```
  1   MESPSAPPHR WCIPWQRLLL TASLLTFWNP PTTAKLTIES TPFNVAEGKE
 51   VLLLVHNLPQ HLFGYSWYKG ERVDGNRQII GYVIGTQQAT PGPAYSGREI
101   IYPNASLLIQ NIIQNDTGFY TLHVIKSDLV NEEATGQFRV YPELPKPSIS
151   SNNSKPVEDK DAVAFTCEPE TQDATYLWWV NNQSLPVSPR LQLSNGNRTL
201   TLFNVTRNDT ASYKCETQNP VSARRSDSVI LNVLYGPDAP TISPLNTSYR
251   SGENLNLSCH AASNPPAQYS WFVNGTFQQS TQELFIPNIT VNNSGSYTCQ
301   AHNSDTGLNR TTVTTITVYA EPPKPFITSN NSNPVEDEDA VALTCEPEIQ
351   NTTYLWWVNN QSLPVSPRLQ LSNDNRTLTL LSVTRNDVGP YECGIQNELS
401   VDHSDPVILN VLYGPDDPTI SPSYTYYRPG VNLSLSCHAA SNPPAQYSWL
451   IDGNIQQHTQ ELFISNITEK NSGLYTCQAN NSASGHSRTT VKTITVSAEL
501   PKPSISSNNS KPVEDKDAVA FTCEPEAQNT TYLWWVNGQS LPVSPRLQLS
551   NGNRTLTLFN VTRNDARAYV CGIQNSVSAN RSDPVTLDVL YGPDTPIISP
601   PDSSYLSGAN LNLSCHSASN PSPQYSWRIN GIPQQHTQVL FIAKITPNNN
651   GTYACFVSNL ATGRNNSIVK SITVSASGTS RAPQSITELC SEYRNTQIYT
701   INDKILSYTE SMAGKREMVI ITFKSGATFQ VEVPGSQHID SQKKAIERMK
751   DTLRITYLTE TKIDKLCVWN NKTPNSIAAI SMEN (SEQ ID NO:13)
```

FIG.5B

Rhesus CEAopt-LTBopt Coding Sequence

```
ATGGGCAGCC CCAGCGCCCC CCTGCACCGC TGGTGCATCC CCTGGCAGAC CCTGCTGCTG ACCGCCAGCC
TGCTGACCTT CTGGAACCCC CCCACCACCG CCCAGCTGAC CATCGAGAGC CGCCCCTTCA ACGTGGCCGA
GGGCAAGGAG GTGCTGCTGC TGGCCCACAA CGTGAGCCAG AACCTGTTCG GCTACATCTG GTACAAGGGC
GAGCGCGTGG ACGCCAGCCG CCGCATCGGC AGCTGCGTGA TCCGCACCCA GCAGATCACC CCCGGCCCCG
CCCACAGCGG CCGCGAGACC ATCGACTTCA ACGCCAGCCT GCTGATCCAC AACGTGACCC AGAGCGACAC
CGGCAGCTAC ACCATCCAGG TGATCAAGGA GGACCTGGTG AACGAGGAGG CCACCGGCCA GTTCCGCGTG
TACCCCGAGC TGCCCAAGCC CTACATCAGC AGCAACAACA GCAACCCCGT GGAGGACAAG GACGCCGTGG
CCCTGACCTG CGAGCCCGAG ACCCAGGACA CCACCTACCT GTGGTGGGTG AACAACCAGA GCCTGCCCGT
GAGCCCCCGC CTGGAGCTGA GCAGCGACAA CCGCACCCTG ACCGTGTTCA ACATCCCCCG CAACGACACC
ACCAGCTACA AGTGCGAGAC CCAGAACCCC GTGAGCGTGC GCCGCAGCGA CCCCGTGACC CTGAACGTGC
TGTACGGCCC CGACGCCCCC ACCATCAGCC CCCTGAACAC CCCCTACCGC GCCGGCGAGA ACCTGAACCT
GACCTGCCAC GCCGCCAGCA ACCCCACCGC CCAGTACTTC TGGTTCGTGA ACGGCACCTT CCAGCAGAGC
ACCCAGGAGC TGTTCATCCC CAACATCACC GTGAACAACA GCGGCAGCTA CATGTGCCAG GCCCACAACA
GCGCCACCGG CCTGAACCGC ACCACCGTGA CCGCCATCAC CGTGTACGCC GAGCTGCCCA AGCCCTACAT
CACCAGCAAC AACAGCAACC CCATCGAGGA CAAGGACGCC GTGACCCTGA CCTGCGAGCC CGAGACCCAG
GACACCACCT ACCTGTGGTG GGTGAACAAC CAGAGCCTGA GCGTGAGCAG CCGCCTGGAG CTGAGCAACG
ACAACCGCAC CCTGACCGTG TTCAACATCC CCCGCAACGA CACCACCTTC TACGAGTGCG AGACCCAGAA
CCCCGTGAGC GTGCGCCGCA GCGACCCCGT GACCCTGAAC GTGCTGTACG GCCCCGACGC CCCCACCATC
AGCCCCCTGA ACACCCCCTA CCGCGCCGGC GAGAACCTGA ACCTGAGCTG CCACGCCGCC AGCAACCCCG
CCGCCCAGTA CAGCTGGTTC GTGAACGGCA CCTTCCAGCA GAGCACCCAG GAGCTGTTCA TCCCCAACAT
CACCGTGAAC AACAGCGGCA GCTACATGTG CCAGGCCCAC AACAGCGCCA CCGGCCTGAA CCGCACCACC
GTGACCGCCA TCACCGTGTA CGTGGAGCTG CCCAAGCCCT ACATCAGCAG CAACAACAGC AACCCCATCG
```

FIG.6A-1

AGGACAAGGA CGCCGTGACC CTGACCTGCG AGCCCGTGGC CGAGAACACC ACCTACCTGT GGTGGGTGAA
CAACCAGAGC CTGAGCGTGA GCCCCCGCCT GCAGCTGAGC AACGGCAACC GCATCCTGAC CCTGCTGAGC
GTGACCCGCA ACGACACCGG CCCCTACGAG TGCGGCATCC AGAACAGCGA GAGCGCCAAG CGCAGCGACC
CCGTGACCCT GAACGTGACC TACGGCCCCG ACACCCCCAT CATCAGCCCC CCCGACCTGA GCTACCGCAG
CGGCGCCAAC CTGAACCTGA GCTGCCACAG CGACAGCAAC CCCAGCCCCC AGTACAGCTG GCTGATCAAC
GGCACCCTGC GCCAGCACAC CCAGGTGCTG TTCATCAGCA AGATCACCAG CAACAACAGC GGCGCCTACG
CCTGCTTCGT GAGCAACCTG GCCACCGGCC GCAACAACAG CATCGTGAAG AACATCAGCG TGAGCAGCGG
CGACAGCTCT AGAGCCCCCC AGAGCATCAC CGAGCTGTGC AGCGAGTACC GGAACACCCA GATCTACACC
ATCAACGACA AGATCCTGAG CTACACCGAG AGCATGGCCG GCAAGAGGGA GATGGTGATC ATCACCTTCA
AGAGCGGCGC CACCTTCCAG GTGGAGGTGC CCGGCAGCCA GCACATCGAC AGCCAGAAGA AGGCCATCGA
GCGGATGAAG GACACCCTGC GGATCACCTA CCTCACCGAG ACCAAGATCG ACAAGCTGTG CGTGTGGAAC
AACAAGACCC CCAACAGCAT CGCCGCCATC AGCATGGAGA ATTGATAA (SEQ ID NO:14)

FIG.6A-2

RhCEAopt-LTBopt Amino Acid Sequence

```
  1  MGSPSAPLHR WCIPWQTLLL TASLLTFWNP PTTAQLTIES RPFNVAEGKE
 51  VLLLAHNVSQ NLFGYIWYKG ERVDASRRIG SCVIRTQQIT PGPAHSGRET
101  IDFNASLLIH NVTQSDTGSY TIQVIKEDLV NEEATGQFRV YPELPKPYIS
151  SNNSNPVEDK DAVALTCEPE TQDTTYLWWV NNQSLPVSPR LELSSDNRTL
201  TVFNIPRNDT TSYKCETQNP VSVRRSDPVT LNVLYGPDAP TISPLNTPYR
251  AGENLNLTCH AASNPTAQYF WFVNGTFQQS TQELFIPNIT VNNSGSYMCQ
301  AHNSATGLNR TTVTAITVYA ELPKPYITSN NSNPIEDKDA VTLTCEPETQ
351  DTTYLWWVNN QSLSVSSRLE LSNDNRTLTV FNIPRNDTTF YECETQNPVS
401  VRRSDPVTLN VLYGPDAPTI SPLNTPYRAG ENLNLSCHAA SNPAAQYSWF
451  VNGTFQQSTQ ELFIPNITVN NSGSYMCQAH NSATGLNRTT VTAITVYVEL
501  PKPYISSNNS NPIEDKDAVT LTCEPVAENT TYLWWVNNQS LSVSPRLQLS
551  NGNRILTLLS VTRNDTGPYE CGIQNSESAK RSDPVTLNVT YGPDTPIISP
601  PDLSYRSGAN LNLSCHSDSN PSPQYSWLIN GTLRQHTQVL FISKITSNNS
651  GAYACFVSNL ATGRNNSIVK NISVSSGDSS RAPQSITELC SEYRNTQIYT
701  INDKILSYTE SMAGKREMVI ITFKSGATFQ VEVPGSQHID SQKKAIERMK
751  DTLRITYLTE TKIDKLCVWN NKTPNSIAAI SMEN (SEQ ID NO:15)
```

FIG.6B

Nucleotide Sequence of First Rhesus Monkey CEA

```
   1 ATGGGGTCTC CCTCAGCCCC TCTTCACAGA TGGTGCATCC CCTGGCAGAC
  51 GCTCCTGCTC ACAGCCTCAC TTCTAACCTT CTGGAACCCG CCCACCACTG
 101 CCCAGCTCAC TATTGAATCC AGGCCGTTCA ATGTTGCAGA GGGGAAGGAG
 151 GTTCTTCTAC TTGCCCACAA TGTGTCCCAG AATCTTTTTG GCTACATTTG
 201 GTACAAGGGA GAAAGAGTGG ATGCCAGCCG TCGAATTGGA TCATGTGTAA
 251 TAAGAACTCA ACAAATTACC CCAGGGCCCG CACACAGCGG TCGAGAGACA
 301 ATAGACTTCA ATGCATCCCT GCTGATCCAC AATGTCACCC AGAGTGACAC
 351 AGGATCCTAC ACCATACAAG TCATAAAGGA AGATCTTGTG AATGAAGAAG
 401 CAACTGGCCA GTTCCGGGTA TACCCGGAGC TGCCCAAGCC CTACATCTCC
 451 AGCAACAACT CCAACCCCGT GGAGGACAAG GATGCTGTGG CCTTAACCTG
 501 TGAACCTGAG ACTCAGGACA CAACCTACCT GTGGTGGGTA AACAATCAGA
 551 GCCTCCCGGT CAGTCCCAGG CTGGAGCTGT CCAGTGACAA CAGGACCCTC
 601 ACTGTATTCA ATATTCCAAG AAATGACACA ACATCCTACA AATGTGAAAC
 651 CCAGAACCCA GTGAGTGTCA GACGCAGCGA CCCAGTCACC CTGAACGTCC
 701 TCTATGGCCC GGATGCGCCC ACCATTTCCC CTCTAAACAC ACCTTACAGA
 751 GCAGGGGAAA ATCTGAACCT CACCTGCCAC GCAGCCTCTA ACCCAACTGC
 801 ACAGTACTTT TGGTTTGTCA ATGGGACGTT CCAGCAATCC ACACAAGAGC
 851 TCTTTATACC CAACATCACC GTGAATAATA GCGGATCCTA TATGTGCCAA
 901 GCCCATAACT CAGCCACTGG CCTCAATAGG ACCACAGTCA CGGCGATCAC
 951 AGTCTACGCG GAGCTGCCCA AGCCCTACAT CACCAGCAAC AACTCCAACC
1001 CCATAGAGGA CAAGGATGCT GTGACCTTAA CCTGTGAACC TGAGACTCAG
1051 GACACAACCT ACCTGTGGTG GGTAAACAAT CAGAGCCTCT CGGTCAGTTC
1101 CAGGCTGGAG CTGTCCAATG ACAACAGGAC CCTCACTGTA TTCAATATTC
1151 CAAGAAACGA CACAACGTTC TACGAATGTG AGACCCAGAA CCCAGTGAGT
1201 GTCAGACGCA GCGACCCAGT CACCCTGAAT GTCCTCTATG GCCCGGATGC
1251 GCCCACCATT TCCCCTCTAA ACACACCTTA CAGAGCAGGG GAAAATCTGA
1301 ACCTCTCCTG CCACGCAGCC TCTAACCCAG CTGCACAGTA CTCTTGGTTT
1351 GTCAATGGGA CGTTCCAGCA ATCCACACAA GAGCTCTTTA TACCCAACAT
1401 CACCGTGAAT AATAGCGGAT CCTATATGTG CCAAGCCCAT AACTCAGCCA
1451 CTGGCCTCAA TAGGACCACA GTCACGGCGA TCACAGTCTA TGTGGAGCTG
1501 CCCAAGCCCT ACATCTCCAG CAACAACTCC AACCCCATAG AGGACAAGGA
1551 TGCTGTGACC TTAACCTGTG AACCTGTGGC TGAGAACACA ACCTACCTGT
1601 GGTGGGTAAA CAATCAGAGC CTCTCGGTCA GTCCCAGGCT GCAGCTCTCC
1651 AATGGCAACA GGATCCTCAC TCTACTCAGT GTCACACGGA ATGACACAGG
1701 ACCCTATGAA TGTGGAATCC AGAACTCAGA GAGTGCAAAA CGCAGTGACC
1751 CAGTCACCCT GAATGTCACC TATGGCCCAG ACACCCCCAT CATATCCCCC
1801 CCAGACTTGT CTTACCGTTC GGGAGCAAAC CTCAACCTCT CCTGCCACTC
```

FIG.7A-1

```
1851   GGACTCTAAC CCATCCCCGC AGTATTCTTG GCTTATCAAT GGGACACTGC
1901   GGCAACACAC ACAAGTTCTC TTTATCTCCA AAATCACATC AAACAATAGC
1951   GGGGCCTATG CCTGTTTTGT CTCTAACTTG GCTACCGGTC GCAATAACTC
2001   CATAGTCAAG AACATCTCAG TCTCCTCTGG CGATTCAGCA CCTGGAAGTT
2051   CTGGTCTCTC AGCTAGGGCT ACTGTCGGCA TCATAATTGG AATGCTGGTT
2101   GGGGTTGCTC TGATGTAG (SEQ ID NO:16)
```

FIG.7A-2

Nucleotide Sequence of Second Rhesus Monkey CEA

```
1     ATGGGGTCTC CCTCAGCCCC TCTTCACAGA TGGTGCATCC CCTGGCAGAC
51    GCTCCTGCTC ACAGCCTCAC TTCTAACCTT CTGGAACCCG CCCACCACTG
101   CCCAGCTCAC TATTGAATCC AGGCCGTTCA ATGTTGCAGA GGGGAAGGAG
151   GTTCTTCTAC TTGCCCACAA TGTGTCCCAG AATCTTTTTG GCTACATTTG
201   GTACAAGGGA GAAAGAGTGG ATGCCAGCCG TCGAATTGGA TCATGTGTAA
251   TAAGAACTCA ACAAATTACC CCAGGGCCCG CACACAGCGG TCGAGAGACA
301   ATAGACTTCA ATGCATCCCT GCTGATCCAC AATGTCACCC AGAGTGACAC
351   AGGATCCTAC ACCATACAAG TCATAAAGGA AGATCTTGTG AATGAAGAAG
401   CAACTGGCCA GTTCCGGGTA TACCCGGAGC TGCCCAAGCC CTACATCTCC
451   AGCAACAACT CCAACCCCGT GGAGGACAAG GATGCTGTGG CCTTAACCTG
501   TGAACCTGAG ACTCAGGACA CAACCTACCT GTGGTGGGTA AACAATCAGA
551   GCCTCCCGGT CAGTCCCAGG CTGGAGCTGT CCAGTGACAA CAGGACCCTC
601   ACTGTATTCA ATATTCCAAG AAATGACACA ACATCCTACA AATGTGAAAC
651   CCAGAACCCA GTGAGTGTCA GACGCAGCGA CCCAGTCACC CTGAACGTCC
701   TCTATGGCCC GGATGCGCCC ACCATTTCCC CTCTAAACAC ACCTTACAGA
751   GCAGGGGAAA ATCTGAACCT CACCTGCCAC GCAGCCTCTA ACCCAACTGC
801   ACAGTACTTT TGGTTTGTCA ATGGGACGTT CCAGCAATCC ACACAAGAGC
851   TCTTTATACC CAACATCACC GTGAATAATA GCGGATCCTA TATGTGCCAA
901   GCCCATAACT CAGCCACTGG CCTCAATAGG ACCACAGTCA CGGCGATCAC
951   AGTCTACGCG GAGCTGCCCA AGCCCTACAT CACCAGCAAC AACTCCAACC
1001  CCATAGAGGA CAAGGATGCT GTGACCTTAA CCTGTGAACC TGAGACTCAG
1051  GACACAACCT ACCTGTGGTG GGTAAACAAT CAGAGCCTCT CGGTCAGTTC
1101  CAGGCTGGAG CTGTCCAATG ACAACAGGAC CCTCACTGTA TTCAATATTC
1151  CAAGAAACGA CACAACGTTC TACGAATGTG AGACCCAGAA CCCAGTGAGT
1201  GTCAGACGCA GCGACCCAGT CACCCTGAAT GTCCTCTATG GCCCGGATGC
1251  GCCCACCATT TCCCCTCTAA ACACACCTTA CAGAGCAGGG GAAAATCTGA
1301  ACCTCTCCTG CCACGCAGCC TCTAACCCAG CTGCACAGTA CTTTTGGTTT
1351  GTCAATGGGA CGTTCCAGCA ATCCACACAA GAGCTCTTTA TACCCAACAT
1401  CACCGTGAAT AATAGCGGAT CCTATATGTG CCAAGCCCAT AACTCAGCCA
1451  CTGGCCTCAA TAGGACCACA GTCACGGCGA TCACAGTCTA TGTGGAGCTG
1501  CCCAAGCCCT ACATCTCCAG CAACAACTCC AACCCCATAG AGGACAAGGA
1551  TGCTGTGACC TTAACCTGTG AACCTGTGGC TGAGAACACA ACCTACCTGT
1601  GGTGGGTAAA CAATCAGAGC CTCTCGGTCA GTCCCAGGCT GCAGCTCTCC
1651  AATGGCAACA GGATCCTCAC TCTACTCAGT GTCACACGGA ATGACACAGG
1701  ACCCTATGAA TGTGGAATCC AGAACTCAGA GAGTGCAAAA CGCAGTGACC
1751  CAGTCACCCT GAATGTCACC TATGGCCCAG ACACCCCCAT CATATCCCCC
1801  CCAGACTTGT CTTACCGTTC GGGAGCAAAC CTCAACCTCT CCTGCCACTC
```

FIG.7B-1

```
1851    GGACTCTAAC CCATCCCCGC AGTATTCTTG GCTTATCAAT GGGACACTGC
1901    GGCAACACAC ACAAGTTCTC TTTATCTCCA AAATCACATC AAACAATAAC
1951    GGGGCCTATG CCTGTTTTGT CTCTAACTTG GCTACCGGTC GCAATAACTC
2001    CATAGTCAAG AACATCTCAG TCTCCTCTGG CGATTCAGCA CCTGGAAGTT
2051    CTGGTCTCTC AGCTAGGGCT ACTGTCGGCA TCATAATTGG AATGCTGGTT
2101    GGGGTTGCTC TGATGTAG (SEQ ID NO:17)
```

FIG.7B-2

Amino Acid Sequence of First Rhesus Monkey CEA Protein

```
  1   MGSPSAPLHR WCIPWQTLLL TASLLTFWNP PTTAQLTIES RPFNVAEGKE
 51   VLLLAHNVSQ NLFGYIWYKG ERVDASRRIG SCVIRTQQIT PGPAHSGRET
101   IDFNASLLIH NVTQSDTGSY TIQVIKEDLV NEEATGQFRV YPELPKPYIS
151   SNNSNPVEDK DAVALTCEPE TQDTTYLWWV NNQSLPVSPR LELSSDNRTL
201   TVFNIPRNDT TSYKCETQNP VSVRRSDPVT LNVLYGPDAP TISPLNTPYR
251   AGENLNLTCH AASNPTAQYF WFVNGTFQQS TQELFIPNIT VNNSGSYMCQ
301   AHNSATGLNR TTVTAITVYA ELPKPYITSN NSNPIEDKDA VTLTCEPETQ
351   DTTYLWWVNN QSLSVSSRLE LSNDNRTLTV FNIPRNDTTF YECETQNPVS
401   VRRSDPVTLN VLYGPDAPTI SPLNTPYRAG ENLNLSCHAA SNPAAQYSWF
451   VNGTFQQSTQ ELFIPNITVN NSGSYMCQAH NSATGLNRTT VTAITVYVEL
501   PKPYISSNNS NPIEDKDAVT LTCEPVAENT TYLWWVNNQS LSVSPRLQLS
551   NGNRILTLLS VTRNDTGPYE CGIQNSESAK RSDPVTLNVT YGPDTPIISP
601   PDLSYRSGAN LNLSCHSDSN PSPQYSWLIN GTLRQHTQVL FISKITSNNS
651   GAYACFVSNL ATGRNNSIVK NISVSSGDSA PGSSGLSARA TVGIIIGMLV
701   GVALM (SEQ ID NO:18)
```

FIG. 7C

Amino Acid Sequence of Second Rhesus Monkey CEA Protein

```
  1   MGSPSAPLHR WCIPWQTLLL TASLLTFWNP PTTAQLTIES RPFNVAEGKE
 51   VLLLAHNVSQ NLFGYIWYKG ERVDASRRIG SCVIRTQQIT PGPAHSGRET
101   IDFNASLLIH NVTQSDTGSY TIQVIKEDLV NEEATGQFRV YPELPKPYIS
151   SNNSNPVEDK DAVALTCEPE TQDTTYLWWV NNQSLPVSPR LELSSDNRTL
201   TVFNIPRNDT TSYKCETQNP VSVRRSDPVT LNVLYGPDAP TISPLNTPYR
251   AGENLNLTCH AASNPTAQYF WFVNGTFQQS TQELFIPNIT VNNSGSYMCQ
301   AHNSATGLNR TTVTAITVYA ELPKPYITSN NSNPIEDKDA VTLTGEPETQ
351   DTTYLWWVNN QSLSVSSRLE LSNDNRTLTV FNIPRNDTTF YECETQNPVS
401   VRRSDPVTLN VLYGPDAPTI SPLNTPYRAG ENLNLSCHAA SNPAAQYFWF
451   VNGTFQQSTQ ELFIPNITVN NSGSYMCQAH NSATGLNRTT VTAITVYVEL
501   PKPYISSNNS NPIEDKDAVT LTCEPVAENT TYLWWVNNQS LSVSPRLQLS
551   NGNRILTLLS VTRNDTGPYE CGIQNSESAK RSDPVTLNVT YGPDTPIISP
601   PDLSYRSGAN LNLSCHSDSN PSPQYSWLIN GTLRQHTQVL FISKITSNNN
651   GAYACFVSNL ATGRNNSIVK NISVSSGDSA PGSSGLSARA TVGIIIGMLV
701   GVALM (SEQ ID NO:19)
```

FIG. 7D

Amino Acid Sequence of Human CEA Protein

```
  1   MESPSAPPHR WCIPWQRLLL TASLLTFWNP PTTAKLTIES TPFNVAEGKE
 51   VLLLVHNLPQ HLFGYSWYKG ERVDGNRQII GYVIGTQQAT PGPAYSGREI
101   IYPNASLLIQ NIIQNDTGFY TLHVIKSDLV NEEATGQFRV YPELPKPSIS
151   SNNSKPVEDK DAVAFTCEPE TQDATYLWWV NNQSLPVSPR LQLSNGNRTL
201   TLFNVTRNDT ASYKCETQNP VSARRSDSVI LNVLYGPDAP TISPLNTSYR
251   SGENLNLSCH AASNPPAQYS WFVNGTFQQS TQELFIPNIT VNNSGSYTCQ
301   AHNSDTGLNR TTVTTITVYA EPPKPFITSN NSNPVEDEDA VALTCEPEIQ
351   NTTYLWWVNN QSLPVSPRLQ LSNDNRTLTL LSVTRNDVGP YECGIQNELS
401   VDHSDPVILN VLYGPDDPTI SPSYTYYRPG VNLSLSCHAA SNPPAQYSWL
451   IDGNIQQHTQ ELFISNITEK NSGLYTCQAN NSASGHSRTT VKTITVSAEL
501   PKPSISSNNS KPVEDKDAVA FTCEPEAQNT TYLWWVNGQS LPVSPRLQLS
551   NGNRTLTLFN VTRNDARAYV CGIQNSVSAN RSDPVTLDVL YGPDTPIISP
601   PDSSYLSGAN LNLSCHSASN PSPQYSWRIN GIPQQHTQVL FIAKITPNNN
651   GTYACFVSNL ATGRNNSIVK SITVSASGTS PGLSAGATVG IMIGULVGVA
701   LI (SEQ ID NO:20)
```

FIG.7E

```
      M E S P  S A P  P H R  W C I P  W Q R·
1     ATGGAGAGCC CCAGCGCCCC CCCCCACCGC TGGTGCATCC CCTGGCAGCG
      ·L L L  T A S L  L T F  W N P  P T T A
51    CCTGCTGCTG ACCGCCAGCC TGCTGACCTT CTGGAACCCC CCCACCACCG
      · K L T  I E S  T P F N  V A E  G K E
101   CCAAGCTGAC CATCGAGAGC ACCCCCTTCA ACGTGGCCGA GGGCAAGGAG
      V L L L  V H N  L P Q  H L F G  Y S W·
151   GTGCTGCTGC TGGTGCACAA CCTGCCCCAG CACCTGTTCG GCTACAGCTG
      ·Y K G  E R V D  G N R  Q I I  G Y V I
201   GTACAAGGGC GAGCGCGTGG ACGGCAACCG CCAGATCATC GGCTACGTGA
      · G T Q  Q A T  P G P A  Y S G  R E I
251   TCGGCACCCA GCAGGCCACC CCCGGCCCCG CCTACAGCGG CCGCGAGATC
      I Y P N  A S L  L I Q  N I I Q  N D T·
301   ATCTACCCCA ACGCCAGCCT GCTGATCCAG AACATCATCC AGAACGACAC
      ·G F Y  T L H V  I K S  D L V  N E E A
351   CGGCTTCTAC ACCCTGCACG TGATCAAGAG CGACCTGGTG AACGAGGAGG
      · T G Q  F R V  Y P E L  P K P  S I S
401   CCACCGGCCA GTTCCGCGTG TACCCCGAGC TGCCCAAGCC CAGCATCAGC
      S N N S  K P V  E D K  D A V A  F T C·
451   AGCAACAACA GCAAGCCCGT GGAGGACAAG GACGCCGTGG CCTTCACCTG
      ·E P E  T Q D A  T Y L  W W V  N N Q S
501   CGAGCCCGAG ACCCAGGACG CCACCTACCT GTGGTGGGTG AACAACCAGA
      · L P V  S P R  L Q L S  N G N  R T L
551   GCCTGCCCGT GAGCCCCCGC CTGCAGCTGA GCAACGGCAA CCGCACCCTG
      T L F N  V T R  N D T  A S Y K  C E T·
601   ACCCTGTTCA ACGTGACCCG CAACGACACC GCCAGCTACA AGTGCGAGAC
      ·Q N P  V S A R  R S D  S V I  L N V L
651   CCAGAACCCC GTGAGCGCCC GCCGCAGCGA CAGCGTGATC CTGAACGTGC
      · Y G P  D A P  T I S P  L N T  S Y R
701   TGTACGGCCC CGACGCCCCC ACCATCAGCC CCCTGAACAC CAGCTACCGC
      S G E N  L N L  S C H  A A S N  P P A·
751   AGCGGCGAGA ACCTGAACCT GAGCTGCCAC GCCGCCAGCA ACCCCCCCGC
      ·Q Y S  W F V N  G T F  Q Q S  T Q E L
801   CCAGTACAGC TGGTTCGTGA ACGGCACCTT CCAGCAGAGC ACCCAGGAGC
      · F I P  N I T  V N N S  G S Y  T C Q
851   TGTTCATCCC CAACATCACC GTGAACAACA GCGGCAGCTA CACCTGCCAG
      A H N S  D T G  L N R  T T V T  T I T·
901   GCCCACAACA GCGACACCGG CCTGAACCGC ACCACCGTGA CCACCATCAC
      ·V Y A  E P P K  P F I  T S N  N S N P
951   CGTGTACGCC GAGCCCCCCA AGCCCTTCAT CACCAGCAAC AACAGCAACC
      · V E D  E D A  V A L T  C E P  E I Q
```

FIG. 26A-1

```
1001  CCGTGGAGGA CGAGGACGCC GTGGCCCTGA CCTGCGAGCC CGAGATCCAG
       N  T  T  Y   L  W  W   V  N  N   Q  S  L  P   V  S  P·
1051  AACACCACCT ACCTGTGGTG GGTGAACAAC CAGAGCCTGC CCGTGAGCCC
      · R  L  Q   L  S  N  D   N  R  T   L  T  L   L  S  V  T·
1101  CCGCCTGCAG CTGAGCAACG ACAACCGCAC CCTGACCCTG CTGAGCGTGA
      ·  R  N  D   V  G  P   Y  E  C  G   I  Q  N   E  L  S
1151  CCCGCAACGA CGTGGGCCCC TACGAGTGCG GCATCCAGAA CGAGCTGAGC
       V  D  H  S   D  P  V   I  L  N   V  L  Y  G   P  D  D·
1201  GTGGACCACA GCGACCCCGT GATCCTGAAC GTGCTGTACG GCCCCGACGA
      · P  T  I   S  P  S  Y   T  Y  Y   R  P  G   V  N  L  S·
1251  CCCCACCATC AGCCCCAGCT ACACCTACTA CCGCCCCGGC GTGAACCTGA
      ·  L  S  C   H  A  A   S  N  P  P   A  Q  Y   S  W  L
1301  GCCTGAGCTG CCACGCCGCC AGCAACCCCC CCGCCCAGTA CAGCTGGCTG
       I  D  G  N   I  Q  Q   H  T  Q   E  L  F  I   S  N  I·
1351  ATCGACGGCA ACATCCAGCA GCACACCCAG GAGCTGTTCA TCAGCAACAT
      · T  E  K   N  S  G  L   Y  T  C   Q  A  N   N  S  A  S·
1401  CACCGAGAAG AACAGCGGCC TGTACACCTG CCAGGCCAAC AACAGCGCCA
      ·  G  H  S   R  T  T   V  K  T  I   T  V  S   A  E  L
1451  GCGGCCACAG CCGCACCACC GTGAAGACCA TCACCGTGAG CGCCGAGCTG
       P  K  P  S   I  S  S   N  N  S   K  P  V  E   D  K  D·
1501  CCCAAGCCCA GCATCAGCAG CAACAACAGC AAGCCCGTGG AGGACAAGGA
      · A  V  A   F  T  C  E   P  E  A   Q  N  T   T  Y  L  W·
1551  CGCCGTGGCC TTCACCTGCG AGCCCGAGGC CCAGAACACC ACCTACCTGT
      ·  W  V  N   G  Q  S   L  P  V  S   P  R  L   Q  L  S
1601  GGTGGGTGAA CGGCCAGAGC CTGCCCGTGA GCCCCCGCCT GCAGCTGAGC
       N  G  N  R   T  L  T   L  F  N   V  T  R  N   D  A  R·
1651  AACGGCAACC GCACCCTGAC CCTGTTCAAC GTGACCCGCA ACGACGCCCG
      · A  Y  V   C  G  I  Q   N  S  V   S  A  N   R  S  D  P
1701  CGCCTACGTG TGCGGCATCC AGAACAGCGT GAGCGCCAAC CGCAGCGACC
      ·  V  T  L   D  V  L   Y  G  P  D   T  P  I   I  S  P
1751  CCGTGACCCT GGACGTGCTG TACGGCCCCG ACACCCCCAT CATCAGCCCC
       P  D  S  S   Y  L  S   G  A  N   L  N  L  S   C  H  S
1801  CCCGACAGCA GCTACCTGAG CGGCGCCAAC CTGAACCTGA GCTGCCACAG
      · A  S  N   P  S  P  Q   Y  S  W   R  I  N   G  I  P  Q
1851  CGCCAGCAAC CCCAGCCCCC AGTACAGCTG GCGCATCAAC GGCATCCCCC
      ·  Q  H  T   Q  V  L   F  I  A  K   I  T  P   N  N  N
1901  AGCAGCACAC CCAGGTGCTG TTCATCGCCA AGATCACCCC CAACAACAAC
       G  T  Y  A   C  F  V   S  N  L   A  T  G  R   N  N  S
1951  GGCACCTACG CCTGCTTCGT GAGCAACCTG GCCACCGGCC GCAACAACAG
      · I  V  K   S  I  T  V   S  A  S   G  T  S   R  S  T  P
2001  CATCGTGAAG AGCATCACCG TGAGCGCCAG CGGCACCTCT AGAAGCACCC
      ·  I  P  F   S  Y  S   K  N  L  D   C  W  V   D  N  E
```

FIG. 26A-2

```
2051 CCATCCCATT CAGCTACAGC AAGAACCTGG ACTGCTGGGT GGACAACGAG
      E  D  I  D   V  I  L   K  K  S   T  I  L  N   L  D  I·
2101 GAGGACATCG ACGTGATCCT GAAGAAGAGC ACCATCCTGA ACCTGGACAT
     ·N  N  D   I  I  S  D   I  S  G   F  N  S   S  V  I  T·
2151 CAACAACGAC ATCATCAGCG ACATCAGCGG CTTCAACAGC AGCGTGATCA
     · Y  P  D   A  Q  L   V  P  G  I   N  G  K   A  I  H
2201 CCTACCCCGA CGCCCAGCTG GTGCCCGGCA TCAACGGCAA GGCCATCCAC
      L  V  N  N   E  S  S   E  V  I   V  H  K  A   M  D  I·
2251 CTGGTGAACA ACGAGAGCAG CGAGGTGATC GTGCACAAGG CCATGGACAT
     ·E  Y  N   D  M  F  N   N  F  T   V  S  F   W  L  R  V·
2301 CGAGTACAAC GACATGTTCA ACAACTTCAC CGTGAGCTTC TGGCTGAGAG
     · P  K  V   S  A  S   H  L  E  Q   Y  G  T   N  E  Y
2351 TGCCTAAGGT GAGCGCCAGC CACCTGGAGC AGTACGGCAC CAACGAGTAC
      S  I  I  S   S  M  K   K  H  S   L  S  I  G   S  G  W·
2401 AGCATCATCA GCAGCATGAA GAAGCACAGC CTGAGCATCG GCAGCGGCTG
     ·S  V  S   L  K  G  N   N  L  I   W  T  L   K  D  S  A·
2451 GAGCGTGAGC CTGAAGGGCA ACAACCTCAT CTGGACCCTG AAGGATAGCG
     · G  E  V   R  Q  I   T  F  R  D   L  P  D   K  F  N
2501 CCGGAGAGGT GAGACAGATC ACCTTCAGAG ACCTGCCCGA CAAGTTCAAT
      A  Y  L  A   N  K  W   V  F  I   T  I  T  N   D  R  L·
2551 GCCTACCTGG CCAACAAGTG GGTGTTCATC ACCATCACCA ACGACAGACT
     ·S  S  A   N  L  Y  I   N  G  V   L  M  G   S  A  E  I·
2601 GAGCAGCGCC AACCTGTACA TCAACGGCGT GCTCATGGGC AGCGCCGAGA
     · T  G  L   G  A  I   R  E  D  N   N  I  T   L  K  L
2651 TCACCGGCCT GGGCGCCATC AGAGAGGACA ACAACATCAC CCTGAAGCTG
      D  R  C  N   N  N  N   Q  Y  V   S  I  D  K   F  R  I·
2701 GACAGATGCA ACAACAACAA CCAGTACGTG AGCATCGACA AGTTCCGGAT
     ·F  C  K   A  L  N  P   K  E  I   E  K  L   Y  T  S  Y·
2751 CTTCTGCAAG GCCCTGAACC CCAAGGAGAT CGAGAAGCTG TACACCAGCT
     · L  S  I   T  F  L   R  D  F  W   G  N  P   L  R  Y
2801 ACCTGAGCAT CACCTTCCTG AGAGACTTCT GGGGCAACCC CCTGAGATAC
      D  T  * (SEQ ID NO:45)
2851 GACACCTAG (SEQ ID NO:21)
```

FIG.26A-3

```
     M  E  S  P   S  A  P   P  H  R   W  C  I   P  W  Q   R  L  L  L
   1 ATGGAGAGCC CCAGCGCCCC CCCCCACCGC TGGTGCATCC CCTGGCAGCG CCTGCTGCTG
     T  A  S  L   L  T  F   W  N  P   P  T  T   A  K  L   T  I  E  S
  61 ACCGCCAGCC TGCTGACCTT CTGGAACCCC CCCACCACCG CCAAGCTGAC CATCGAGAGC
     T  P  F  N   V  A  E   G  K  E   V  L  L   L  V  H   N  L  P  Q
 121 ACCCCCTTCA ACGTGGCCGA GGGCAAGGAG GTGCTGCTGC TGGTGCACAA CCTGCCCCAG
     H  L  F  G   Y  S  W   Y  K  G   E  R  V   D  G  N   R  Q  I  I
 181 CACCTGTTCG GCTACAGCTG GTACAAGGGC GAGCGCGTGG ACGGCAACCG CCAGATCATC
     G  Y  V  I   G  T  Q   Q  A  T   P  G  P   A  Y  S   G  R  E  I
 241 GGCTACGTGA TCGGCACCCA GCAGGCCACC CCCGGCCCCG CCTACAGCGG CCGCGAGATC
     I  Y  P  N   A  S  L   L  I  Q   N  I  I   Q  N  D   T  G  F  Y
 301 ATCTACCCCA ACGCCAGCCT GCTGATCCAG AACATCATCC AGAACGACAC CGGCTTCTAC
     T  L  H  V   I  K  S   D  L  V   N  E  E   A  T  G   Q  F  R  V
 361 ACCCTGCACG TGATCAAGAG CGACCTGGTG AACGAGGAGG CCACCGGCCA GTTCCGCGTG
     Y  P  E  L   P  K  P   S  I  S   S  N  N   S  K  P   V  E  D  K
 421 TACCCCGAGC TGCCCAAGCC CAGCATCAGC AGCAACAACA GCAAGCCCGT GGAGGACAAG
     D  A  V  A   F  T  C   E  P  E   T  Q  D   A  T  Y   L  W  W  V
 481 GACGCCGTGG CCTTCACCTG CGAGCCCGAG ACCCAGGACG CCACCTACCT GTGGTGGGTG
     N  N  Q  S   L  P  V   S  P  R   L  Q  L   S  N  G   N  R  T  L
 541 AACAACCAGA GCCTGCCCGT GAGCCCCCGC CTGCAGCTGA GCAACGGCAA CCGCACCCTG
     T  L  F  N   V  T  R   N  D  T   A  S  Y   K  C  E   T  Q  N  P
 601 ACCCTGTTCA ACGTGACCCG CAACGACACC GCCAGCTACA AGTGCGAGAC CCAGAACCCC
     V  S  A  R   R  S  D   S  V  I   L  N  V   L  Y  G   P  D  A  P
 661 GTGAGCGCCC GCCGCAGCGA CAGCGTGATC CTGAACGTGC TGTACGGCCC CGACGCCCCC
     T  I  S  P   L  N  T   S  Y  R   S  G  E   N  L  N   L  S  C  H
 721 ACCATCAGCC CCCTGAACAC CAGCTACCGC AGCGGCGAGA ACCTGAACCT GAGCTGCCAC
     A  A  S  N   P  P  A   Q  Y  S   W  F  V   N  G  T   F  Q  Q  S
 781 GCCGCCAGCA ACCCCCCCGC CCAGTACAGC TGGTTCGTGA ACGGCACCTT CCAGCAGAGC
     T  Q  E  L   F  I  P   N  I  T   V  N  N   S  G  S   Y  T  C  Q
 841 ACCCAGGAGC TGTTCATCCC CAACATCACC GTGAACAACA GCGGCAGCTA CACCTGCCAG
     A  H  N  S   D  T  G   L  N  R   T  T  V   T  T  I   T  V  Y  A
 901 GCCCACAACA GCGACACCGG CCTGAACCGC ACCACCGTGA CCACCATCAC CGTGTACGCC
     E  P  P  K   P  F  I   T  S  N   N  S  N   P  V  E   D  E  D  A
 961 GAGCCCCCCA AGCCCTTCAT CACCAGCAAC AACAGCAACC CCGTGGAGGA CGAGGACGCC
     V  A  L  T   C  E  P   E  I  Q   N  T  T   Y  L  W   W  V  N  N
1021 GTGGCCCTGA CCTGCGAGCC CGAGATCCAG AACACCACCT ACCTGTGGTG GGTGAACAAC
     Q  S  L  P   V  S  P   R  L  Q   L  S  N   D  N  R   T  L  T  L
1081 CAGAGCCTGC CCGTGAGCCC CCGCCTGCAG CTGAGCAACG ACAACCGCAC CCTGACCCTG
     L  S  V  T   R  N  D   V  G  P   Y  E  C   G  I  Q   N  E  L  S
1141 CTGAGCGTGA CCCGCAACGA CGTGGGCCCC TACGAGTGCG GCATCCAGAA CGAGCTGAGC
     V  D  H  S   D  P  V   I  L  N   V  L  Y   G  P  D   D  P  T  I
```

FIG.27A-1

```
1201 GTGGACCACA GCGACCCCGT GATCCTGAAC GTGCTGTACG GCCCCGACGA CCCCACCATC
      S  P  S  Y   T  Y  Y   R  P  G   V  N  L  S   L  S  C   H  A  A
1261 AGCCCCAGCT ACACCTACTA CCGCCCCGGC GTGAACCTGA GCCTGAGCTG CCACGCCGCC
      S  N  P  P   A  Q  Y   S  W  L   I  D  G  N   I  Q  Q   H  T  Q
1321 AGCAACCCCC CCGCCCAGTA CAGCTGGCTG ATCGACGGCA ACATCCAGCA GCACACCCAG
      E  L  F  I   S  N  I   T  E  K   N  S  G  L   Y  T  C   Q  A  N
1381 GAGCTGTTCA TCAGCAACAT CACCGAGAAG AACAGCGGCC TGTACACCTG CCAGGCCAAC
      N  S  A  S   G  H  S   R  T  T   V  K  T  I   T  V  S   A  E  L
1441 AACAGCGCCA GCGGCCACAG CCGCACCACC GTGAAGACCA TCACCGTGAG CGCCGAGCTG
      P  K  P  S   I  S  S   N  N  S   K  P  V  E   D  K  D   A  V  A
1501 CCCAAGCCCA GCATCAGCAG CAACAACAGC AAGCCCGTGG AGGACAAGGA CGCCGTGGCC
      F  T  C  E   P  E  A   Q  N  T   T  Y  L  W   W  V  N   G  Q  S
1561 TTCACCTGCG AGCCCGAGGC CCAGAACACC ACCTACCTGT GGTGGGTGAA CGGCCAGAGC
      L  P  V  S   P  R  L   Q  L  S   N  G  N  R   T  L  T   L  F  N
1621 CTGCCCGTGA GCCCCCGCCT GCAGCTGAGC AACGGCAACC GCACCCTGAC CCTGTTCAAC
      V  T  R  N   D  A  R   A  Y  V   C  G  I  Q   N  S  V   S  A  N
1681 GTGACCCGCA ACGACGCCCG CGCCTACGTG TGCGGCATCC AGAACAGCGT GAGCGCCAAC
      R  S  D  P   V  T  L   D  V  L   Y  G  P  D   T  P  I   I  S  P
1741 CGCAGCGACC CCGTGACCCT GGACGTGCTG TACGGCCCCG ACACCCCCAT CATCAGCCCC
      P  D  S  S   Y  L  S   G  A  N   L  N  L  S   C  H  S   A  S  N
1801 CCCGACAGCA GCTACCTGAG CGGCGCCAAC CTGAACCTGA GCTGCCACAG CGCCAGCAAC
      P  S  P  Q   Y  S  W   R  I  N   G  I  P  Q   Q  H  T   Q  V  L
1861 CCCAGCCCCC AGTACAGCTG GCGCATCAAC GGCATCCCCC AGCAGCACAC CCAGGTGCTG
      F  I  A  K   I  T  P   N  N  N   G  T  Y  A   C  F  V   S  N  L
1921 TTCATCGCCA AGATCACCCC CAACAACAAC GGCACCTACG CCTGCTTCGT GAGCAACCTG
      A  T  G  R   N  N  S   I  V  K   S  I  T  V   S  A  S   G  T  S
1981 GCCACCGGCC GCAACAACAG CATCGTGAAG AGCATCACCG TGAGCGCCAG CGGCACCTCT
      R  K  T  H   T  C  P   P  C  P   A  P  E  L   L  G  G   P  S  V
2041 AGAAAGACCC ACACCTGCCC CCCTTGCCCT GCCCCTGAGC TGCTGGGCGG ACCCAGCGTG
      F  L  F  P   P  K  P   K  D  T   L  M  I  S   R  T  P   E  V  T
2101 TTCCTGTTCC CCCCCAAGCC TAAGGACACC CTCATGATCA GCAGAACCCC CGAGGTGACC
      C  V  V  V   D  V  S   H  E  D   P  E  V  K   F  N  W   Y  V  D
2161 TGCGTGGTGG TGGACGTGAG CCACGAGGAT CCCGAGGTGA AGTTCAACTG GTACGTGGAC
      G  V  E  V   H  N  A   K  T  K   P  R  E  E   Q  Y  N   S  T  Y
2221 GGCGTGGAGG TGCACAATGC CAAGACCAAG CCCAGAGAGG AGCAGTACAA CAGCACCTAC
      R  V  V  S   V  L  T   V  L  H   Q  D  W  L   N  G  K   E  Y  K
2281 AGAGTGGTGA GCGTGCTCAC CGTGCTGCAC CAGGATTGGC TGAACGGCAA GGAGTACAAG
      C  K  V  S   N  K  A   L  P  A   P  I  E  K   T  I  S   K  A  K
2341 TGCAAGGTGA GCAACAAGGC CCTGCCTGCC CCCATCGAGA AAACCATCAG CAAGGCCAAG
      G  Q  P  R   E  P  Q   V  Y  T   L  P  P  S   R  D  E   L  T  K
```

FIG.27A-2

```
2401 GGCCAGCCCA GAGAGCCCCA GGTGTACACC CTGCCCCCTA GCAGAGATGA GTTGACCAAG
      N  Q  V  S  L  T  C  L  V  K  G  F  Y  P  S  D  I  A  V  E
2461 AACCAGGTGA GCCTCACATG CCTGGTGAAG GGCTTCTACC CCAGCGACAT CGCCGTGGAG
      W  E  S  N  G  Q  P  E  N  N  Y  K  T  T  P  P  V  L  D  S
2521 TGGGAGAGCA ACGGCCAGCC CGAGAACAAC TACAAGACCA CCCCCCCTGT GCTGGACAGC
      D  G  S  F  F  L  Y  S  K  L  T  V  D  K  S  R  W  Q  Q  G
2581 GATGGCAGCT TCTTCCTGTA CAGCAAGCTC ACCGTGGACA AGAGCAGATG GCAGCAGGGC
      N  V  F  S  C  S  V  M  H  E  A  L  H  N  H  Y  T  Q  K  S
2641 AACGTGTTCA GCTGCAGCGT GATGCACGAG GCCCTGCACA ATCACTACAC CCAGAAGAGC
      L  S  L  S  P  G  K  * (SEQ ID NO:46)
2701 CTGAGCCTGA GCCCCGGCAA GTAA   (SEQ ID NO:25)
```

FIG.27A-3

```
atggagtctc cctcggcccc tccccacaga tggtgcatcc cctggcagag gctcctgctc 60
acagcctcac ttctaacctt ctggaacccg cccaccactg ccaagctcac tattgaatcc 120
acgccgttca atgtcgcaga ggggaaggag gtgcttctac ttgtccacaa tctgccccag 180
catctttttg gctacagctg gtacaaaggt gaaagagtgg atggcaaccg tcaaattata 240
ggatatgtaa taggaactca acaagctacc ccagggcccg catacagtgg tcgagagata 300
atataccccca atgcatccct gctgatccag aacatcatcc agaatgacac aggattctac 360
accctacacg tcataaagtc agatcttgtg aatgaagaag caactggcca gttccgggta 420
tacccggagc tgcccaagcc ctccatctcc agcaacaact ccaaacccgt ggaggacaag 480
gatgctgtgg ccttcacctg tgaacctgag actcaggacg caacctacct gtggtgggta 540
aacaatcaga gcctcccggt cagtcccagg ctgcagctgt ccaatggcaa caggaccctc 600
actctattca atgtcacaag aaatgacaca gcaagctaca aatgtgaaac ccagaaccca 660
gtgagtgcca ggcgcagtga ttcagtcatc ctgaatgtcc tctatggccc ggatgccccc 720
accatttccc ctctaaacac atcttacaga tcaggggaaa atctgaacct ctcctgccac 780
gcagcctcta acccacctgc acagtactct tggtttgtca atgggacttt ccagcaatcc 840
acccaagagc tctttatccc caacatcact gtgaataata gtggatccta tacgtgccaa 900
gcccataact cagacactgg cctcaatagg accacagtca cgacgatcac agtctatgca 960
gagccaccca aacccttcat caccagcaac aactccaacc ccgtggagga tgaggatgct 1020
gtagccttaa cctgtgaacc tgagattcag aacacaacct acctgtggtg ggtaaataat 1080
cagagcctcc cggtcagtcc caggctgcag ctgtccaatg acaacaggac cctcactcta 1140
ctcagtgtca caaggaatga tgtaggaccc tatgagtgtg gaatccagaa cgaattaagt 1200
gttgaccaca gcgacccagt catcctgaat gtcctctatg gcccagacga ccccaccatt 1260
tccccctcat acacctatta ccgtccaggg gtgaacctca gcctctcctg ccatgcagcc 1320
tctaacccac ctgcacagta ttcttggctg attgatggga acatccagca acacacacaa 1380
gagctcttta tctccaacat cactgagaag aacagcggac tctatacctg ccaggccaat 1440
aactcagcca gtggccacag caggactaca gtcaagacaa tcacagtctc tgcggagctg 1500
cccaagccct ccatctccag caacaactcc aaacccgtgg aggacaagga tgctgtggcc 1560
ttcacctgtg aacctgaggc tcagaacaca acctacctgt ggtgggtaaa tggtcagagc 1620
ctcccagtca gtcccaggct gcagctgtcc aatggcaaca ggaccctcac tctattcaat 1680
gtcacaagaa atgacgcaag agcctatgta tgtggaatcc agaactcagt gagtgcaaac 1740
cgcagtgacc cagtcaccct ggatgtcctc tatgggccgg acacccccat catttccccc 1800
ccagactcgt cttacctttc gggagcgaac ctcaacctct cctgccactc ggcctctaac 1860
ccatccccgc agtattcttg gcgtatcaat gggataccgc agcaacacac acaagttctc 1920
tttatcgcca aaatcacgcc aaataataac gggacctatg cctgttttgt ctctaacttg 1980
gctactggcc gcaataattc catagtcaag agcatcacag tctctgcatc tggaact(SEQ ID NO:22)
```

FIG.28A

```
1    MESPSAPPHR WCIPWQRLLL TASLLTFWNP PTTAKLTIES TPFNVAEGKE
51   VLLLVHNLPQ HLFGYSWYKG ERVDGNRQII GYVIGTQQAT PGPAYSGREI
101  IYPNASLLIQ NIIQNDTGFY TLHVIKSDLV NEEATGQFRV YPELPKPSIS
151  SNNSKPVEDK DAVAFTCEPE TQDATYLWWV NNQSLPVSPR LQLSNGNRTL
201  TLFNVTRNDT ASYKCETQNP VSARRSDSVI LNVLYGPDAP TISPLNTSYR
251  SGENLNLSCH AASNPPAQYS WFVNGTFQQS TQELFIPNIT VNNSGSYTCQ
301  AHNSDTGLNR TTVTTITVYA EPPKPFITSN NSNPVEDEDA VALTCEPEIQ
351  NTTYLWWVNN QSLPVSPRLQ LSNDNRTLTL LSVTRNDVGP YECGIQNELS
401  VDHSDPVILN VLYGPDDPTI SPSYTYYRPG VNLSLSCHAA SNPPAQYSWL
451  IDGNIQQHTQ ELFISNITEK NSGLYTCQAN NSASGHSRTT VKTITVSAEL
501  PKPSISSNNS KPVEDKDAVA FTCEPEAQNT TYLWWVNGQS LPVSPRLQLS
551  NGNRTLTLFN VTRNDARAYV CGIQNSVSAN RSDPVTLDVL YGPDTPIISP
601  PDSSYLSGAN LNLSCHSASN PSPQYSWRIN GIPQQHTQVL FIAKITPNNN
651  GTYACFVSNL ATGRNNSIVK SITVSASGT (SEQ ID NO:23)
```

FIG.28B

```
     D  S  T  P  I  P  F  S  Y  S  K  N  L  D  C  W  V  D  N  E
1    GATTCAACAC CAATTCCATT TTCTTATTCT AAAAATCTGG ATTGTTGGGT TGATAATGAA
     E  D  I  D  V  I  L  K  K  S  T  I  L  N  L  D  I  N  N  D
61   GAAGATATAG ATGTTATATT AAAAAAGAGT ACAATTTTAA ATTTAGATAT TAATAATGAT
     I  I  S  D  I  S  G  F  N  S  S  V  I  T  Y  P  D  A  Q  L
121  ATTATATCAG ATATATCTGG GTTTAATTCA TCTGTAATAA CATATCCAGA TGCTCAATTG
     V  P  G  I  N  G  K  A  I  H  L  V  N  N  E  S  S  E  V  I
181  GTGCCCGGAA TAAATGGCAA AGCAATACAT TTAGTAAACA ATGAATCTTC TGAAGTTATA
     V  H  K  A  M  D  I  E  Y  N  D  M  F  N  N  F  T  V  S  F
241  GTGCATAAAG CTATGGATAT TGAATATAAT GATATGTTTA ATAATTTTAC CGTTAGCTTT
     W  L  R  V  P  K  V  S  A  S  H  L  E  Q  Y  G  T  N  E  Y
301  TGGTTGAGGG TTCCTAAAGT ATCTGCTAGT CATTTAGAAC AATATGGCAC AAATGAGTAT
     S  I  I  S  S  M  K  K  H  S  L  S  I  G  S  G  W  S  V  S
361  TCAATAATTA GCTCTATGAA AAAACATAGT CTATCAATAG GATCTGGTTG GAGTGTATCA
     L  K  G  N  N  L  I  W  T  L  K  D  S  A  G  E  V  R  Q  I
421  CTTAAAGGTA ATAACTTAAT ATGGACTTTA AAAGATTCCG CGGGAGAAGT TAGACAAATA
     T  F  R  D  L  P  D  K  F  N  A  Y  L  A  N  K  W  V  F  I
481  ACTTTTAGGG ATTTACCTGA TAAATTTAAT GCTTATTTAG CAAATAAATG GGTTTTTATA
     T  I  T  N  D  R  L  S  S  A  N  L  Y  I  N  G  V  L  M  G
541  ACTATTACTA ATGATAGATT ATCTTCTGCT AATTTGTATA TAAATGGAGT ACTTATGGGA
     S  A  E  I  T  G  L  G  A  I  R  E  D  N  N  I  T  L  K  L
601  AGTGCAGAAA TTACTGGTTT AGGAGCTATT AGAGAGGATA ATAATATAAC ATTAAAACTA
     D  R  C  N  N  N  N  Q  Y  V  S  I  D  K  F  R  I  F  C  K
661  GATAGATGTA ATAATAATAA TCAATACGTT TCTATTGATA AATTTAGGAT ATTTTGCAAA
     A  L  N  P  K  E  I  E  K  L  Y  T  S  Y  L  S  I  T  F  L
721  GCATTAAATC CAAAAGAGAT TGAAAAATTA TACACAAGTT ATTTATCTAT AACCTTTTTA
     R  D  F  W  G  N  P  L  R  Y  D  T  D  R  *(SEQ ID NO:48)
781  AGAGACTTCT GGGGAAACCC TTTACGATAT GATACAGATA GGTAG (SEQ ID NO:47)
```

FIG. 29

```
1     ATGGAGTCTC CCTCGGCCCC TCCCCACAGA TGGTGCATCC CCTGGCAGAG GCTCCTGCTC
61    ACAGCCTCAC TTCTAACCTT CTGGAACCCG CCCACCACTG CCAAGCTCAC TATTGAATCC
121   ACGCCGTTCA ATGTCGCAGA GGGGAAGGAG GTGCTTCTAC TTGTCCACAA TCTGCCCCAG
181   CATCTTTTTG GCTACAGCTG GTACAAAGGT GAAAGAGTGG ATGGCAACCG TCAAATTATA
241   GGATATGTAA TAGGAACTCA ACAAGCTACC CCAGGGCCCG CATACAGTGG TCGAGAGATA
301   ATATACCCCA ATGCATCCCT GCTGATCCAG AACATCATCC AGAATGACAC AGGATTCTAC
361   ACCCTACACG TCATAAAGTC AGATCTTGTG AATGAAGAAG CAACTGGCCA GTTCCGGGTA
421   TACCCGGAGC TGCCCAAGCC CTCCATCTCC AGCAACAACT CCAAACCCGT GGAGGACAAG
481   GATGCTGTGG CCTTCACCTG TGAACCTGAG ACTCAGGACG CAACCTACCT GTGGTGGGTA
541   AACAATCAGA GCCTCCCGGT CAGTCCCAGG CTGCAGCTGT CCAATGGCAA CAGGACCCTC
601   ACTCTATTCA ATGTCACAAG AAATGACACA GCAAGCTACA AATGTGAAAC CCAGAACCCA
661   GTGAGTGCCA GGCGCAGTGA TTCAGTCATC CTGAATGTCC TCTATGGCCC GGATGCCCCC
721   ACCATTTCCC CTCTAAACAC ATCTTACAGA TCAGGGGAAA ATCTGAACCT CTCCTGCCAC
781   GCAGCCTCTA ACCCACCTGC ACAGTACTCT TGGTTTGTCA ATGGGACTTT CCAGCAATCC
841   ACCCAAGAGC TCTTTATCCC CAACATCACT GTGAATAATA GTGGATCCTA TACGTGCCAA
901   GCCCATAACT CAGACACTGG CCTCAATAGG ACCACAGTCA CGACGATCAC AGTCTATGCA
961   GAGCCACCCA AACCCTTCAT CACCAGCAAC AACTCCAACC CCGTGGAGGA TGAGGATGCT
1021  GTAGCCTTAA CCTGTGAACC TGAGATTCAG AACACAACCT ACCTGTGGTG GGTAAATAAT
1081  CAGAGCCTCC CGGTCAGTCC CAGGCTGCAG CTGTCCAATG ACAACAGGAC CCTCACTCTA
1141  CTCAGTGTCA CAAGGAATGA TGTAGGACCC TATGAGTGTG GAATCCAGAA CGAATTAAGT
1201  GTTGACCACA GCGACCCAGT CATCCTGAAT GTCCTCTATG GCCCAGACGA CCCCACCATT
1261  TCCCCCTCAT ACACCTATTA CCGTCCAGGG GTGAACCTCA GCCTCTCCTG CCATGCAGCC
1321  TCTAACCCAC CTGCACAGTA TTCTTGGCTG ATTGATGGGA ACATCCAGCA ACACACACAA
1381  GAGCTCTTTA TCTCCAACAT CACTGAGAAG AACAGCGGAC TCTATACCTG CCAGGCCAAT
1441  AACTCAGCCA GTGGCCACAG CAGGACTACA GTCAAGACAA TCACAGTCTC TGCGGAGCTG
1501  CCCAAGCCCT CCATCTCCAG CAACAACTCC AAACCCGTGG AGGACAAGGA TGCTGTGGCC
1561  TTCACCTGTG AACCTGAGGC TCAGAACACA ACCTACCTGT GGTGGGTAAA TGGTCAGAGC
1621  CTCCCAGTCA GTCCCAGGCT GCAGCTGTCC AATGGCAACA GGACCCTCAC TCTATTCAAT
1681  GTCACAAGAA ATGACGCAAG AGCCTATGTA TGTGGAATCC AGAACTCAGT GAGTGCAAAC
1741  CGCAGTGACC CAGTCACCCT GGATGTCCTC TATGGGCCGG ACACCCCCAT CATTTCCCCC
1801  CCAGACTCGT CTTACCTTTC GGGAGCGAAC CTCAACCTCT CCTGCCACTC GGCCTCTAAC
1861  CCATCCCCGC AGTATTGGTG GCGTATCAAT GGGATACCGC AGCAACACAC ACAAGTTCTC
1921  TTTATCGCCA AAATCACGCC AAATAATAAC GGGACCTATG CCTGTTTTGT CTCTAACTTG
1981  GCTACTGGCC GCAATAATTC CATAGTCAAG AGCATCACAG TCTCTGCATC TGGAACTCTA
2041  GATTCAACAC CAATTCCATT TTCTTATTCT AAAAATCTGG ATTGTTGGGT TGATAATGAA
2101  GAAGATATAG ATGTTATATT AAAAAAGAGT ACAATTTTAA ATTTAGATAT TAATAATGAT
2161  ATTATATCAG ATATATCTGG GTTTAATTCA TCTGTAATAA CATATCCAGA TGCTCAATTG
2221  GTGCCCGGAA TAAATGGCAA AGCAATACAT TTAGTAAACA ATGAATCTTC TGAAGTTATA
2281  GTGCATAAAG CTATGGATAT TGAATATAAT GATATGTTTA ATAATTTTAC CGTTAGCTTT
2341  TGGTTGAGGG TTCCTAAAGT ATCTGCTAGT CATTTAGAAC AATATGGCAC AAATGAGTAT
2401  TCAATAATTA GCTCTATGAA AAAACATAGT CTATCAATAG GATCTGGTTG GAGTGTATCA
```

FIG.30A-1

```
2461 CTTAAAGGTA ATAACTTAAT ATGGACTTTA AAAGATTCCG CGGGAGAAGT TAGACAAATA
2521 ACTTTTAGGG ATTTACCTGA TAAATTTAAT GCTTATTTAG CAAATAAATG GGTTTTTATA
2581 ACTATTACTA ATGATAGATT ATCTTCTGCT AATTTGTATA TAAATGGAGT ACTTATGGGA
2641 AGTGCAGAAA TTACTGGTTT AGGAGCTATT AGAGAGGATA ATAATATAAC ATTAAAACTA
2701 GATAGATGTA ATAATAATAA TCAATACGTT TCTATTGATA AATTTAGGAT ATTTTGCAAA
2761 GCATTAAATC CAAAAGAGAT TGAAAAATTA TACACAAGTT ATTTATCTAT AACCTTTTTA
2821 AGAGACTTCT GGGGAAACCC TTTACGATAT GATATAG (SEQ ID NO:49)
```

FIG.30A-2

```
1     ATGGGCAGCC CCAGCGCCCC CCTGCACCGC TGGTGCATCC CCTGGCAGAC
      CCTGCTGCTG ACCGCCAGCC TGCTGACCTT CTGGAACCCC CCCACCACCG
101   CCCAGCTGAC CATCGAGAGC CGCCCCTTCA ACGTGGCCGA GGGCAAGGAG
      GTGCTGCTGC TGGCCCACAA CGTGAGCCAG AACCTGTTCG GCTACATCTG
201   GTACAAGGGC GAGCGCGTGG ACGCCAGCCG CCGCATCGGC AGCTGCGTGA
      TCCGCACCCA GCAGATCACC CCCGGCCCCG CCCACAGCGG CCGCGAGACC
301   ATCGACTTCA ACGCCAGCCT GCTGATCCAC AACGTGACCC AGAGCGACAC
      CGGCAGCTAC ACCATCCAGG TGATCAAGGA GGACCTGGTG AACGAGGAGG
401   CCACCGGCCA GTTCCGCGTG TACCCCGAGC TGCCCAAGCC CTACATCAGC
      AGCAACAACA GCAACCCCGT GGAGGACAAG GACGCCGTGG CCCTGACCTG
501   CGAGCCCGAG ACCCAGGACA CCACCTACCT GTGGTGGGTG AACAACCAGA
      GCCTGCCCGT GAGCCCCCGC CTGGAGCTGA GCAGCGACAA CCGCACCCTG
601   ACCGTGTTCA ACATCCCCCG CAACGACACC ACCAGCTACA AGTGCGAGAC
      CCAGAACCCC GTGAGCGTGC GCCGCAGCGA CCCCGTGACC CTGAACGTGC
701   TGTACGGCCC CGACGCCCCC ACCATCAGCC CCCTGAACAC CCCCTACCGC
      GCCGGCGAGA ACCTGAACCT GACCTGCCAC GCCGCCAGCA ACCCCACCGC
801   CCAGTACTTC TGGTTCGTGA ACGGCACCTT CCAGCAGAGC ACCCAGGAGC
      TGTTCATCCC CAACATCACC GTGAACAACA GCGGCAGCTA CATGTGCCAG
901   GCCCACAACA GCGCCACCGG CCTGAACCGC ACCACCGTGA CCGCCATCAC
      CGTGTACGCC GAGCTGCCCA AGCCCTACAT CACCAGCAAC AACAGCAACC
1001  CCATCGAGGA CAAGGACGCC GTGACCCTGA CCTGCGAGCC CGAGACCCAG
      GACACCACCT ACCTGTGGTG GGTGAACAAC CAGAGCCTGA GCGTGAGCAG
1101  CCGCCTGGAG CTGAGCAACG ACAACCGCAC CCTGACCGTG TTCAACATCC
      CCCGCAACGA CACCACCTTC TACGAGTGCG AGACCCAGAA CCCCGTGAGC
1201  GTGCGCCGCA GCGACCCCGT GACCCTGAAC GTGCTGTACG GCCCCGACGC
      CCCCACCATC AGCCCCCTGA ACACCCCCTA CCGCGCCGGC GAGAACCTGA
1301  ACCTGAGCTG CCACGCCGCC AGCAACCCCG CCGCCCAGTA CAGCTGGTTC
      GTGAACGGCA CCTTCCAGCA GAGCACCCAG GAGCTGTTCA TCCCCAACAT
1401  CACCGTGAAC AACAGCGGCA GCTACATGTG CCAGGCCCAC AACAGCGCCA
      CCGGCCTGAA CCGCACCACC GTGACCGCCA TCACCGTGTA CGTGGAGCTG
1501  CCCAAGCCCT ACATCAGCAG CAACAACAGC AACCCCATCG AGGACAAGGA
      CGCCGTGACC CTGACCTGCG AGCCCGTGGC CGAGAACACC ACCTACCTGT
1601  GGTGGGTGAA CAACCAGAGC CTGAGCGTGA GCCCCCGCCT GCAGCTGAGC
      AACGGCAACC GCATCCTGAC CCTGCTGAGC GTGACCCGCA ACGACACCGG
1701  CCCCTACGAG TGCGGCATCC AGAACAGCGA GAGCGCCAAG CGCAGCGACC
      CCGTGACCCT GAACGTGACC TACGGCCCCG ACACCCCCAT CATCAGCCCC
1801  CCCGACCTGA GCTACCGCAG CGGCGCCAAC CTGAACCTGA GCTGCCACAG
      CGACAGCAAC CCCAGCCCCC AGTACAGCTG GCTGATCAAC GGCACCCTGC
1901  GCCAGCACAC CCAGGTGCTG TTCATCAGCA AGATCACCAG CAACAACAGC
      GGCGCCTACG CCTGCTTCGT GAGCAACCTG GCCACCGGCC GCAACAACAG
2001  CATCGTGAAG AACATCAGCG TGAGCAGCGG CGACAGCTCT AGAAGCACCC
      CCATCCCATT CAGCTACAGC AAGAACCTGG ACTGCTGGGT GGACAACGAG
```

FIG.31A-1

```
2101  GAGGACATCG ACGTGATCCT GAAGAAGAGC ACCATCCTGA ACCTGGACAT
      CAACAACGAC ATCATCAGCG ACATCAGCGG CTTCAACAGC AGCGTGATCA
2201  CCTACCCCGA CGCCCAGCTG GTGCCCGGCA TCAACGGCAA GGCCATCCAC
      CTGGTGAACA ACGAGAGCAG CGAGGTGATC GTGCACAAGG CCATGGACAT
2301  CGAGTACAAC GACATGTTCA ACAACTTCAC CGTGAGCTTC TGGCTGAGAG
      TGCCTAAGGT GAGCGCCAGC CACCTGGAGC AGTACGGCAC CAACGAGTAC
2401  AGCATCATCA GCAGCATGAA GAAGCACAGC CTGAGCATCG GCAGCGGCTG
      GAGCGTGAGC CTGAAGGGCA ACAACCTCAT CTGGACCCTG AAGGATAGCG
2501  CCGGAGAGGT GAGACAGATC ACCTTCAGAG ACCTGCCCGA CAAGTTCAAT
      GCCTACCTGG CCAACAAGTG GGTGTTCATC ACCATCACCA ACGACAGACT
2601  GAGCAGCGCC AACCTGTACA TCAACGGCGT GCTCATGGGC AGCGCCGAGA
      TCACCGGCCT GGGCGCCATC AGAGAGGACA ACAACATCAC CCTGAAGCTG
2701  GACAGATGCA ACAACAACAA CCAGTACGTG AGCATCGACA AGTTCCGGAT
      CTTCTGCAAG GCCCTGAACC CCAAGGAGAT CGAGAAGCTG TACACCAGCT
2801  ACCTGAGCAT CACCTTCCTG AGAGACTTCT GGGGCAACCC CCTGAGATAC
      GACACCTAG (SEQ ID NO:50)
```

FIG.31A-2

```
  1  MGSPSAPLHR WCIPWQTLLL TASLLTFWNP PTTAQLTIES RPFNVAEGKE
 51  VLLLAHNVSQ NLFGYIWYKG ERVDASRRIG SCVIRTQQIT PGPAHSGRET
101  IDFNASLLIH NVTQSDTGSY TIQVIKEDLV NEEATGQFRV YPELPKPYIS
151  SNNSNPVEDK DAVALTCEPE TQDTTYLWWV NNQSLPVSPR LELSSDNRTL
201  TVFNIPRNDT TSYKCETQNP VSVRRSDPVT LNVLYGPDAP TISPLNTPYR
251  AGENLNLTCH AASNPTAQYF WFVNGTFQQS TQELFIPNIT VNNSGSYMCQ
301  AHNSATGLNR TTVTAITVYA ELPKPYITSN NSNPIEDKDA VTLTCEPETQ
351  DTTYLWWVNN QSLSVSSRLE LSNDNRTLTV FNIPRNDTTF YECETQNPVS
401  VRRSDPVTLN VLYGPDAPTI SPLNTPYRAG ENLNLSCHAA SNPAAQYSWF
451  VNGTFQQSTQ ELFIPNITVN NSGSYMCQAH NSATGLNRTT VTAITVYVEL
501  PKPYISSNNS NPIEDKDAVT LTCEPVAENT TYLWWVNNQS LSVSPRLQLS
551  NGNRILTLLS VTRNDTGPYE CGIQNSESAK RSDPVTLNVT YGPDTPIISP
601  PDLSYRSGAN LNLSCHSDSN PSPQYSWLIN GTLRQHTQVL FISKITSNNS
651  GAYACFVSNL ATGRNNSIVK NISVSSGDSS RSTPIPFSYS KNLDCWVDNE
701  EDIDVILKKS TILNLDINND IISDISGFNS SVITYPDAQL VPGINGKAIH
751  LVNNESSEVI VHKAMDIEYN DMFNNFTVSF WLRVPKVSAS HLEQYGTNEY
801  SIISSMKKHS LSIGSGWSVS LKGNNLIWTL KDSAGEVRQI TFRDLPDKFN
851  AYLANKWVFI TITNDRLSSA NLYINGVLMG SAEITGLGAI REDNNITLKL
901  DRCNNNNQYV SIDKFRIFCK ALNPKEIEKL YTSYLSITFL RDFWGNPLRY
951  DT* (SEQ ID NO:51)
```

FIG.31B

```
1     ATGGGCAGCC CCAGCGCCCC CCTGCACCGC TGGTGCATCC CCTGGCAGAC
      CCTGCTGCTG ACCGCCAGCC TGCTGACCTT CTGGAACCCC CCCACCACCG
101   CCCAGCTGAC CATCGAGAGC CGCCCCTTCA ACGTGGCCGA GGGCAAGGAG
      GTGCTGCTGC TGGCCCACAA CGTGAGCCAG AACCTGTTCG GCTACATCTG
201   GTACAAGGGC GAGCGCGTGG ACGCCAGCCG CCGCATCGGC AGCTGCGTGA
      TCCGCACCCA GCAGATCACC CCCGGCCCCG CCCACAGCGG CCGCGAGACC
301   ATCGACTTCA ACGCCAGCCT GCTGATCCAC AACGTGACCC AGAGCGACAC
      CGGCAGCTAC ACCATCCAGG TGATCAAGGA GGACCTGGTG AACGAGGAGG
401   CCACCGGCCA GTTCCGCGTG TACCCCGAGC TGCCCAAGCC CTACATCAGC
      AGCAACAACA GCAACCCCGT GGAGGACAAG GACGCCGTGG CCCTGACCTG
501   CGAGCCCGAG ACCCAGGACA CCACCTACCT GTGGTGGGTG AACAACCAGA
      GCCTGCCCGT GAGCCCCCGC CTGGAGCTGA GCAGCGACAA CCGCACCCTG
601   ACCGTGTTCA ACATCCCCCG CAACGACACC ACCAGCTACA AGTGCGAGAC
      CCAGAACCCC GTGAGCGTGC GCCGCAGCGA CCCCGTGACC CTGAACGTGC
701   TGTACGGCCC CGACGCCCCC ACCATCAGCC CCCTGAACAC CCCCTACCGC
      GCCGGCGAGA ACCTGAACCT GACCTGCCAC GCCGCCAGCA ACCCCACCGC
801   CCAGTACTTC TGGTTCGTGA ACGGCACCTT CCAGCAGAGC ACCCAGGAGC
      TGTTCATCCC CAACATCACC GTGAACAACA GCGGCAGCTA CATGTGCCAG
901   GCCCACAACA GCGCCACCGG CCTGAACCGC ACCACCGTGA CCGCCATCAC
      CGTGTACGCC GAGCTGCCCA AGCCCTACAT CACCAGCAAC AACAGCAACC
1001  CCATCGAGGA CAAGGACGCC GTGACCCTGA CCTGCGAGCC CGAGACCCAG
      GACACCACCT ACCTGTGGTG GGTGAACAAC CAGAGCCTGA GCGTGAGCAG
1101  CCGCCTGGAG CTGAGCAACG ACAACCGCAC CCTGACCGTG TTCAACATCC
      CCCGCAACGA CACCACCTTC TACGAGTGCG AGACCCAGAA CCCCGTGAGC
1201  GTGCGCCGCA GCGACCCCGT GACCCTGAAC GTGCTGTACG GCCCCGACGC
      CCCCACCATC AGCCCCCTGA ACACCCCCTA CCGCGCCGGC GAGAACCTGA
1301  ACCTGAGCTG CCACGCCGCC AGCAACCCCG CCGCCCAGTA CAGCTGGTTC
      GTGAACGGCA CCTTCCAGCA GAGCACCCAG GAGCTGTTCA TCCCCAACAT
1401  CACCGTGAAC AACAGCGGCA GCTACATGTG CCAGGCCCAC AACAGCGCCA
      CCGGCCTGAA CCGCACCACC GTGACCGCCA TCACCGTGTA CGTGGAGCTG
1501  CCCAAGCCCT ACATCAGCAG CAACAACAGC AACCCCATCG AGGACAAGGA
      CGCCGTGACC CTGACCTGCG AGCCCGTGGC CGAGAACACC ACCTACCTGT
1601  GGTGGGTGAA CAACCAGAGC CTGAGCGTGA GCCCCCGCCT GCAGCTGAGC
      AACGGCAACC GCATCCTGAC CCTGCTGAGC GTGACCCGCA ACGACACCGG
1701  CCCCTACGAG TGCGGCATCC AGAACAGCGA GAGCGCCAAG CGCAGCGACC
      CCGTGACCCT GAACGTGACC TACGGCCCCG ACACCCCCAT CATCAGCCCC
1801  CCCGACCTGA GCTACCGCAG CGGCGCCAAC CTGAACCTGA GCTGCCACAG
      CGACAGCAAC CCCAGCCCCC AGTACAGCTG GCTGATCAAC GGCACCCTGC
1901  GCCAGCACAC CCAGGTGCTG TTCATCAGCA AGATCACCAG CAACAACAGC
      GGCGCCTACG CCTGCTTCGT GAGCAACCTG GCCACCGGCC GCAACAACAG
2001  CATCGTGAAG AACATCAGCG TGAGCAGCGG CGACAGCTCT AGAACCCCTC
      AGAACATCAC CGATCTGTGC GCCGAGTACC ACAACACCCA GATCTACACC
```

FIG.32A-1

```
2101  CTGAACGACA AGATCTTCAG CTACACCGAG AGCCTGGCCG GCAAGAGAGA
      GATGGCCATC ATCACCTTCA AGAACGGCGC CATCTTCCAG GTGGAGGTGC
2201  CCGGCAGCCA GCACATCGAC AGCCAGAAGA AGGCCATCGA GCGGATGAAG
      GACACCCTGC GGATCGCCTA CCTCACCGAG GCCAAGGTGG AGAAGCTGTG
2301  CGTGTGGAAC AACAAGACCC CTCACGCCAT CGCCGCCATC AGCATGGCCA
      ATTGATAAG (SEQ ID NO:52)
```

FIG.32A-2

```
  1   MGSPSAPLHR WCIPWQTLLL TASLLTFWNP PTTAQLTIES RPFNVAEGKE
 51   VLLLAHNVSQ NLFGYIWYKG ERVDASRRIG SCVIRTQQIT PGPAHSGRET
101   IDFNASLLIH NVTQSDTGSY TIQVIKEDLV NEEATGQFRV YPELPKPYIS
151   SNNSNPVEDK DAVALTCEPE TQDTTYLWWV NNQSLPVSPR LELSSDNRTL
201   TVFNIPRNDT TSYKCETQNP VSVRRSDPVT LNVLYGPDAP TISPLNTPYR
251   AGENLNLTCH AASNPTAQYF WFVNGTFQQS TQELFIPNIT VNNSGSYMCQ
301   AHNSATGLNR TTVTAITVYA ELPKPYITSN NSNPIEDKDA VTLTCEPETQ
351   DTTYLWWVNN QSLSVSSRLE LSNDNRTLTV FNIPRNDTTF YECETQNPVS
401   VRRSDPVTLN VLYGPDAPTI SPLNTPYRAG ENLNLSCHAA SNPAAQYSWF
451   VNGTFQQSTQ ELFIPNITVN NSGSYMCQAH NSATGLNRTT VTAITVYVEL
501   PKPYISSNNS NPIEDKDAVT LTCEPVAENT TYLWWVNNQS LSVSPRLQLS
551   NGNRILTLLS VTRNDTGPYE CGIQNSESAK RSDPVTLNVT YGPDTPIISP
601   PDLSYRSGAN LNLSCHSDSN PSPQYSWLIN GTLRQHTQVL FISKITSNNS
651   GAYACFVSNL ATGRNNSIVK NISVSSGDSS RTPQNITDLC AEYHNTQIYT
701   LNDKIFSYTE SLAGKREMAI ITFKNGAIFQ VEVPGSQHID SQKKAIERMK
751   DTLRIAYLTE AKVEKLCVWN NKTPHAIAAI SMAN** (SEQ ID NO:53)
```

FIG.32B

SEQUENCE LISTING

```
<160> NUMBER OF SEQ ID NOS: 54

<210> SEQ ID NO 1
<211> LENGTH: 31
<212> TYPE: DNA
<213> ORGANISM: Artificial Sequence
<220> FEATURE:
<223> OTHER INFORMATION: PCR Primer, chemically synthesized

<400> SEQUENCE: 1

tattctagat gctccccaga ctattacaga a                                 31


<210> SEQ ID NO 2
<211> LENGTH: 35
<212> TYPE: DNA
<213> ORGANISM: Artificial Sequence
<220> FEATURE:
<223> OTHER INFORMATION: PCR Primer, chemically synthesized

<400> SEQUENCE: 2

tatgcggccg cctagttttc catactgatt gccgc                             35
```

<210> SEQ ID NO 3
<211> LENGTH: 35
<212> TYPE: DNA
<213> ORGANISM: Artificial Sequence
<220> FEATURE:
<223> OTHER INFORMATION: PCR Primer, chemically synthesized

<400> SEQUENCE: 3
gctctagagc cccccagagc atcaccgagc tgtgc 35

<210> SEQ ID NO 4
<211> LENGTH: 38
<212> TYPE: DNA
<213> ORGANISM: Artificial Sequence
<220> FEATURE:
<223> OTHER INFORMATION: PCR Primer, chemically synthesized

<400> SEQUENCE: 4
gctctagaac ccctcagaac atcaccgatc tgtgcgcc 38

<210> SEQ ID NO 5
<211> LENGTH: 30
<212> TYPE: DNA
<213> ORGANISM: Artificial Sequence
<220> FEATURE:
<223> OTHER INFORMATION: PCR Primer, chemically synthesized

<400> SEQUENCE: 5
tattctagat aatggcgaca aattataccg 30

<210> SEQ ID NO 6
<211> LENGTH: 35
<212> TYPE: DNA
<213> ORGANISM: Artificial Sequence
<220> FEATURE:
<223> OTHER INFORMATION: PCR Primer, chemically synthesized

<400> SEQUENCE: 6
tatgcggccg ctcataattc atcccgaatt ctgtt 35

<210> SEQ ID NO 7
<211> LENGTH: 2766
<212> TYPE: DNA
<213> ORGANISM: Artificial Sequence
<220> FEATURE:
<223> OTHER INFORMATION: CEA-LTA fusion

<400> SEQUENCE: 7
atggagtctc cctcggcccc tccccacaga tggtgcatcc cctggcagag gctcctgctc 60
acagcctcac ttctaacctt ctggaacccg cccaccactg ccaagctcac tattgaatcc 120
acgccgttca atgtcgcaga ggggaaggag gtgcttctac ttgtccacaa tctgccccag 180
catctttttg gctacagctg gtacaaaggt gaaagagtgg atggcaaccg tcaaattata 240
ggatatgtaa taggaactca acaagctacc ccagggcccg catacagtgg tcgagagata 300
atatacccca atgcatccct gctgatccag aacatcatcc agaatgacac aggattctac 360
accctacacg tcataaagtc agatcttgtg aatgaagaag caactggcca gttccgggta 420
tacccggagc tgcccaagcc ctccatctcc agcaacaact ccaaacccgt ggaggacaag 480
gatgctgtgg ccttcacctg tgaacctgag actcaggacg caacctacct gtggtgggta 540
aacaatcaga gcctcccggt cagtcccagg ctgcagctgt ccaatggcaa caggaccctc 600
actctattca atgtcacaag aaatgacaca gcaagctaca aatgtgaaac ccagaaccca 660
gtgagtgcca ggcgcagtga ttcagtcatc ctgaatgtcc tctatggccc ggatgccccc 720

```
accatttccc ctctaaacac atcttacaga tcaggggaaa atctgaacct ctcctgccac    780

gcagcctcta acccacctgc acagtactct tggtttgtca atgggacttt ccagcaatcc    840

acccaagagc tctttatccc caacatcact gtgaataata gtggatccta tacgtgccaa    900

gcccataact cagacactgg cctcaatagg accacagtca cgacgatcac agtctatgca    960

gagccaccca aacccttcat caccagcaac aactccaacc ccgtggagga tgaggatgct   1020

gtagccttaa cctgtgaacc tgagattcag aacacaacct acctgtggtg ggtaaataat   1080

cagagcctcc cggtcagtcc caggctgcag ctgtccaatg acaacaggac cctcactcta   1140

ctcagtgtca caaggaatga tgtaggaccc tatgagtgtg gaatccagaa cgaattaagt   1200

gttgaccaca gcgacccagt catcctgaat gtcctctatg gcccagacga ccccaccatt   1260

tccccctcat acacctatta ccgtccaggg gtgaacctca gcctctcctg ccatgcagcc   1320

tctaacccac ctgcacagta ttcttggctg attgatggga acatccagca acacacacaa   1380

gagctcttta tctccaacat cactgagaag aacagcggac tctatacctg ccaggccaat   1440

aactcagcca gtggccacag caggactaca gtcaagacaa tcacagtctc tgcggagctg   1500

cccaagccct ccatctccag caacaactcc aaacccgtgg aggacaagga tgctgtggcc   1560

ttcacctgtg aacctgaggc tcagaacaca acctacctgt ggtgggtaaa tggtcagagc   1620

ctcccagtca gtcccaggct gcagctgtcc aatggcaaca ggaccctcac tctattcaat   1680

gtcacaagaa atgacgcaag agcctatgta tgtggaatcc agaactcagt gagtgcaaac   1740

cgcagtgacc cagtcaccct ggatgtcctc tatgggccgg acacccccat catttccccc   1800

ccagactcgt cttacctttc gggagcgaac ctcaacctct cctgccactc ggcctctaac   1860

ccatccccgc agtattcttg gcgtatcaat gggataccgc agcaacacac acaagttctc   1920

tttatcgcca aaatcacgcc aaataataac gggacctatg cctgttttgt ctctaacttg   1980

gctactggcc gcaataattc catagtcaag agcatcacag tctctgcatc tggaactcta   2040

gttaatggcg acaaattata ccgtgctgac tctagacccc cagatgaaat aaaacgttcc   2100

ggaggtctta tgcccagagg gcataatgag tacttcgata gaggaactca aatgaatatt   2160

aatctttatg atcacgcgag aggaacacaa accggctttg tcagatatga tgacggatat   2220

gtttccactt ctcttagttt gagaagtgct cacttagcag gacagtctat attatcagga   2280

tattccactt actatatata tgttatagcg acagcaccaa atatgtttaa tgttaatgat   2340

gtattaggcg tatacagccc tcacccatat gaacaggagg tttctgcgtt aggtggaata   2400

ccatattctc agatatatgg atggtatcgt gttaattttg gtgtaattga tgaacgatta   2460

catcgtaaca gggaatatag agaccggtat tacagaaatc tgaatatagc tccggcagag   2520

gatggttaca gattagcagg tttcccaccg gatcaccaag cttggagaga agaaccctgg   2580

attcatcatg caccacaagg ttgtggaaat tcatcaagaa caattacaga tgatacttgt   2640

aatgaggaga cccagaatct gagcacaata tatctcagga aatatcaatc aaaagttaag   2700

aggcagatat tttcagacta tcagtcagag gttgacatat ataacagaat tcgggatgaa   2760

ttatga                                                              2766
```

<210> SEQ ID NO 8
<211> LENGTH: 921
<212> TYPE: PRT
<213> ORGANISM: Artificial Sequence
<220> FEATURE:
<223> OTHER INFORMATION: CEA-LTB fusion

<400> SEQUENCE: 8

```
Met Glu Ser Pro Ser Ala Pro Pro His Arg Trp Cys Ile Pro Trp Gln
 1               5                  10                  15

Arg Leu Leu Leu Thr Ala Ser Leu Leu Thr Phe Trp Asn Pro Pro Thr
            20                  25                  30

Thr Ala Lys Leu Thr Ile Glu Ser Thr Pro Phe Asn Val Ala Glu Gly
        35                  40                  45

Lys Glu Val Leu Leu Leu Val His Asn Leu Pro Gln His Leu Phe Gly
    50                  55                  60

Tyr Ser Trp Tyr Lys Gly Glu Arg Val Asp Gly Asn Arg Gln Ile Ile
65                  70                  75                  80

Gly Tyr Val Ile Gly Thr Gln Gln Ala Thr Pro Gly Pro Ala Tyr Ser
                85                  90                  95

Gly Arg Glu Ile Ile Tyr Pro Asn Ala Ser Leu Leu Ile Gln Asn Ile
            100                 105                 110

Ile Gln Asn Asp Thr Gly Phe Tyr Thr Leu His Val Ile Lys Ser Asp
        115                 120                 125

Leu Val Asn Glu Glu Ala Thr Gly Gln Phe Arg Val Tyr Pro Glu Leu
    130                 135                 140

Pro Lys Pro Ser Ile Ser Ser Asn Asn Ser Lys Pro Val Glu Asp Lys
145                 150                 155                 160

Asp Ala Val Ala Phe Thr Cys Glu Pro Glu Thr Gln Asp Ala Thr Tyr
                165                 170                 175

Leu Trp Trp Val Asn Asn Gln Ser Leu Pro Val Ser Pro Arg Leu Gln
            180                 185                 190

Leu Ser Asn Gly Asn Arg Thr Leu Thr Leu Phe Asn Val Thr Arg Asn
        195                 200                 205

Asp Thr Ala Ser Tyr Lys Cys Glu Thr Gln Asn Pro Val Ser Ala Arg
    210                 215                 220

Arg Ser Asp Ser Val Ile Leu Asn Val Leu Tyr Gly Pro Asp Ala Pro
225                 230                 235                 240

Thr Ile Ser Pro Leu Asn Thr Ser Tyr Arg Ser Gly Glu Asn Leu Asn
                245                 250                 255

Leu Ser Cys His Ala Ala Ser Asn Pro Pro Ala Gln Tyr Ser Trp Phe
            260                 265                 270

Val Asn Gly Thr Phe Gln Gln Ser Thr Gln Glu Leu Phe Ile Pro Asn
        275                 280                 285

Ile Thr Val Asn Asn Ser Gly Ser Tyr Thr Cys Gln Ala His Asn Ser
    290                 295                 300

Asp Thr Gly Leu Asn Arg Thr Thr Val Thr Thr Ile Thr Val Tyr Ala
305                 310                 315                 320

Glu Pro Pro Lys Pro Phe Ile Thr Ser Asn Asn Ser Asn Pro Val Glu
                325                 330                 335

Asp Glu Asp Ala Val Ala Leu Thr Cys Glu Pro Glu Ile Gln Asn Thr
            340                 345                 350

Thr Tyr Leu Trp Trp Val Asn Asn Gln Ser Leu Pro Val Ser Pro Arg
        355                 360                 365

Leu Gln Leu Ser Asn Asp Asn Arg Thr Leu Thr Leu Leu Ser Val Thr
    370                 375                 380

Arg Asn Asp Val Gly Pro Tyr Glu Cys Gly Ile Gln Asn Glu Leu Ser
385                 390                 395                 400

Val Asp His Ser Asp Pro Val Ile Leu Asn Val Leu Tyr Gly Pro Asp
                405                 410                 415

Asp Pro Thr Ile Ser Pro Ser Tyr Thr Tyr Tyr Arg Pro Gly Val Asn
```

```
            420                 425                 430

Leu Ser Leu Ser Cys His Ala Ala Ser Asn Pro Pro Ala Gln Tyr Ser
        435                 440                 445

Trp Leu Ile Asp Gly Asn Ile Gln Gln His Thr Gln Glu Leu Phe Ile
    450                 455                 460

Ser Asn Ile Thr Glu Lys Asn Ser Gly Leu Tyr Thr Cys Gln Ala Asn
465                 470                 475                 480

Asn Ser Ala Ser Gly His Ser Arg Thr Thr Val Lys Thr Ile Thr Val
                485                 490                 495

Ser Ala Glu Leu Pro Lys Pro Ser Ile Ser Ser Asn Asn Ser Lys Pro
            500                 505                 510

Val Glu Asp Lys Asp Ala Val Ala Phe Thr Cys Glu Pro Glu Ala Gln
        515                 520                 525

Asn Thr Thr Tyr Leu Trp Trp Val Asn Gly Gln Ser Leu Pro Val Ser
    530                 535                 540

Pro Arg Leu Gln Leu Ser Asn Gly Asn Arg Thr Leu Thr Leu Phe Asn
545                 550                 555                 560

Val Thr Arg Asn Asp Ala Arg Ala Tyr Val Cys Gly Ile Gln Asn Ser
                565                 570                 575

Val Ser Ala Asn Arg Ser Asp Pro Val Thr Leu Asp Val Leu Tyr Gly
            580                 585                 590

Pro Asp Thr Pro Ile Ile Ser Pro Pro Asp Ser Ser Tyr Leu Ser Gly
        595                 600                 605

Ala Asn Leu Asn Leu Ser Cys His Ser Ala Ser Asn Pro Ser Pro Gln
    610                 615                 620

Tyr Ser Trp Arg Ile Asn Gly Ile Pro Gln Gln His Thr Gln Val Leu
625                 630                 635                 640

Phe Ile Ala Lys Ile Thr Pro Asn Asn Asn Gly Thr Tyr Ala Cys Phe
                645                 650                 655

Val Ser Asn Leu Ala Thr Gly Arg Asn Asn Ser Ile Val Lys Ser Ile
            660                 665                 670

Thr Val Ser Ala Ser Gly Thr Leu Val Asn Gly Asp Lys Leu Tyr Arg
        675                 680                 685

Ala Asp Ser Arg Pro Pro Asp Glu Ile Lys Arg Ser Gly Gly Leu Met
    690                 695                 700

Pro Arg Gly His Asn Glu Tyr Phe Asp Arg Gly Thr Gln Met Asn Ile
705                 710                 715                 720

Asn Leu Tyr Asp His Ala Arg Gly Thr Gln Thr Gly Phe Val Arg Tyr
                725                 730                 735

Asp Asp Gly Tyr Val Ser Thr Ser Leu Ser Leu Arg Ser Ala His Leu
            740                 745                 750

Ala Gly Gln Ser Ile Leu Ser Gly Tyr Ser Thr Tyr Tyr Ile Tyr Val
        755                 760                 765

Ile Ala Thr Ala Pro Asn Met Phe Asn Val Asn Asp Val Leu Gly Val
    770                 775                 780

Tyr Ser Pro His Pro Tyr Glu Gln Glu Val Ser Ala Leu Gly Gly Ile
785                 790                 795                 800

Pro Tyr Ser Gln Ile Tyr Gly Trp Tyr Arg Val Asn Phe Gly Val Ile
                805                 810                 815

Asp Glu Arg Leu His Arg Asn Arg Glu Tyr Arg Asp Arg Tyr Tyr Arg
            820                 825                 830

Asn Leu Asn Ile Ala Pro Ala Glu Asp Gly Tyr Arg Leu Ala Gly Phe
        835                 840                 845
```

```
Pro Pro Asp His Gln Ala Trp Arg Glu Glu Pro Trp Ile His His Ala
    850                 855                 860

Pro Gln Gly Cys Gly Asn Ser Ser Arg Thr Ile Thr Asp Asp Thr Cys
865                 870                 875                 880

Asn Glu Glu Thr Gln Asn Leu Ser Thr Ile Tyr Leu Arg Lys Tyr Gln
                885                 890                 895

Ser Lys Val Lys Arg Gln Ile Phe Ser Asp Tyr Gln Ser Glu Val Asp
            900                 905                 910

Ile Tyr Asn Arg Ile Arg Asp Glu Leu
        915                 920


<210> SEQ ID NO 9
<211> LENGTH: 2355
<212> TYPE: DNA
<213> ORGANISM: Artificial Sequence
<220> FEATURE:
<223> OTHER INFORMATION: CEA-LTB fusion

<400> SEQUENCE: 9

atggagtctc cctcggcccc tccccacaga tggtgcatcc cctggcagag gctcctgctc      60

acagcctcac ttctaacctt ctggaacccg cccaccactg ccaagctcac tattgaatcc     120

acgccgttca atgtcgcaga ggggaaggag gtgcttctac ttgtccacaa tctgccccag     180

catctttttg gctacagctg gtacaaaggt gaaagagtgg atggcaaccg tcaaattata     240

ggatatgtaa taggaactca acaagctacc ccagggcccg catacagtgg tcgagagata     300

atatacccca atgcatccct gctgatccag aacatcatcc agaatgacac aggattctac     360

accctacacg tcataaagtc agatcttgtg aatgaagaag caactggcca gttccgggta     420

tacccggagc tgcccaagcc ctccatctcc agcaacaact ccaaacccgt ggaggacaag     480

gatgctgtgg ccttcacctg tgaacctgag actcaggacg caacctacct gtggtgggta     540

aacaatcaga gcctcccggt cagtcccagg ctgcagctgt ccaatggcaa caggaccctc     600

actctattca atgtcacaag aaatgacaca gcaagctaca aatgtgaaac ccagaaccca     660

gtgagtgcca ggcgcagtga ttcagtcatc ctgaatgtcc tctatggccc ggatgccccc     720

accatttccc ctctaaacac atcttacaga tcaggggaaa atctgaacct ctcctgccac     780

gcagcctcta acccacctgc acagtactct tggtttgtca atgggacttt ccagcaatcc     840

acccaagagc tctttatccc caacatcact gtgaataata gtggatccta tacgtgccaa     900

gcccataact cagacactgg cctcaatagg accacagtca cgacgatcac agtctatgca     960

gagccaccca aacccttcat caccagcaac aactccaacc ccgtggagga tgaggatgct    1020

gtagccttaa cctgtgaacc tgagattcag aacacaacct acctgtggtg ggtaaataat    1080

cagagcctcc cggtcagtcc caggctgcag ctgtccaatg acaacaggac cctcactcta    1140

ctcagtgtca caaggaatga tgtaggaccc tatgagtgtg gaatccagaa cgaattaagt    1200

gttgaccaca gcgacccagt catcctgaat gtcctctatg gcccagacga ccccaccatt    1260

tcccctcat acacctatta ccgtccaggg gtgaacctca gcctctcctg ccatgcagcc    1320

tctaacccac ctgcacagta ttcttggctg attgatggga acatccagca acacacacaa    1380

gagctcttta tctccaacat cactgagaag aacagcggac tctatacctg ccaggccaat    1440

aactcagcca gtggccacag caggactaca gtcaagacaa tcacagtctc tgcggagctg    1500

cccaagccct ccatctccag caacaactcc aaacccgtgg aggacaagga tgctgtggcc    1560

ttcacctgtg aacctgaggc tcagaacaca acctacctgt ggtgggtaaa tggtcagagc    1620

ctcccagtca gtcccaggct gcagctgtcc aatggcaaca ggaccctcac tctattcaat    1680
```

```
gtcacaagaa atgacgcaag agcctatgta tgtggaatcc agaactcagt gagtgcaaac   1740

cgcagtgacc cagtcaccct ggatgtcctc tatgggccgg acacccccat catttccccc   1800

ccagactcgt cttacctttc gggagcgaac ctcaacctct cctgccactc ggcctctaac   1860

ccatccccgc agtattcttg gcgtatcaat gggataccgc agcaacacac acaagttctc   1920

tttatcgcca aaatcacgcc aaataataac gggacctatg cctgttttgt ctctaacttg   1980

gctactggcc gcaataattc catagtcaag agcatcacag tctctgcatc tggaactcta   2040

gatgctcccc agtctattac agaactatgt tcggaatatc gcaacacaca aatatatacg   2100

ataaatgaca agatactatc atatacggaa tcgatggcag gtaaaagaga aatggttatc   2160

attacattta agagcggcgc aacatttcag gtcgaagtcc cgggcagtca acatatagac   2220

tcccaaaaaa aagccattga aaggatgaag gacacattaa gaatcacata tctgaccgag   2280

accaaaattg ataaattatg tgtatggaat aataaaaccc ccaattcaat tgcggcaatc   2340

agtatggaaa actag                                                    2355
```

<210> SEQ ID NO 10
<211> LENGTH: 784
<212> TYPE: PRT
<213> ORGANISM: Artificial Sequence
<220> FEATURE:
<223> OTHER INFORMATION: CEA-LTB fusion

<400> SEQUENCE: 10

```
Met Glu Ser Pro Ser Ala Pro Pro His Arg Trp Cys Ile Pro Trp Gln
 1               5                  10                  15

Arg Leu Leu Leu Thr Ala Ser Leu Leu Thr Phe Trp Asn Pro Pro Thr
            20                  25                  30

Thr Ala Lys Leu Thr Ile Glu Ser Thr Pro Phe Asn Val Ala Glu Gly
        35                  40                  45

Lys Glu Val Leu Leu Leu Val His Asn Leu Pro Gln His Leu Phe Gly
    50                  55                  60

Tyr Ser Trp Tyr Lys Gly Glu Arg Val Asp Gly Asn Arg Gln Ile Ile
65                  70                  75                  80

Gly Tyr Val Ile Gly Thr Gln Gln Ala Thr Pro Gly Pro Ala Tyr Ser
                85                  90                  95

Gly Arg Glu Ile Ile Tyr Pro Asn Ala Ser Leu Leu Ile Gln Asn Ile
            100                 105                 110

Ile Gln Asn Asp Thr Gly Phe Tyr Thr Leu His Val Ile Lys Ser Asp
        115                 120                 125

Leu Val Asn Glu Glu Ala Thr Gly Gln Phe Arg Val Tyr Pro Glu Leu
    130                 135                 140

Pro Lys Pro Ser Ile Ser Ser Asn Asn Ser Lys Pro Val Glu Asp Lys
145                 150                 155                 160

Asp Ala Val Ala Phe Thr Cys Glu Pro Glu Thr Gln Asp Ala Thr Tyr
                165                 170                 175

Leu Trp Trp Val Asn Asn Gln Ser Leu Pro Val Ser Pro Arg Leu Gln
            180                 185                 190

Leu Ser Asn Gly Asn Arg Thr Leu Thr Leu Phe Asn Val Thr Arg Asn
        195                 200                 205

Asp Thr Ala Ser Tyr Lys Cys Glu Thr Gln Asn Pro Val Ser Ala Arg
    210                 215                 220

Arg Ser Asp Ser Val Ile Leu Asn Val Leu Tyr Gly Pro Asp Ala Pro
225                 230                 235                 240
```

```
Thr Ile Ser Pro Leu Asn Thr Ser Tyr Arg Ser Gly Glu Asn Leu Asn
                245                 250                 255

Leu Ser Cys His Ala Ala Ser Asn Pro Pro Ala Gln Tyr Ser Trp Phe
            260                 265                 270

Val Asn Gly Thr Phe Gln Gln Ser Thr Gln Glu Leu Phe Ile Pro Asn
        275                 280                 285

Ile Thr Val Asn Asn Ser Gly Ser Tyr Thr Cys Gln Ala His Asn Ser
    290                 295                 300

Asp Thr Gly Leu Asn Arg Thr Thr Val Thr Thr Ile Thr Val Tyr Ala
305                 310                 315                 320

Glu Pro Pro Lys Pro Phe Ile Thr Ser Asn Asn Ser Asn Pro Val Glu
                325                 330                 335

Asp Glu Asp Ala Val Ala Leu Thr Cys Glu Pro Glu Ile Gln Asn Thr
            340                 345                 350

Thr Tyr Leu Trp Trp Val Asn Asn Gln Ser Leu Pro Val Ser Pro Arg
        355                 360                 365

Leu Gln Leu Ser Asn Asp Asn Arg Thr Leu Thr Leu Leu Ser Val Thr
    370                 375                 380

Arg Asn Asp Val Gly Pro Tyr Glu Cys Gly Ile Gln Asn Glu Leu Ser
385                 390                 395                 400

Val Asp His Ser Asp Pro Val Ile Leu Asn Val Leu Tyr Gly Pro Asp
                405                 410                 415

Asp Pro Thr Ile Ser Pro Ser Tyr Thr Tyr Tyr Arg Pro Gly Val Asn
            420                 425                 430

Leu Ser Leu Ser Cys His Ala Ala Ser Asn Pro Pro Ala Gln Tyr Ser
        435                 440                 445

Trp Leu Ile Asp Gly Asn Ile Gln Gln His Thr Gln Glu Leu Phe Ile
    450                 455                 460

Ser Asn Ile Thr Glu Lys Asn Ser Gly Leu Tyr Thr Cys Gln Ala Asn
465                 470                 475                 480

Asn Ser Ala Ser Gly His Ser Arg Thr Thr Val Lys Thr Ile Thr Val
                485                 490                 495

Ser Ala Glu Leu Pro Lys Pro Ser Ile Ser Ser Asn Asn Ser Lys Pro
            500                 505                 510

Val Glu Asp Lys Asp Ala Val Ala Phe Thr Cys Glu Pro Glu Ala Gln
        515                 520                 525

Asn Thr Thr Tyr Leu Trp Trp Val Asn Gly Gln Ser Leu Pro Val Ser
    530                 535                 540

Pro Arg Leu Gln Leu Ser Asn Gly Asn Arg Thr Leu Thr Leu Phe Asn
545                 550                 555                 560

Val Thr Arg Asn Asp Ala Arg Ala Tyr Val Cys Gly Ile Gln Asn Ser
                565                 570                 575

Val Ser Ala Asn Arg Ser Asp Pro Val Thr Leu Asp Val Leu Tyr Gly
            580                 585                 590

Pro Asp Thr Pro Ile Ile Ser Pro Pro Asp Ser Ser Tyr Leu Ser Gly
        595                 600                 605

Ala Asn Leu Asn Leu Ser Cys His Ser Ala Ser Asn Pro Ser Pro Gln
    610                 615                 620

Tyr Ser Trp Arg Ile Asn Gly Ile Pro Gln Gln His Thr Gln Val Leu
625                 630                 635                 640

Phe Ile Ala Lys Ile Thr Pro Asn Asn Asn Gly Thr Tyr Ala Cys Phe
                645                 650                 655

Val Ser Asn Leu Ala Thr Gly Arg Asn Asn Ser Ile Val Lys Ser Ile
            660                 665                 670
```

```
Thr Val Ser Ala Ser Gly Thr Leu Asp Ala Pro Gln Ser Ile Thr Glu
        675                 680                 685

Leu Cys Ser Glu Tyr Arg Asn Thr Gln Ile Tyr Thr Ile Asn Asp Lys
    690                 695                 700

Ile Leu Ser Tyr Thr Glu Ser Met Ala Gly Lys Arg Glu Met Val Ile
705                 710                 715                 720

Ile Thr Phe Lys Ser Gly Ala Thr Phe Gln Val Glu Val Pro Gly Ser
                725                 730                 735

Gln His Ile Asp Ser Gln Lys Lys Ala Ile Glu Arg Met Lys Asp Thr
            740                 745                 750

Leu Arg Ile Thr Tyr Leu Thr Glu Thr Lys Ile Asp Lys Leu Cys Val
        755                 760                 765

Trp Asn Asn Lys Thr Pro Asn Ser Ile Ala Ala Ile Ser Met Glu Asn
    770                 775                 780
```

<210> SEQ ID NO 11
<211> LENGTH: 2355
<212> TYPE: DNA
<213> ORGANISM: Artificial Sequence
<220> FEATURE:
<223> OTHER INFORMATION: CEAopt-LTB fusion

<400> SEQUENCE: 11

```
atggagagcc ccagcgcccc cccccaccgc tggtgcatcc cctggcagcg cctgctgctg     60

accgccagcc tgctgacctt ctggaacccc cccaccaccg ccaagctgac catcgagagc    120

accccccttca acgtggccga gggcaaggag gtgctgctgc tggtgcacaa cctgccccag    180

cacctgttcg gctacagctg gtacaagggc gagcgcgtgg acggcaaccg ccagatcatc    240

ggctacgtga tcggcaccca gcaggccacc cccggccccg cctacagcgg ccgcgagatc    300

atctacccca acgccagcct gctgatccag aacatcatcc agaacgacac cggcttctac    360

accctgcacg tgatcaagag cgacctggtg aacgaggagg ccaccggcca gttccgcgtg    420

taccccgagc tgcccaagcc cagcatcagc agcaacaaca gcaagcccgt ggaggacaag    480

gacgccgtgg ccttcacctg cgagcccgag acccaggacg ccacctacct gtggtgggtg    540

aacaaccaga gcctgcccgt gagcccccgc ctgcagctga gcaacggcaa ccgcaccctg    600

accctgttca acgtgacccg caacgacacc gccagctaca agtgcgagac ccagaacccc    660

gtgagcgccc gccgcagcga cagcgtgatc ctgaacgtgc tgtacggccc cgacgccccc    720

accatcagcc ccctgaacac cagctaccgc agcggcgaga acctgaacct gagctgccac    780

gccgccagca accccccccgc ccagtacagc tggttcgtga acggcacctt ccagcagagc    840

acccaggagc tgttcatccc caacatcacc gtgaacaaca gcggcagcta cacctgccag    900

gcccacaaca gcgacaccgg cctgaaccgc accaccgtga ccaccatcac cgtgtacgcc    960

gagcccccca agcccttcat caccagcaac aacagcaacc ccgtggagga cgaggacgcc   1020

gtggccctga cctgcgagcc cgagatccag aacaccacct acctgtggtg ggtgaacaac   1080

cagagcctgc ccgtgagccc ccgcctgcag ctgagcaacg acaaccgcac cctgaccctg   1140

ctgagcgtga cccgcaacga cgtgggcccc tacgagtgcg gcatccagaa cgagctgagc   1200

gtggaccaca gcgaccccgt gatcctgaac gtgctgtacg gccccgacga ccccaccatc   1260

agccccagct acacctacta ccgccccggc gtgaacctga gcctgagctg ccacgccgcc   1320

agcaaccccc ccgcccagta cagctggctg atcgacggca acatccagca gcacacccag   1380

gagctgttca tcagcaacat caccgagaag aacagcggcc tgtacacctg ccaggccaac   1440
```

```
aacagcgcca gcggccacag ccgcaccacc gtgaagacca tcaccgtgag cgccgagctg   1500

cccaagccca gcatcagcag caacaacagc aagcccgtgg aggacaagga cgccgtggcc   1560

ttcacctgcg agcccgaggc ccagaacacc acctacctgt ggtgggtgaa cggccagagc   1620

ctgcccgtga gcccccgcct gcagctgagc aacggcaacc gcaccctgac cctgttcaac   1680

gtgacccgca acgacgcccg cgcctacgtg tgcggcatcc agaacagcgt gagcgccaac   1740

cgcagcgacc ccgtgaccct ggacgtgctg tacggccccg acacccccat catcagcccc   1800

cccgacagca gctacctgag cggcgccaac ctgaacctga gctgccacag cgccagcaac   1860

cccagccccc agtacagctg gcgcatcaac ggcatccccc agcagcacac ccaggtgctg   1920

ttcatcgcca agatcacccc caacaacaac ggcacctacg cctgcttcgt gagcaacctg   1980

gccaccggcc gcaacaacag catcgtgaag agcatcaccg tgagcgccag cggcacctct   2040

agagctcccc agactattac agaactatgt tcggaatatc gcaacacaca aatatatacg   2100

ataaatgaca agatactatc atatacggaa tcgatggcag gcaaaagaga aatggttatc   2160

attacattta agagcggcga aacatttcag gtcgaagtcc cgggcagtca acatatagac   2220

tcccagaaaa aagccattga aaggatgaag gacacattaa gaatcacata tctgaccgag   2280

accaaaattg ataaattatg tgtatggaat aataaaaccc ccaattcaat tgcggcaatc   2340

agtatggaaa actag                                                      2355
```

```
<210> SEQ ID NO 12
<211> LENGTH: 2358
<212> TYPE: DNA
<213> ORGANISM: Artificial Sequence
<220> FEATURE:
<223> OTHER INFORMATION: CEAopt-LTBopt fusion

<400> SEQUENCE: 12

atggagagcc ccagcgcccc cccccaccgc tggtgcatcc cctggcagcg cctgctgctg     60

accgccagcc tgctgacctt ctggaacccc cccaccaccg ccaagctgac catcgagagc    120

accccctica acgtggccga gggcaaggag gtgctgctgc tggtgcacaa cctgccccag    180

cacctgttcg gctacagctg gtacaagggc gagcgcgtgg acggcaaccg ccagatcatc    240

ggctacgtga tcggcaccca gcaggccacc cccggccccg cctacagcgg ccgcgagatc    300

atctacccca acgccagcct gctgatccag aacatcatcc agaacgacac cggcttctac    360

accctgcacg tgatcaagag cgacctggtg aacgaggagg ccaccggcca gttccgcgtg    420

taccccgagc tgcccaagcc cagcatcagc agcaacaaca gcaagcccgt ggaggacaag    480

gacgccgtgg ccttcacctg cgagcccgag acccaggacg ccacctacct gtggtgggtg    540

aacaaccaga gcctgcccgt gagcccccgc ctgcagctga gcaacggcaa ccgcaccctg    600

accctgttca acgtgacccg caacgacacc gccagctaca agtgcgagac ccagaacccc    660

gtgagcgccc gccgcagcga cagcgtgatc ctgaacgtgc tgtacggccc cgacgccccc    720

accatcagcc ccctgaacac cagctaccgc agcggcgaga acctgaacct gagctgccac    780

gccgccagca acccccccgc ccagtacagc tggttcgtga acggcacctt ccagcagagc    840

acccaggagc tgttcatccc caacatcacc gtgaacaaca gcggcagcta cacctgccag    900

gcccacaaca gcgacaccgg cctgaaccgc accaccgtga ccaccatcac cgtgtacgcc    960

gagcccccca agcccttcat caccagcaac aacagcaacc ccgtggagga cgaggacgcc   1020

gtggccctga cctgcgagcc cgagatccag aacaccacct acctgtggtg ggtgaacaac   1080

cagagcctgc ccgtgagccc ccgcctgcag ctgagcaacg acaaccgcac cctgaccctg   1140
```

```
ctgagcgtga cccgcaacga cgtgggcccc tacgagtgcg gcatccagaa cgagctgagc   1200

gtggaccaca gcgaccccgt gatcctgaac gtgctgtacg gccccgacga ccccaccatc   1260

agccccagct acacctacta ccgccccggc gtgaacctga gcctgagctg ccacgccgcc   1320

agcaaccccc ccgcccagta cagctggctg atcgacggca acatccagca gcacacccag   1380

gagctgttca tcagcaacat caccgagaag aacagcggcc tgtacacctg ccaggccaac   1440

aacagcgcca gcggccacag ccgcaccacc gtgaagacca tcaccgtgag cgccgagctg   1500

cccaagccca gcatcagcag caacaacagc aagcccgtgg aggacaagga cgccgtggcc   1560

ttcacctgcg agcccgaggc ccagaacacc acctacctgt ggtgggtgaa cggccagagc   1620

ctgcccgtga gcccccgcct gcagctgagc aacggcaacc gcaccctgac cctgttcaac   1680

gtgacccgca acgacgcccg cgcctacgtg tgcggcatcc agaacagcgt gagcgccaac   1740

cgcagcgacc ccgtgaccct ggacgtgctg tacggccccg acacccccat catcagcccc   1800

cccgacagca gctacctgag cggcgccaac ctgaacctga gctgccacag cgccagcaac   1860

cccagccccc agtacagctg gcgcatcaac ggcatccccc agcagcacac ccaggtgctg   1920

ttcatcgcca agatcacccc caacaacaac ggcacctacg cctgcttcgt gagcaacctg   1980

gccaccggcc gcaacaacag catcgtgaag agcatcaccg tgagcgccag cggcacctct   2040

agagcccccc agagcatcac cgagctgtgc agcgagtacc ggaacaccca gatctacacc   2100

atcaacgaca agatcctgag ctacaccgag agcatggccg gcaagaggga gatggtgatc   2160

atcaccttca agagcggcgc caccttccag gtggaggtgc ccggcagcca gcacatcgac   2220

agccagaaga aggccatcga gcggatgaag gacaccctgc ggatcaccta cctcaccgag   2280

accaagatcg acaagctgtg cgtgtggaac aacaagaccc ccaacagcat cgccgccatc   2340

agcatggaga attgataa                                                  2358
```

<210> SEQ ID NO 13
<211> LENGTH: 784
<212> TYPE: PRT
<213> ORGANISM: Artificial Sequence
<220> FEATURE:
<223> OTHER INFORMATION: CEAopt-LTBopt fusion

<400> SEQUENCE: 13

```
Met Glu Ser Pro Ser Ala Pro Pro His Arg Trp Cys Ile Pro Trp Gln
 1               5                  10                  15

Arg Leu Leu Leu Thr Ala Ser Leu Leu Thr Phe Trp Asn Pro Pro Thr
            20                  25                  30

Thr Ala Lys Leu Thr Ile Glu Ser Thr Pro Phe Asn Val Ala Glu Gly
        35                  40                  45

Lys Glu Val Leu Leu Leu Val His Asn Leu Pro Gln His Leu Phe Gly
    50                  55                  60

Tyr Ser Trp Tyr Lys Gly Glu Arg Val Asp Gly Asn Arg Gln Ile Ile
65                  70                  75                  80

Gly Tyr Val Ile Gly Thr Gln Gln Ala Thr Pro Gly Pro Ala Tyr Ser
                85                  90                  95

Gly Arg Glu Ile Ile Tyr Pro Asn Ala Ser Leu Leu Ile Gln Asn Ile
            100                 105                 110

Ile Gln Asn Asp Thr Gly Phe Tyr Thr Leu His Val Ile Lys Ser Asp
        115                 120                 125

Leu Val Asn Glu Glu Ala Thr Gly Gln Phe Arg Val Tyr Pro Glu Leu
    130                 135                 140

Pro Lys Pro Ser Ile Ser Ser Asn Asn Ser Lys Pro Val Glu Asp Lys
```

```
145                 150                 155                 160

Asp Ala Val Ala Phe Thr Cys Glu Pro Glu Thr Gln Asp Ala Thr Tyr
                165                 170                 175

Leu Trp Trp Val Asn Asn Gln Ser Leu Pro Val Ser Pro Arg Leu Gln
            180                 185                 190

Leu Ser Asn Gly Asn Arg Thr Leu Thr Leu Phe Asn Val Thr Arg Asn
        195                 200                 205

Asp Thr Ala Ser Tyr Lys Cys Glu Thr Gln Asn Pro Val Ser Ala Arg
    210                 215                 220

Arg Ser Asp Ser Val Ile Leu Asn Val Leu Tyr Gly Pro Asp Ala Pro
225                 230                 235                 240

Thr Ile Ser Pro Leu Asn Thr Ser Tyr Arg Ser Gly Glu Asn Leu Asn
                245                 250                 255

Leu Ser Cys His Ala Ala Ser Asn Pro Pro Ala Gln Tyr Ser Trp Phe
            260                 265                 270

Val Asn Gly Thr Phe Gln Gln Ser Thr Gln Glu Leu Phe Ile Pro Asn
        275                 280                 285

Ile Thr Val Asn Asn Ser Gly Ser Tyr Thr Cys Gln Ala His Asn Ser
    290                 295                 300

Asp Thr Gly Leu Asn Arg Thr Thr Val Thr Thr Ile Thr Val Tyr Ala
305                 310                 315                 320

Glu Pro Pro Lys Pro Phe Ile Thr Ser Asn Asn Ser Asn Pro Val Glu
                325                 330                 335

Asp Glu Asp Ala Val Ala Leu Thr Cys Glu Pro Glu Ile Gln Asn Thr
            340                 345                 350

Thr Tyr Leu Trp Trp Val Asn Asn Gln Ser Leu Pro Val Ser Pro Arg
        355                 360                 365

Leu Gln Leu Ser Asn Asp Asn Arg Thr Leu Thr Leu Leu Ser Val Thr
    370                 375                 380

Arg Asn Asp Val Gly Pro Tyr Glu Cys Gly Ile Gln Asn Glu Leu Ser
385                 390                 395                 400

Val Asp His Ser Asp Pro Val Ile Leu Asn Val Leu Tyr Gly Pro Asp
                405                 410                 415

Asp Pro Thr Ile Ser Pro Ser Tyr Thr Tyr Tyr Arg Pro Gly Val Asn
            420                 425                 430

Leu Ser Leu Ser Cys His Ala Ala Ser Asn Pro Pro Ala Gln Tyr Ser
        435                 440                 445

Trp Leu Ile Asp Gly Asn Ile Gln Gln His Thr Gln Glu Leu Phe Ile
    450                 455                 460

Ser Asn Ile Thr Glu Lys Asn Ser Gly Leu Tyr Thr Cys Gln Ala Asn
465                 470                 475                 480

Asn Ser Ala Ser Gly His Ser Arg Thr Thr Val Lys Thr Ile Thr Val
                485                 490                 495

Ser Ala Glu Leu Pro Lys Pro Ser Ile Ser Ser Asn Asn Ser Lys Pro
            500                 505                 510

Val Glu Asp Lys Asp Ala Val Ala Phe Thr Cys Glu Pro Glu Ala Gln
        515                 520                 525

Asn Thr Thr Tyr Leu Trp Trp Val Asn Gly Gln Ser Leu Pro Val Ser
    530                 535                 540

Pro Arg Leu Gln Leu Ser Asn Gly Asn Arg Thr Leu Thr Leu Phe Asn
545                 550                 555                 560

Val Thr Arg Asn Asp Ala Arg Ala Tyr Val Cys Gly Ile Gln Asn Ser
                565                 570                 575
```

```
Val Ser Ala Asn Arg Ser Asp Pro Val Thr Leu Asp Val Leu Tyr Gly
            580                 585                 590

Pro Asp Thr Pro Ile Ile Ser Pro Pro Asp Ser Ser Tyr Leu Ser Gly
        595                 600                 605

Ala Asn Leu Asn Leu Ser Cys His Ser Ala Ser Asn Pro Ser Pro Gln
    610                 615                 620

Tyr Ser Trp Arg Ile Asn Gly Ile Pro Gln Gln His Thr Gln Val Leu
625                 630                 635                 640

Phe Ile Ala Lys Ile Thr Pro Asn Asn Asn Gly Thr Tyr Ala Cys Phe
                645                 650                 655

Val Ser Asn Leu Ala Thr Gly Arg Asn Asn Ser Ile Val Lys Ser Ile
            660                 665                 670

Thr Val Ser Ala Ser Gly Thr Ser Arg Ala Pro Gln Ser Ile Thr Glu
        675                 680                 685

Leu Cys Ser Glu Tyr Arg Asn Thr Gln Ile Tyr Thr Ile Asn Asp Lys
    690                 695                 700

Ile Leu Ser Tyr Thr Glu Ser Met Ala Gly Lys Arg Glu Met Val Ile
705                 710                 715                 720

Ile Thr Phe Lys Ser Gly Ala Thr Phe Gln Val Glu Val Pro Gly Ser
                725                 730                 735

Gln His Ile Asp Ser Gln Lys Lys Ala Ile Glu Arg Met Lys Asp Thr
            740                 745                 750

Leu Arg Ile Thr Tyr Leu Thr Glu Thr Lys Ile Asp Lys Leu Cys Val
        755                 760                 765

Trp Asn Asn Lys Thr Pro Asn Ser Ile Ala Ala Ile Ser Met Glu Asn
    770                 775                 780
```

```
<210> SEQ ID NO 14
<211> LENGTH: 2358
<212> TYPE: DNA
<213> ORGANISM: Artificial Sequence
<220> FEATURE:
<223> OTHER INFORMATION: rhCEAopt-LTBopt fusion

<400> SEQUENCE: 14

atgggcagcc ccagcgcccc cctgcaccgc tggtgcatcc cctggcagac cctgctgctg      60

accgccagcc tgctgacctt ctggaacccc cccaccaccg cccagctgac catcgagagc     120

cgccccttca acgtggccga gggcaaggag gtgctgctgc tggcccacaa cgtgagccag     180

aacctgttcg gctacatctg gtacaagggc gagcgcgtgg acgccagccg ccgcatcggc     240

agctgcgtga tccgcaccca gcagatcacc cccggccccg cccacagcgg ccgcgagacc     300

atcgacttca acgccagcct gctgatccac aacgtgaccc agagcgacac cggcagctac     360

accatccagg tgatcaagga ggacctggtg aacgaggagg ccaccggcca gttccgcgtg     420

taccccgagc tgcccaagcc ctacatcagc agcaacaaca gcaaccccgt ggaggacaag     480

gacgccgtgg ccctgacctg cgagcccgag acccaggaca ccacctacct gtggtgggtg     540

aacaaccaga gcctgcccgt gagcccccgc ctggagctga gcagcgacaa ccgcaccctg     600

accgtgttca acatccccg caacgacacc accagctaca agtgcgagac ccagaacccc     660

gtgagcgtgc gccgcagcga ccccgtgacc ctgaacgtgc tgtacggccc cgacgccccc     720

accatcagcc ccctgaacac ccccctaccgc gccggcgaga acctgaacct gacctgccac     780

gccgccagca accccacgc ccagtacttc tggttcgtga acggcacctt ccagcagagc     840

acccaggagc tgttcatccc caacatcacc gtgaacaaca gcggcagcta catgtgccag     900

gcccacaaca gcgccaccgg cctgaaccgc accaccgtga ccgccatcac cgtgtacgcc     960
```

```
gagctgccca agccctacat caccagcaac aacagcaacc ccatcgagga caaggacgcc   1020

gtgaccctga cctgcgagcc cgagacccag gacaccacct acctgtggtg ggtgaacaac   1080

cagagcctga gcgtgagcag ccgcctggag ctgagcaacg acaaccgcac cctgaccgtg   1140

ttcaacatcc cccgcaacga caccaccttc tacgagtgcg agacccagaa ccccgtgagc   1200

gtgcgccgca gcgaccccgt gaccctgaac gtgctgtacg gccccgacgc ccccaccatc   1260

agcccccctga acacccccta ccgcgccggc gagaacctga acctgagctg ccacgccgcc   1320

agcaaccccg ccgcccagta cagctggttc gtgaacggca ccttccagca gagcacccag   1380

gagctgttca tccccaacat caccgtgaac aacagcggca gctacatgtg ccaggcccac   1440

aacagcgcca ccggcctgaa ccgcaccacc gtgaccgcca tcaccgtgta cgtggagctg   1500

cccaagccct acatcagcag caacaacagc aaccccatcg aggacaagga cgccgtgacc   1560

ctgacctgcg agcccgtggc cgagaacacc acctacctgt ggtgggtgaa caaccagagc   1620

ctgagcgtga gcccccgcct gcagctgagc aacggcaacc gcatcctgac cctgctgagc   1680

gtgacccgca acgacaccgg cccctacgag tgcggcatcc agaacagcga gagcgccaag   1740

cgcagcgacc ccgtgaccct gaacgtgacc tacggccccg acacccccat catcagcccc   1800

cccgacctga gctaccgcag cggcgccaac ctgaacctga gctgccacag cgacagcaac   1860

cccagccccc agtacagctg gctgatcaac ggcaccctgc gccagcacac ccaggtgctg   1920

ttcatcagca agatcaccag caacaacagc ggcgcctacg cctgcttcgt gagcaacctg   1980

gccaccggcc gcaacaacag catcgtgaag aacatcagcg tgagcagcgg cgacagctct   2040

agagcccccc agagcatcac cgagctgtgc agcgagtacc ggaacaccca gatctacacc   2100

atcaacgaca agatcctgag ctacaccgag agcatggccg gcaagaggga gatggtgatc   2160

atcaccttca agagcggcgc caccttccag gtggaggtgc ccggcagcca gcacatcgac   2220

agccagaaga aggccatcga gcggatgaag gacaccctgc ggatcaccta cctcaccgag   2280

accaagatcg acaagctgtg cgtgtggaac aacaagaccc ccaacagcat cgccgccatc   2340

agcatggaga attgataa                                                 2358
```

```
<210> SEQ ID NO 15
<211> LENGTH: 784
<212> TYPE: PRT
<213> ORGANISM: Artificial Sequence
<220> FEATURE:
<223> OTHER INFORMATION: rhCEAopt-LTBopt fusion

<400> SEQUENCE: 15

Met Gly Ser Pro Ser Ala Pro Leu His Arg Trp Cys Ile Pro Trp Gln
 1               5                  10                  15

Thr Leu Leu Leu Thr Ala Ser Leu Leu Thr Phe Trp Asn Pro Pro Thr
            20                  25                  30

Thr Ala Gln Leu Thr Ile Glu Ser Arg Pro Phe Asn Val Ala Glu Gly
        35                  40                  45

Lys Glu Val Leu Leu Leu Ala His Asn Val Ser Gln Asn Leu Phe Gly
    50                  55                  60

Tyr Ile Trp Tyr Lys Gly Glu Arg Val Asp Ala Ser Arg Arg Ile Gly
65                  70                  75                  80

Ser Cys Val Ile Arg Thr Gln Gln Ile Thr Pro Gly Pro Ala His Ser
                85                  90                  95

Gly Arg Glu Thr Ile Asp Phe Asn Ala Ser Leu Leu Ile His Asn Val
            100                 105                 110
```

```
Thr Gln Ser Asp Thr Gly Ser Tyr Thr Ile Gln Val Ile Lys Glu Asp
        115                 120                 125

Leu Val Asn Glu Glu Ala Thr Gly Gln Phe Arg Val Tyr Pro Glu Leu
    130                 135                 140

Pro Lys Pro Tyr Ile Ser Ser Asn Asn Ser Asn Pro Val Glu Asp Lys
145                 150                 155                 160

Asp Ala Val Ala Leu Thr Cys Glu Pro Glu Thr Gln Asp Thr Thr Tyr
                165                 170                 175

Leu Trp Trp Val Asn Asn Gln Ser Leu Pro Val Ser Pro Arg Leu Glu
            180                 185                 190

Leu Ser Ser Asp Asn Arg Thr Leu Thr Val Phe Asn Ile Pro Arg Asn
        195                 200                 205

Asp Thr Thr Ser Tyr Lys Cys Glu Thr Gln Asn Pro Val Ser Val Arg
    210                 215                 220

Arg Ser Asp Pro Val Thr Leu Asn Val Leu Tyr Gly Pro Asp Ala Pro
225                 230                 235                 240

Thr Ile Ser Pro Leu Asn Thr Pro Tyr Arg Ala Gly Glu Asn Leu Asn
                245                 250                 255

Leu Thr Cys His Ala Ala Ser Asn Pro Thr Ala Gln Tyr Phe Trp Phe
            260                 265                 270

Val Asn Gly Thr Phe Gln Gln Ser Thr Gln Glu Leu Phe Ile Pro Asn
        275                 280                 285

Ile Thr Val Asn Asn Ser Gly Ser Tyr Met Cys Gln Ala His Asn Ser
    290                 295                 300

Ala Thr Gly Leu Asn Arg Thr Thr Val Thr Ala Ile Thr Val Tyr Ala
305                 310                 315                 320

Glu Leu Pro Lys Pro Tyr Ile Thr Ser Asn Asn Ser Asn Pro Ile Glu
                325                 330                 335

Asp Lys Asp Ala Val Thr Leu Thr Cys Glu Pro Glu Thr Gln Asp Thr
            340                 345                 350

Thr Tyr Leu Trp Trp Val Asn Asn Gln Ser Leu Ser Val Ser Ser Arg
        355                 360                 365

Leu Glu Leu Ser Asn Asp Asn Arg Thr Leu Thr Val Phe Asn Ile Pro
    370                 375                 380

Arg Asn Asp Thr Thr Phe Tyr Glu Cys Glu Thr Gln Asn Pro Val Ser
385                 390                 395                 400

Val Arg Arg Ser Asp Pro Val Thr Leu Asn Val Leu Tyr Gly Pro Asp
                405                 410                 415

Ala Pro Thr Ile Ser Pro Leu Asn Thr Pro Tyr Arg Ala Gly Glu Asn
            420                 425                 430

Leu Asn Leu Ser Cys His Ala Ala Ser Asn Pro Ala Ala Gln Tyr Ser
        435                 440                 445

Trp Phe Val Asn Gly Thr Phe Gln Gln Ser Thr Gln Glu Leu Phe Ile
    450                 455                 460

Pro Asn Ile Thr Val Asn Asn Ser Gly Ser Tyr Met Cys Gln Ala His
465                 470                 475                 480

Asn Ser Ala Thr Gly Leu Asn Arg Thr Thr Val Thr Ala Ile Thr Val
                485                 490                 495

Tyr Val Glu Leu Pro Lys Pro Tyr Ile Ser Ser Asn Asn Ser Asn Pro
            500                 505                 510

Ile Glu Asp Lys Asp Ala Val Thr Leu Thr Cys Glu Pro Val Ala Glu
        515                 520                 525

Asn Thr Thr Tyr Leu Trp Trp Val Asn Asn Gln Ser Leu Ser Val Ser
    530                 535                 540
```

```
Pro Arg Leu Gln Leu Ser Asn Gly Asn Arg Ile Leu Thr Leu Leu Ser
545                 550                 555                 560

Val Thr Arg Asn Asp Thr Gly Pro Tyr Glu Cys Gly Ile Gln Asn Ser
                565                 570                 575

Glu Ser Ala Lys Arg Ser Asp Pro Val Thr Leu Asn Val Thr Tyr Gly
            580                 585                 590

Pro Asp Thr Pro Ile Ile Ser Pro Pro Asp Leu Ser Tyr Arg Ser Gly
        595                 600                 605

Ala Asn Leu Asn Leu Ser Cys His Ser Asp Ser Asn Pro Ser Pro Gln
    610                 615                 620

Tyr Ser Trp Leu Ile Asn Gly Thr Leu Arg Gln His Thr Gln Val Leu
625                 630                 635                 640

Phe Ile Ser Lys Ile Thr Ser Asn Asn Ser Gly Ala Tyr Ala Cys Phe
                645                 650                 655

Val Ser Asn Leu Ala Thr Gly Arg Asn Asn Ser Ile Val Lys Asn Ile
            660                 665                 670

Ser Val Ser Ser Gly Asp Ser Ser Arg Ala Pro Gln Ser Ile Thr Glu
        675                 680                 685

Leu Cys Ser Glu Tyr Arg Asn Thr Gln Ile Tyr Thr Ile Asn Asp Lys
    690                 695                 700

Ile Leu Ser Tyr Thr Glu Ser Met Ala Gly Lys Arg Glu Met Val Ile
705                 710                 715                 720

Ile Thr Phe Lys Ser Gly Ala Thr Phe Gln Val Glu Val Pro Gly Ser
                725                 730                 735

Gln His Ile Asp Ser Gln Lys Lys Ala Ile Glu Arg Met Lys Asp Thr
            740                 745                 750

Leu Arg Ile Thr Tyr Leu Thr Glu Thr Lys Ile Asp Lys Leu Cys Val
        755                 760                 765

Trp Asn Asn Lys Thr Pro Asn Ser Ile Ala Ala Ile Ser Met Glu Asn
    770                 775                 780
```

```
<210> SEQ ID NO 16
<211> LENGTH: 2118
<212> TYPE: DNA
<213> ORGANISM: Macaca mulatta

<400> SEQUENCE: 16

atggggtctc cctcagcccc tcttcacaga tggtgcatcc cctggcagac gctcctgctc      60

acagcctcac ttctaacctt ctggaacccg cccaccactg cccagctcac tattgaatcc     120

aggccgttca atgttgcaga ggggaaggag gttcttctac ttgcccacaa tgtgtcccag     180

aatctttttg gctacatttg gtacaaggga gaaagagtgg atgccagccg tcgaattgga     240

tcatgtgtaa taagaactca acaaattacc ccagggcccg cacacagcgg tcgagagaca     300

atagacttca atgcatccct gctgatccac aatgtcaccc agagtgacac aggatcctac     360

accatacaag tcataaagga agatcttgtg aatgaagaag caactggcca gttccgggta     420

tacccggagc tgcccaagcc ctacatctcc agcaacaact ccaaccccgt ggaggacaag     480

gatgctgtgg ccttaacctg tgaacctgag actcaggaca caacctacct gtggtgggta     540

aacaatcaga gcctcccggt cagtcccagg ctggagctgt ccagtgacaa caggaccctc     600

actgtattca atattccaag aaatgacaca acatcctaca aatgtgaaac ccagaaccca     660

gtgagtgtca gacgcagcga cccagtcacc ctgaacgtcc tctatggccc ggatgcgccc     720

accatttccc ctctaaacac accttacaga gcaggggaaa atctgaacct cacctgccac     780
```

```
gcagcctcta acccaactgc acagtacttt tggtttgtca atgggacgtt ccagcaatcc    840

acacaagagc tctttatacc caacatcacc gtgaataata gcggatccta tatgtgccaa    900

gcccataact cagccactgg cctcaatagg accacagtca cggcgatcac agtctacgcg    960

gagctgccca agccctacat caccagcaac aactccaacc ccatagagga caaggatgct   1020

gtgaccttaa cctgtgaacc tgagactcag gacacaacct acctgtggtg ggtaaacaat   1080

cagagcctct cggtcagttc caggctggag ctgtccaatg acaacaggac cctcactgta   1140

ttcaatattc caagaaacga cacaacgttc tacgaatgtg agacccagaa cccagtgagt   1200

gtcagacgca gcgacccagt caccctgaat gtcctctatg gcccggatgc gcccaccatt   1260

tcccctctaa acacacctta cagagcaggg gaaaatctga acctctcctg ccacgcagcc   1320

tctaacccag ctgcacagta ctcttggttt gtcaatggga cgttccagca atccacacaa   1380

gagctcttta tacccaacat caccgtgaat aatagcggat cctatatgtg ccaagcccat   1440

aactcagcca ctggcctcaa taggaccaca gtcacggcga tcacagtcta tgtggagctg   1500

cccaagccct acatctccag caacaactcc aaccccatag aggacaagga tgctgtgacc   1560

ttaacctgtg aacctgtggc tgagaacaca acctacctgt ggtgggtaaa caatcagagc   1620

ctctcggtca gtcccaggct gcagctctcc aatggcaaca ggatcctcac tctactcagt   1680

gtcacacgga atgacacagg accctatgaa tgtggaatcc agaactcaga gagtgcaaaa   1740

cgcagtgacc cagtcaccct gaatgtcacc tatggcccag acacccccat catatccccc   1800

ccagacttgt cttaccgttc gggagcaaac ctcaacctct cctgccactc ggactctaac   1860

ccatccccgc agtattcttg gcttatcaat gggacactgc ggcaacacac acaagttctc   1920

tttatctcca aaatcacatc aaacaatagc ggggcctatg cctgttttgt ctctaacttg   1980

gctaccggtc gcaataactc catagtcaag aacatctcag tctcctctgg cgattcagca   2040

cctggaagtt ctggtctctc agctagggct actgtcggca tcataattgg aatgctggtt   2100

ggggttgctc tgatgtag                                                 2118
```

<210> SEQ ID NO 17
<211> LENGTH: 2118
<212> TYPE: DNA
<213> ORGANISM: Macaca mulatta

<400> SEQUENCE: 17

```
atggggtctc cctcagcccc tcttcacaga tggtgcatcc cctggcagac gctcctgctc     60

acagcctcac ttctaacctt ctggaacccg cccaccactg cccagctcac tattgaatcc    120

aggccgttca atgttgcaga ggggaaggag gttcttctac ttgcccacaa tgtgtcccag    180

aatctttttg gctacatttg gtacaaggga gaaagagtgg atgccagccg tcgaattgga    240

tcatgtgtaa taagaactca acaaattacc ccagggcccg cacacagcgg tcgagagaca    300

atagacttca atgcatccct gctgatccac aatgtcaccc agagtgacac aggatcctac    360

accatacaag tcataaagga agatcttgtg aatgaagaag caactggcca gttccgggta    420

tacccggagc tgcccaagcc ctacatctcc agcaacaact ccaaccccgt ggaggacaag    480

gatgctgtgg ccttaacctg tgaacctgag actcaggaca caacctacct gtggtgggta    540

aacaatcaga gcctcccggt cagtcccagg ctggagctgt ccagtgacaa caggaccctc    600

actgtattca atattccaag aaatgacaca acatcctaca aatgtgaaac ccagaaccca    660

gtgagtgtca gacgcagcga cccagtcacc ctgaacgtcc tctatggccc ggatgcgccc    720

accatttccc ctctaaacac accttacaga gcaggggaaa atctgaacct cacctgccac    780
```

```
gcagcctcta acccaactgc acagtacttt tggtttgtca atgggacgtt ccagcaatcc    840

acacaagagc tctttatacc caacatcacc gtgaataata gcggatccta tatgtgccaa    900

gcccataact cagccactgg cctcaatagg accacagtca cggcgatcac agtctacgcg    960

gagctgccca agccctacat caccagcaac aactccaacc ccatagagga caaggatgct   1020

gtgaccttaa cctgtgaacc tgagactcag gacacaacct acctgtggtg ggtaaacaat   1080

cagagcctct cggtcagttc caggctggag ctgtccaatg acaacaggac cctcactgta   1140

ttcaatattc caagaaacga cacaacgttc tacgaatgtg agacccagaa cccagtgagt   1200

gtcagacgca gcgacccagt caccctgaat gtcctctatg gcccggatgc gcccaccatt   1260

tcccctctaa acacacctta cagagcaggg gaaaatctga acctctcctg ccacgcagcc   1320

tctaacccag ctgcacagta cttttggttt gtcaatggga cgttccagca atccacacaa   1380

gagctcttta tacccaacat caccgtgaat aatagcggat cctatatgtg ccaagcccat   1440

aactcagcca ctggcctcaa taggaccaca gtcacggcga tcacagtcta tgtggagctg   1500

cccaagccct acatctccag caacaactcc aaccccatag aggacaagga tgctgtgacc   1560

ttaacctgtg aacctgtggc tgagaacaca acctacctgt ggtgggtaaa caatcagagc   1620

ctctcggtca gtcccaggct gcagctctcc aatggcaaca ggatcctcac tctactcagt   1680

gtcacacgga atgacacagg accctatgaa tgtggaatcc agaactcaga gagtgcaaaa   1740

cgcagtgacc cagtcaccct gaatgtcacc tatggcccag acacccccat catatccccc   1800

ccagacttgt cttaccgttc gggagcaaac ctcaacctct cctgccactc ggactctaac   1860

ccatccccgc agtattcttg gcttatcaat gggacactgc ggcaacacac acaagttctc   1920

tttatctcca aaatcacatc aaacaataac ggggcctatg cctgttttgt ctctaacttg   1980

gctaccggtc gcaataactc catagtcaag aacatctcag tctcctctgg cgattcagca   2040

cctggaagtt ctggtctctc agctagggct actgtcggca tcataattgg aatgctggtt   2100

ggggttgctc tgatgtag                                                 2118
```

```
<210> SEQ ID NO 18
<211> LENGTH: 705
<212> TYPE: PRT
<213> ORGANISM: Macaca mulatta

<400> SEQUENCE: 18

Met Gly Ser Pro Ser Ala Pro Leu His Arg Trp Cys Ile Pro Trp Gln
1               5                   10                  15

Thr Leu Leu Leu Thr Ala Ser Leu Leu Thr Phe Trp Asn Pro Pro Thr
            20                  25                  30

Thr Ala Gln Leu Thr Ile Glu Ser Arg Pro Phe Asn Val Ala Glu Gly
        35                  40                  45

Lys Glu Val Leu Leu Leu Ala His Asn Val Ser Gln Asn Leu Phe Gly
    50                  55                  60

Tyr Ile Trp Tyr Lys Gly Glu Arg Val Asp Ala Ser Arg Arg Ile Gly
65                  70                  75                  80

Ser Cys Val Ile Arg Thr Gln Gln Ile Thr Pro Gly Pro Ala His Ser
                85                  90                  95

Gly Arg Glu Thr Ile Asp Phe Asn Ala Ser Leu Leu Ile His Asn Val
            100                 105                 110

Thr Gln Ser Asp Thr Gly Ser Tyr Thr Ile Gln Val Ile Lys Glu Asp
        115                 120                 125

Leu Val Asn Glu Glu Ala Thr Gly Gln Phe Arg Val Tyr Pro Glu Leu
    130                 135                 140
```

-continued

```
Pro Lys Pro Tyr Ile Ser Ser Asn Asn Ser Asn Pro Val Glu Asp Lys
145                 150                 155                 160

Asp Ala Val Ala Leu Thr Cys Glu Pro Glu Thr Gln Asp Thr Thr Tyr
                165                 170                 175

Leu Trp Trp Val Asn Asn Gln Ser Leu Pro Val Ser Pro Arg Leu Glu
            180                 185                 190

Leu Ser Ser Asp Asn Arg Thr Leu Thr Val Phe Asn Ile Pro Arg Asn
        195                 200                 205

Asp Thr Thr Ser Tyr Lys Cys Glu Thr Gln Asn Pro Val Ser Val Arg
    210                 215                 220

Arg Ser Asp Pro Val Thr Leu Asn Val Leu Tyr Gly Pro Asp Ala Pro
225                 230                 235                 240

Thr Ile Ser Pro Leu Asn Thr Pro Tyr Arg Ala Gly Glu Asn Leu Asn
                245                 250                 255

Leu Thr Cys His Ala Ala Ser Asn Pro Thr Ala Gln Tyr Phe Trp Phe
            260                 265                 270

Val Asn Gly Thr Phe Gln Gln Ser Thr Gln Glu Leu Phe Ile Pro Asn
        275                 280                 285

Ile Thr Val Asn Asn Ser Gly Ser Tyr Met Cys Gln Ala His Asn Ser
    290                 295                 300

Ala Thr Gly Leu Asn Arg Thr Thr Val Thr Ala Ile Thr Val Tyr Ala
305                 310                 315                 320

Glu Leu Pro Lys Pro Tyr Ile Thr Ser Asn Asn Ser Asn Pro Ile Glu
                325                 330                 335

Asp Lys Asp Ala Val Thr Leu Thr Cys Glu Pro Glu Thr Gln Asp Thr
            340                 345                 350

Thr Tyr Leu Trp Trp Val Asn Asn Gln Ser Leu Ser Val Ser Ser Arg
        355                 360                 365

Leu Glu Leu Ser Asn Asp Asn Arg Thr Leu Thr Val Phe Asn Ile Pro
    370                 375                 380

Arg Asn Asp Thr Thr Phe Tyr Glu Cys Glu Thr Gln Asn Pro Val Ser
385                 390                 395                 400

Val Arg Arg Ser Asp Pro Val Thr Leu Asn Val Leu Tyr Gly Pro Asp
                405                 410                 415

Ala Pro Thr Ile Ser Pro Leu Asn Thr Pro Tyr Arg Ala Gly Glu Asn
            420                 425                 430

Leu Asn Leu Ser Cys His Ala Ala Ser Asn Pro Ala Ala Gln Tyr Ser
        435                 440                 445

Trp Phe Val Asn Gly Thr Phe Gln Gln Ser Thr Gln Glu Leu Phe Ile
    450                 455                 460

Pro Asn Ile Thr Val Asn Asn Ser Gly Ser Tyr Met Cys Gln Ala His
465                 470                 475                 480

Asn Ser Ala Thr Gly Leu Asn Arg Thr Thr Val Thr Ala Ile Thr Val
                485                 490                 495

Tyr Val Glu Leu Pro Lys Pro Tyr Ile Ser Ser Asn Asn Ser Asn Pro
            500                 505                 510

Ile Glu Asp Lys Asp Ala Val Thr Leu Thr Cys Glu Pro Val Ala Glu
        515                 520                 525

Asn Thr Thr Tyr Leu Trp Trp Val Asn Asn Gln Ser Leu Ser Val Ser
    530                 535                 540

Pro Arg Leu Gln Leu Ser Asn Gly Asn Arg Ile Leu Thr Leu Leu Ser
545                 550                 555                 560

Val Thr Arg Asn Asp Thr Gly Pro Tyr Glu Cys Gly Ile Gln Asn Ser
```

```
                565                 570                 575

Glu Ser Ala Lys Arg Ser Asp Pro Val Thr Leu Asn Val Thr Tyr Gly
            580                 585                 590

Pro Asp Thr Pro Ile Ile Ser Pro Pro Asp Leu Ser Tyr Arg Ser Gly
        595                 600                 605

Ala Asn Leu Asn Leu Ser Cys His Ser Asp Ser Asn Pro Ser Pro Gln
    610                 615                 620

Tyr Ser Trp Leu Ile Asn Gly Thr Leu Arg Gln His Thr Gln Val Leu
625                 630                 635                 640

Phe Ile Ser Lys Ile Thr Ser Asn Asn Ser Gly Ala Tyr Ala Cys Phe
                645                 650                 655

Val Ser Asn Leu Ala Thr Gly Arg Asn Asn Ser Ile Val Lys Asn Ile
            660                 665                 670

Ser Val Ser Ser Gly Asp Ser Ala Pro Gly Ser Ser Gly Leu Ser Ala
        675                 680                 685

Arg Ala Thr Val Gly Ile Ile Ile Gly Met Leu Val Gly Val Ala Leu
    690                 695                 700

Met
705


<210> SEQ ID NO 19
<211> LENGTH: 705
<212> TYPE: PRT
<213> ORGANISM: Macaca mulatta

<400> SEQUENCE: 19

Met Gly Ser Pro Ser Ala Pro Leu His Arg Trp Cys Ile Pro Trp Gln
 1               5                  10                  15

Thr Leu Leu Leu Thr Ala Ser Leu Leu Thr Phe Trp Asn Pro Pro Thr
            20                  25                  30

Thr Ala Gln Leu Thr Ile Glu Ser Arg Pro Phe Asn Val Ala Glu Gly
        35                  40                  45

Lys Glu Val Leu Leu Leu Ala His Asn Val Ser Gln Asn Leu Phe Gly
    50                  55                  60

Tyr Ile Trp Tyr Lys Gly Glu Arg Val Asp Ala Ser Arg Arg Ile Gly
65                  70                  75                  80

Ser Cys Val Ile Arg Thr Gln Gln Ile Thr Pro Gly Pro Ala His Ser
                85                  90                  95

Gly Arg Glu Thr Ile Asp Phe Asn Ala Ser Leu Leu Ile His Asn Val
            100                 105                 110

Thr Gln Ser Asp Thr Gly Ser Tyr Thr Ile Gln Val Ile Lys Glu Asp
        115                 120                 125

Leu Val Asn Glu Glu Ala Thr Gly Gln Phe Arg Val Tyr Pro Glu Leu
    130                 135                 140

Pro Lys Pro Tyr Ile Ser Ser Asn Asn Ser Asn Pro Val Glu Asp Lys
145                 150                 155                 160

Asp Ala Val Ala Leu Thr Cys Glu Pro Glu Thr Gln Asp Thr Thr Tyr
                165                 170                 175

Leu Trp Trp Val Asn Asn Gln Ser Leu Pro Val Ser Pro Arg Leu Glu
            180                 185                 190

Leu Ser Ser Asp Asn Arg Thr Leu Thr Val Phe Asn Ile Pro Arg Asn
        195                 200                 205

Asp Thr Thr Ser Tyr Lys Cys Glu Thr Gln Asn Pro Val Ser Val Arg
    210                 215                 220

Arg Ser Asp Pro Val Thr Leu Asn Val Leu Tyr Gly Pro Asp Ala Pro
```

```
225                 230                 235                 240

Thr Ile Ser Pro Leu Asn Thr Pro Tyr Arg Ala Gly Glu Asn Leu Asn
                245                 250                 255

Leu Thr Cys His Ala Ala Ser Asn Pro Thr Ala Gln Tyr Phe Trp Phe
            260                 265                 270

Val Asn Gly Thr Phe Gln Gln Ser Thr Gln Glu Leu Phe Ile Pro Asn
        275                 280                 285

Ile Thr Val Asn Asn Ser Gly Ser Tyr Met Cys Gln Ala His Asn Ser
    290                 295                 300

Ala Thr Gly Leu Asn Arg Thr Thr Val Thr Ala Ile Thr Val Tyr Ala
305                 310                 315                 320

Glu Leu Pro Lys Pro Tyr Ile Thr Ser Asn Asn Ser Asn Pro Ile Glu
                325                 330                 335

Asp Lys Asp Ala Val Thr Leu Thr Cys Glu Pro Glu Thr Gln Asp Thr
            340                 345                 350

Thr Tyr Leu Trp Trp Val Asn Asn Gln Ser Leu Ser Val Ser Ser Arg
        355                 360                 365

Leu Glu Leu Ser Asn Asp Asn Arg Thr Leu Thr Val Phe Asn Ile Pro
    370                 375                 380

Arg Asn Asp Thr Thr Phe Tyr Glu Cys Glu Thr Gln Asn Pro Val Ser
385                 390                 395                 400

Val Arg Arg Ser Asp Pro Val Thr Leu Asn Val Leu Tyr Gly Pro Asp
                405                 410                 415

Ala Pro Thr Ile Ser Pro Leu Asn Thr Pro Tyr Arg Ala Gly Glu Asn
            420                 425                 430

Leu Asn Leu Ser Cys His Ala Ala Ser Asn Pro Ala Ala Gln Tyr Phe
        435                 440                 445

Trp Phe Val Asn Gly Thr Phe Gln Gln Ser Thr Gln Glu Leu Phe Ile
    450                 455                 460

Pro Asn Ile Thr Val Asn Asn Ser Gly Ser Tyr Met Cys Gln Ala His
465                 470                 475                 480

Asn Ser Ala Thr Gly Leu Asn Arg Thr Thr Val Thr Ala Ile Thr Val
                485                 490                 495

Tyr Val Glu Leu Pro Lys Pro Tyr Ile Ser Ser Asn Asn Ser Asn Pro
            500                 505                 510

Ile Glu Asp Lys Asp Ala Val Thr Leu Thr Cys Glu Pro Val Ala Glu
        515                 520                 525

Asn Thr Thr Tyr Leu Trp Trp Val Asn Asn Gln Ser Leu Ser Val Ser
    530                 535                 540

Pro Arg Leu Gln Leu Ser Asn Gly Asn Arg Ile Leu Thr Leu Leu Ser
545                 550                 555                 560

Val Thr Arg Asn Asp Thr Gly Pro Tyr Glu Cys Gly Ile Gln Asn Ser
                565                 570                 575

Glu Ser Ala Lys Arg Ser Asp Pro Val Thr Leu Asn Val Thr Tyr Gly
            580                 585                 590

Pro Asp Thr Pro Ile Ile Ser Pro Pro Asp Leu Ser Tyr Arg Ser Gly
        595                 600                 605

Ala Asn Leu Asn Leu Ser Cys His Ser Asp Ser Asn Pro Ser Pro Gln
    610                 615                 620

Tyr Ser Trp Leu Ile Asn Gly Thr Leu Arg Gln His Thr Gln Val Leu
625                 630                 635                 640

Phe Ile Ser Lys Ile Thr Ser Asn Asn Asn Gly Ala Tyr Ala Cys Phe
                645                 650                 655
```

```
Val Ser Asn Leu Ala Thr Gly Arg Asn Asn Ser Ile Val Lys Asn Ile
            660                 665                 670

Ser Val Ser Ser Gly Asp Ser Ala Pro Gly Ser Ser Gly Leu Ser Ala
        675                 680                 685

Arg Ala Thr Val Gly Ile Ile Ile Gly Met Leu Val Gly Val Ala Leu
    690                 695                 700

Met
705


<210> SEQ ID NO 20
<211> LENGTH: 702
<212> TYPE: PRT
<213> ORGANISM: Homo sapiens

<400> SEQUENCE: 20

Met Glu Ser Pro Ser Ala Pro Pro His Arg Trp Cys Ile Pro Trp Gln
 1               5                  10                  15

Arg Leu Leu Leu Thr Ala Ser Leu Leu Thr Phe Trp Asn Pro Pro Thr
            20                  25                  30

Thr Ala Lys Leu Thr Ile Glu Ser Thr Pro Phe Asn Val Ala Glu Gly
        35                  40                  45

Lys Glu Val Leu Leu Leu Val His Asn Leu Pro Gln His Leu Phe Gly
    50                  55                  60

Tyr Ser Trp Tyr Lys Gly Glu Arg Val Asp Gly Asn Arg Gln Ile Ile
65                  70                  75                  80

Gly Tyr Val Ile Gly Thr Gln Gln Ala Thr Pro Gly Pro Ala Tyr Ser
                85                  90                  95

Gly Arg Glu Ile Ile Tyr Pro Asn Ala Ser Leu Leu Ile Gln Asn Ile
            100                 105                 110

Ile Gln Asn Asp Thr Gly Phe Tyr Thr Leu His Val Ile Lys Ser Asp
        115                 120                 125

Leu Val Asn Glu Glu Ala Thr Gly Gln Phe Arg Val Tyr Pro Glu Leu
    130                 135                 140

Pro Lys Pro Ser Ile Ser Ser Asn Asn Ser Lys Pro Val Glu Asp Lys
145                 150                 155                 160

Asp Ala Val Ala Phe Thr Cys Glu Pro Glu Thr Gln Asp Ala Thr Tyr
                165                 170                 175

Leu Trp Trp Val Asn Asn Gln Ser Leu Pro Val Ser Pro Arg Leu Gln
            180                 185                 190

Leu Ser Asn Gly Asn Arg Thr Leu Thr Leu Phe Asn Val Thr Arg Asn
        195                 200                 205

Asp Thr Ala Ser Tyr Lys Cys Glu Thr Gln Asn Pro Val Ser Ala Arg
    210                 215                 220

Arg Ser Asp Ser Val Ile Leu Asn Val Leu Tyr Gly Pro Asp Ala Pro
225                 230                 235                 240

Thr Ile Ser Pro Leu Asn Thr Ser Tyr Arg Ser Gly Glu Asn Leu Asn
                245                 250                 255

Leu Ser Cys His Ala Ala Ser Asn Pro Pro Ala Gln Tyr Ser Trp Phe
            260                 265                 270

Val Asn Gly Thr Phe Gln Gln Ser Thr Gln Glu Leu Phe Ile Pro Asn
        275                 280                 285

Ile Thr Val Asn Asn Ser Gly Ser Tyr Thr Cys Gln Ala His Asn Ser
    290                 295                 300

Asp Thr Gly Leu Asn Arg Thr Thr Val Thr Thr Ile Thr Val Tyr Ala
305                 310                 315                 320
```

```
Glu Pro Pro Lys Pro Phe Ile Thr Ser Asn Asn Ser Asn Pro Val Glu
                325                 330                 335

Asp Glu Asp Ala Val Ala Leu Thr Cys Glu Pro Glu Ile Gln Asn Thr
            340                 345                 350

Thr Tyr Leu Trp Trp Val Asn Asn Gln Ser Leu Pro Val Ser Pro Arg
        355                 360                 365

Leu Gln Leu Ser Asn Asp Asn Arg Thr Leu Thr Leu Leu Ser Val Thr
    370                 375                 380

Arg Asn Asp Val Gly Pro Tyr Glu Cys Gly Ile Gln Asn Glu Leu Ser
385                 390                 395                 400

Val Asp His Ser Asp Pro Val Ile Leu Asn Val Leu Tyr Gly Pro Asp
                405                 410                 415

Asp Pro Thr Ile Ser Pro Ser Tyr Thr Tyr Tyr Arg Pro Gly Val Asn
            420                 425                 430

Leu Ser Leu Ser Cys His Ala Ala Ser Asn Pro Pro Ala Gln Tyr Ser
        435                 440                 445

Trp Leu Ile Asp Gly Asn Ile Gln Gln His Thr Gln Glu Leu Phe Ile
    450                 455                 460

Ser Asn Ile Thr Glu Lys Asn Ser Gly Leu Tyr Thr Cys Gln Ala Asn
465                 470                 475                 480

Asn Ser Ala Ser Gly His Ser Arg Thr Thr Val Lys Thr Ile Thr Val
                485                 490                 495

Ser Ala Glu Leu Pro Lys Pro Ser Ile Ser Ser Asn Asn Ser Lys Pro
            500                 505                 510

Val Glu Asp Lys Asp Ala Val Ala Phe Thr Cys Glu Pro Glu Ala Gln
        515                 520                 525

Asn Thr Thr Tyr Leu Trp Trp Val Asn Gly Gln Ser Leu Pro Val Ser
    530                 535                 540

Pro Arg Leu Gln Leu Ser Asn Gly Asn Arg Thr Leu Thr Leu Phe Asn
545                 550                 555                 560

Val Thr Arg Asn Asp Ala Arg Ala Tyr Val Cys Gly Ile Gln Asn Ser
                565                 570                 575

Val Ser Ala Asn Arg Ser Asp Pro Val Thr Leu Asp Val Leu Tyr Gly
            580                 585                 590

Pro Asp Thr Pro Ile Ile Ser Pro Pro Asp Ser Ser Tyr Leu Ser Gly
        595                 600                 605

Ala Asn Leu Asn Leu Ser Cys His Ser Ala Ser Asn Pro Ser Pro Gln
    610                 615                 620

Tyr Ser Trp Arg Ile Asn Gly Ile Pro Gln Gln His Thr Gln Val Leu
625                 630                 635                 640

Phe Ile Ala Lys Ile Thr Pro Asn Asn Asn Gly Thr Tyr Ala Cys Phe
                645                 650                 655

Val Ser Asn Leu Ala Thr Gly Arg Asn Asn Ser Ile Val Lys Ser Ile
            660                 665                 670

Thr Val Ser Ala Ser Gly Thr Ser Pro Gly Leu Ser Ala Gly Ala Thr
        675                 680                 685

Val Gly Ile Met Ile Gly Val Leu Val Gly Val Ala Leu Ile
    690                 695                 700


<210> SEQ ID NO 21
<211> LENGTH: 2859
<212> TYPE: DNA
<213> ORGANISM: Artificial Sequence
<220> FEATURE:
<223> OTHER INFORMATION: CEAoptDOMopt fusion
```

<400> SEQUENCE: 21

```
atggagagcc ccagcgcccc cccccaccgc tggtgcatcc cctggcagcg cctgctgctg     60
accgccagcc tgctgacctt ctggaacccc cccaccaccg ccaagctgac catcgagagc    120
accccccttca acgtggccga gggcaaggag gtgctgctgc tggtgcacaa cctgccccag    180
cacctgttcg gctacagctg gtacaagggc gagcgcgtgg acggcaaccg ccagatcatc    240
ggctacgtga tcggcaccca gcaggccacc cccggccccg cctacagcgg ccgcgagatc    300
atctacccca acgccagcct gctgatccag aacatcatcc agaacgacac cggcttctac    360
accctgcacg tgatcaagag cgacctggtg aacgaggagg ccaccggcca gttccgcgtg    420
taccccgagc tgcccaagcc cagcatcagc agcaacaaca gcaagcccgt ggaggacaag    480
gacgccgtgg ccttcacctg cgagcccgag acccaggacg ccacctacct gtggtgggtg    540
aacaaccaga gcctgcccgt gagcccccgc ctgcagctga gcaacggcaa ccgcaccctg    600
accctgttca acgtgacccg caacgacacc gccagctaca agtgcgagac ccagaacccc    660
gtgagcgccc gccgcagcga cagcgtgatc ctgaacgtgc tgtacggccc cgacgccccc    720
accatcagcc ccctgaacac cagctaccgc agcggcgaga acctgaacct gagctgccac    780
gccgccagca acccccccgc ccagtacagc tggttcgtga acggcacctt ccagcagagc    840
acccaggagc tgttcatccc caacatcacc gtgaacaaca gcggcagcta cacctgccag    900
gcccacaaca gcgacaccgg cctgaaccgc accaccgtga ccaccatcac cgtgtacgcc    960
gagcccccca agcccttcat caccagcaac aacagcaacc ccgtggagga cgaggacgcc   1020
gtggccctga cctgcgagcc cgagatccag aacaccacct acctgtggtg ggtgaacaac   1080
cagagcctgc ccgtgagccc ccgcctgcag ctgagcaacg acaaccgcac cctgaccctg   1140
ctgagcgtga cccgcaacga cgtgggcccc tacgagtgcg gcatccagaa cgagctgagc   1200
gtggaccaca gcgaccccgt gatcctgaac gtgctgtacg gccccgacga ccccaccatc   1260
agccccagct acacctacta ccgccccggc gtgaacctga gcctgagctg ccacgccgcc   1320
agcaaccccc ccgcccagta cagctggctg atcgacggca acatccagca gcacacccag   1380
gagctgttca tcagcaacat caccgagaag aacagcggcc tgtacacctg ccaggccaac   1440
aacagcgcca gcggccacag ccgcaccacc gtgaagacca tcaccgtgag cgccgagctg   1500
cccaagccca gcatcagcag caacaacagc aagcccgtgg aggacaagga cgccgtggcc   1560
ttcacctgcg agcccgaggc ccagaacacc acctacctgt ggtgggtgaa cggccagagc   1620
ctgcccgtga gcccccgcct gcagctgagc aacggcaacc gcaccctgac cctgttcaac   1680
gtgacccgca acgacgcccg cgcctacgtg tgcggcatcc agaacagcgt gagcgccaac   1740
cgcagcgacc ccgtgaccct ggacgtgctg tacggccccg acacccccat catcagcccc   1800
cccgacagca gctacctgag cggcgccaac ctgaacctga gctgccacag cgccagcaac   1860
cccagccccc agtacagctg gcgcatcaac ggcatccccc agcagcacac ccaggtgctg   1920
ttcatcgcca agatcacccc caacaacaac ggcacctacg cctgcttcgt gagcaacctg   1980
gccaccggcc gcaacaacag catcgtgaag agcatcaccg tgagcgccag cggcacctct   2040
agaagcaccc ccatcccatt cagctacagc aagaacctgg actgctgggt ggacaacgag   2100
gaggacatcg acgtgatcct gaagaagagc accatcctga acctggacat caacaacgac   2160
atcatcagcg acatcagcgg cttcaacagc agcgtgatca cctaccccga cgcccagctg   2220
gtgcccggca tcaacggcaa ggccatccac ctggtgaaca acgagagcag cgaggtgatc   2280
gtgcacaagg ccatggacat cgagtacaac gacatgttca acaacttcac cgtgagcttc   2340
```

tggctgagag tgcctaaggt gagcgccagc cacctggagc agtacggcac caacgagtac 2400
agcatcatca gcagcatgaa gaagcacagc ctgagcatcg gcagcggctg gagcgtgagc 2460
ctgaagggca acaacctcat ctggaccctg aaggatagcg ccggagaggt gagacagatc 2520
accttcagag acctgcccga caagttcaat gcctacctgg ccaacaagtg ggtgttcatc 2580
accatcacca acgacagact gagcagcgcc aacctgtaca tcaacggcgt gctcatgggc 2640
agcgccgaga tcaccggcct gggcgccatc agagaggaca acaacatcac cctgaagctg 2700
gacagatgca acaacaacaa ccagtacgtg agcatcgaca agttccggat cttctgcaag 2760
gccctgaacc ccaaggagat cgagaagctg tacaccagct acctgagcat caccttcctg 2820
agagacttct ggggcaaccc cctgagatac gacacctag 2859

<210> SEQ ID NO 22
<211> LENGTH: 2037
<212> TYPE: DNA
<213> ORGANISM: Artificial Sequence
<220> FEATURE:
<223> OTHER INFORMATION: deleted human CEA

<400> SEQUENCE: 22
atggagtctc cctcggcccc tccccacaga tggtgcatcc cctggcagag gctcctgctc 60
acagcctcac ttctaacctt ctggaacccg cccaccactg ccaagctcac tattgaatcc 120
acgccgttca atgtcgcaga ggggaaggag gtgcttctac ttgtccacaa tctgccccag 180
catctttttg gctacagctg gtacaaaggt gaaagagtgg atggcaaccg tcaaattata 240
ggatatgtaa taggaactca acaagctacc ccagggcccg catacagtgg tcgagagata 300 atataccccca atgcatccct gctgatccag aacatcatcc agaatgacac aggattctac 360
accctacacg tcataaagtc agatcttgtg aatgaagaag caactggcca gttccgggta 420
tacccggagc tgcccaagcc ctccatctcc agcaacaact ccaaacccgt ggaggacaag 480
gatgctgtgg ccttcacctg tgaacctgag actcaggacg caacctacct gtggtgggta 540
aacaatcaga gcctcccggt cagtcccagg ctgcagctgt ccaatggcaa caggaccctc 600
actctattca atgtcacaag aaatgacaca gcaagctaca aatgtgaaac ccagaaccca 660
gtgagtgcca ggcgcagtga ttcagtcatc ctgaatgtcc tctatggccc ggatgccccc 720
accatttccc ctctaaacac atcttacaga tcaggggaaa atctgaacct ctcctgccac 780
gcagcctcta acccacctgc acagtactct tggtttgtca atgggacttt ccagcaatcc 840
acccaagagc tctttatccc caacatcact gtgaataata gtggatccta tacgtgccaa 900
gcccataact cagacactgg cctcaatagg accacagtca cgacgatcac agtctatgca 960
gagccaccca aacccttcat caccagcaac aactccaacc ccgtggagga tgaggatgct 1020
gtagccttaa cctgtgaacc tgagattcag aacacaacct acctgtggtg ggtaaataat 1080
cagagcctcc cggtcagtcc caggctgcag ctgtccaatg acaacaggac cctcactcta 1140
ctcagtgtca caaggaatga tgtaggaccc tatgagtgtg gaatccagaa cgaattaagt 1200
gttgaccaca gcgacccagt catcctgaat gtcctctatg gcccagacga ccccaccatt 1260 tcccctcat acacctatta ccgtccaggg gtgaacctca gcctctcctg ccatgcagcc 1320
tctaacccac ctgcacagta ttcttggctg attgatggga acatccagca acacacacaa 1380
gagctcttta tctccaacat cactgagaag aacagcggac tctatacctg ccaggccaat 1440
aactcagcca gtggccacag caggactaca gtcaagacaa tcacagtctc tgcggagctg 1500
cccaagccct ccatctccag caacaactcc aaacccgtgg aggacaagga tgctgtggcc 1560

```
ttcacctgtg aacctgaggc tcagaacaca acctacctgt ggtgggtaaa tggtcagagc   1620

ctcccagtca gtcccaggct gcagctgtcc aatggcaaca ggaccctcac tctattcaat   1680

gtcacaagaa atgacgcaag agcctatgta tgtggaatcc agaactcagt gagtgcaaac   1740

cgcagtgacc cagtcaccct ggatgtcctc tatgggccgg acacccccat catttccccc   1800

ccagactcgt cttacctttc gggagcgaac ctcaacctct cctgccactc ggcctctaac   1860

ccatccccgc agtattcttg gcgtatcaat gggataccgc agcaacacac acaagttctc   1920

tttatcgcca aaatcacgcc aaataataac gggacctatg cctgttttgt ctctaacttg   1980

gctactggcc gcaataattc catagtcaag agcatcacag tctctgcatc tggaact      2037
```

```
<210> SEQ ID NO 23
<211> LENGTH: 679
<212> TYPE: PRT
<213> ORGANISM: Artificial Sequence
<220> FEATURE:
<223> OTHER INFORMATION: deleted human CEA

<400> SEQUENCE: 23

Met Glu Ser Pro Ser Ala Pro Pro His Arg Trp Cys Ile Pro Trp Gln
 1               5                  10                  15

Arg Leu Leu Leu Thr Ala Ser Leu Leu Thr Phe Trp Asn Pro Pro Thr
            20                  25                  30

Thr Ala Lys Leu Thr Ile Glu Ser Thr Pro Phe Asn Val Ala Glu Gly
        35                  40                  45

Lys Glu Val Leu Leu Leu Val His Asn Leu Pro Gln His Leu Phe Gly
    50                  55                  60

Tyr Ser Trp Tyr Lys Gly Glu Arg Val Asp Gly Asn Arg Gln Ile Ile
65                  70                  75                  80

Gly Tyr Val Ile Gly Thr Gln Gln Ala Thr Pro Gly Pro Ala Tyr Ser
                85                  90                  95

Gly Arg Glu Ile Ile Tyr Pro Asn Ala Ser Leu Leu Ile Gln Asn Ile
            100                 105                 110

Ile Gln Asn Asp Thr Gly Phe Tyr Thr Leu His Val Ile Lys Ser Asp
        115                 120                 125

Leu Val Asn Glu Glu Ala Thr Gly Gln Phe Arg Val Tyr Pro Glu Leu
    130                 135                 140

Pro Lys Pro Ser Ile Ser Ser Asn Asn Ser Lys Pro Val Glu Asp Lys
145                 150                 155                 160

Asp Ala Val Ala Phe Thr Cys Glu Pro Glu Thr Gln Asp Ala Thr Tyr
                165                 170                 175

Leu Trp Trp Val Asn Asn Gln Ser Leu Pro Val Ser Pro Arg Leu Gln
            180                 185                 190

Leu Ser Asn Gly Asn Arg Thr Leu Thr Leu Phe Asn Val Thr Arg Asn
        195                 200                 205

Asp Thr Ala Ser Tyr Lys Cys Glu Thr Gln Asn Pro Val Ser Ala Arg
    210                 215                 220

Arg Ser Asp Ser Val Ile Leu Asn Val Leu Tyr Gly Pro Asp Ala Pro
225                 230                 235                 240

Thr Ile Ser Pro Leu Asn Thr Ser Tyr Arg Ser Gly Glu Asn Leu Asn
                245                 250                 255

Leu Ser Cys His Ala Ala Ser Asn Pro Pro Ala Gln Tyr Ser Trp Phe
            260                 265                 270

Val Asn Gly Thr Phe Gln Gln Ser Thr Gln Glu Leu Phe Ile Pro Asn
        275                 280                 285
```

```
Ile Thr Val Asn Asn Ser Gly Ser Tyr Thr Cys Gln Ala His Asn Ser
    290                 295                 300

Asp Thr Gly Leu Asn Arg Thr Thr Val Thr Thr Ile Thr Val Tyr Ala
305                 310                 315                 320

Glu Pro Pro Lys Pro Phe Ile Thr Ser Asn Asn Ser Asn Pro Val Glu
                325                 330                 335

Asp Glu Asp Ala Val Ala Leu Thr Cys Glu Pro Glu Ile Gln Asn Thr
            340                 345                 350

Thr Tyr Leu Trp Trp Val Asn Asn Gln Ser Leu Pro Val Ser Pro Arg
        355                 360                 365

Leu Gln Leu Ser Asn Asp Asn Arg Thr Leu Thr Leu Leu Ser Val Thr
    370                 375                 380

Arg Asn Asp Val Gly Pro Tyr Glu Cys Gly Ile Gln Asn Glu Leu Ser
385                 390                 395                 400

Val Asp His Ser Asp Pro Val Ile Leu Asn Val Leu Tyr Gly Pro Asp
                405                 410                 415

Asp Pro Thr Ile Ser Pro Ser Tyr Thr Tyr Tyr Arg Pro Gly Val Asn
            420                 425                 430

Leu Ser Leu Ser Cys His Ala Ala Ser Asn Pro Pro Ala Gln Tyr Ser
        435                 440                 445

Trp Leu Ile Asp Gly Asn Ile Gln Gln His Thr Gln Glu Leu Phe Ile
    450                 455                 460

Ser Asn Ile Thr Glu Lys Asn Ser Gly Leu Tyr Thr Cys Gln Ala Asn
465                 470                 475                 480

Asn Ser Ala Ser Gly His Ser Arg Thr Thr Val Lys Thr Ile Thr Val
                485                 490                 495

Ser Ala Glu Leu Pro Lys Pro Ser Ile Ser Ser Asn Asn Ser Lys Pro
            500                 505                 510

Val Glu Asp Lys Asp Ala Val Ala Phe Thr Cys Glu Pro Glu Ala Gln
        515                 520                 525

Asn Thr Thr Tyr Leu Trp Trp Val Asn Gly Gln Ser Leu Pro Val Ser
    530                 535                 540

Pro Arg Leu Gln Leu Ser Asn Gly Asn Arg Thr Leu Thr Leu Phe Asn
545                 550                 555                 560

Val Thr Arg Asn Asp Ala Arg Ala Tyr Val Cys Gly Ile Gln Asn Ser
                565                 570                 575

Val Ser Ala Asn Arg Ser Asp Pro Val Thr Leu Asp Val Leu Tyr Gly
            580                 585                 590

Pro Asp Thr Pro Ile Ile Ser Pro Pro Asp Ser Ser Tyr Leu Ser Gly
        595                 600                 605

Ala Asn Leu Asn Leu Ser Cys His Ser Ala Ser Asn Pro Ser Pro Gln
    610                 615                 620

Tyr Ser Trp Arg Ile Asn Gly Ile Pro Gln Gln His Thr Gln Val Leu
625                 630                 635                 640

Phe Ile Ala Lys Ile Thr Pro Asn Asn Asn Gly Thr Tyr Ala Cys Phe
                645                 650                 655

Val Ser Asn Leu Ala Thr Gly Arg Asn Asn Ser Ile Val Lys Ser Ile
            660                 665                 670

Thr Val Ser Ala Ser Gly Thr
        675
```

<210> SEQ ID NO 24
<211> LENGTH: 3426
<212> TYPE: DNA
<213> ORGANISM: Artificial Sequence
<220> FEATURE:
<223> OTHER INFORMATION: CEA-FRC fusion

<400> SEQUENCE: 24

```
atggagtctc cctcggcccc tccccacaga tggtgcatcc cctggcagag gctcctgctc     60
acagcctcac ttctaacctt ctggaacccg cccaccactg ccaagctcac tattgaatcc    120
acgccgttca atgtcgcaga ggggaaggag gtgcttctac ttgtccacaa tctgccccag    180
catctttttg gctacagctg gtacaaaggt gaaagagtgg atggcaaccg tcaaattata    240
ggatatgtaa taggaactca acaagctacc ccagggcccg catacagtgg tcgagagata    300
atatacccca atgcatccct gctgatccag aacatcatcc agaatgacac aggattctac    360
accctacacg tcataaagtc agatcttgtg aatgaagaag caactggcca gttccgggta    420
tacccggagc tgcccaagcc ctccatctcc agcaacaact ccaaacccgt ggaggacaag    480
gatgctgtgg ccttcacctg tgaacctgag actcaggacg caacctacct gtggtgggta    540
aacaatcaga gcctcccggt cagtcccagg ctgcagctgt ccaatggcaa caggaccctc    600
actctattca atgtcacaag aaatgacaca gcaagctaca aatgtgaaac ccagaaccca    660
gtgagtgcca ggcgcagtga ttcagtcatc ctgaatgtcc tctatggccc ggatgccccc    720
accatttccc ctctaaacac atcttacaga tcaggggaaa atctgaacct ctcctgccac    780
gcagcctcta acccacctgc acagtactct tggtttgtca atgggacttt ccagcaatcc    840
acccaagagc tctttatccc caacatcact gtgaataata gtggatccta tacgtgccaa    900
gcccataact cagacactgg cctcaatagg accacagtca cgacgatcac agtctatgca    960
gagccaccca aacccttcat caccagcaac aactccaacc ccgtggagga tgaggatgct   1020
gtagccttaa cctgtgaacc tgagattcag aacacaacct acctgtggtg ggtaaataat   1080
cagagcctcc cggtcagtcc caggctgcag ctgtccaatg acaacaggac cctcactcta   1140
ctcagtgtca caaggaatga tgtaggaccc tatgagtgtg gaatccagaa cgaattaagt   1200
gttgaccaca gcgacccagt catcctgaat gtcctctatg gcccagacga ccccaccatt   1260
tccccctcat acacctatta ccgtccaggg gtgaacctca gcctctcctg ccatgcagcc   1320
tctaacccac ctgcacagta ttcttggctg attgatggga acatccagca acacacacaa   1380
gagctcttta tctccaacat cactgagaag aacagcggac tctatacctg ccaggccaat   1440
aactcagcca gtggccacag caggactaca gtcaagacaa tcacagtctc tgcggagctg   1500
cccaagccct ccatctccag caacaactcc aaacccgtgg aggacaagga tgctgtggcc   1560
ttcacctgtg aacctgaggc tcagaacaca acctacctgt ggtgggtaaa tggtcagagc   1620
ctcccagtca gtcccaggct gcagctgtcc aatggcaaca ggaccctcac tctattcaat   1680
gtcacaagaa atgacgcaag agcctatgta tgtggaatcc agaactcagt gagtgcaaac   1740
cgcagtgacc cagtcaccct ggatgtcctc tatgggccgg acacccccat catttccccc   1800
ccagactcgt cttacctttc gggagcgaac ctcaacctct cctgccactc ggcctctaac   1860
ccatccccgc agtattcttg gcgtatcaat gggataccgc agcaacacac acaagttctc   1920
tttatcgcca aaatcacgcc aaataataac gggacctatg cctgttttgt ctctaacttg   1980
gctactggcc gcaataattc catagtcaag agcatcacag tctctgcatc tggaactcta   2040
gattcaacac caattccatt ttcttattct aaaaatctgg attgttgggt tgataatgaa   2100
gaagatatag atgttatatt aaaaaagagt acaattttaa atttagatat taataatgat   2160
attatatcag atatatctgg gtttaattca tctgtaataa catatccaga tgctcaattg   2220
gtgcccggaa taaatggcaa agcaatacat ttagtaaaca atgaatcttc tgaagttata   2280
```

```
gtgcataaag ctatggatat tgaatataat gatatgttta ataattttac cgttagcttt   2340

tggttgaggg ttcctaaagt atctgctagt catttagaac aatatggcac aaatgagtat   2400

tcaataatta gctctatgaa aaaacatagt ctatcaatag gatctggttg gagtgtatca   2460

cttaaaggta ataacttaat atggacttta aaagattccg cgggagaagt tagacaaata   2520

acttttaggg atttacctga taaatttaat gcttatttag caaataaatg ggtttttata   2580

actattacta atgatagatt atcttctgct aatttgtata taaatggagt acttatggga   2640

agtgcagaaa ttactggttt aggagctatt agagaggata ataatataac attaaaacta   2700

gatagatgta ataataataa tcaatacgtt tctattgata aatttaggat attttgcaaa   2760

gcattaaatc caaaagagat tgaaaaatta tacacaagtt atttatctat aacctttttta   2820

agagacttct ggggaaaccc tttacgatat gatacagaat attatttaat accagtagct   2880

tctagttcta aagatgttca attgaaaaat ataacagatt atatgtattt gacaaatgcg   2940

ccatcgtata ctaacggaaa attgaatata tattatagaa ggttatataa tggactaaaa   3000

tttattataa aaagatatac acctaataat gaaatagatt cttttgttaa atcaggtgat   3060

tttattaaat tatatgtatc atataacaat aatgagcaca ttgtaggtta tccgaaagat   3120

ggaaatgcct ttaataatct tgatagaatt ctaagagtag gttataatgc cccaggtatc   3180

cctctttata aaaaaatgga agcagtaaaa ttgcgtgatt taaaaaccta ttctgtacaa   3240

cttaaattat atgatgataa aaatgcatct ttaggactag taggtaccca taatggtcaa   3300

ataggcaacg atccaaatag ggatatatta attgcaagca actggtactt taatcattta   3360

aaagataaaa ttttaggatg tgattggtac tttgtaccta cagatgaagg atggacaaat   3420

gattaa                                                              3426
```

<210> SEQ ID NO 25
<211> LENGTH: 2664
<212> TYPE: DNA
<213> ORGANISM: Artificial Sequence
<220> FEATURE:
<223> OTHER INFORMATION: CEA-FcIgG fusion

<400> SEQUENCE: 25

```
atggagagcc ccagcgcccc cccccaccgc tggtgcatcc cctggcagcg cctgctgctg     60

accgccagcc tgctgacctt ctggaacccc cccaccaccg ccaagctgac catcgagagc    120

acccccttca acgtggccga gggcaaggag gtgctgctgc tggtgcacaa cctgccccag    180

cacctgttcg gctacagctg gtacaagggc gagcgcgtgg acggcaaccg ccagatcatc    240

ggctacgtga tcggcaccca gcaggccacc cccggccccg cctacagcgg ccgcgagatc    300

atctacccca acgccagcct gctgatccag aacatcatcc agaacgacac cggcttctac    360

accctgcacg tgatcaagag cgacctggtg aacgaggagg ccaccggcca gttccgcgtg    420

taccccgagc tgcccaagcc cagcatcagc agcaacaaca gcaagcccgt ggaggacaag    480

gacgccgtgg ccttcacctg cgagcccgag acccaggacg ccacctacct gtggtgggtg    540

aacaaccaga gcctgcccgt gagcccccgc ctgcagctga gcaacggcaa ccgcaccctg    600

accctgttca acgtgacccg caacgacacc gccagctaca agtgcgagac ccagaacccc    660

gtgagcgccc gccgcagcga cagcgtgatc ctgaacgtgc tgtacggccc cgacgccccc    720

accatcagcc ccctgaacac cagctaccgc agcggcgaga acctgaacct gagctgccac    780

gccgccagca acccccccgc ccagtacagc tggttcgtga acggcacctt ccagcagagc    840

acccaggagc tgttcatccc caacatcacc gtgaacaaca gcggcagcta cacctgccag    900
```

```
gcccacaaca gcgacaccgg cctgaaccgc accaccgtga ccaccatcac cgtgtacgcc     960
gagcccccca agcccttcat caccagcaac aacagcaacc ccgtggagga cgaggacgcc    1020
gtggccctga cctgcgagcc cgagatccag aacaccacct acctgtggtg ggtgaacaac    1080
cagagcctgc ccgtgagccc ccgcctgcag ctgagcaacg acaaccgcac cctgaccctg    1140
ctgagcgtga cccgcaacga cgtgggcccc tacgagtgcg gcatccagaa cgagctgagc    1200
gtggaccaca gcgaccccgt gatcctgaac gtgctgtacg gccccgacga ccccaccatc    1260
agccccagct acacctacta ccgccccggc gtgaacctga gcctgagctg ccacgccgcc    1320
agcaaccccc ccgcccagta cagctggctg atcgacggca acatccagca gcacacccag    1380
gagctgttca tcagcaacat caccgagaag aacagcggcc tgtacacctg ccaggccaac    1440
aacagcgcca gcggccacag ccgcaccacc gtgaagacca tcaccgtgag cgccgagctg    1500
cccaagccca gcatcagcag caacaacagc aagcccgtgg aggacaagga cgccgtggcc    1560
ttcacctgcg agcccgaggc ccagaacacc acctacctgt ggtgggtgaa cggccagagc    1620
ctgcccgtga gcccccgcct gcagctgagc aacggcaacc gcaccctgac cctgttcaac    1680
cgcagcgacc ccgtgaccct ggacgtgctg tacggccccg acacccccat catcagcccc    1740
cccgacagca gctacctgag cggcgccaac ctgaacctga gctgccacag cgccagcaac    1800
cccagccccc agtacagctg gcgcatcaac ggcatccccc agcagcacac ccaggtgctg    1860
ttcatcgcca agatcacccc caacaacaac ggcacctacg cctgcttcgt gagcaacctg    1920
gccaccggcc gcaacaacag catcgtgaag agcatcaccg tgagcgccag cggcacctct    1980
agaaagaccc acacctgccc cccttgccct gcccctgagc tgctgggcgg acccagcgtg    2040
ttcctgttcc cccccaagcc taaggacacc ctcatgatca gcagaacccc cgaggtgacc    2100
tgcgtggtgg tggacgtgag ccacgaggat cccgaggtga agttcaactg gtacgtggac    2160
ggcgtggagg tgcacaatgc caagaccaag cccagagagg agcagtacaa cagcacctac    2220
agagtggtga gcgtgctcac cgtgctgcac caggattggc tgaacggcaa ggagtacaag    2280
tgcaaggtga gcaacaaggc cctgcctgcc cccatcgaga aaaccatcag caaggccaag    2340
ggccagccca gagagcccca ggtgtacacc ctgcccccta gcagagatga gttgaccaag    2400
aaccaggtga gcctcacatg cctggtgaag ggcttctacc ccagcgacat cgccgtggag    2460
tgggagagca acggccagcc cgagaacaac tacaagacca ccccccctgt gctggacagc    2520
gatggcagct tcttcctgta cagcaagctc accgtggaca agagcagatg gcagcagggc    2580
aacgtgttca gctgcagcgt gatgcacgag gccctgcaca atcactacac ccagaagagc    2640
ctgagcctga gccccggcaa gtaa                                           2664
```

<210> SEQ ID NO 26
<211> LENGTH: 2167
<212> TYPE: DNA
<213> ORGANISM: Artificial Sequence
<220> FEATURE:
<223> OTHER INFORMATION: CEA-LAMP fusion

<400> SEQUENCE: 26

```
catggagtct ccctcggccc ctccccacag atggtgcatc ccctggcaga ggctcctgct      60
cacagcctca cttctaacct tctggaaccc gcccaccact gccaagctca ctattgaatc     120
cacgccgttc aatgtcgcag aggggaagga ggtgcttcta cttgtccaca atctgcccca     180
gcatcttttt ggctacagct ggtacaaagg tgaaagagtg gatggcaacc gtcaaattat     240
aggatatgta ataggaactc aacaagctac cccagggccc gcatacagtg gtcgagagat     300
```

```
aatatacccc aatgcatccc tgctgatcca gaacatcatc cagaatgaca caggattcta    360

caccctacac gtcataaagt cagatcttgt gaatgaagaa gcaactggcc agttccgggt    420

atacccggag ctgcccaagc cctccatctc cagcaacaac tccaaacccg tggaggacaa    480

ggatgctgtg gccttcacct gtgaacctga gactcaggac gcaacctacc tgtggtgggt    540

aaacaatcag agcctcccgg tcagtcccag gctgcagctg tccaatggca acaggaccct    600

cactctattc aatgtcacaa gaaatgacac agcaagctac aaatgtgaaa cccagaaccc    660

agtgagtgcc aggcgcagtg attcagtcat cctgaatgtc ctctatggcc cggatgcccc    720

caccatttcc cctctaaaca catcttacag atcaggggaa aatctgaacc tctcctgcca    780

cgcagcctct aacccacctg cacagtactc ttggtttgtc aatgggactt tccagcaatc    840

cacccaagag ctctttatcc ccaacatcac tgtgaataat agtggatcct atacgtgcca    900

agcccataac tcagacactg gcctcaatag gaccacagtc acgacgatca cagtctatgc    960

agagccaccc aaacccttca tcaccagcaa caactccaac cccgtggagg atgaggatgc   1020

tgtagcctta acctgtgaac ctgagattca gaacacaacc tacctgtggt gggtaaataa   1080

tcagagcctc ccggtcagtc ccaggctgca gctgtccaat gacaacagga ccctcactct   1140

actcagtgtc acaaggaatg atgtaggacc ctatgagtgt ggaatccaga acgaattaag   1200

tgttgaccac agcgacccag tcatcctgaa tgtcctctat ggcccagacg accccaccat   1260

ttccccctca tacacctatt accgtccagg ggtgaacctc agcctctcct gccatgcagc   1320

ctctaaccca cctgcacagt attcttggct gattgatggg aacatccagc aacacacaca   1380

agagctcttt atctccaaca tcactgagaa gaacagcgga ctctatacct gccaggccaa   1440

taactcagcc agtggccaca gcaggactac agtcaagaca atcacagtct ctgcggagct   1500

gcccaagccc tccatctcca gcaacaactc caaacccgtg gaggacaagg atgctgtggc   1560

cttcacctgt gaacctgagg ctcagaacac aacctacctg tggtgggtaa atggtcagag   1620

cctcccagtc agtcccaggc tgcagctgtc caatggcaac aggaccctca ctctattcaa   1680

tgtcacaaga aatgacgcaa gagcctatgt atgtggaatc cagaactcag tgagtgcaaa   1740

ccgcagtgac ccagtcaccc tggatgtcct ctatgggccg gacaccccca tcatttcccc   1800

cccagactcg tcttaccttt cgggagcgaa cctcaacctc tcctgccact cggcctctaa   1860

cccatccccg cagtattctt ggcgtatcaa tgggataccg cagcaacaca cacaagttct   1920

ctttatcgcc aaaatcacgc caaataataa cgggacctat gcctgttttg tctctaactt   1980

ggctactggc cgcaataatt ccatagtcaa gagcatcaca gtctctgcat ctggaactct   2040

agatgatggt aacaacatgt tgatccccat tgctgtgggc ggtgccctgg cagggctgat   2100

cctcatcgtc ctcattgcct acctcattgg caggaagagg agtcacgccg gctatcagac   2160

catctag                                                              2167
```

<210> SEQ ID NO 27
<211> LENGTH: 3921
<212> TYPE: DNA
<213> ORGANISM: Artificial Sequence
<220> FEATURE:
<223> OTHER INFORMATION: CEA-HSP70 fusion

<400> SEQUENCE: 27

```
atggagtctc cctcggcccc tccccacaga tggtgcatcc cctggcagag gctcctgctc     60

acagcctcac ttctaacctt ctggaacccg cccaccactg ccaagctcac tattgaatcc    120

acgccgttca atgtcgcaga ggggaaggag gtgcttctac ttgtccacaa tctgccccag    180
```

```
catctttttg gctacagctg gtacaaaggt gaaagagtgg atggcaaccg tcaaattata    240
ggatatgtaa taggaactca acaagctacc ccagggcccg catacagtgg tcgagagata    300
atatacccca atgcatccct gctgatccag aacatcatcc agaatgacac aggattctac    360
accctacacg tcataaagtc agatcttgtg aatgaagaag caactggcca gttccgggta    420
tacccggagc tgcccaagcc ctccatctcc agcaacaact ccaaacccgt ggaggacaag    480
gatgctgtgg ccttcacctg tgaacctgag actcaggacg caacctacct gtggtgggta    540
aacaatcaga gcctcccggt cagtcccagg ctgcagctgt ccaatggcaa caggaccctc    600
actctattca atgtcacaag aaatgacaca gcaagctaca aatgtgaaac ccagaaccca    660
gtgagtgcca ggcgcagtga ttcagtcatc ctgaatgtcc tctatggccc ggatgccccc    720
accatttccc ctctaaacac atcttacaga tcaggggaaa atctgaacct ctcctgccac    780
gcagcctcta acccacctgc acagtactct tggtttgtca atgggacttt ccagcaatcc    840
acccaagagc tctttatccc caacatcact gtgaataata gtggatccta tacgtgccaa    900
gcccataact cagacactgg cctcaatagg accacagtca cgacgatcac agtctatgca    960
gagccaccca aacccttcat caccagcaac aactccaacc ccgtggagga tgaggatgct   1020
gtagccttaa cctgtgaacc tgagattcag aacacaacct acctgtggtg ggtaaataat   1080
cagagcctcc cggtcagtcc caggctgcag ctgtccaatg acaacaggac cctcactcta   1140
ctcagtgtca caaggaatga tgtaggaccc tatgagtgtg gaatccagaa cgaattaagt   1200
gttgaccaca gcgacccagt catcctgaat gtcctctatg gcccagacga ccccaccatt   1260
tccccctcat acacctatta ccgtccaggg gtgaacctca gcctctcctg ccatgcagcc   1320
tctaacccac ctgcacagta ttcttggctg attgatggga acatccagca acacacacaa   1380
gagctcttta tctccaacat cactgagaag aacagcggac tctatacctg ccaggccaat   1440
aactcagcca gtggccacag caggactaca gtcaagacaa tcacagtctc tgcggagctg   1500
cccaagccct ccatctccag caacaactcc aaacccgtgg aggacaagga tgctgtggcc   1560
ttcacctgtg aacctgaggc tcagaacaca acctacctgt ggtgggtaaa tggtcagagc   1620
ctcccagtca gtcccaggct gcagctgtcc aatggcaaca ggaccctcac tctattcaat   1680
gtcacaagaa atgacgcaag agcctatgta tgtggaatcc agaactcagt gagtgcaaac   1740
cgcagtgacc cagtcaccct ggatgtcctc tatgggccgg acacccccat catttccccc   1800
ccagactcgt cttacctttc gggagcgaac ctcaacctct cctgccactc ggcctctaac   1860
ccatccccgc agtattcttg gcgtatcaat gggataccgc agcaacacac acaagttctc   1920
tttatcgcca aaatcacgcc aaataataac gggacctatg cctgttttgt ctctaacttg   1980
gctactggcc gcaataattc catagtcaag agcatcacag tctctgcatc tggaactcta   2040
gatatggctc gtgcggtcgg gatcgacctc gggaccacca actccgtcgt ctcggttctg   2100
gaaggtggcg acccggtcgt cgtcgccaac tccgagggct ccaggaccac cccgtcaatt   2160
gtcgcgttcg cccgcaacgg tgaggtgctg gtcggccagc ccgccaagaa ccaggcggtg   2220
accaacgtcg atcgcaccgt gcgctcggtc aagcgacaca tgggcagcga ctggtccata   2280
gagattgacg gcaagaaata caccgcgccg gagatcagcg cccgcattct gatgaagctg   2340
aagcgcgacg ccgaggccta cctcggtgag gacattaccg acgcggttat cacgacgccc   2400
gcctacttca atgacgccca gcgtcaggcc accaaggacg ccggccagat cgccggcctc   2460
aacgtgctgc ggatcgtcaa cgagccgacc gcggccgcgc tggcctacgg cctcgacaag   2520
ggcgagaagg agcagcgaat cctggtcttc gacttgggtg gtggcacttt cgacgtttcc   2580
```

```
ctgctggaga tcggcgaggg tgtggttgag gtccgtgcca cttcgggtga caaccacctc   2640
ggcggcgacg actgggacca gcgggtcgtc gattggctgg tggacaagtt caagggcacc   2700
agcggcatcg atctgaccaa ggacaagatg gcgatgcagc ggctgcggga agccgccgag   2760
aaggcaaagg tcgagctgag ttcgagtcag tccacctcga tcaacctgcc ctacatcacc   2820
gtcgacgcag acaagaaccc gttgttctta gacgagcagc tgacccgcgc ggagttccaa   2880
cggatcactc aggacctgct ggaccgcact cgcaagccgt tccagtcggt gatcgctgac   2940
accggcattt cggtgtcgga gatcgatcac gttgtgctcg tgggtggttc gacccggatg   3000
cccgcggtga ccgatctggt caaggaactc accggcggca aggaacccaa caagggcgtc   3060
aaccccgatg aggttgtcgc ggtgggagcc gctctgcagg ccggcgtcct caagggcgag   3120
gtgaaagacg ttctgctgct tgatgttacc ccgctgagcc tgggtatcga gaccaagggc   3180
ggggtgatga ccaggctcat cgagcgcaac accacgatcc cctccaagcg gtcggagact   3240
ttcaccaccg ccgacgacaa ccaaccgtcg gtgcagatcc aggtctatca gggggagtgt   3300
gagatcgccg cgcacaacaa gttgcccggg tccttcgagc tgaccggcat cccgccggcg   3360
ccgcggggga ttccgcagat cgaggtcact ttcgacatcg acgccaacgg cattgtgcac   3420
gtcaccgcca aggacaaggg caccggcaag gagaacacga tccgaatcca ggaaggctcg   3480
ggcctgtcca aggaagacat tgaccgcatg atcaaggacg ccgaagcgca cgccgaggag   3540
gatcgcaagc gtcgcgagga ggccgatgtt cgtaatcaag ccgagacatt ggtctaccag   3600
acggagaagt tcgtcaaaga acagcgtgag gccgagggtg gttcgaaggt acctgaagac   3660
acgctgaaca aggttgatgc cgcggtggcg gaagcgaagg cggcacttgg cggatcggat   3720
atttcggcca tcaagtcggc gatggagaag ctgggccagg agtcgcaggc tctggggcaa   3780
gcgatctacg aagcagctca ggctgcgtca ctggccactg gcgctgccca ccccggcggc   3840
gagccgggcg gtgcccaccc cggctcggct gatgacgttg tggacgcgga ggtggtcgac   3900
gacggccggg aggccaagtg a                                             3921
```

<210> SEQ ID NO 28
<211> LENGTH: 3585
<212> TYPE: DNA
<213> ORGANISM: Artificial Sequence
<220> FEATURE:
<223> OTHER INFORMATION: CEA-VSVG fusion

<400> SEQUENCE: 28

```
atggagtctc cctcggcccc tccccacaga tggtgcatcc cctggcagag gctcctgctc     60
acagcctcac ttctaacctt ctggaacccg cccaccactg ccaagctcac tattgaatcc    120
acgccgttca atgtcgcaga ggggaaggag gtgcttctac ttgtccacaa tctgccccag    180
catctttttg gctacagctg gtacaaaggt gaaagagtgg atggcaaccg tcaaattata    240
ggatatgtaa taggaactca acaagctacc ccagggcccg catacagtgg tcgagagata    300
atatacccca atgcatccct gctgatccag aacatcatcc agaatgacac aggattctac    360
accctacacg tcataaagtc agatcttgtg aatgaagaag caactggcca gttccgggta    420
tacccggagc tgcccaagcc ctccatctcc agcaacaact ccaaacccgt ggaggacaag    480
gatgctgtgg ccttcacctg tgaacctgag actcaggacg caacctacct gtggtgggta    540
aacaatcaga gcctcccggt cagtcccagg ctgcagctgt ccaatggcaa caggaccctc    600
actctattca atgtcacaag aaatgacaca gcaagctaca aatgtgaaac ccagaaccca    660
gtgagtgcca ggcgcagtga ttcagtcatc ctgaatgtcc tctatggccc ggatgccccc    720
```

```
accatttccc ctctaaacac atcttacaga tcaggggaaa atctgaacct ctcctgccac    780
gcagcctcta acccacctgc acagtactct tggtttgtca atgggacttt ccagcaatcc    840
acccaagagc tctttatccc caacatcact gtgaataata gtggatccta tacgtgccaa    900
gcccataact cagacactgg cctcaatagg accacagtca cgacgatcac agtctatgca    960
gagccaccca aacccttcat caccagcaac aactccaacc ccgtggagga tgaggatgct   1020
gtagccttaa cctgtgaacc tgagattcag aacacaacct acctgtggtg ggtaaataat   1080
cagagcctcc cggtcagtcc caggctgcag ctgtccaatg acaacaggac cctcactcta   1140
ctcagtgtca caaggaatga tgtaggaccc tatgagtgtg gaatccagaa cgaattaagt   1200
gttgaccaca gcgacccagt catcctgaat gtcctctatg gcccagacga ccccaccatt   1260
tccccctcat acacctatta ccgtccaggg gtgaacctca gcctctcctg ccatgcagcc   1320
tctaacccac ctgcacagta ttcttggctg attgatggga acatccagca acacacacaa   1380
gagctcttta tctccaacat cactgagaag aacagcggac tctatacctg ccaggccaat   1440
aactcagcca gtggccacag caggactaca gtcaagacaa tcacagtctc tgcggagctg   1500
cccaagccct ccatctccag caacaactcc aaacccgtgg aggacaagga tgctgtggcc   1560
ttcacctgtg aacctgaggc tcagaacaca acctacctgt ggtgggtaaa tggtcagagc   1620
ctcccagtca gtcccaggct gcagctgtcc aatggcaaca ggaccctcac tctattcaat   1680
gtcacaagaa atgacgcaag agcctatgta tgtggaatcc agaactcagt gagtgcaaac   1740
cgcagtgacc cagtcaccct ggatgtcctc tatgggccgg acacccccat catttccccc   1800
ccagactcgt cttacctttc gggagcgaac ctcaacctct cctgccactc ggcctctaac   1860
ccatccccgc agtattcttg gcgtatcaat gggataccgc agcaacacac acaagttctc   1920
tttatcgcca aaatcacgcc aaataataac gggacctatg cctgttttgt ctctaacttg   1980
gctactggcc gcaataattc catagtcaag agcatcacag tctctgcatc tggaactcta   2040
gatgaattca tgaagtgctt tttgtactta gctttttttat tcatcggggt gaattgcaag   2100
ttcaccatag tttttccaca caaccaaaaa ggaaactgga aaaatgttcc ttccaattac   2160
cattattgcc cgtcaagctc agatttaaat tggcataatg acttaatagg cacaggctta   2220
caagtcaaaa tgcccaagag tcacaaggct attcaagcag acggttggat gtgtcatgct   2280
tccaaatggg tcactacttg tgatttccgc tggtacggac cgaagtatat aacacattcc   2340
atccgatcct tcactccatc tgtagaacaa tgcaaggaaa gcattgaaca aacgaaacaa   2400
ggaacttggc tgaatccagg cttccctcct caaagttgtg gatatgcaac tgtgacggat   2460
gccgaagcag tgattgtcca ggtgactcct caccatgtgc ttgttgatga atacacagga   2520
gaatgggttg attcacagtt catcaacgga aaatgcagca atgacatatg ccccactgtc   2580
cataactcca caacctggca ttccgactat aaggtcaaag ggctatgtga ttctaacctc   2640
atttccacgg acatcacctt cttctcagag gacagagagc tatcatccct aggaaaggag   2700
ggcacagggt tcagaagtaa ctactttgct tatgaaactg gagacaaggc ctgcaaaatg   2760
cagtactgca agcattgggg agtcagactc ccatcaggtg tctggttcga gatggctgat   2820
aaggatctct ttgctgcagc cagattccct gaatgcccag aagggtcaag tatctctgct   2880
ccatctcaga cctcagtgga tgtaagtctc attcaggacg ttgagaggat cttggattat   2940
tccctctgcc aagaaacctg gagcaaaatc agagcgggtc ttcccatctc tccagtggat   3000
ctcagctatc ttgctcctaa aaacccagga accggtcctg cctttaccat aatcaatggt   3060
accctaaaat actttgagac cagatacatc agagtcgata ttgctgctcc aatcctctca   3120
```

```
agaatggtcg gaatgatcag tggaactacc acagaaaggg aactgtggga tgactgggct   3180

ccatatgaag acgtggaaat tggacccaat ggagttctga ggaccagttc aggatataag   3240

tttcctttat atatgattgg acatggtatg ttggactccg gtcttcatct tagctcaaag   3300

gctcaggtgt ttgaacatcc tcacattcaa gacgctgctt cgcagcttcc tgatgatgag   3360

attttatttt ttggtgatac tgggctatcc aaaaatccaa tcgactttgt cgaaggttgg   3420

ttcagtagtt ggaagagctc cattgcctct tttttcttta tcatagggtt aatcattgga   3480

ctattcttgg ttctccgagt tggtatttat ctttacatta aattaaagca caccaagaaa   3540

agacagattt atacagacat agagatgaac cgacttggaa ggtaa                   3585


<210> SEQ ID NO 29
<211> LENGTH: 36
<212> TYPE: DNA
<213> ORGANISM: Artificial Sequence
<220> FEATURE:
<223> OTHER INFORMATION: PCR Primer, chemically synthesized

<400> SEQUENCE: 29

tattctagat tcaacaccaa ttccattttc ttattc                               36


<210> SEQ ID NO 30
<211> LENGTH: 33
<212> TYPE: DNA
<213> ORGANISM: Artificial Sequence
<220> FEATURE:
<223> OTHER INFORMATION: PCR Primer, chemically synthesized

<400> SEQUENCE: 30

gcggccgcta gaatcatttg tccatccttc atc                                  33


<210> SEQ ID NO 31
<211> LENGTH: 36
<212> TYPE: DNA
<213> ORGANISM: Artificial Sequence
<220> FEATURE:
<223> OTHER INFORMATION: PCR Primer, chemically synthesized

<400> SEQUENCE: 31

tattctagat tcaacaccaa ttccattttc ttattc                               36


<210> SEQ ID NO 32
<211> LENGTH: 36
<212> TYPE: DNA
<213> ORGANISM: Artificial Sequence
<220> FEATURE:
<223> OTHER INFORMATION: PCR Primer, chemically synthesized

<400> SEQUENCE: 32

ttagcggccg ctagttctgt atcatatcgt aaaggg                               36


<210> SEQ ID NO 33
<211> LENGTH: 25
<212> TYPE: DNA
<213> ORGANISM: Artificial Sequence
<220> FEATURE:
<223> OTHER INFORMATION: PCR Primer, chemically synthesized

<400> SEQUENCE: 33

tctagataaa actcacacat gccca                                           25


<210> SEQ ID NO 34
<211> LENGTH: 28
```

<212> TYPE: DNA
<213> ORGANISM: Artificial Sequence
<220> FEATURE:
<223> OTHER INFORMATION: PCR Primer, chemically synthesized

<400> SEQUENCE: 34
gccgactcat ttacccggag acagggag 28

<210> SEQ ID NO 35
<211> LENGTH: 37
<212> TYPE: DNA
<213> ORGANISM: Artificial Sequence
<220> FEATURE:
<223> OTHER INFORMATION: PCR Primer, chemically synthesized

<400> SEQUENCE: 35
tctagatttg atccccattg ctgtgggcgg tgccctg 37

<210> SEQ ID NO 36
<211> LENGTH: 39
<212> TYPE: DNA
<213> ORGANISM: Artificial Sequence
<220> FEATURE:
<223> OTHER INFORMATION: PCR Primer, chemically synthesized

<400> SEQUENCE: 36
ggcgtgactc ctcttcctgc caatgaggta ggcaatgag 39

<210> SEQ ID NO 37
<211> LENGTH: 35
<212> TYPE: DNA
<213> ORGANISM: Artificial Sequence
<220> FEATURE:
<223> OTHER INFORMATION: PCR Primer, chemically synthesized

<400> SEQUENCE: 37
atatctagat ttcaccatag tttttccaca caacc 35

<210> SEQ ID NO 38
<211> LENGTH: 36
<212> TYPE: DNA
<213> ORGANISM: Artificial Sequence
<220> FEATURE:
<223> OTHER INFORMATION: PCR Primer, chemically synthesized

<400> SEQUENCE: 38
gcggccgcct tccttccaag tcggttcatc tctatg 36

<210> SEQ ID NO 39
<211> LENGTH: 34
<212> TYPE: DNA
<213> ORGANISM: Artificial Sequence
<220> FEATURE:
<223> OTHER INFORMATION: PCR Primer, chemically synthesized

<400> SEQUENCE: 39
gctctagata tggctcgtgc ggtcgggatc gacc 34

<210> SEQ ID NO 40
<211> LENGTH: 36
<212> TYPE: DNA
<213> ORGANISM: Artificial Sequence
<220> FEATURE:
<223> OTHER INFORMATION: PCR Primer, chemically synthesized

<400> SEQUENCE: 40
gccgcggccg ctcacttggc ctcccggccg tcgtcg 36

<210> SEQ ID NO 41
<211> LENGTH: 24
<212> TYPE: DNA
<213> ORGANISM: Artificial Sequence
<220> FEATURE:
<223> OTHER INFORMATION: PCR Primer, chemically synthesized

<400> SEQUENCE: 41
gttatctaga agcaccccca tccc 24

<210> SEQ ID NO 42
<211> LENGTH: 36
<212> TYPE: DNA
<213> ORGANISM: Artificial Sequence
<220> FEATURE:
<223> OTHER INFORMATION: PCR Primer, chemically synthesized

<400> SEQUENCE: 42
ttaagatctc taagatctgg tgtcgtatct cagggg 36

<210> SEQ ID NO 43
<211> LENGTH: 33
<212> TYPE: DNA
<213> ORGANISM: Artificial Sequence
<220> FEATURE:
<223> OTHER INFORMATION: PCR Primer, chemically synthesized

<400> SEQUENCE: 43
ttatctagaa agacccacac ctgcccccct tgc 33

<210> SEQ ID NO 44
<211> LENGTH: 31
<212> TYPE: DNA
<213> ORGANISM: Artificial Sequence
<220> FEATURE:
<223> OTHER INFORMATION: PCR Primer, chemically synthesized

<400> SEQUENCE: 44
tatagatctt agggtacctt acttgccggg g 31

<210> SEQ ID NO 45
<211> LENGTH: 952
<212> TYPE: PRT
<213> ORGANISM: Artificial Sequence
<220> FEATURE:
<223> OTHER INFORMATION: CEA-Dom fusion

<400> SEQUENCE: 45

Met Glu Ser Pro Ser Ala Pro Pro His Arg Trp Cys Ile Pro Trp Gln
1               5                   10                  15

Arg Leu Leu Leu Thr Ala Ser Leu Leu Thr Phe Trp Asn Pro Pro Thr
            20                  25                  30

Thr Ala Lys Leu Thr Ile Glu Ser Thr Pro Phe Asn Val Ala Glu Gly
        35                  40                  45

Lys Glu Val Leu Leu Leu Val His Asn Leu Pro Gln His Leu Phe Gly
    50                  55                  60

Tyr Ser Trp Tyr Lys Gly Glu Arg Val Asp Gly Asn Arg Gln Ile Ile
65                  70                  75                  80

Gly Tyr Val Ile Gly Thr Gln Gln Ala Thr Pro Gly Pro Ala Tyr Ser
                85                  90                  95

Gly Arg Glu Ile Ile Tyr Pro Asn Ala Ser Leu Leu Ile Gln Asn Ile
            100                 105                 110

```
Ile Gln Asn Asp Thr Gly Phe Tyr Thr Leu His Val Ile Lys Ser Asp
        115                 120                 125

Leu Val Asn Glu Glu Ala Thr Gly Gln Phe Arg Val Tyr Pro Glu Leu
    130                 135                 140

Pro Lys Pro Ser Ile Ser Ser Asn Asn Ser Lys Pro Val Glu Asp Lys
145                 150                 155                 160

Asp Ala Val Ala Phe Thr Cys Glu Pro Glu Thr Gln Asp Ala Thr Tyr
                165                 170                 175

Leu Trp Trp Val Asn Asn Gln Ser Leu Pro Val Ser Pro Arg Leu Gln
            180                 185                 190

Leu Ser Asn Gly Asn Arg Thr Leu Thr Leu Phe Asn Val Thr Arg Asn
        195                 200                 205

Asp Thr Ala Ser Tyr Lys Cys Glu Thr Gln Asn Pro Val Ser Ala Arg
    210                 215                 220

Arg Ser Asp Ser Val Ile Leu Asn Val Leu Tyr Gly Pro Asp Ala Pro
225                 230                 235                 240

Thr Ile Ser Pro Leu Asn Thr Ser Tyr Arg Ser Gly Glu Asn Leu Asn
                245                 250                 255

Leu Ser Cys His Ala Ala Ser Asn Pro Pro Ala Gln Tyr Ser Trp Phe
            260                 265                 270

Val Asn Gly Thr Phe Gln Gln Ser Thr Gln Glu Leu Phe Ile Pro Asn
        275                 280                 285

Ile Thr Val Asn Asn Ser Gly Ser Tyr Thr Cys Gln Ala His Asn Ser
    290                 295                 300

Asp Thr Gly Leu Asn Arg Thr Thr Val Thr Thr Ile Thr Val Tyr Ala
305                 310                 315                 320

Glu Pro Pro Lys Pro Phe Ile Thr Ser Asn Asn Ser Asn Pro Val Glu
                325                 330                 335

Asp Glu Asp Ala Val Ala Leu Thr Cys Glu Pro Glu Ile Gln Asn Thr
            340                 345                 350

Thr Tyr Leu Trp Trp Val Asn Asn Gln Ser Leu Pro Val Ser Pro Arg
        355                 360                 365

Leu Gln Leu Ser Asn Asp Asn Arg Thr Leu Thr Leu Leu Ser Val Thr
    370                 375                 380

Arg Asn Asp Val Gly Pro Tyr Glu Cys Gly Ile Gln Asn Glu Leu Ser
385                 390                 395                 400

Val Asp His Ser Asp Pro Val Ile Leu Asn Val Leu Tyr Gly Pro Asp
                405                 410                 415

Asp Pro Thr Ile Ser Pro Ser Tyr Thr Tyr Tyr Arg Pro Gly Val Asn
            420                 425                 430

Leu Ser Leu Ser Cys His Ala Ala Ser Asn Pro Pro Ala Gln Tyr Ser
        435                 440                 445

Trp Leu Ile Asp Gly Asn Ile Gln Gln His Thr Gln Glu Leu Phe Ile
    450                 455                 460

Ser Asn Ile Thr Glu Lys Asn Ser Gly Leu Tyr Thr Cys Gln Ala Asn
465                 470                 475                 480

Asn Ser Ala Ser Gly His Ser Arg Thr Thr Val Lys Thr Ile Thr Val
                485                 490                 495

Ser Ala Glu Leu Pro Lys Pro Ser Ile Ser Ser Asn Asn Ser Lys Pro
            500                 505                 510

Val Glu Asp Lys Asp Ala Val Ala Phe Thr Cys Glu Pro Glu Ala Gln
        515                 520                 525

Asn Thr Thr Tyr Leu Trp Trp Val Asn Gly Gln Ser Leu Pro Val Ser
    530                 535                 540
```

```
Pro Arg Leu Gln Leu Ser Asn Gly Asn Arg Thr Leu Thr Leu Phe Asn
545                 550                 555                 560

Val Thr Arg Asn Asp Ala Arg Ala Tyr Val Cys Gly Ile Gln Asn Ser
                565                 570                 575

Val Ser Ala Asn Arg Ser Asp Pro Val Thr Leu Asp Val Leu Tyr Gly
            580                 585                 590

Pro Asp Thr Pro Ile Ile Ser Pro Pro Asp Ser Ser Tyr Leu Ser Gly
        595                 600                 605

Ala Asn Leu Asn Leu Ser Cys His Ser Ala Ser Asn Pro Ser Pro Gln
    610                 615                 620

Tyr Ser Trp Arg Ile Asn Gly Ile Pro Gln Gln His Thr Gln Val Leu
625                 630                 635                 640

Phe Ile Ala Lys Ile Thr Pro Asn Asn Asn Gly Thr Tyr Ala Cys Phe
                645                 650                 655

Val Ser Asn Leu Ala Thr Gly Arg Asn Asn Ser Ile Val Lys Ser Ile
            660                 665                 670

Thr Val Ser Ala Ser Gly Thr Ser Arg Ser Thr Pro Ile Pro Phe Ser
        675                 680                 685

Tyr Ser Lys Asn Leu Asp Cys Trp Val Asp Asn Glu Glu Asp Ile Asp
    690                 695                 700

Val Ile Leu Lys Lys Ser Thr Ile Leu Asn Leu Asp Ile Asn Asn Asp
705                 710                 715                 720

Ile Ile Ser Asp Ile Ser Gly Phe Asn Ser Ser Val Ile Thr Tyr Pro
                725                 730                 735

Asp Ala Gln Leu Val Pro Gly Ile Asn Gly Lys Ala Ile His Leu Val
            740                 745                 750

Asn Asn Glu Ser Ser Glu Val Ile Val His Lys Ala Met Asp Ile Glu
        755                 760                 765

Tyr Asn Asp Met Phe Asn Asn Phe Thr Val Ser Phe Trp Leu Arg Val
    770                 775                 780

Pro Lys Val Ser Ala Ser His Leu Glu Gln Tyr Gly Thr Asn Glu Tyr
785                 790                 795                 800

Ser Ile Ile Ser Ser Met Lys Lys His Ser Leu Ser Ile Gly Ser Gly
                805                 810                 815

Trp Ser Val Ser Leu Lys Gly Asn Asn Leu Ile Trp Thr Leu Lys Asp
            820                 825                 830

Ser Ala Gly Glu Val Arg Gln Ile Thr Phe Arg Asp Leu Pro Asp Lys
        835                 840                 845

Phe Asn Ala Tyr Leu Ala Asn Lys Trp Val Phe Ile Thr Ile Thr Asn
    850                 855                 860

Asp Arg Leu Ser Ser Ala Asn Leu Tyr Ile Asn Gly Val Leu Met Gly
865                 870                 875                 880

Ser Ala Glu Ile Thr Gly Leu Gly Ala Ile Arg Glu Asp Asn Asn Ile
                885                 890                 895

Thr Leu Lys Leu Asp Arg Cys Asn Asn Asn Asn Gln Tyr Val Ser Ile
            900                 905                 910

Asp Lys Phe Arg Ile Phe Cys Lys Ala Leu Asn Pro Lys Glu Ile Glu
        915                 920                 925

Lys Leu Tyr Thr Ser Tyr Leu Ser Ile Thr Phe Leu Arg Asp Phe Trp
    930                 935                 940

Gly Asn Pro Leu Arg Tyr Asp Thr
945                 950
```

<210> SEQ ID NO 46
<211> LENGTH: 907
<212> TYPE: PRT
<213> ORGANISM: Artificial Sequence
<220> FEATURE:
<223> OTHER INFORMATION: CEA-FcIgG fusion

<400> SEQUENCE: 46

```
Met Glu Ser Pro Ser Ala Pro Pro His Arg Trp Cys Ile Pro Trp Gln
1               5                   10                  15

Arg Leu Leu Leu Thr Ala Ser Leu Leu Thr Phe Trp Asn Pro Pro Thr
            20                  25                  30

Thr Ala Lys Leu Thr Ile Glu Ser Thr Pro Phe Asn Val Ala Glu Gly
        35                  40                  45

Lys Glu Val Leu Leu Leu Val His Asn Leu Pro Gln His Leu Phe Gly
    50                  55                  60

Tyr Ser Trp Tyr Lys Gly Glu Arg Val Asp Gly Asn Arg Gln Ile Ile
65                  70                  75                  80

Gly Tyr Val Ile Gly Thr Gln Gln Ala Thr Pro Gly Pro Ala Tyr Ser
                85                  90                  95

Gly Arg Glu Ile Ile Tyr Pro Asn Ala Ser Leu Leu Ile Gln Asn Ile
            100                 105                 110

Ile Gln Asn Asp Thr Gly Phe Tyr Thr Leu His Val Ile Lys Ser Asp
        115                 120                 125

Leu Val Asn Glu Glu Ala Thr Gly Gln Phe Arg Val Tyr Pro Glu Leu
    130                 135                 140

Pro Lys Pro Ser Ile Ser Ser Asn Asn Ser Lys Pro Val Glu Asp Lys
145                 150                 155                 160

Asp Ala Val Ala Phe Thr Cys Glu Pro Glu Thr Gln Asp Ala Thr Tyr
                165                 170                 175

Leu Trp Trp Val Asn Asn Gln Ser Leu Pro Val Ser Pro Arg Leu Gln
            180                 185                 190

Leu Ser Asn Gly Asn Arg Thr Leu Thr Leu Phe Asn Val Thr Arg Asn
        195                 200                 205

Asp Thr Ala Ser Tyr Lys Cys Glu Thr Gln Asn Pro Val Ser Ala Arg
    210                 215                 220

Arg Ser Asp Ser Val Ile Leu Asn Val Leu Tyr Gly Pro Asp Ala Pro
225                 230                 235                 240

Thr Ile Ser Pro Leu Asn Thr Ser Tyr Arg Ser Gly Glu Asn Leu Asn
                245                 250                 255

Leu Ser Cys His Ala Ala Ser Asn Pro Pro Ala Gln Tyr Ser Trp Phe
            260                 265                 270

Val Asn Gly Thr Phe Gln Gln Ser Thr Gln Glu Leu Phe Ile Pro Asn
        275                 280                 285

Ile Thr Val Asn Asn Ser Gly Ser Tyr Thr Cys Gln Ala His Asn Ser
    290                 295                 300

Asp Thr Gly Leu Asn Arg Thr Thr Val Thr Thr Ile Thr Val Tyr Ala
305                 310                 315                 320

Glu Pro Pro Lys Pro Phe Ile Thr Ser Asn Asn Ser Asn Pro Val Glu
                325                 330                 335

Asp Glu Asp Ala Val Ala Leu Thr Cys Glu Pro Glu Ile Gln Asn Thr
            340                 345                 350

Thr Tyr Leu Trp Trp Val Asn Asn Gln Ser Leu Pro Val Ser Pro Arg
        355                 360                 365

Leu Gln Leu Ser Asn Asp Asn Arg Thr Leu Thr Leu Leu Ser Val Thr
    370                 375                 380
```

```
Arg Asn Asp Val Gly Pro Tyr Glu Cys Gly Ile Gln Asn Glu Leu Ser
385                 390                 395                 400

Val Asp His Ser Asp Pro Val Ile Leu Asn Val Leu Tyr Gly Pro Asp
                405                 410                 415

Asp Pro Thr Ile Ser Pro Ser Tyr Thr Tyr Tyr Arg Pro Gly Val Asn
            420                 425                 430

Leu Ser Leu Ser Cys His Ala Ala Ser Asn Pro Pro Ala Gln Tyr Ser
        435                 440                 445

Trp Leu Ile Asp Gly Asn Ile Gln Gln His Thr Gln Glu Leu Phe Ile
    450                 455                 460

Ser Asn Ile Thr Glu Lys Asn Ser Gly Leu Tyr Thr Cys Gln Ala Asn
465                 470                 475                 480

Asn Ser Ala Ser Gly His Ser Arg Thr Thr Val Lys Thr Ile Thr Val
                485                 490                 495

Ser Ala Glu Leu Pro Lys Pro Ser Ile Ser Ser Asn Asn Ser Lys Pro
            500                 505                 510

Val Glu Asp Lys Asp Ala Val Ala Phe Thr Cys Glu Pro Glu Ala Gln
        515                 520                 525

Asn Thr Thr Tyr Leu Trp Trp Val Asn Gly Gln Ser Leu Pro Val Ser
    530                 535                 540

Pro Arg Leu Gln Leu Ser Asn Gly Asn Arg Thr Leu Thr Leu Phe Asn
545                 550                 555                 560

Val Thr Arg Asn Asp Ala Arg Ala Tyr Val Cys Gly Ile Gln Asn Ser
                565                 570                 575

Val Ser Ala Asn Arg Ser Asp Pro Val Thr Leu Asp Val Leu Tyr Gly
            580                 585                 590

Pro Asp Thr Pro Ile Ile Ser Pro Pro Asp Ser Ser Tyr Leu Ser Gly
        595                 600                 605

Ala Asn Leu Asn Leu Ser Cys His Ser Ala Ser Asn Pro Ser Pro Gln
    610                 615                 620

Tyr Ser Trp Arg Ile Asn Gly Ile Pro Gln Gln His Thr Gln Val Leu
625                 630                 635                 640

Phe Ile Ala Lys Ile Thr Pro Asn Asn Asn Gly Thr Tyr Ala Cys Phe
                645                 650                 655

Val Ser Asn Leu Ala Thr Gly Arg Asn Asn Ser Ile Val Lys Ser Ile
            660                 665                 670

Thr Val Ser Ala Ser Gly Thr Ser Arg Lys Thr His Thr Cys Pro Pro
        675                 680                 685

Cys Pro Ala Pro Glu Leu Leu Gly Gly Pro Ser Val Phe Leu Phe Pro
    690                 695                 700

Pro Lys Pro Lys Asp Thr Leu Met Ile Ser Arg Thr Pro Glu Val Thr
705                 710                 715                 720

Cys Val Val Val Asp Val Ser His Glu Asp Pro Glu Val Lys Phe Asn
                725                 730                 735

Trp Tyr Val Asp Gly Val Glu Val His Asn Ala Lys Thr Lys Pro Arg
            740                 745                 750

Glu Glu Gln Tyr Asn Ser Thr Tyr Arg Val Val Ser Val Leu Thr Val
        755                 760                 765

Leu His Gln Asp Trp Leu Asn Gly Lys Glu Tyr Lys Cys Lys Val Ser
    770                 775                 780

Asn Lys Ala Leu Pro Ala Pro Ile Glu Lys Thr Ile Ser Lys Ala Lys
785                 790                 795                 800

Gly Gln Pro Arg Glu Pro Gln Val Tyr Thr Leu Pro Pro Ser Arg Asp
```

```
                805                 810                 815

Glu Leu Thr Lys Asn Gln Val Ser Leu Thr Cys Leu Val Lys Gly Phe
            820                 825                 830

Tyr Pro Ser Asp Ile Ala Val Glu Trp Glu Ser Asn Gly Gln Pro Glu
        835                 840                 845

Asn Asn Tyr Lys Thr Thr Pro Pro Val Leu Asp Ser Asp Gly Ser Phe
    850                 855                 860

Phe Leu Tyr Ser Lys Leu Thr Val Asp Lys Ser Arg Trp Gln Gln Gly
865                 870                 875                 880

Asn Val Phe Ser Cys Ser Val Met His Glu Ala Leu His Asn His Tyr
                885                 890                 895

Thr Gln Lys Ser Leu Ser Leu Ser Pro Gly Lys
            900                 905
```

<210> SEQ ID NO 47
<211> LENGTH: 825
<212> TYPE: DNA
<213> ORGANISM: Artificial Sequence
<220> FEATURE:
<223> OTHER INFORMATION: N-terminal domain of fragment C of tetanus toxin

<400> SEQUENCE: 47

```
gattcaacac caattccatt ttcttattct aaaaatctgg attgttgggt tgataatgaa     60

gaagatatag atgttatatt aaaaaagagt acaattttaa atttagatat taataatgat    120

attatatcag atatatctgg gtttaattca tctgtaataa catatccaga tgctcaattg    180

gtgcccggaa taaatggcaa agcaatacat ttagtaaaca atgaatcttc tgaagttata    240

gtgcataaag ctatggatat tgaatataat gatatgttta ataattttac cgttagcttt    300

tggttgaggg ttcctaaagt atctgctagt catttagaac aatatggcac aaatgagtat    360

tcaataatta gctctatgaa aaaacatagt ctatcaatag gatctggttg gagtgtatca    420

cttaaaggta ataacttaat atggacttta aaagattccg cgggagaagt tagacaaata    480

acttttaggg atttacctga taaatttaat gcttatttag caaataaatg ggtttttata    540

actattacta atgatagatt atcttctgct aatttgtata taaatggagt acttatggga    600

agtgcagaaa ttactggttt aggagctatt agagaggata ataatataac attaaaacta    660

gatagatgta ataataataa tcaatacgtt tctattgata aatttaggat attttgcaaa    720

gcattaaatc caaaagagat tgaaaaatta tacacaagtt atttatctat aacctttta     780

agagacttct ggggaaaccc tttacgatat gatacagata ggtag                    825
```

<210> SEQ ID NO 48
<211> LENGTH: 274
<212> TYPE: PRT
<213> ORGANISM: Artificial Sequence
<220> FEATURE:
<223> OTHER INFORMATION: N-terminal domain of fragment C of tetanus toxin

<400> SEQUENCE: 48

```
Asp Ser Thr Pro Ile Pro Phe Ser Tyr Ser Lys Asn Leu Asp Cys Trp
 1               5                  10                  15

Val Asp Asn Glu Glu Asp Ile Asp Val Ile Leu Lys Lys Ser Thr Ile
            20                  25                  30

Leu Asn Leu Asp Ile Asn Asn Asp Ile Ile Ser Asp Ile Ser Gly Phe
        35                  40                  45

Asn Ser Ser Val Ile Thr Tyr Pro Asp Ala Gln Leu Val Pro Gly Ile
```

```
    50                  55                  60

Asn Gly Lys Ala Ile His Leu Val Asn Asn Glu Ser Ser Glu Val Ile
65                  70                  75                  80

Val His Lys Ala Met Asp Ile Glu Tyr Asn Asp Met Phe Asn Asn Phe
                85                  90                  95

Thr Val Ser Phe Trp Leu Arg Val Pro Lys Val Ser Ala Ser His Leu
            100                 105                 110

Glu Gln Tyr Gly Thr Asn Glu Tyr Ser Ile Ile Ser Ser Met Lys Lys
        115                 120                 125

His Ser Leu Ser Ile Gly Ser Gly Trp Ser Val Ser Leu Lys Gly Asn
    130                 135                 140

Asn Leu Ile Trp Thr Leu Lys Asp Ser Ala Gly Glu Val Arg Gln Ile
145                 150                 155                 160

Thr Phe Arg Asp Leu Pro Asp Lys Phe Asn Ala Tyr Leu Ala Asn Lys
                165                 170                 175

Trp Val Phe Ile Thr Ile Thr Asn Asp Arg Leu Ser Ser Ala Asn Leu
            180                 185                 190

Tyr Ile Asn Gly Val Leu Met Gly Ser Ala Glu Ile Thr Gly Leu Gly
        195                 200                 205

Ala Ile Arg Glu Asp Asn Asn Ile Thr Leu Lys Leu Asp Arg Cys Asn
    210                 215                 220

Asn Asn Asn Gln Tyr Val Ser Ile Asp Lys Phe Arg Ile Phe Cys Lys
225                 230                 235                 240

Ala Leu Asn Pro Lys Glu Ile Glu Lys Leu Tyr Thr Ser Tyr Leu Ser
                245                 250                 255

Ile Thr Phe Leu Arg Asp Phe Trp Gly Asn Pro Leu Arg Tyr Asp Thr
            260                 265                 270

Asp Arg
```

<210> SEQ ID NO 49
<211> LENGTH: 2857
<212> TYPE: DNA
<213> ORGANISM: Artificial Sequence
<220> FEATURE:
<223> OTHER INFORMATION: CEA-DOM fusion

<400> SEQUENCE: 49

```
atggagtctc cctcggcccc tccccacaga tggtgcatcc cctggcagag gctcctgctc     60

acagcctcac ttctaacctt ctggaacccg cccaccactg ccaagctcac tattgaatcc    120

acgccgttca atgtcgcaga ggggaaggag gtgcttctac ttgtccacaa tctgccccag    180

catctttttg gctacagctg gtacaaaggt gaaagagtgg atggcaaccg tcaaattata    240

ggatatgtaa taggaactca acaagctacc ccagggcccg catacagtgg tcgagagata    300

atatacccca atgcatccct gctgatccag aacatcatcc agaatgacac aggattctac    360

accctacacg tcataaagtc agatcttgtg aatgaagaag caactggcca gttccgggta    420

tacccggagc tgcccaagcc ctccatctcc agcaacaact ccaaacccgt ggaggacaag    480

gatgctgtgg ccttcacctg tgaacctgag actcaggacg caacctacct gtggtgggta    540

aacaatcaga gcctcccggt cagtcccagg ctgcagctgt ccaatggcaa caggaccctc    600

actctattca atgtcacaag aaatgacaca gcaagctaca aatgtgaaac ccagaaccca    660

gtgagtgcca ggcgcagtga ttcagtcatc ctgaatgtcc tctatggccc ggatgccccc    720

accatttccc ctctaaacac atcttacaga tcaggggaaa atctgaacct ctcctgccac    780

gcagcctcta acccacctgc acagtactct tggtttgtca atgggacttt ccagcaatcc    840
```

```
acccaagagc tctttatccc caacatcact gtgaataata gtggatccta tacgtgccaa    900

gcccataact cagacactgg cctcaatagg accacagtca cgacgatcac agtctatgca    960

gagccaccca aacccttcat caccagcaac aactccaacc ccgtggagga tgaggatgct   1020

gtagccttaa cctgtgaacc tgagattcag aacacaacct acctgtggtg ggtaaataat   1080

cagagcctcc cggtcagtcc caggctgcag ctgtccaatg acaacaggac cctcactcta   1140

ctcagtgtca caaggaatga tgtaggaccc tatgagtgtg gaatccagaa cgaattaagt   1200

gttgaccaca gcgacccagt catcctgaat gtcctctatg gcccagacga ccccaccatt   1260

tcccccctcat acacctatta ccgtccaggg gtgaacctca gcctctcctg ccatgcagcc   1320

tctaacccac ctgcacagta ttcttggctg attgatggga acatccagca acacacacaa   1380

gagctcttta tctccaacat cactgagaag aacagcggac tctatacctg ccaggccaat   1440

aactcagcca gtggccacag caggactaca gtcaagacaa tcacagtctc tgcggagctg   1500

cccaagccct ccatctccag caacaactcc aaacccgtgg aggacaagga tgctgtggcc   1560

ttcacctgtg aacctgaggc tcagaacaca acctacctgt ggtgggtaaa tggtcagagc   1620

ctcccagtca gtcccaggct gcagctgtcc aatggcaaca ggaccctcac tctattcaat   1680

gtcacaagaa atgacgcaag agcctatgta tgtggaatcc agaactcagt gagtgcaaac   1740

cgcagtgacc cagtcaccct ggatgtcctc tatgggccgg acacccccat catttccccc   1800

ccagactcgt cttacctttc gggagcgaac ctcaacctct cctgccactc ggcctctaac   1860

ccatccccgc agtattcttg gcgtatcaat gggataccgc agcaacacac acaagttctc   1920

tttatcgcca aaatcacgcc aaataataac gggacctatg cctgttttgt ctctaacttg   1980

gctactggcc gcaataattc catagtcaag agcatcacag tctctgcatc tggaactcta   2040

gattcaacac caattccatt ttcttattct aaaaatctgg attgttgggt tgataatgaa   2100

gaagatatag atgttatatt aaaaaagagt acaattttaa atttagatat taataatgat   2160

attatatcag atatatctgg gtttaattca tctgtaataa catatccaga tgctcaattg   2220

gtgcccggaa taaatggcaa agcaatacat ttagtaaaca atgaatcttc tgaagttata   2280

gtgcataaag ctatggatat tgaatataat gatatgttta ataattttac cgttagcttt   2340

tggttgaggg ttcctaaagt atctgctagt catttagaac aatatggcac aaatgagtat   2400

tcaataatta gctctatgaa aaaacatagt ctatcaatag gatctggttg gagtgtatca   2460

cttaaaggta ataacttaat atggacttta aaagattccg cgggagaagt tagacaaata   2520

acttttaggg atttacctga taaatttaat gcttatttag caaataaatg ggtttttata   2580

actattacta atgatagatt atcttctgct aatttgtata taaatggagt acttatggga   2640

agtgcagaaa ttactggttt aggagctatt agagaggata ataatataac attaaaacta   2700

gatagatgta ataataataa tcaatacgtt tctattgata aatttaggat attttgcaaa   2760

gcattaaatc caaaagagat tgaaaaatta tacacaagtt atttatctat aacctttttta   2820

agagacttct ggggaaaccc tttacgatat gatatag                            2857
```

<210> SEQ ID NO 50
<211> LENGTH: 2859
<212> TYPE: DNA
<213> ORGANISM: Artificial Sequence
<220> FEATURE:
<223> OTHER INFORMATION: rhCEA-DOMopt fusion

<400> SEQUENCE: 50

```
atgggcagcc ccagcgcccc cctgcaccgc tggtgcatcc cctggcagac cctgctgctg     60
```

```
accgccagcc tgctgacctt ctggaacccc cccaccaccg cccagctgac catcgagagc    120
cgccccttca acgtggccga gggcaaggag gtgctgctgc tggcccacaa cgtgagccag    180
aacctgttcg gctacatctg gtacaagggc gagcgcgtgg acgccagccg ccgcatcggc    240
agctgcgtga tccgcaccca gcagatcacc cccggccccg cccacagcgg ccgcgagacc    300
atcgacttca acgccagcct gctgatccac aacgtgaccc agagcgacac cggcagctac    360
accatccagg tgatcaagga ggacctggtg aacgaggagg ccaccggcca gttccgcgtg    420
taccccgagc tgcccaagcc ctacatcagc agcaacaaca gcaaccccgt ggaggacaag    480
gacgccgtgg ccctgacctg cgagcccgag acccaggaca ccacctacct gtggtgggtg    540
aacaaccaga gcctgcccgt gagcccccgc ctggagctga gcagcgacaa ccgcaccctg    600
accgtgttca acatcccccg caacgacacc accagctaca agtgcgagac ccagaacccc    660
gtgagcgtgc gccgcagcga ccccgtgacc ctgaacgtgc tgtacggccc cgacgccccc    720
accatcagcc ccctgaacac cccctaccgc gccggcgaga acctgaacct gacctgccac    780
gccgccagca accccaccgc ccagtacttc tggttcgtga acggcacctt ccagcagagc    840
acccaggagc tgttcatccc caacatcacc gtgaacaaca gcggcagcta catgtgccag    900
gcccacaaca gcgccaccgg cctgaaccgc accaccgtga ccgccatcac cgtgtacgcc    960
gagctgccca agccctacat caccagcaac aacagcaacc ccatcgagga caaggacgcc   1020
gtgaccctga cctgcgagcc cgagacccag gacaccacct acctgtggtg ggtgaacaac   1080
cagagcctga gcgtgagcag ccgcctggag ctgagcaacg acaaccgcac cctgaccgtg   1140
ttcaacatcc cccgcaacga caccaccttc tacgagtgcg agacccagaa ccccgtgagc   1200
gtgcgccgca gcgaccccgt gaccctgaac gtgctgtacg gccccgacgc ccccaccatc   1260
agcccccctga acaccccccta ccgcgccggc gagaacctga acctgagctg ccacgccgcc   1320
agcaaccccg ccgcccagta cagctggttc gtgaacggca ccttccagca gagcacccag   1380
gagctgttca tccccaacat caccgtgaac aacagcggca gctacatgtg ccaggcccac   1440
aacagcgcca ccggcctgaa ccgcaccacc gtgaccgcca tcaccgtgta cgtggagctg   1500
cccaagccct acatcagcag caacaacagc aaccccatcg aggacaagga cgccgtgacc   1560
ctgacctgcg agcccgtggc cgagaacacc acctacctgt ggtgggtgaa caaccagagc   1620
ctgagcgtga gcccccgcct gcagctgagc aacggcaacc gcatcctgac cctgctgagc   1680
gtgacccgca acgacaccgg cccctacgag tgcggcatcc agaacagcga gagcgccaag   1740
cgcagcgacc ccgtgaccct gaacgtgacc tacggccccg acacccccat catcagcccc   1800
cccgacctga gctaccgcag cggcgccaac ctgaacctga gctgccacag cgacagcaac   1860
cccagccccc agtacagctg gctgatcaac ggcaccctgc gccagcacac ccaggtgctg   1920
ttcatcagca agatcaccag caacaacagc ggcgcctacg cctgcttcgt gagcaacctg   1980
gccaccggcc gcaacaacag catcgtgaag aacatcagcg tgagcagcgg cgacagctct   2040
agaagcaccc ccatcccatt cagctacagc aagaacctgg actgctgggt ggacaacgag   2100
gaggacatcg acgtgatcct gaagaagagc accatcctga acctggacat caacaacgac   2160
atcatcagcg acatcagcgg cttcaacagc agcgtgatca cctaccccga cgcccagctg   2220
gtgcccggca tcaacggcaa ggccatccac ctggtgaaca acgagagcag cgaggtgatc   2280
gtgcacaagg ccatggacat cgagtacaac gacatgttca acaacttcac cgtgagcttc   2340
tggctgagag tgcctaaggt gagcgccagc cacctggagc agtacggcac caacgagtac   2400
agcatcatca gcagcatgaa gaagcacagc ctgagcatcg gcagcggctg gagcgtgagc   2460
```

```
ctgaagggca acaacctcat ctggaccctg aaggatagcg ccggagaggt gagacagatc   2520

accttcagag acctgcccga caagttcaat gcctacctgg ccaacaagtg ggtgttcatc   2580

accatcacca acgacagact gagcagcgcc aacctgtaca tcaacggcgt gctcatgggc   2640

agcgccgaga tcaccggcct gggcgccatc agagaggaca acaacatcac cctgaagctg   2700

gacagatgca acaacaacaa ccagtacgtg agcatcgaca agttccggat cttctgcaag   2760

gccctgaacc ccaaggagat cgagaagctg tacaccagct acctgagcat caccttcctg   2820

agagacttct ggggcaaccc cctgagatac gacacctag                          2859
```

<210> SEQ ID NO 51
<211> LENGTH: 952
<212> TYPE: PRT
<213> ORGANISM: Artificial Sequence
<220> FEATURE:
<223> OTHER INFORMATION: rhCEA-DOMopt fusion

<400> SEQUENCE: 51

```
Met Gly Ser Pro Ser Ala Pro Leu His Arg Trp Cys Ile Pro Trp Gln
 1               5                  10                  15

Thr Leu Leu Leu Thr Ala Ser Leu Leu Thr Phe Trp Asn Pro Pro Thr
            20                  25                  30

Thr Ala Gln Leu Thr Ile Glu Ser Arg Pro Phe Asn Val Ala Glu Gly
        35                  40                  45

Lys Glu Val Leu Leu Leu Ala His Asn Val Ser Gln Asn Leu Phe Gly
    50                  55                  60

Tyr Ile Trp Tyr Lys Gly Glu Arg Val Asp Ala Ser Arg Arg Ile Gly
65                  70                  75                  80

Ser Cys Val Ile Arg Thr Gln Gln Ile Thr Pro Gly Pro Ala His Ser
                85                  90                  95

Gly Arg Glu Thr Ile Asp Phe Asn Ala Ser Leu Leu Ile His Asn Val
            100                 105                 110

Thr Gln Ser Asp Thr Gly Ser Tyr Thr Ile Gln Val Ile Lys Glu Asp
        115                 120                 125

Leu Val Asn Glu Glu Ala Thr Gly Gln Phe Arg Val Tyr Pro Glu Leu
    130                 135                 140

Pro Lys Pro Tyr Ile Ser Ser Asn Asn Ser Asn Pro Val Glu Asp Lys
145                 150                 155                 160

Asp Ala Val Ala Leu Thr Cys Glu Pro Glu Thr Gln Asp Thr Thr Tyr
                165                 170                 175

Leu Trp Trp Val Asn Asn Gln Ser Leu Pro Val Ser Pro Arg Leu Glu
            180                 185                 190

Leu Ser Ser Asp Asn Arg Thr Leu Thr Val Phe Asn Ile Pro Arg Asn
        195                 200                 205

Asp Thr Thr Ser Tyr Lys Cys Glu Thr Gln Asn Pro Val Ser Val Arg
    210                 215                 220

Arg Ser Asp Pro Val Thr Leu Asn Val Leu Tyr Gly Pro Asp Ala Pro
225                 230                 235                 240

Thr Ile Ser Pro Leu Asn Thr Pro Tyr Arg Ala Gly Glu Asn Leu Asn
                245                 250                 255

Leu Thr Cys His Ala Ala Ser Asn Pro Thr Ala Gln Tyr Phe Trp Phe
            260                 265                 270

Val Asn Gly Thr Phe Gln Gln Ser Thr Gln Glu Leu Phe Ile Pro Asn
        275                 280                 285

Ile Thr Val Asn Asn Ser Gly Ser Tyr Met Cys Gln Ala His Asn Ser
```

```
    290                 295                 300

Ala Thr Gly Leu Asn Arg Thr Thr Val Thr Ala Ile Thr Val Tyr Ala
305                 310                 315                 320

Glu Leu Pro Lys Pro Tyr Ile Thr Ser Asn Asn Ser Asn Pro Ile Glu
                325                 330                 335

Asp Lys Asp Ala Val Thr Leu Thr Cys Glu Pro Glu Thr Gln Asp Thr
            340                 345                 350

Thr Tyr Leu Trp Trp Val Asn Asn Gln Ser Leu Ser Val Ser Ser Arg
        355                 360                 365

Leu Glu Leu Ser Asn Asp Asn Arg Thr Leu Thr Val Phe Asn Ile Pro
    370                 375                 380

Arg Asn Asp Thr Thr Phe Tyr Glu Cys Glu Thr Gln Asn Pro Val Ser
385                 390                 395                 400

Val Arg Arg Ser Asp Pro Val Thr Leu Asn Val Leu Tyr Gly Pro Asp
                405                 410                 415

Ala Pro Thr Ile Ser Pro Leu Asn Thr Pro Tyr Arg Ala Gly Glu Asn
            420                 425                 430

Leu Asn Leu Ser Cys His Ala Ala Ser Asn Pro Ala Ala Gln Tyr Ser
        435                 440                 445

Trp Phe Val Asn Gly Thr Phe Gln Gln Ser Thr Gln Glu Leu Phe Ile
    450                 455                 460

Pro Asn Ile Thr Val Asn Asn Ser Gly Ser Tyr Met Cys Gln Ala His
465                 470                 475                 480

Asn Ser Ala Thr Gly Leu Asn Arg Thr Thr Val Thr Ala Ile Thr Val
                485                 490                 495

Tyr Val Glu Leu Pro Lys Pro Tyr Ile Ser Ser Asn Asn Ser Asn Pro
            500                 505                 510

Ile Glu Asp Lys Asp Ala Val Thr Leu Thr Cys Glu Pro Val Ala Glu
        515                 520                 525

Asn Thr Thr Tyr Leu Trp Trp Val Asn Asn Gln Ser Leu Ser Val Ser
    530                 535                 540

Pro Arg Leu Gln Leu Ser Asn Gly Asn Arg Ile Leu Thr Leu Leu Ser
545                 550                 555                 560

Val Thr Arg Asn Asp Thr Gly Pro Tyr Glu Cys Gly Ile Gln Asn Ser
                565                 570                 575

Glu Ser Ala Lys Arg Ser Asp Pro Val Thr Leu Asn Val Thr Tyr Gly
            580                 585                 590

Pro Asp Thr Pro Ile Ile Ser Pro Pro Asp Leu Ser Tyr Arg Ser Gly
        595                 600                 605

Ala Asn Leu Asn Leu Ser Cys His Ser Asp Ser Asn Pro Ser Pro Gln
    610                 615                 620

Tyr Ser Trp Leu Ile Asn Gly Thr Leu Arg Gln His Thr Gln Val Leu
625                 630                 635                 640

Phe Ile Ser Lys Ile Thr Ser Asn Asn Ser Gly Ala Tyr Ala Cys Phe
                645                 650                 655

Val Ser Asn Leu Ala Thr Gly Arg Asn Asn Ser Ile Val Lys Asn Ile
            660                 665                 670

Ser Val Ser Ser Gly Asp Ser Ser Arg Ser Thr Pro Ile Pro Phe Ser
        675                 680                 685

Tyr Ser Lys Asn Leu Asp Cys Trp Val Asp Asn Glu Glu Asp Ile Asp
    690                 695                 700

Val Ile Leu Lys Lys Ser Thr Ile Leu Asn Leu Asp Ile Asn Asn Asp
705                 710                 715                 720
```

```
Ile Ile Ser Asp Ile Ser Gly Phe Asn Ser Ser Val Ile Thr Tyr Pro
                725                 730                 735

Asp Ala Gln Leu Val Pro Gly Ile Asn Gly Lys Ala Ile His Leu Val
            740                 745                 750

Asn Asn Glu Ser Ser Glu Val Ile Val His Lys Ala Met Asp Ile Glu
        755                 760                 765

Tyr Asn Asp Met Phe Asn Asn Phe Thr Val Ser Phe Trp Leu Arg Val
    770                 775                 780

Pro Lys Val Ser Ala Ser His Leu Glu Gln Tyr Gly Thr Asn Glu Tyr
785                 790                 795                 800

Ser Ile Ile Ser Ser Met Lys Lys His Ser Leu Ser Ile Gly Ser Gly
                805                 810                 815

Trp Ser Val Ser Leu Lys Gly Asn Asn Leu Ile Trp Thr Leu Lys Asp
            820                 825                 830

Ser Ala Gly Glu Val Arg Gln Ile Thr Phe Arg Asp Leu Pro Asp Lys
        835                 840                 845

Phe Asn Ala Tyr Leu Ala Asn Lys Trp Val Phe Ile Thr Ile Thr Asn
    850                 855                 860

Asp Arg Leu Ser Ser Ala Asn Leu Tyr Ile Asn Gly Val Leu Met Gly
865                 870                 875                 880

Ser Ala Glu Ile Thr Gly Leu Gly Ala Ile Arg Glu Asp Asn Asn Ile
                885                 890                 895

Thr Leu Lys Leu Asp Arg Cys Asn Asn Asn Asn Gln Tyr Val Ser Ile
            900                 905                 910

Asp Lys Phe Arg Ile Phe Cys Lys Ala Leu Asn Pro Lys Glu Ile Glu
        915                 920                 925

Lys Leu Tyr Thr Ser Tyr Leu Ser Ile Thr Phe Leu Arg Asp Phe Trp
    930                 935                 940

Gly Asn Pro Leu Arg Tyr Asp Thr
945                 950
```

<210> SEQ ID NO 52
<211> LENGTH: 2359
<212> TYPE: DNA
<213> ORGANISM: Artificial Sequence
<220> FEATURE:
<223> OTHER INFORMATION: rhCEA-CTBopt fusion

<400> SEQUENCE: 52

```
atgggcagcc ccagcgcccc cctgcaccgc tggtgcatcc cctggcagac cctgctgctg     60

accgccagcc tgctgacctt ctggaacccc cccaccaccg cccagctgac catcgagagc    120

cgcccettca acgtggccga gggcaaggag gtgctgctgc tggcccacaa cgtgagccag    180

aacctgttcg gctacatctg gtacaagggc gagcgcgtgg acgccagccg ccgcatcggc    240

agctgcgtga tccgcaccca gcagatcacc cccggccccg cccacagcgg ccgcgagacc    300

atcgacttca acgccagcct gctgatccac aacgtgaccc agagcgacac cggcagctac    360

accatccagg tgatcaagga ggacctggtg aacgaggagg ccaccggcca gttccgcgtg    420

taccccgagc tgcccaagcc ctacatcagc agcaacaaca gcaaccccgt ggaggacaag    480

gacgccgtgg ccctgacctg cgagcccgag acccaggaca ccacctacct gtggtgggtg    540

aacaaccaga gcctgcccgt gagcccccgc ctggagctga gcagcgacaa ccgcaccctg    600

accgtgttca acatcccccg caacgacacc accagctaca agtgcgagac ccagaacccc    660

gtgagcgtgc gccgcagcga ccccgtgacc ctgaacgtgc tgtacggccc cgacgccccc    720

accatcagcc ccctgaacac cccctaccgc gccggcgaga acctgaacct gacctgccac    780
```

```
gccgccagca accccaccgc ccagtacttc tggttcgtga acggcacctt ccagcagagc    840

acccaggagc tgttcatccc caacatcacc gtgaacaaca gcggcagcta catgtgccag    900

gcccacaaca gcgccaccgg cctgaaccgc accaccgtga ccgccatcac cgtgtacgcc    960

gagctgccca agccctacat caccagcaac aacagcaacc ccatcgagga caaggacgcc   1020

gtgaccctga cctgcgagcc cgagacccag gacaccacct acctgtggtg ggtgaacaac   1080

cagagcctga gcgtgagcag ccgcctggag ctgagcaacg acaaccgcac cctgaccgtg   1140

ttcaacatcc cccgcaacga caccaccttc tacgagtgcg agacccagaa ccccgtgagc   1200

gtgcgccgca gcgaccccgt gaccctgaac gtgctgtacg gccccgacgc ccccaccatc   1260

agcccccctga acacccccta ccgcgccggc gagaacctga acctgagctg ccacgccgcc   1320

agcaaccccg ccgcccagta cagctggttc gtgaacggca ccttccagca gagcacccag   1380

gagctgttca tccccaacat caccgtgaac aacagcggca gctacatgtg ccaggcccac   1440

aacagcgcca ccggcctgaa ccgcaccacc gtgaccgcca tcaccgtgta cgtggagctg   1500

cccaagccct acatcagcag caacaacagc aaccccatcg aggacaagga cgccgtgacc   1560

ctgacctgcg agcccgtggc cgagaacacc acctacctgt ggtgggtgaa caaccagagc   1620

ctgagcgtga gcccccgcct gcagctgagc aacggcaacc gcatcctgac cctgctgagc   1680

gtgacccgca acgacaccgg cccctacgag tgcggcatcc agaacagcga gagcgccaag   1740

cgcagcgacc ccgtgaccct gaacgtgacc tacggccccg acacccccat catcagcccc   1800

cccgacctga gctaccgcag cggcgccaac ctgaacctga gctgccacag cgacagcaac   1860

cccagccccc agtacagctg gctgatcaac ggcaccctgc gccagcacac ccaggtgctg   1920

ttcatcagca agatcaccag caacaacagc ggcgcctacg cctgcttcgt gagcaacctg   1980

gccaccggcc gcaacaacag catcgtgaag aacatcagcg tgagcagcgg cgacagctct   2040

agaacccctc agaacatcac cgatctgtgc gccgagtacc acaacaccca gatctacacc   2100

ctgaacgaca agatcttcag ctacaccgag agcctggccg gcaagagaga gatggccatc   2160

atcaccttca agaacggcgc catcttccag gtggaggtgc ccggcagcca gcacatcgac   2220

agccagaaga aggccatcga gcggatgaag gacaccctgc ggatcgccta cctcaccgag   2280

gccaaggtgg agaagctgtg cgtgtggaac aacaagaccc ctcacgccat cgccgccatc   2340

agcatggcca attgataag                                                2359
```

```
<210> SEQ ID NO 53
<211> LENGTH: 784
<212> TYPE: PRT
<213> ORGANISM: Artificial Sequence
<220> FEATURE:
<223> OTHER INFORMATION: rhCEA-CTBopt fusion

<400> SEQUENCE: 53

Met Gly Ser Pro Ser Ala Pro Leu His Arg Trp Cys Ile Pro Trp Gln
 1               5                  10                  15

Thr Leu Leu Leu Thr Ala Ser Leu Leu Thr Phe Trp Asn Pro Pro Thr
            20                  25                  30

Thr Ala Gln Leu Thr Ile Glu Ser Arg Pro Phe Asn Val Ala Glu Gly
        35                  40                  45

Lys Glu Val Leu Leu Leu Ala His Asn Val Ser Gln Asn Leu Phe Gly
    50                  55                  60

Tyr Ile Trp Tyr Lys Gly Glu Arg Val Asp Ala Ser Arg Arg Ile Gly
65                  70                  75                  80
```

```
Ser Cys Val Ile Arg Thr Gln Gln Ile Thr Pro Gly Pro Ala His Ser
                85                  90                  95

Gly Arg Glu Thr Ile Asp Phe Asn Ala Ser Leu Leu Ile His Asn Val
            100                 105                 110

Thr Gln Ser Asp Thr Gly Ser Tyr Thr Ile Gln Val Ile Lys Glu Asp
        115                 120                 125

Leu Val Asn Glu Glu Ala Thr Gly Gln Phe Arg Val Tyr Pro Glu Leu
    130                 135                 140

Pro Lys Pro Tyr Ile Ser Ser Asn Asn Ser Asn Pro Val Glu Asp Lys
145                 150                 155                 160

Asp Ala Val Ala Leu Thr Cys Glu Pro Glu Thr Gln Asp Thr Thr Tyr
                165                 170                 175

Leu Trp Trp Val Asn Asn Gln Ser Leu Pro Val Ser Pro Arg Leu Glu
            180                 185                 190

Leu Ser Ser Asp Asn Arg Thr Leu Thr Val Phe Asn Ile Pro Arg Asn
        195                 200                 205

Asp Thr Thr Ser Tyr Lys Cys Glu Thr Gln Asn Pro Val Ser Val Arg
    210                 215                 220

Arg Ser Asp Pro Val Thr Leu Asn Val Leu Tyr Gly Pro Asp Ala Pro
225                 230                 235                 240

Thr Ile Ser Pro Leu Asn Thr Pro Tyr Arg Ala Gly Glu Asn Leu Asn
                245                 250                 255

Leu Thr Cys His Ala Ala Ser Asn Pro Thr Ala Gln Tyr Phe Trp Phe
            260                 265                 270

Val Asn Gly Thr Phe Gln Gln Ser Thr Gln Glu Leu Phe Ile Pro Asn
        275                 280                 285

Ile Thr Val Asn Asn Ser Gly Ser Tyr Met Cys Gln Ala His Asn Ser
    290                 295                 300

Ala Thr Gly Leu Asn Arg Thr Thr Val Thr Ala Ile Thr Val Tyr Ala
305                 310                 315                 320

Glu Leu Pro Lys Pro Tyr Ile Thr Ser Asn Asn Ser Asn Pro Ile Glu
                325                 330                 335

Asp Lys Asp Ala Val Thr Leu Thr Cys Glu Pro Glu Thr Gln Asp Thr
            340                 345                 350

Thr Tyr Leu Trp Trp Val Asn Asn Gln Ser Leu Ser Val Ser Ser Arg
        355                 360                 365

Leu Glu Leu Ser Asn Asp Asn Arg Thr Leu Thr Val Phe Asn Ile Pro
    370                 375                 380

Arg Asn Asp Thr Thr Phe Tyr Glu Cys Glu Thr Gln Asn Pro Val Ser
385                 390                 395                 400

Val Arg Arg Ser Asp Pro Val Thr Leu Asn Val Leu Tyr Gly Pro Asp
                405                 410                 415

Ala Pro Thr Ile Ser Pro Leu Asn Thr Pro Tyr Arg Ala Gly Glu Asn
            420                 425                 430

Leu Asn Leu Ser Cys His Ala Ala Ser Asn Pro Ala Ala Gln Tyr Ser
        435                 440                 445

Trp Phe Val Asn Gly Thr Phe Gln Gln Ser Thr Gln Glu Leu Phe Ile
    450                 455                 460

Pro Asn Ile Thr Val Asn Asn Ser Gly Ser Tyr Met Cys Gln Ala His
465                 470                 475                 480

Asn Ser Ala Thr Gly Leu Asn Arg Thr Thr Val Thr Ala Ile Thr Val
                485                 490                 495

Tyr Val Glu Leu Pro Lys Pro Tyr Ile Ser Ser Asn Asn Ser Asn Pro
            500                 505                 510
```

```
Ile Glu Asp Lys Asp Ala Val Thr Leu Thr Cys Glu Pro Val Ala Glu
        515                 520                 525

Asn Thr Thr Tyr Leu Trp Trp Val Asn Asn Gln Ser Leu Ser Val Ser
    530                 535                 540

Pro Arg Leu Gln Leu Ser Asn Gly Asn Arg Ile Leu Thr Leu Leu Ser
545                 550                 555                 560

Val Thr Arg Asn Asp Thr Gly Pro Tyr Glu Cys Gly Ile Gln Asn Ser
                565                 570                 575

Glu Ser Ala Lys Arg Ser Asp Pro Val Thr Leu Asn Val Thr Tyr Gly
            580                 585                 590

Pro Asp Thr Pro Ile Ile Ser Pro Pro Asp Leu Ser Tyr Arg Ser Gly
        595                 600                 605

Ala Asn Leu Asn Leu Ser Cys His Ser Asp Ser Asn Pro Ser Pro Gln
    610                 615                 620

Tyr Ser Trp Leu Ile Asn Gly Thr Leu Arg Gln His Thr Gln Val Leu
625                 630                 635                 640

Phe Ile Ser Lys Ile Thr Ser Asn Asn Ser Gly Ala Tyr Ala Cys Phe
                645                 650                 655

Val Ser Asn Leu Ala Thr Gly Arg Asn Asn Ser Ile Val Lys Asn Ile
            660                 665                 670

Ser Val Ser Ser Gly Asp Ser Ser Arg Thr Pro Gln Asn Ile Thr Asp
        675                 680                 685

Leu Cys Ala Glu Tyr His Asn Thr Gln Ile Tyr Thr Leu Asn Asp Lys
    690                 695                 700

Ile Phe Ser Tyr Thr Glu Ser Leu Ala Gly Lys Arg Glu Met Ala Ile
705                 710                 715                 720

Ile Thr Phe Lys Asn Gly Ala Ile Phe Gln Val Glu Val Pro Gly Ser
                725                 730                 735

Gln His Ile Asp Ser Gln Lys Lys Ala Ile Glu Arg Met Lys Asp Thr
            740                 745                 750

Leu Arg Ile Ala Tyr Leu Thr Glu Ala Lys Val Glu Lys Leu Cys Val
        755                 760                 765

Trp Asn Asn Lys Thr Pro His Ala Ile Ala Ala Ile Ser Met Ala Asn
    770                 775                 780


<210> SEQ ID NO 54
<211> LENGTH: 20
<212> TYPE: PRT
<213> ORGANISM: Artificial Sequence
<220> FEATURE:
<223> OTHER INFORMATION: chemically synthesized

<400> SEQUENCE: 54

Asn Asn Phe Thr Val Ser Phe Trp Leu Arg Val Pro Lys Val Ser Ala
 1               5                  10                  15

Ser His Leu Glu
            20
```

CARCINOEMBRYONIC ANTIGEN FUSIONS AND USES THEREOF

CROSS-REFERENCE TO RELATED APPLICATIONS

This application is a §371 National Stage Application of PCT/EP2005/001114, international filing date of Feb. 3, 2005, which claims the benefit of U.S. Provisional Application No. 60/543,649 filed Feb. 11, 2004, now expired, and claims the benefit of U.S. Provisional Application 60/635,791, filed Dec. 14, 2004, now expired.

FIELD OF THE INVENTION

The present invention relates generally to the therapy of cancer. More specifically, the present invention relates to polynucleotides encoding fusion proteins wherein the fusion proteins comprise at least a portion of the tumor associated polypeptide carcinoembryonic antigen. The present invention also provides recombinant vectors and hosts comprising said polynucleotides, purified fusion proteins and methods for enhancing an immune response against CEA using the compositions and molecules disclosed herein.

BACKGROUND OF THE INVENTION

The immunoglobulin superfamily (IgSF) consists of numerous genes that code for proteins with diverse functions, one of which is intercellular adhesion. IgSF proteins contain at least one Ig-related domain that is important for maintaining proper intermolecular binding interactions. Because such interactions are necessary to the diverse biological functions of the IgSF members, disruption or aberrant expression of many IgSF adhesion molecules has been correlated with many human diseases.

The carcinoembryonic antigen (CEA) belongs to a subfamily of the Ig superfamily consisting of cell surface glycoproteins known as CEA-related cell adhesion molecules (CEACAMs). CEACAMs have been shown to act as both homotypic and heterotypic intercellular adhesion molecules (Benchimol et al., *Cell* 57: 327-334 (1989)). In addition to cell adhesion, CEA (also known as CEACAM5) inhibits cell death resulting from detachment of cells from the extracellular matrix and can contribute to cellular transformation associated with certain proto-oncogenes such as Bcl2 and C-Myc (see Berinstein, *J. Clin Oncol.* 20(8): 2197-2207 (2002)). Sequences coding for human CEA have been cloned and characterized (U.S. Pat. Nos. 5,274,087; 5,571,710; and 5,843,761. See also Beauchemin et al., *Mol. Cell. Biol.* 7:3221-3230 (1987); Zimmerman et al., *Proc. Natl. Acad. Sci. USA* 84:920-924 (1987); Thompson et al. *Proc. Natl. Acad; Sci. USA* 84(9):2965-69 (1987)).

Normal expression of CEA has been detected during fetal development and in adult colonic mucosa. CEA overexpression was first detected in human colon tumors over thirty years ago (Gold and Freedman, *J. Exp. Med.* 121:439-462 (1965)) and has since been found in nearly all colorectal tumors. Additionally, CEA overexpression is detectable in a high percentage of adenocarcinomas of the pancreas, liver, breast, ovary, cervix, and lung. Because of its prevalence in these tumor types and limited normal tissue expression, CEA is considered a self tumor-associated antigen and a target for active and passive immunotherapy. Recent clinical data have established that different vaccine strategies can generate human B and T cells specific for CEA, providing additional evidence that CEA is a target for molecular and immunological intervention for treatment of these cancer types.

Therapeutic approaches targeting CEA include the use of anti-CEA antibodies (see Chester et al., *Cancer Chemother. Pharmacol.* 46 (Suppl): S8-S12 (2000)), as well as CEA-based vaccines (for review, see Berinstein, supra). The development and commercialization of many vaccines have been hindered by difficulties associated with obtaining high expression levels of exogenous genes. Success of DNA-based vaccines has also been hindered by an inability to generate an immune response of sufficient magnitude in treated individuals. Although DNA vaccines targeting various proteins have been developed, the resulting immune responses have been relatively weak compared with conventional vaccines.

The ease of DNA manipulation has offered an opportunity to develop vaccines incorporating gene fusion strategies in which antigens are linked to various immunoenhancing elements. Enhancement of immune response to target antigens has been demonstrated in animal models by vectors encoding antigens fused to heat shock protein (HSP) 70 (Liu et al., *J. Virol.* 74: 2888-94 (2000); Cheng et al. *J. Immunol.* 166: 6218-26 (2001); Chen et al., *Cancer Res.* 60: 1035-42 (2000)), to Fc portion of IgG1 (You et al., *J. Immunol.* 165: 4581-92 (2000)), to lysosome-associated membrane protein (LAMP) (Su et al., *Cancer Res.* 62: 5041-48 (2002)), and universal Th epitope from tetanus toxin (Renard et al., *J. Immunol.* 171:1588-95 (2003); King et al., *Nature Med.* 4: 1281-86 (1998); Lund et al., *Cancer Gene Ther.* 10: 365-76 (2003); Padua et al., *Nature Med.* 9(11): 1413-17 (2003); Savelyeva et al., *Nature Biotechnol.* 19: 760-64 (2001); Wahren et al., WO 2004/092216). The enhancement of immune responses to target antigens is particularly relevant for cancer vaccines in view of the limited immunogenicity of tumor antigens and of the need to overcome tolerance to exert effective antitumor effects.

Therefore, despite the identification of the wild-type nucleotide sequences encoding CEA proteins described above, it would be highly desirable to develop a vaccine which is capable of eliciting an enhanced CEA-specific immune response relative to a wild-type full-length CEA cDNA, when delivered to a mammal. It would also be desirable to develop methods for treating or preventing CEA-associated cancers which utilize nucleic acid molecules or proteins that safely and effectively potentiate a CEA-specific immune response.

SUMMARY OF THE INVENTION

The present invention provides polynucleotides encoding fusion proteins wherein the fusion proteins comprise at least a portion of the tumor associated polypeptide carcinoembryonic antigen, fused to a substantial portion of an immunoenhancing element, such as a bacterial toxin. In preferred embodiments, the CEA portion of the encoded CEA fusion protein is deleted of its C-terminal anchoring domain. In preferred embodiments, the immunoenhancing element is the A or B subunit of the heat labile enterotoxin of *E. coli*, or substantial portion thereof. In other preferred embodiments, the immunoenhancing element is the minimized domain of tetanus toxin fragment C (DOM), or substantial portion thereof. The present invention also provides recombinant vectors, including but not limited to, adenovirus and plasmid vectors, comprising said polynucleotides and host cells comprising said recombinant vectors. Also provided herein are purified fusion proteins encoded by invention polynucleotides.

The present invention further provides methods for inhibiting or preventing the development of a cancer in a mammal by eliciting an immune response to the CEA protein by administering a vaccine or pharmaceutical composition comprising the CEA fusions or CEA fusion proteins described herein. In preferred embodiments of the methods herein, the immune response is enhanced relative to the response elicited by a wild-type CEA vaccine.

As used throughout the specification and in the appended claims, the singular forms "a," "an," and "the" include the plural reference unless the context clearly dictates otherwise.

As used throughout the specification and appended claims, the following definitions and abbreviations apply:

The term "promoter" refers to a recognition site on a DNA strand to which the RNA polymerase binds. The promoter forms an initiation complex with RNA polymerase to initiate and drive transcriptional activity. The complex can be modified by activating sequences termed "enhancers" or inhibiting sequences termed "silencers".

The term "cassette" refers to a nucleotide or gene sequence that is to be expressed from a vector, for example, the nucleotide or gene sequence encoding the hCEA-LTB fusion. In general, a cassette comprises a gene sequence that can be inserted into a vector, which in some embodiments, provides regulatory sequences for expressing the nucleotide or gene sequence. In other embodiments, the nucleotide or gene sequence provides the regulatory sequences for its expression. In further embodiments, the vector provides some regulatory sequences and the nucleotide or gene sequence provides other regulatory sequences. For example, the vector can provide a promoter for transcribing the nucleotide or gene sequence and the nucleotide or gene sequence provides a transcription termination sequence. The regulatory sequences that can be provided by the vector include, but are not limited to, enhancers, transcription termination sequences, splice acceptor and donor sequences, introns, ribosome binding sequences, and poly(A) addition sequences.

The term "vector" refers to some means by which DNA fragments can be introduced into a host organism or host tissue. There are various types of vectors including plasmid, virus (including adenovirus), bacteriophages and cosmids.

The term "first generation," as used in reference to adenoviral vectors, describes adenoviral vectors that are replication-defective. First generation adenovirus vectors typically have a deleted or inactivated E1 gene region, and preferably have a deleted or inactivated E3 gene region.

The abbreviation "DOM" refers generally to the N-terminal domain of fragment C of tetanus toxoid.

The abbreviation "LT" refers generally to the heat labile enterotoxin of *E. coli*. "LT" may refer to the complete enterotoxin, comprising subunits A and B or a substantial portion of subunit A, or a substantial portion of subunit B. The abbreviation "LTA" refers to the A subunit of the heat labile enterotoxin of *E. coli*, or substantial portion thereof, including subunits which are truncated on the C-terminal or N-terminal end but maintain biological activity, as well as subunits that contain internal amino acid insertions, deletions, or substitutions but maintain biological activity. The abbreviation "LTB" refers to the B subunit of the heat labile enterotoxin of *E. coli*, or substantial portion thereof, including subunits which are truncated on the C-terminal or N-terminal end but maintain biological activity, as well as subunits that contain internal amino acid insertions, deletions, or substitutions but maintain biological activity.

The designation "pV1J/hCEAopt" refers to a plasmid construct, disclosed herein, comprising the CMV immediate-early (IE) promoter with intron A, a full-length codon-optimized human CEA gene, bovine growth hormone-derived polyadenylation and transcriptional termination sequences, and a minimal pUC backbone (see EXAMPLE 2). The designation "pV1J/hCEA" refers to a construct essentially as described above, except the construct comprises a wild-type human CEA gene instead of a codon-optimized human CEA gene.

The designation "pV1J/hCEA-LTB" refers to a plasmid construct, disclosed herein, comprising the CMV immediate-early (IE) promoter with intron A, a human CEA gene devoid of its GPI anchor coding sequence, fused at its C-terminal end to the B subunit of *E. coli* heat labile enterotoxin, bovine growth hormone-derived polyadenylation and transcriptional termination sequences, and a minimal pUC backbone.

The designation "pV1J/hCEAopt-LTB" refers to a construct essentially as described immediately above, except the construct comprises a codon-optimized human CEA gene devoid of its GPI anchor coding sequence instead of the corresponding portion of the wild-type human CEA gene.

The designation "pV1J/hCEAopt-LTBopt" refers to a plasmid construct essentially as described immediately above, except that both the CEA sequences and the LTB sequences are codon-optimized for high level expression in human cells.

The designation "pV1J/rhCEAopt-LTBopt" refers to a construct essentially as described above except that the human codon-optimized CEA gene is replaced with a rhesus monkey CEA gene, codon-optimized for high-level expression in human cells.

The designation "pV1J/hCEA-LTA" refers to a plasmid construct, disclosed herein, comprising the CMV immediate-early (IE) promoter with intron A, a human CEA gene devoid of the GPI anchor coding sequence, fused at its C-terminal end to the A subunit of *E. coli* heat labile enterotoxin, bovine growth hormone-derived polyadenylation and transcriptional termination sequences, and a minimal pUC backbone. Construction of plasmid vectors comprising various CEA-LT fusions is described in EXAMPLE 2.

The designation "pV1J/hCEA-DOM" refers to a plasmid construct, disclosed herein, comprising the CMV immediate-early (IE) promoter with intron A, a human CEA gene devoid of its GPI anchor coding sequence, fused at its C-terminal end to the N-terminal domain of Fragment C of tetanus toxoid (DOM), bovine growth hormone-derived polyadenylation and transcriptional termination sequences, and a minimal pUC backbone (EXAMPLE 2).

The designation "pV1J/rhCEAopt-DOMopt" refers to a construct essentially as described above except that the human codon-optimized CEA gene is replaced with a rhesus monkey CEA gene, codon-optimized for high-level expression in human cells.

The designation "pV1J/hCEA-FcIgG" refers to a plasmid construct, disclosed herein, comprising the CMV immediate-early (IE) promoter with intron A, a human CEA gene devoid of the GPI anchor coding sequence, fused at its C-terminal end to the heavy fragment of constant chain of immunoglobulin G1, bovine growth hormone-derived polyadenylation and transcriptional termination sequences, and a minimal pUC backbone. (EXAMPLE 2). pV1J/hCEAopt-FcIgGopt refers to a construct essentially as described, except the nucleotide sequences encoding CEA and FcIgG have been codon-optimized for high-level expression in human cells.

The designations "Ad5/hCEAopt" and "Ad5/hCEA" refer to two constructs, disclosed herein, which comprise an Ad5 adenoviral genome deleted of the E1 and E3 regions. In the "Ad5/hCEAopt" construct, the E1 region is replaced by a codon-optimized human CEA gene in an E1 parallel orientation under the control of a human CMV promoter without intron A, followed by a bovine growth hormone polyadenylation signal. The "Ad5/hCEA" construct is essentially as described above, except the E1 region of the Ad5 genome is replaced with a wild-type human CEA sequence. The designation "Ad5/hCEAopt-LTB" refers to an Ad5 construct, essentially as described above, except that the codon-optimized human CEA sequence is devoid of the GPI anchor coding sequence and is fused at its C-terminus to the B subunit of *E. coli* heat labile enterotoxin. Construction of adenovirus vectors comprising various CEA-LT fusions is described in EXAMPLE 3.

"Immunoenhancing element" refers to a portion of the CEA fusion proteins of the present invention which is capable of stimulating or enhancing the immune response to the associated CEA protein, relative to full-length wild-type CEA. Immunoenhancing elements of the present invention are selected from the group consisting of: heat shock protein (HSP) 70, lysosome-associated membrane protein (LAMP), fragment C of tetanus toxoid (FrC), the N-terminal domain of FrC (DOM), the heavy fragment of constant chain of immune globulin G1 (FcIgG), the vesicular stomatitis virus glycoprotein (VSV-G), cholera toxin (CT) from *Vibrio cholerae*, and heat labile enterotoxin of *E. coli* (LT). The term "immunoenhancing element" is used interchangeably herein with the term "adjuvant."

As used herein, a "fusion protein" refers to a protein having at least two polypeptides covalently linked in which one polypeptide comes from one protein sequence or domain and the other polypeptide comes from a second protein sequence or domain. The fusion proteins of the present invention comprise a CEA polypeptide or fragment or variant thereof, and a second polypeptide, which comprises a substantial portion of an immunoenhancing element, which, in some cases, is a bacterial toxin. The CEA polypeptide, fragment or variant thereof may be a human CEA or CEA homolog from another species. The polypeptides that comprise the fusion protein are preferably linked N-terminus to C-terminus. The CEA polypeptide and the toxin subunit can be fused in any order. In some embodiments of this invention, the C-terminus of the CEA polypeptide is fused to the N-terminus of the toxin subunit, as exemplified in FIG. 1A. However, fusion proteins in which the immunoenhancing element is fused to the N-terminus of the CEA polypeptide are also contemplated. The term "CEA fusion protein" is intended to be a general term which refers to a fusion as described above, which comprises a CEA polypeptide or fragment or variant thereof fused to a polypeptide comprising an immunoenhancing element.

The term "CEA-LT fusion" refers to a nucleic acid sequence in which at least a portion of the CEA gene is fused to a substantial portion of either the LTA or the LTB subunit of *E. coli* heat labile enterotoxin. The term "CEA-LT fusion protein" refers to a polypeptide encoded by a CEA-LT fusion as described. The terms "CEA-LT fusion" and "CEA-LT fusion protein" are also understood to refer to fragments thereof, homologs thereof, and functional equivalents thereof (collectively referred to as "variants"), such as those in which one or more amino acids is inserted, deleted or replaced by other amino acid(s). The CEA-LT fusions of the present invention, upon administration to a mammal such as a human being, can stimulate an immune response by helper T cells or cytotoxic T cells, or stimulate the production of antibodies at least as well as a "wild-type" CEA sequence. In preferred embodiments of the invention, the CEA-LT fusion can enhance the immune response as compared to a wild-type CEA.

The term "CEA-DOM fusion" refers to a nucleic acid sequence in which at least a portion of the CEA gene is fused to a substantial portion of the minimized domain of tetanus toxin fragment C, unless the context clearly dictates that said term refers to the protein sequence. The term "CEA-DOM fusion protein" refers to a polypeptide encoded by a CEA-DOM fusion as described. The terms "CEA-DOM fusion" and "CEA-DOM fusion protein" are also understood to refer to fragments thereof, homologs thereof, and functional equivalents thereof (collectively referred to as "variants"), such as those in which one or more amino acids is inserted, deleted or replaced by other amino acid(s). The CEA-DOM fusions of the present invention, upon administration to a mammal such as a human being, can stimulate an immune response by helper T cells or cytotoxic T cells, or stimulate the production of antibodies at least as well as a "wild-type" CEA sequence. In preferred embodiments of the invention, the CEA-DOM fusion can enhance the immune response as compared to a wild-type CEA.

The abbreviation "AD" refers to the anchoring domain of a CEA gene or protein. The anchoring domain of the wild-type human CEA is located from about amino acid 679 to about amino acid 702 of SEQ ID NO:20.

The term "treatment" refers to both therapeutic treatment and prophylactic or preventative measures. Those in need of treatment include those already with the disorder as well as those prone to have the disorder or those in which the disorder is to be prevented.

A "disorder" is any condition that would benefit from treatment with the molecules of the present invention, including the nucleic acid molecules described herein and the fusion proteins that are encoded by said nucleic acid molecules. Encompassed by the term "disorder" are chronic and acute disorders or diseases including those pathological conditions which predispose the mammal to the disorder in question. The molecules of the present invention are intended for use as treatments for disorders or conditions characterized by aberrant cell proliferation, including, but not limited to, breast cancer, colorectal cancer, and lung cancer.

The term "effective amount" means sufficient vaccine composition is introduced to produce the adequate levels of the polypeptide, so that an immune response results. One skilled in the art recognizes that this level may vary.

A "conservative amino acid substitution" refers to the replacement of one amino acid residue by another, chemically similar, amino acid residue. Examples of such conservative substitutions are: substitution of one hydrophobic residue (isoleucine, leucine, valine, or methionine) for another; substitution of one polar residue for another polar residue of the same charge (e.g., arginine for lysine; glutamic acid for aspartic acid).

"hCEA" and "hCEAopt" refer to a human carcinoembryonic antigen and a human codon-optimized carcinoembryonic antigen, respectively.

"rhCEA" and "rhCEAopt" refer to a rhesus monkey carcinoembryonic antigen and a rhesus monkey codon-optimized carcinoembryonic antigen, respectively.

"Substantially similar" means that a given nucleic acid or amino acid sequence shares at least 75%, preferably 85%, more preferably 90%, and even more preferably 95% identity with a reference sequence. In the present invention, the reference sequence can be relevant portions of the wild-type human CEA nucleotide or amino acid sequence, or the wild-type nucleotide or amino acid sequence of a bacterial toxin or subunit thereof, such as the LTB or LTA subunits of the *E. coli* heat labile enterotoxin, as dictated by the context of the text. The reference sequence may also be, for example, the wild-type rhesus monkey CEA sequence. Thus, a CEA protein sequence that is "substantially similar" to the wild-type human CEA protein or fragment thereof will share at least 75% identity with the relevant fragment of the wild-type human CEA, along the length of the fragment, preferably 85% identity, more preferably 90% identity and even more preferably 95% identity. Whether a given CEA, LTB, or LTA protein or nucleotide sequence is "substantially similar" to a reference sequence can be determined for example, by comparing sequence information using sequence analysis software such as the GAP computer program, version 6.0, available from the University of Wisconsin Genetics Computer Group (UWGCG). The GAP program utilizes the alignment method of Needleman and Wunsch (*J. Mol. Biol.* 48:443, 1970), as revised by Smith and Waterman (*Adv. Appl. Math.* 2:482, 1981).

A "substantial portion" of a gene, variant, fragment, or subunit thereof, means a portion of at least 50%, preferably 75%, more preferably 90%, and even more preferably 95% of a reference sequence.

A "gene" refers to a nucleic acid molecule whose nucleotide sequence codes for a polypeptide molecule. Genes may be uninterrupted sequences of nucleotides or they may include such intervening segments as introns, promoter regions, splicing sites and repetitive sequences. A gene can be either RNA or DNA. A preferred gene is one that encodes the invention peptide.

The term "nucleic acid" or "nucleic acid molecule" is intended for ribonucleic acid (RNA) or deoxyribonucleic acid (DNA), probes, oligonucleotides, fragment or portions thereof, and primers. DNA can be either complementary DNA (cDNA) or genomic DNA, e.g. a gene encoding a CEA fusion protein.

"Wild-type CEA" or "wild-type protein" or "wt protein" refers to a protein comprising a naturally occurring sequence of amino acids or variant thereof. The amino acid sequence of wild-type human CEA is shown in FIG. 7E (SEQ ID NO:20). The amino acid sequence of the wild-type rhesus monkey CEA was previously described (WO 2004/072287, see FIGS. 7A-7B).

"Wild-type CEA gene" refers to a gene comprising a sequence of nucleotides that encodes a naturally occurring CEA protein, including proteins of human origin or proteins obtained from another organism, including, but not limited to, other mammals such as rat, mouse and rhesus monkey. The nucleotide sequence of the human CEA gene is available in the art (supra). See also Beauchemin et al., *Mol. Cell. Biol.* 7:3221-3230 (1987); Zimmerman et al., *Proc. Natl. Acad. Sci. USA* 84:920-924 (1987); and Thompson et al. *Proc. Natl. Acad. Sci. USA* 84(9):2965-69 (1987). The nucleotide sequence of the wild-type rhesus monkey gene is shown in FIGS. 7C-7D.

The term "mammalian" refers to any mammal, including a human being.

The abbreviation "Ag" refers to an antigen.

The abbreviations "Ab" and "mAb" refer to an antibody and a monoclonal antibody, respectively.

The abbreviation "ORF" refers to the open reading frame of a gene.

BRIEF DESCRIPTION OF THE DRAWINGS

FIG. 3 shows the nucleotide (SEQ ID NO:9, Panel A) and amino acid sequence (SEQ ID NO:10, Panel B) of an exemplary hCEA-LTB fusion. The LTB nucleotide sequence is shown in bold.

FIG. 4 shows the nucleotide sequence of an exemplary hCEAopt-LTB fusion (SEQ ID NO:11). The LTB nucleotide sequence is shown in bold.

FIG. 5 shows the nucleotide (SEQ ID NO:12, Panel A) and amino acid sequence (SEQ ID NO:13, Panel B) of an exemplary fully optimized hCEA-LTB fusion, designated herein hCEAopt-LTBopt. The LTB nucleotide and amino acid sequences are shown in bold. Junction sequences, created by the cloning strategy employed to fuse the CEA and LTB sequences are underlined.

FIG. 6 shows the nucleotide (SEQ ID NO:14, Panel A) and amino acid sequence (SEQ ID NO:15, Panel B) of a fully optimized rhesus monkey CEA-LTB fusion, designated herein rhCEAoptLTBopt. LTB nucleotide and amino acid sequences are shown in bold. Junction sequences, created by the cloning strategy employed to fuse the CEA and LTB sequences, are underlined.

FIG. 7 shows nucleotide sequences of wild-type genes encoding rhesus monkey CEA (Panels A and B, SEQ ID NOs:16 and 17) and the amino acid sequences of the corresponding proteins (Panels C and D, SEQ ID NOs:18 and 19), as previously described (U.S. Ser. No. 60/447,203). Panel E shows the amino acid sequence of wild-type human CEA (SEQ ID NO:20), which was previously described (see, e.g., U.S. Pat. No. 5,274,087).

FIG. 26 shows the nucleotide sequence (SEQ ID NO:21) of an exemplary, fully optimized hCEA-DOM fusion, herein designated hCEAoptDOMopt. The amino acid sequence of the encoded protein is also shown (SEQ ID NO:45). The CEA portion of the nucleotide sequence of this particular CEA fusion consists of nucleotides 1 to 2037, which are codon-optimized for high-level expression in a human host cell. The DOM portion of the nucleotide sequence is shown in bold and is also codon-optimized for high-level expression in human cells. Junction sequences, created by the cloning strategy employed to fuse the CEA and LTB sequences are underlined.

FIG. 27 shows an exemplary nucleotide (SEQ ID NO:25) sequence of a hCEA-FcIgGopt fusion, herein designated hCEAoptFcIgGopt. The sequence of the encoded protein (SEQ ID NO:46) is also shown. The CEA portion of the nucleotide sequence of this particular CEA fusion consists of nucleotides 1 to 2037, which are codon-optimized for high-level expression in a human host cell. The FcIgG portion of the nucleotide sequence, which is also codon-optimized for high-level expression in human cells, is shown in bold. Junction sequences, created by the cloning strategy employed to fuse the CEA and LTB sequences are underlined.

FIG. 28 shows the nucleotide sequence of a portion of the wild-type human CEA cDNA from nt 1 to nt 2037 (SEQ ID NO:22, Panel A), encoding a portion of the hCEA protein from aa 1 to aa 679 (SEQ ID NO:23, Panel B).

FIG. 29 shows the non-optimized nucleotide sequence of the minimized domain of tetanus toxin fragment C (DOM) cDNA from nt 1 to nt 825 (SEQ ID NO:47), encoding the DOM protein, also shown (SEQ ID NO:48).

FIG. 30 shows the non-optimized nucleotide sequence of an exemplary human CEA-DOM fusion (SEQ ID NO:49). The CEA portion of the nucleotide sequence of this particular CEA fusion consists of nucleotides 1 to 2037. The DOM portion of the nucleotide sequence is shown in bold.

FIG. 31 shows an exemplary nucleotide sequence (SEQ ID NO:50) of a rhesus monkey CEA-DOM fusion, herein designated rhCEA-DOMopt. The sequence of the encoded fusion protein (SEQ ID NO:51) is also shown. The CEA portion of the nucleotide sequence of this particular CEA fusion consists of nucleotides 1 to 2037, which are codon-optimized for high-level expression in a human host cell. The DOM portion of the nucleotide sequence, which is also codon-optimized for high-level expression in human cells, is shown in bold.

FIG. 32 shows an exemplary nucleotide sequence (SEQ ID NO:52) of a rhesus monkey CEA-CTB fusion, herein designated rhCEA-CTBopt. The sequence of the encoded fusion protein (SEQ ID NO:53) is also shown. The CEA portion of the nucleotide sequence of this particular CEA fusion consists of nucleotides 1 to 2037, which are codon-optimized for high-level expression in a human host cell. The CTB portion of the nucleotide sequence, which is also codon-optimized for high-level expression in human cells, is shown in bold.

DETAILED DESCRIPTION OF THE INVENTION

Figure 1:
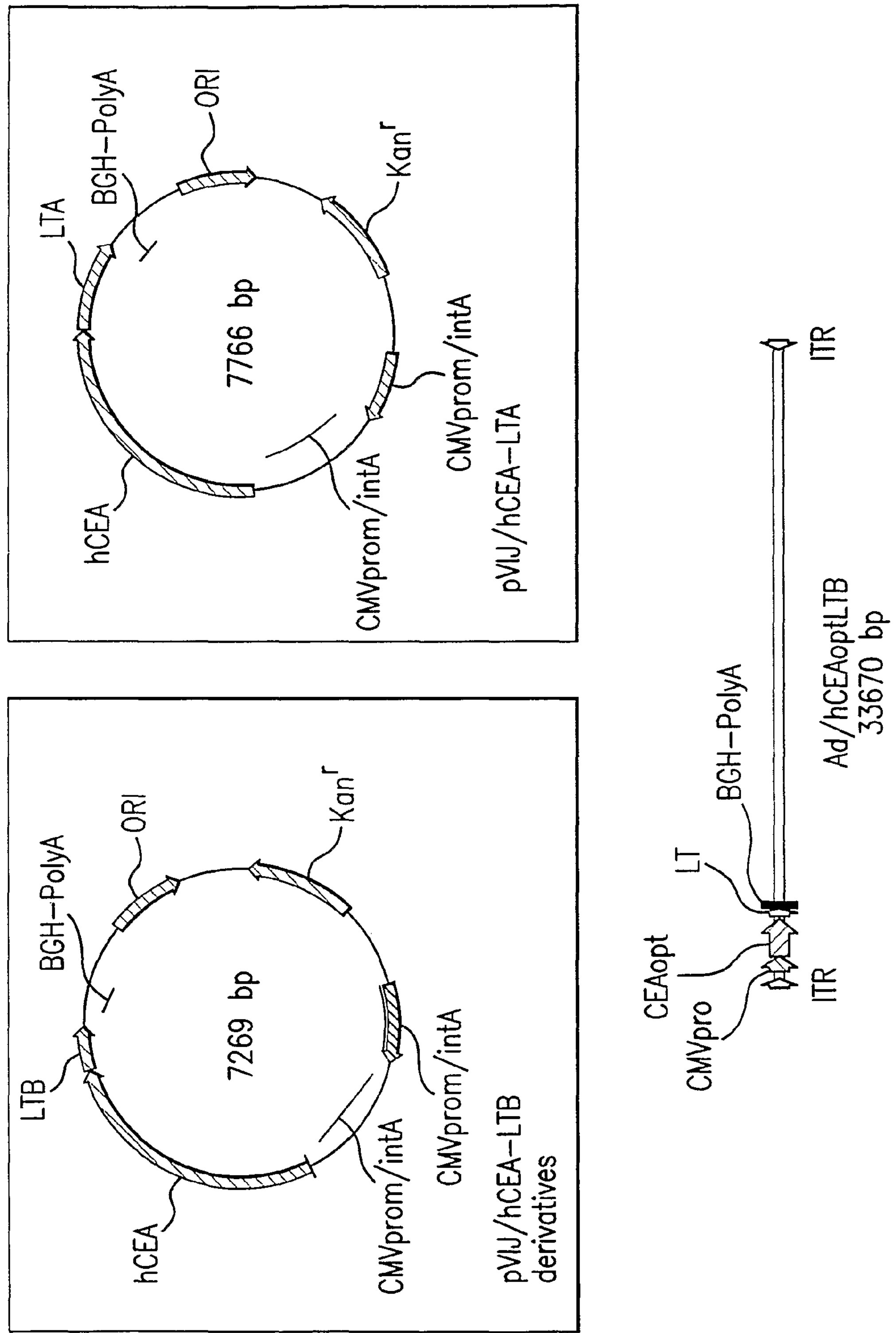
FIG. 1 shows a schematic representation of the vectors developed in this study. The essential features of the plasmid and Ad vectors encoding the CEA-LTA and CEA-LTB fusions are indicated. The inverted terminal repeats (ITR) of the Ad5 genome are also shown.

Carcinoembryonic antigen (CEA) is commonly associated with the development of adenocarcinomas. The present invention relates to compositions and methods to elicit or enhance immunity to the protein product expressed by the CEA tumor-associated antigen, wherein aberrant CEA expression is associated with the carcinoma or its development. Association of aberrant CEA expression with a carcinoma does not require that the CEA protein be expressed in tumor tissue at all timepoints of its development, as abnormal CEA expression may be present at tumor initiation and not be detectable late into tumor progression or vice-versa.

To this end, the present invention provides polynucleotides, vectors, host cells, and encoded proteins comprising a CEA sequence or variant thereof for use in vaccines and pharmaceutical compositions for the treatment and/or prevention of a cancer. The polynucleotides of the present invention comprise a nucleotide sequence encoding a CEA protein or variant thereof, fused to a nucleotide sequence encoding at least a subunit of an immunoenhancing element, such as a bacterial enterotoxin or substantial portion thereof, which can effectively adjuvant an immune response to the associated CEA.

The CEA nucleotide sequences of the present invention can be of human origin or can be a CEA homolog from another species. The wild-type human CEA nucleotide sequence has been reported (see, e.g., U.S. Pat. Nos. 5,274,087; 5,571,710; and 5,843,761). The rhesus monkey CEA sequence was recently described (WO 2004/072287). The CEA portion of the CEA fusion may be full-length, or any variant sufficient to elicit a CEA-specific immune response in a mammal. CEA variants of the present invention include, but are not limited to sequences that are C- or N-terminally truncated, sequences with conservative substitutions, and sequences with internal deletions or insertions.

In preferred embodiments of the present invention, the CEA portion of the CEA fusion is human CEA or a functional equivalent thereof. In other preferred embodiments, the CEA portion is a rhesus monkey CEA, or functional equivalent thereof.

Accordingly, the present invention relates to a synthetic polynucleotide comprising a sequence of nucleotides encoding a CEA fusion protein, said fusion protein comprising a CEA protein or a biologically active fragment or mutant form of a CEA protein fused to an immunoenhancing element or subunit thereof, which can effectively enhance the immune response to the CEA protein. Said mutant forms of the CEA protein include, but are not limited to: conservative amino acid substitutions, amino-terminal truncations, carboxy-terminal truncations, deletions, or additions. Any such biologically active fragment and/or mutant will encode either a protein or protein fragment which at least substantially mimics the immunological properties of the CEA protein as set forth in SEQ ID NO:20. The synthetic polynucleotides of the present invention encode mRNA molecules that express a functional CEA fusion protein so as to be useful in the development of a therapeutic or prophylactic cancer vaccine.

In preferred embodiments of the present invention, the CEA portion of the encoded CEA fusion protein is human CEA (SEQ ID NO: 20) or a functional equivalent thereof, for example, a human CEA deleted of its C-terminal anchoring domain (AD) (SEQ ID NO: 23), which is located from about amino acid 679 to about amino acid 702 of the human full-length CEA. While not being bound by theory, deletion of the anchoring domain increases secretion of the CEA fusion protein, thereby enhancing cross priming of the CEA-LTB immune response. In other preferred embodiments, the CEA portion is a rhesus monkey CEA (SEQ ID NOs:18 and 19), or functional equivalent thereof.

The immunoenhancing element portion of the CEA fusion proteins of the present invention are capable of stimulating or enhancing the immune response to the associated CEA protein and are selected from the group consisting of: heat shock protein (HSP) 70, lysosome-associated membrane protein (LAMP), fragment C of tetanus toxoid (FrC), the N-terminal domain of FrC (DOM), the heavy fragment of constant chain of immune globulin G1 (FcIgG), the vesicular stomatitis virus glycoprotein (VSV-G), cholera toxin (CT) from *Vibrio cholerae*, and heat labile enterotoxin of *E. coli* (LT). In preferred embodiments of the present invention, the adjuvant portion of the CEA fusion comprises the N-terminal domain of FrC (DOM), which has been shown to strongly potentiate the immunogenicity of codelivered antigens. In further preferred embodiments, the adjuvant portion of the CEA fusion comprises a subunit of LT, or substantial portion thereof. In still further preferred embodiments, the adjuvant portion of the CEA fusion is a substantial portion of FcIgG.

A CEA fusion comprising a truncated human CEA fused to a single epitope of tetanus toxin (Q830-L844) has been described (Lund et al. *Cancer Gene Therapy* 10: 365-376 (2003)). Unlike this single-epitope fusion, the CEA fusions of the present invention comprise a substantial portion of an immunoenhancing element or subunit thereof, as described above, which is capable of enhancing the immunogenicity of a CEA protein or variant thereof. A substantial portion of an immunoenhancing element to be used for the compositions and methods described herein does not include portions that are less than 50% of a full-length toxin subunit. The strategy used herein, which utilizes full-length adjuvant subunits or substantial portions thereof, was employed to ensure a greater immune response to the fused CEA sequence. While not being bound by theory, it is believed that if the bacterial toxin chosen as adjuvant comprises greater than one helper epitope, limiting the toxin sequence of the fusion protein to a single epitope would arguably lead to a reduced effect on the immunogenicity of the target protein. Additionally, it is believed that if the adjuvant-mediated enhancement of the immune response is dependent on the interaction of the adjuvant with specific cell receptors and not based on a universal epitope, then the receptor interaction could depend on a specific structural configuration that would require a substantial portion of the immunoenhancing element to exert an adjuvant effect. In such a case, a short adjuvant sequence comprising a single epitope would be insufficient in mediating an increase of the immune response.

Also contemplated for use in the present invention are nucleotide sequences encoding variants or mutants of the immunoenhancing elements described herein, including but not necessarily limited to: nucleotide substitutions, deletions, additions, amino-terminal truncations and carboxy-terminal truncations. In some cases, it may be advantageous to add specific point mutations to the nucleotide sequence encoding the adjuvant or subunit thereof to reduce or eliminate toxicity of the encoded protein. In exemplary embodiments of this aspect of the present invention, an LT subunit is fused to the CEA sequence of the CEA fusion, wherein the LT subunit is truncated of its signal sequence. While not being bound by theory, deletion of the toxin signal sequence, e.g. the LTB signal sequence, ensures that posttranslational processing of the CEA fusion is driven by the CEA signal sequence.

The immunoenhancing element, subunit, or substantial portion thereof may be fused to the amino terminus or the carboxy terminus of the CEA sequence. Further, the immunoenhancing element sequence and the CEA sequence can be fused N-terminus to N-terminus, C-terminus to C-terminus, C-terminus to N-terminus or N-terminus to N-terminus. In preferred embodiments of the present invention, the C-terminus of the CEA polypeptide is fused to the N-terminus of the immunoenhancing element.

The present invention relates to a synthetic nucleic acid molecule (polynucleotide) comprising a sequence of nucleotides which encodes mRNA that expresses a novel CEA fusion protein; for example, nucleotide sequences encoding the fusion proteins as set forth in SEQ ID NOs:8, 10, 13, 15, 45, 46, 51 and 53. The nucleic acid molecules of the present invention are substantially free from other nucleic acids.

The present invention also relates to recombinant vectors and recombinant host cells, both prokaryotic and eukaryotic, which contain the nucleic acid molecules disclosed throughout this specification. The synthetic DNA molecules, associated vectors, and hosts of the present invention are useful for the development of a cancer vaccine.

Exemplary nucleic acid molecules of the present invention comprise a nucleotide sequence selected from the group consisting of: SEQ ID NOs: 7, 9, 11, 12, 14, 21, 25, 49, 50, and 52, as shown in FIGS. 2-6, 26-27, 30-32, which encode exemplary CEA-LTA, CEA-LTB, CEA-DOM, CEA-FcIgG, and CEA-CTB fusion proteins of the present invention.

The present invention also includes biologically active fragments or mutants of SEQ ID NOs: 7, 9, 11, 12, 14, 21, 25, 49, 50, and 52, which encode mRNA expressing exemplary CEA fusion proteins. Any such biologically active fragment and/or mutant will encode either a protein or protein fragment which at least substantially mimics the pharmacological properties of the hCEA protein, including but not limited to the hCEA protein as set forth in SEQ ID NO:20. Any such polynucleotide includes but is not necessarily limited to:

nucleotide substitutions, deletions, additions, amino-terminal truncations and carboxy-terminal truncations. The mutations of the present invention encode mRNA molecules that express a functional CEA fusion protein in a eukaryotic cell so as to be useful in cancer vaccine development.

Also included within the scope of this invention are mutations in the DNA sequence that do not substantially alter the ultimate physical properties of the expressed protein. For example, substitution of valine for leucine, arginine for lysine, or asparagine for glutamine may not cause a change in the functionality of the polypeptide.

As stated above, the present invention further relates to recombinant vectors that comprise the nucleic acid molecules disclosed throughout this specification. These vectors may be comprised of DNA or RNA. For most cloning purposes, DNA vectors are preferred. Typical vectors include plasmids, modified viruses, baculovirus, bacteriophage, cosmids, yeast artificial chromosomes, and other forms of episomal or integrated DNA that can encode a CEA fusion protein. It is well within the purview of the skilled artisan to determine an appropriate vector for a particular gene transfer or other use.

Also provided by the present invention are purified CEA fusion proteins encoded by the nucleic acids disclosed throughout this specification. In exemplary embodiments of this aspect of the invention, the CEA fusion protein comprises a sequence of amino acids selected from the group consisting of: SEQ ID NOs: 8, 10, 13, 15, 45, 46, 51 and 53.

Included in the present invention are DNA sequences that hybridize to SEQ ID NOs: 7, 9, 11, 12, 14, 21, 25, 49, 50, or 52 under stringent conditions. By way of example, and not limitation, a procedure using conditions of high stringency is as follows. Prehybridization of filters containing DNA is carried out for about 2 hours to overnight at about 65° C. in buffer composed of 6×SSC, 5× Denhardt's solution, and 100 μg/ml denatured salmon sperm DNA. Filters are hybridized for about 12 to 48 hrs at 65° C. in prehybridization mixture containing 100 μg/ml denatured salmon sperm DNA and 5-20×$10^6$ cpm of $^{32}$P-labeled probe. Washing of filters is done at 37° C. for about 1 hour in a solution containing 2×SSC, 0.1% SDS. This is followed by a wash in 0.1×SSC, 0.1% SDS at 50° C. for 45 minutes before autoradiography. Other procedures using conditions of high stringency would include either a hybridization step carried out in 5×SSC, 5× Denhardt's solution, 50% formamide at about 42° C. for about 12 to 48 hours or a washing step carried out in 0.2×SSPE, 0.2% SDS at about 65° C. for about 30 to 60 minutes. Reagents mentioned in the foregoing procedures for carrying out high stringency hybridization are well known in the art. Details of the composition of these reagents can be found in Sambrook et al., Molecular Cloning: A Laboratory Manual 2$^{nd}$ Edition; Cold Spring Harbor Laboratory Press, Cold Spring Harbor, N.Y., (1989) or Sambrook and Russell, Molecular Cloning: A Laboratory Manual, 3rd Edition. Cold Spring Harbor Laboratory Press, Plainview, N.Y. (2001). In addition to the foregoing, other conditions of high stringency which may be used are also well known in the art.

An expression vector containing a CEA fusion protein-encoding nucleic acid molecule may be used for high-level expression of CEA fusion protein in a recombinant host cell. Expression vectors may include, but are not limited to, cloning vectors, modified cloning vectors, specifically designed plasmids or viruses. Also, a variety of bacterial expression vectors may be used to express recombinant CEA fusion sequences in bacterial cells if desired. In addition, a variety of fungal cell expression vectors may be used to express recombinant CEA fusion sequences in fungal cells. Further, a variety of insect cell expression vectors may be used to express recombinant protein in insect cells.

The present invention also relates to host cells transformed or transfected with vectors comprising the nucleic acid molecules of the present invention. Recombinant host cells may be prokaryotic or eukaryotic, including but not limited to, bacteria such as *E. coli*, fungal cells such as yeast, mammalian cells including, but not limited to, cell lines of bovine, porcine, monkey and rodent origin; and insect cells including but not limited to *Drosophila* and silkworm derived cell lines. Such recombinant host cells can be cultured under suitable conditions to produce a CEA fusion protein or a biologically equivalent form. In a preferred embodiment of the present invention, the host cell is human. As defined herein, the term "host cell" is not intended to include a host cell in the body of a transgenic human being, human fetus, or human embryo.

As noted above, an expression vector containing DNA encoding a CEA fusion protein may be used for expression of CEA fusion protein in a recombinant host cell. Therefore, another aspect of this invention is a process for expressing a CEA fusion protein in a recombinant host cell, comprising: (a) introducing a vector comprising a nucleic acid comprising a sequence of nucleotides that encodes a CEA fusion protein into a suitable human host cell, wherein the CEA fusion protein comprises a CEA protein or variant thereof, fused to a substantial portion of an immunoenhancing element or subunit thereof, wherein the immunoenhancing element or subunit thereof is selected from the group consisting of: heat shock protein (HSP) 70, lysosome-associated membrane protein (LAMP), fragment C of tetanus toxoid (FrC), the N-terminal domain of FrC (DOM), the heavy fragment of constant chain of immune globulin G1 (FcIgG), the vesicular stomatitis virus glycoprotein (VSV-G), cholera toxin (CT) from *Vibrio cholerae*, and heat labile enterotoxin of *E. coli* (LT); and wherein the fusion protein is capable of producing an immune response in a mammal; and, (b) culturing the host cell under conditions which allow expression of said CEA fusion protein.

Preferred immunoenhancing elements for use in this aspect of the invention are selected from the group consisting of: LTB, LTA, DOM, and FcIgG.

In a further preferred embodiment of this aspect of the invention, the nucleotide sequence of the CEA portion of the fusion and/or the immunoenhancing element portion of the fusion are codon-optimized for high-level expression in human cells.

This invention also provides a process for expressing a CEA-LT fusion protein in a recombinant host cell, comprising: (a) introducing a vector comprising a nucleic acid comprising a sequence of nucleotides that encodes a CEA-LT fusion protein into a suitable human host cell, wherein the CEA fusion protein comprises a CEA protein or variant thereof, fused to a substantial portion of an LT subunit, and wherein the fusion protein is capable of producing an immune response in a mammal; and, (b) culturing the host cell under conditions which allow expression of said CEA-LT fusion protein.

In preferred embodiments of the process for expressing a CEA-LT fusion protein described above, the LT subunit is a substantial portion of LTB, wherein the LTB sequence is deleted of its signal sequence. In other embodiments, the LT subunit is LTA, or a substantial portion thereof.

This invention also provides a process for expressing a CEA-DOM fusion protein in a recombinant host cell, comprising: (a) introducing a vector comprising a nucleic acid comprising a sequence of nucleotides that encodes a CEA-DOM fusion protein into a suitable human host cell, wherein the CEA fusion protein comprises a CEA protein or variant thereof, fused to a substantial portion of the N-terminal domain of fragment C of tetanus toxin (DOM), and wherein the fusion protein is capable of producing an immune response in a mammal; and, (b) culturing the host cell under conditions which allow expression of said CEA-DOM fusion protein.

In preferred embodiments of the process for expressing a CEA-DOM fusion protein described above, the DOM portion is codon-optimized for high-level expression in human cells. In other preferred embodiments, the CEA portion of the CEA fusion is codon-optimized for high-level expression in human cells. In still further preferred embodiments, both the CEA and the DOM portions are codon-optimized for high-level expression in human cells.

Following expression of a CEA fusion in a host cell, CEA fusion protein may be recovered to provide CEA fusion protein in active form. Several protein purification procedures are available and suitable for use. Recombinant protein may be purified from cell lysates and extracts by various combinations of, or individual application of salt fractionation, ion exchange chromatography, size exclusion chromatography, hydroxylapatite adsorption chromatography and hydrophobic interaction chromatography. In addition, recombinant CEA fusion protein can be separated from other cellular proteins by use of an immunoaffinity column made with monoclonal or polyclonal antibodies specific for a CEA protein, or polypeptide fragments of a CEA protein.

The nucleic acid molecules comprising CEA fusions and the encoded fusion proteins of this invention were designed to enhance the CEA-specific immune response, relative to full-length cDNA encoding CEA, for use in vaccine development. To further enhance the immunogenic properties of the CEA fusion sequences of the present invention, in some embodiments described herein, the polynucleotides encoding CEA fusion proteins comprise optimized codons for further high level expression in a host cell, as described below. In these embodiments, at least a portion of the codons of the CEA fusions are designed so as to use the codons preferred by the projected host cell, which in preferred embodiments is a human cell. The optimized CEA fusions may be used for the development of recombinant adenovirus or plasmid-based DNA vaccines, which provide effective immunoprophylaxis against CEA-associated cancer through neutralizing antibody and cell-mediated immunity. The synthetic molecules may be used as an immunogenic composition. This invention provides codon-optimized CEA fusion polynucleotides which, when directly introduced into a vertebrate in vivo, including mammals such as primates and humans, induce the expression of encoded proteins within the animal.

As stated above, in some embodiments of the present invention, the synthetic molecules comprise a sequence of nucleotides, wherein some of the nucleotides have been altered so as to use the codons preferred by a human cell, thus allowing for high-level fusion protein expression in a human host cell. The synthetic molecules may be used as a source of a CEA fusion protein, for example, CEA-LTB fusion protein, which may be used in a cancer vaccine to provide effective immunoprophylaxis against CEA-associated carcinomas through neutralizing antibody and cell-mediated immunity. The nucleic acid molecules disclosed herein may also serve as the basis for a DNA-based cancer vaccine.

A "triplet" codon of four possible nucleotide bases can exist in over 60 variant forms. Because these codons provide the message for only 20 different amino acids (as well as transcription initiation and termination), some amino acids can be coded for by more than one codon, a phenomenon known as codon redundancy. For reasons not completely understood, alternative codons are not uniformly present in the endogenous DNA of differing types of cells. Indeed, there appears to exist a variable natural hierarchy or "preference" for certain codons in certain types of cells. As one example, the amino acid leucine is specified by any of six DNA codons including CTA, CTC, CTG, CTT, TTA, and TTG. Exhaustive analysis of genome codon frequencies for microorganisms has revealed endogenous DNA of *E. coli* most commonly contains the CTG leucine-specifying codon, while the DNA of yeasts and slime molds most commonly includes a TTA leucine-specifying codon. In view of this hierarchy, it is generally believed that the likelihood of obtaining high levels of expression of a leucine-rich polypeptide by an *E. coli* host will depend to some extent on the frequency of codon use. For example, it is likely that a gene rich in TTA codons will be poorly expressed in *E. coli*, whereas a CTG rich gene will probably be highly expressed in this host. Similarly, a preferred codon for expression of a leucine-rich polypeptide in yeast host cells would be TTA.

The implications of codon preference phenomena on recombinant DNA techniques are manifest, and the phenomenon may serve to explain many prior failures to achieve high expression levels of exogenous genes in successfully transformed host organisms—a less "preferred" codon may be repeatedly present in the inserted gene and the host cell machinery for expression may not operate as efficiently. This phenomenon suggests that synthetic genes which have been designed to include a projected host cell's preferred codons provide an optimal form of foreign genetic material for practice of recombinant DNA techniques. Thus, one aspect of this invention is a CEA fusion gene that is codon-optimized for expression in a human cell. In a preferred embodiment of this invention, it has been found that the use of alternative codons encoding the same protein sequence may remove the constraints on expression of exogenous CEA fusion protein in human cells.

In accordance with some embodiments of the present invention, the nucleic acid molecules which encode the CEA fusion proteins are converted to a polynucleotide sequence having an identical translated sequence but with alternative codon usage as described by Lathe, "Synthetic Oligonucleotide Probes Deduced from Amino Acid Sequence Data: Theoretical and Practical Considerations" *J. Molec. Biol.* 183:1-12 (1985), which is hereby incorporated by reference. The methodology generally consists of identifying codons in the wild-type sequence that are not commonly associated with highly expressed human genes and replacing them with optimal codons for high expression in human cells. The new gene sequence is then inspected for undesired sequences generated by these codon replacements (e.g., "ATTTA" sequences, inadvertent creation of intron splice recognition sites, unwanted restriction enzyme sites, etc.). Undesirable sequences are eliminated by substitution of the existing codons with different codons coding for the same amino acid. The synthetic gene segments are then tested for improved expression.

The methods described above were used to create synthetic gene sequences which encode CEA fusion proteins, resulting in a gene comprising codons optimized for high level expression. While the above procedure provides a summary of our methodology for designing codon-optimized genes for use in cancer vaccines, it is understood by one skilled in the art that similar vaccine efficacy or increased expression of genes may be achieved by minor variations in the procedure or by minor variations in the sequence.

One of skill in the art will also recognize that additional nucleic acid molecules may be constructed that provide for high levels of CEA fusion expression in human cells, wherein only a portion of the codons of the DNA molecules are codon-optimized. For example, in some embodiments of the present invention, codons comprising the CEA portion of the CEA fusion are optimized for high-level expression in human cells, and codons comprising the adjuvant portion of the CEA fusion are substantially similar to the wild-type adjuvant-encoding nucleotide sequence. In other embodiments of the present invention, codons comprising the adjuvant portion of the CEA fusion are optimized for high-level expression in human cells, and codons comprising the CEA portion of the CEA fusion are substantially similar to a wild-type CEA gene. In still other embodiments of the present invention, both the CEA and the adjuvant portions of the CEA fusion are codon-optimized for high-level expression in human cells. CEA fusions in which only a subset of codons are optimized within the CEA and/or the adjuvant portion of the CEA fusion are also contemplated by this invention.

The nucleic acids of the present invention may be assembled into an expression cassette which comprises sequences designed to provide for efficient expression of the protein in a human cell. The cassette preferably contains CEA fusion protein-encoding gene, with related transcriptional and translations control sequences operatively linked to it, such as a promoter, and termination sequences. In a preferred embodiment, the promoter is the cytomegalovirus promoter without the intron A sequence (CMV), although those skilled in the art will recognize that any of a number of other known promoters such as the strong immunoglobulin, or other eukaryotic gene promoters may be used. A preferred transcriptional terminator is the bovine growth hormone terminator, although other known transcriptional terminators may also be used. The combination of CMV-BGH terminator is particularly preferred.

In accordance with this invention, the CEA fusion expression cassette is inserted into a vector. The vector is preferably an adenoviral or plasmid vector, although linear DNA linked to a promoter, or other vectors, such as adeno-associated virus or a modified vaccinia virus, retroviral or lentiviral vector may also be used.

If the vector chosen is an adenovirus, it is preferred that the vector be a so-called first-generation adenoviral vector. These adenoviral vectors are characterized by having a non-functional E1 gene region, and preferably a deleted adenoviral E1 gene region. In some embodiments, the expression cassette is inserted in the position where the adenoviral E1 gene is normally located. In addition, these vectors optionally have a non-functional or deleted E3 region. It is preferred that the adenovirus genome used be deleted of both the E1 and E3 regions (ΔE1ΔE3). The adenoviruses can be multiplied in known cell lines which express the viral E1 gene, such as 293 cells, or PERC.6 cells, or in cell lines derived from 293 or PERC.6 cell which are transiently or stablily transformed to express an extra protein. For examples, when using constructs that have a controlled gene expression, such as a tetracycline regulatable promoter system, the cell line may express components involved in the regulatory system. One example of such a cell line is T-Rex-293; others are known in the art.

For convenience in manipulating the adenoviral vector, the adenovirus may be in a shuttle plasmid form. This invention is also directed to a shuttle plasmid vector which comprises a plasmid portion and an adenovirus portion, the adenovirus portion comprising an adenoviral genome which has a deleted E1 and optional E3 deletion, and has an inserted expression cassette comprising a CEA fusion protein encoding nucleotide sequence. In preferred embodiments, there is a restriction site flanking the adenoviral portion of the plasmid so that the adenoviral vector can easily be removed. The shuttle plasmid may be replicated in prokaryotic cells or eukaryotic cells.

In a preferred embodiment of the invention, the expression cassette is inserted into the pMRKAd5-HV0 adenovirus plasmid (See Emini et al., WO 02/22080, which is hereby incorporated by reference). This plasmid comprises an Ad5 adenoviral genome deleted of the E1 and E3 regions. The design of the pMRKAd5-HV0 plasmid was improved over prior adenovectors by extending the 5' cis-acting packaging region further into the E1 gene to incorporate elements found to be important in optimizing viral packaging, resulting in enhanced virus amplification. Advantageously, this enhanced adenoviral vector is capable of maintaining genetic stability following high passage propagation.

Standard techniques of molecular biology for preparing and purifying DNA constructs enable the preparation of the adenoviruses, shuttle plasmids, and DNA immunogens of this invention.

It has been determined in accordance with the present invention that the CEA-LT fusion protein-encoding molecules described herein (e.g. SEQ ID NO:12), which comprise a substantial portion of the LTA or LTB subunits of *E. coli* heat labile enterotoxin, are expressed with equivalent efficiency compared to the corresponding wild type CEA sequence (See EXAMPLE 4). It has also been shown herein that plasmids pV1J/hCEA-LTA and pV1J/hCEA-LTB elicited a greater antibody response than pV1J/hCEA, confirming the adjuvant effect exerted by the LT subunits on the CEA specific immune response (See EXAMPLE 11). Thus, the data described herein demonstrate that fusion of the CEA coding sequence to the LTA or LTB cDNA results in an increase the CEA specific immune response. It appears that LTB exerts a greater enhancing effect on the immune response with a prevalent induction of $CD8^+$ T cells, whereas LTA elicits a predominant $CD4^+$ response.

It has also been shown in accordance with the present invention that tolerance to the CEA self antigen can be broken more efficiently, relative to the full-length wild-type CEA cDNA, due to the increased immunogenic properties of the CEA-LTB fusion. The enhancing effect of LTB on the immunogenic properties of CEA was also observed upon injection of a plasmid carrying a fully codon optimized cDNA of the CEA-LTB fusion. Lastly, the results described herein, using adenovirus vectors carrying CEA-LT fusions, indicate that that enhanced immunogenicity of CEA-LT fusions is not limited to plasmid DNA immunization (see EXAMPLE 13).

It has further been shown in accordance with the present invention that plasmids pV1J/hCEA-DOM and pV1J/hCEA-FcIgG elicited a greater CEA-specific cell-mediated and humoral immune response than CEA (See EXAMPLE 15). It has also been shown in accordance with the present invention that tolerance to the CEA self antigen can be broken more efficiently with the DOM and FcIgG CEA fusions described herein, relative to the full-length wild-type CEA cDNA, due to the increased immunogenic properties of the CEA fusions. The enhanced immunogenic properties of these fusion proteins were observed upon immunization with DNA or Ad vectors, indicating that enhanced immunogenicity of CEA-LT fusions is not limited to plasmid DNA immunization (see EXAMPLE 16).

Therefore, the vectors described above may be used in immunogenic compositions and vaccines for preventing the development of adenocarcinomas associated with aberrant CEA expression and/or for treating existing cancers. The vectors of the present invention allow for vaccine development and commercialization by eliminating difficulties with obtaining high expression levels of exogenous CEA in successfully transformed host organisms and by providing a CEA fusion protein which can elicit an enhanced immune response when administered to a mammal such as a human being.

To this end, one aspect of the instant invention is a method of preventing or treating CEA-associated cancer comprising administering to a mammal a vaccine vector comprising a polynucleotide comprising a sequence of nucleotides that encodes a CEA fusion protein, wherein the CEA fusion protein comprises a CEA protein or variant thereof, fused to a substantial portion of an immunoenhancing element selected from the group consisting of: heat shock protein (HSP) 70, lysosome-associated membrane protein (LAMP), fragment C of tetanus toxoid (FrC), the N-terminal domain of FrC (DOM), the heavy fragment of constant chain of immune globulin G1 (FcIgG), the vesicular stomatitis virus glycoprotein (VSV-G), cholera toxin (CT) from *Vibrio cholerae*, and heat labile enterotoxin of *E. coli* (LT); and wherein the fusion protein is capable of producing an immune response in a mammal.

In preferred embodiments of the methods described herein, the immunoenhancing element is selected from the group consisting of: LTA, LTB, DOM and FcIgG.

In accordance with the method described above, the vaccine vector may be administered for the treatment or prevention of a cancer in any mammal, including but not limited to: lung cancer, breast cancer, and colorectal cancer. In a preferred embodiment of the invention, the mammal is a human.

Further, one of skill in the art may choose any type of vector for use in the treatment and prevention method described. Preferably, the vector is an adenovirus vector or a plasmid vector. In a preferred embodiment of the invention, the vector is an adenoviral vector comprising an adenoviral genome with a deletion in the adenovirus E1 region, and an insert in the adenovirus E1 region, wherein the insert comprises an expression cassette comprising: (a) a sequence of nucleotides that encodes a CEA fusion protein, wherein the CEA fusion protein comprises a CEA protein or variant thereof, fused to an immunoenhancing element or substantial portion thereof; wherein the immunoenhancing element is selected from the group consisting of: heat shock protein (HSP) 70, lysosome-associated membrane protein (LAMP), fragment C of tetanus toxoid (FrC), the N-terminal domain of FrC (DOM), the heavy fragment of constant chain of immune globulin G1 (FcIgG), the vesicular stomatitis virus glycoprotein (VSV-G), cholera toxin (CT) from *Vibrio cholerae*, and heat labile enterotoxin of *E. coli* (LT); and wherein the fusion protein is capable of producing an immune response in a mammal; and (b) a promoter operably linked to the polynucleotide.

The instant invention further relates to an adenovirus vaccine vector comprising an adenoviral genome with a deletion in the E1 region, and an insert in the E1 region, wherein the insert comprises an expression cassette comprising: (a) a sequence of nucleotides that encodes a CEA fusion protein, wherein the CEA fusion protein comprises a CEA protein or variant thereof, fused to a substantial portion of an immunoenhancing element; wherein the immunoenhancing element is selected from the group consisting of: HSP70, LAMP, FrC, DOM, FcIgG, VSV-G, CT, LTA and LTB; and wherein the fusion protein is capable of producing an immune response in a mammal; and (b) a promoter operably linked to the polynucleotide.

In a preferred embodiment of this aspect of the invention, the adenovirus vector is an Ad 5 vector.

In another preferred embodiment of the invention, the adenovirus vector is an Ad 6 vector.

In yet another preferred embodiment, the adenovirus vector is an Ad 24 vector.

Also contemplated for use in the present invention is an adenovirus vaccine vector comprising a adenovirus genome that naturally infects a species other than human, including, but not limited to, chimpanzee adenoviral vectors. A preferred embodiment of this aspect of the invention is a chimp Ad 3 vaccine vector.

In another aspect, the invention relates to a vaccine plasmid comprising a plasmid portion and an expression cassette portion, the expression cassette portion comprising: (a) a sequence of nucleotides that encodes a CEA fusion protein, wherein the CEA fusion protein comprises a CEA protein or variant thereof, fused to an immunoenhancing element or substantial portion thereof, selected from the group consisting of: HSP70, LAMP, FrC, DOM, the FcIgG, VSV-G, CT, LTA and LTB; and wherein the fusion protein is capable of producing an immune response in a mammal; and (b) a promoter operably linked to the polynucleotide.

In some embodiments of this invention, the recombinant adenovirus and plasmid-based polynucleotide vaccines disclosed herein are used in various prime/boost combinations in order to induce an enhanced immune response. In this case, the two vectors are administered in a "prime and boost" regimen. For example the first type of vector is administered one or more times, then after a predetermined amount of time, for example, 2 weeks, 1 month, 2 months, six months, or other appropriate interval, a second type of vector is administered one or more times. Preferably the vectors carry expression cassettes encoding the same polynucleotide or combination of polynucleotides. In the embodiment where a plasmid DNA is also used, it is preferred that the vector contain one or more promoters recognized by mammalian or insect cells. In a preferred embodiment, the plasmid would contain a strong promoter such as, but not limited to, the CMV promoter. The synthetic CEA fusion gene or other gene to be expressed would be linked to such a promoter. An example of such a plasmid would be the mammalian expression plasmid V1Jns as described (J. Shiver et. al. in *DNA Vaccines*, M. Liu et al. eds., N.Y. Acad. Sci., N.Y., 772:198-208 (1996), which is herein incorporated by reference).

As stated above, an adenoviral vector vaccine and a plasmid vaccine may be administered to a vertebrate as part of a single therapeutic regime to induce an immune response. To this end, the present invention relates to a method of protecting a mammal from a CEA-associated cancer comprising: (a) introducing into the mammal a first vector comprising: i) a sequence of nucleotides that encodes a CEA fusion protein, wherein the CEA fusion protein comprises a CEA protein or variant thereof, fused to a substantial portion of an immunoenhancing element selected from the group consisting of: HSP70, LAMP, FrC, DOM, the FcIgG, VSV-G, CT, LTA and LTB; and wherein the fusion protein is capable of producing an immune response in a mammal; and ii) a promoter operably linked to the polynucleotide; (b) allowing a predetermined amount of time to pass; and (c) introducing into the mammal a second vector comprising: i) a sequence of nucleotides that encodes a CEA fusion protein, wherein the CEA fusion protein comprises a CEA protein or variant thereof, fused to a substantial portion of an immunoenhancing element selected from the group consisting of: HSP70, LAMP, FrC, DOM, the FcIgG, VSV-G, CT, LTA and LTB; and wherein the fusion protein is capable of producing an immune response in a mammal; and ii) a promoter operably linked to the polynucleotide.

In one embodiment of the method of protection described above, the first vector is a plasmid and the second vector is an adenovirus vector. In an alternative embodiment, the first vector is an adenovirus vector and the second vector is a plasmid.

In the method described above, the first type of vector may be administered more than once, with each administration of the vector separated by a predetermined amount of time. Such a series of administration of the first type of vector may be followed by administration of a second type of vector one or more times, after a predetermined amount of time has passed. Similar to treatment with the first type of vector, the second type of vector may also be given one time or more than once, following predetermined intervals of time.

The instant invention further relates to a method of treating a mammal suffering from a CEA-associated adenocarcinoma comprising: (a) introducing into the mammal a first vector comprising: i) a sequence of nucleotides that encodes a CEA fusion protein, wherein the CEA fusion protein comprises a CEA protein or variant thereof, fused to a substantial portion of an immunoenhancing element selected from the group consisting of: HSP70, LAMP, FrC, DOM, the FcIgG, VSV-G, CT and LT; and wherein the fusion protein is capable of producing an immune response in a mammal; and ii) a promoter operably linked to the polynucleotide; (b) allowing a predetermined amount of time to pass; and (c) introducing into the mammal a second vector comprising: i) a sequence of nucleotides that encodes a CEA fusion protein, wherein the CEA fusion protein comprises a CEA protein or variant thereof, fused to a substantial portion of an immunoenhancing element selected from the group consisting of: HSP70, LAMP, FrC, DOM, the FcIgG, VSV-G, CT and LT; and wherein the fusion protein is capable of producing an immune response in a mammal; and ii) a promoter operably linked to the polynucleotide.

In one embodiment of the method of treatment described above, the first vector is a plasmid and the second vector is an adenovirus vector. In an alternative embodiment, the first vector is an adenovirus vector and the second vector is a plasmid.

In preferred embodiments of the methods described above, the vectors comprise a sequence of nucleotides that encode a CEA-LT fusion protein, wherein the CEA fusion protein comprises a CEA protein or variant thereof, fused to a substantial portion of a LT subunit. In further preferred embodiments, the vector comprises a sequence of nucleotides that encodes a CEA-LTB fusion protein. In further preferred embodiments of the methods described above, the vectors comprise a sequence of nucleotides that encode a CEA-DOM fusion protein, wherein the CEA fusion protein comprises a CEA protein or variant thereof, fused to a substantial portion of a DOM subunit. In still further preferred embodiments, the vector comprises a sequence of nucleotides that encodes a CEA-FcIgG fusion protein.

The amount of expressible DNA or transcribed RNA to be introduced into a vaccine recipient will depend partially on the strength of the promoters used and on the immunogenicity of the expressed gene product. In general, an immunologically or prophylactically effective dose of about 1 ng to 100 mg, and preferably about 10 μg to 300 μg of a plasmid vaccine vector is administered directly into muscle tissue. An effective dose for recombinant adenovirus is approximately $10^6$-$10^{12}$ particles and preferably about $10^7$-$10^{11}$ particles. Subcutaneous injection, intradermal introduction, impression though the skin, and other modes of administration such as intraperitoneal, intravenous, intramuscular or inhalation delivery are also contemplated.

In preferred embodiments of the present invention, the vaccine vectors are introduced to the recipient through intramuscular injection.

The vaccine vectors of this invention may be naked, i.e., unassociated with any proteins, or other agents which impact on the recipient's immune system. In this case, it is desirable for the vaccine vectors to be in a physiologically acceptable solution, such as, but not limited to, sterile saline or sterile buffered saline. Alternatively, it may be advantageous to administer an agent which assists in the cellular uptake of DNA, such as, but not limited to calcium ion. These agents are generally referred to as transfection facilitating reagents and pharmaceutically acceptable carriers. Those of skill in the art will be able to determine the particular reagent or pharmaceutically acceptable carrier as well as the appropriate time and mode of administration.

All publications mentioned herein are incorporated by reference for the purpose of describing and disclosing methodologies and materials that might be used in connection with the present invention. Nothing herein is to be construed as an admission that the invention is not entitled to antedate such disclosure by virtue of prior invention.

Having described preferred embodiments of the invention with reference to the accompanying drawings, it is to be understood that the invention is not limited to those precise embodiments, and that various changes and modifications may be effected therein by one skilled in the art without departing from the scope or spirit of the invention as defined in the appended claims.

The following examples illustrate, but do not limit the invention.

EXAMPLE 1

Construction of CEA Fusion Proteins

Figure 18A:
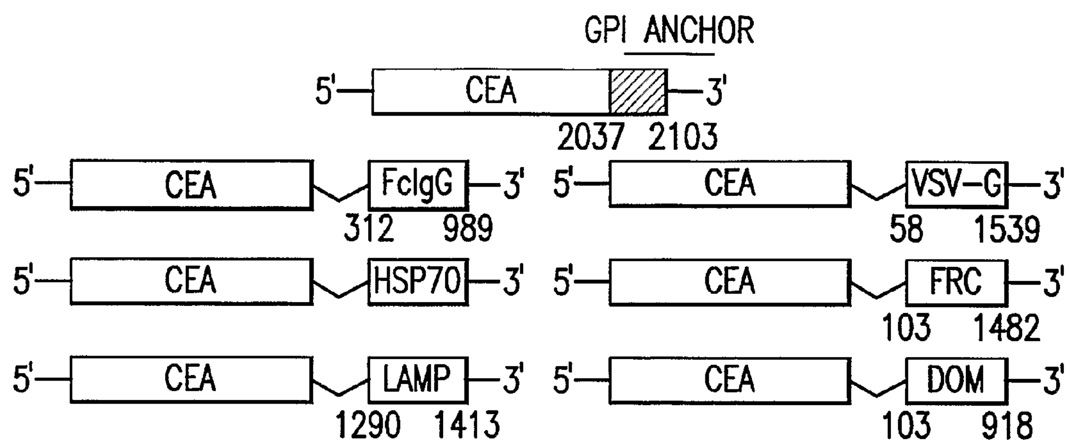

To determine the immunogenicity of CEA fusion proteins, a series of vectors were constructed encoding amino acids (hereinafter aa) 1 to 679 of the human CEA protein fused to a panel of selected polypeptides (see EXAMPLE 2). These sequences were chosen in view of their reported immunoenhancing properties, which have been demonstrated in a variety of experimental systems. The CEA fusions were engineered by joining the cDNA of the CEA protein deleted of the GPI anchoring sequence to the foreign polypeptides (exemplary constructs are depicted in FIG. 18A). The tumor antigen was linked to the HSP70, FcIgG or LAMP sequences to determine whether enhancement of antigen uptake or retargeting to the endosomal compartment would lead to an increased immune response. Similarly, fusion to fragment C of tetanus toxin (FrC) or to a minimal domain devoid of potentially competitive MHC class I binding epitopes (DOM, see FIG. 29) (Rice et al. *J. Immunol.* 169: 3908-13 (2002)) was constructed to promote humoral and $CD4^+$ T cell responses. CEA was also linked to the VSV-G coding sequence to determine whether fusion to a viral glycoprotein would influence the immunogenic properties of CEA.

The coding sequences of these CEA-fusions were cloned into vectors pV1Jns under the control of the human CMV/intron A promoter plus the bovine growth hormone (BGH) polyadenylation signal (EXAMPLE 2). Plasmids pV1J/CEA-FRC, pV1J/CEA-DOM, pV1J/CEA-FcIgG, pV1J/CEA-LAMP, pV1J/CEA-VSV-G, and pV1J/CEA-HSP70 carry the wild type cDNA of CEA fused to the coding sequences of the indicated foreign polypeptides. Exemplary nucleotide and amino acid sequences of hCEA-DOM and hCEA-FcIgG fusions are shown in FIGS. 26, 27, and 30.

To assess the effect of LTA and LTB subunits of the *E. coli* heat labile enterotoxin on CEA immunogenicity, a series of additional fusion constructs were generated encoding amino acids 1 to 679 of CEA protein fused to either the LTA (aa 18 to 259) or the LTB (aa 21 to 125) coding sequence. A schematic representation of the structure of exemplary CEA-LTA and CEA-LTB fusions developed for this study are shown in FIG. 1. Exemplary nucleotide and amino acid sequences of CEA-LT fusions are shown in FIGS. 2-6.

CEA-LT fusions were engineered by joining the cDNA of the CEA protein deleted of the anchoring sequence to the LT subunits to which the signal peptide coding sequence had been removed. The CEA-fusions coding sequences were cloned into vectors pV1Jns under the control of the human cytomegalovirus (CMV)/intron A promoter plus the bovine growth hormone (BGH) polyadenylation signal. Plasmids pV1J/hCEA-LTA and pV1J/hCEA-LTB carry the wild type cDNA of CEA fused to the coding sequences of LTA and LTB, respectively (see EXAMPLE 2).

All constructs carrying the CEA-LTB fusion were generated by fusing the CEA cDNA from nt 1 to 2037, with the LTB cDNA fragment encompassing nt 64 to 375. The LTB coding sequence was obtained by PCR amplification of *E. coli* genomic DNA using sequence specific primers LTB-S1 5'-TATTCTAGATGCTCCCCAGACTATTACAGAA-3' (SEQ ID NO:1)and LTB-A1 5'-TATGCGGCCGCCTAGTTTTCCATACTGATTGCCGC-3' (SEQ ID NO:2). The amplified DNA was introduced at the 3' end of the CEA coding sequence generating plasmids.

EXAMPLE 2

Plasmid Constructs pV1J/CEA$_{opt}$ and pV1J/CEA: These two constructs carry the codon usage optimized and wild type cDNA of CEA, respectively. The CEA coding sequence is located between the CMV/intronA immediate early promoter of cytomegalovirus and the bovine growth hormone polyadenylation signal. For generation of pV1J/hCEA$_{opt}$, plasmid pCR-hCEAopt was digested with EcoRI for 1 hr at 37° C. The resulting 2156 bp insert was purified and cloned into the EcoRI site of plasmid pV1JnsB ((Montgomery et al. *DNA Cell Biol* 12(9): 777-83 (1993)).

For generation of pV1J/hCEA, plasmid pCI/hCEA (Song et al. Regulation of T-helper-1 versus T-helper-2 activity and enhancement of tumour immunity by combined DNA-based vaccination and nonviral cytokine gene transfer. *Gene Therapy* 7: 481-492 (2000)) was digested with EcoRI. The resulting 2109 bp insert was cloned into the EcoRI site of plasmid pV1JnsA (Montgomery et al., supra).

pV1J/hCEA-LTB and pV1J/hCEA$_{opt}$-LTB: The codon optimized cDNA of LTB was synthetized by oligonucleotide assembly (Geneart GmbH, Regensburg, Germany) and cloned in pCR-script vector (Stratagene, LA Jolla, Calif.). To generate pV1J/hCEA$_{opt}$-LTB$_{opt}$, LTB$_{opt}$ was amplified by PCR using the following PCR primers: LTBopt-5'XbaI (5' end) 5'-GCTCTAGAGCCCCCCAGAGCATCACCGAGCTGTGC-3' (SEQ ID NO:3)and LTBopt-3'BglII (3' end) 5'-GCTCTAGAACCCCTCAGAACATCACCGATCTGTGCGCC-3' (SEQ ID NO:4). The amplified product was then inserted into the XbaI/BglII sites of plasmid pV1J/hCEA$_{opt}$.

pV1J/hCEA-LTA: The LTA coding sequence corresponding to nt 54 to 774 that encode aa 18 to 259, was amplified by PCR from genomic DNA of *E. coli* using sequence specific primers LTA-S1 5' -TATTCTAGATAATGGCGACAAATTATACCG-3' (SEQ ID NO:5) and LTA-A1 5' -TATGCGGCCGCTCATAATTCATCCCGAATTCTGTT-3' (SEQ ID NO:6). The amplified DNA was digested with appropriate restriction enzymes and inserted into plasmid pV1J/hCEA.

pV1J/rhCEAopt-LTB: A 3' fragment of the rhesus monkey CEA cDNA (nt 1641 to 2026), which was codon-optimized for high level expression in human cells, was amplified by PCR from pV1J-rhCEAopt. The amplified cDNA lacked the GPI anchor coding sequence and carried the XbaI/BglII restriction sites. This fragment was inserted into the PstI site of pCR-blunt-rhCEAopt, thus obtaining the intermediate pCR-blunt-rhCEAopt XbaI/BglII. rhCEAopt was extracted as a BglII/SalI fragment and cloned in the same sites in pV1J-nsB, thus obtaining pV1J-rhCEAopt XbaI/BglII. LTBopt was amplified by PCR from pCR-script-LTBopt adding XbaI and BglII sites at 5' and 3' ends, respectively, and was cloned in pV1J-rhCEAopt XbaI/BglII, thus obtaining pV1J-rhCEAopt-LTBopt.

pV1J/CEA-FrC, pV1J/CEA-DOM, pV1J/CEA-FcIgG, pV1J/CEA-LAMP, pV1J/CEA-HSP70 and pV1J/CEA-VSV-G: All the constructs encoding the referenced CEA fusion proteins were generated by fusing the CEA cDNA from nt 1 to nt 2037 (SEQ ID NO:22, FIG. 28A), corresponding to aa 1 to aa 679 (SEQ ID NO:23, FIG. 28B), with the cDNA fragment corresponding to the following: fragment C of tetanus toxoid (CEA-FrC, SEQ ID NO:24), the N-terminal domain of FrC (CEA-DOM, SEQ ID NOs:21 and 49), the heavy fragment of constant chain of immune globulin G1 (CEA-FcIgG, SEQ ID NO:25), the lysosome-associated membrane protein (CEA-LAMP, SEQ ID NO:26), the heat shock protein 70 (CEA-HSP70, SEQ ID NO:27), or the vesicular stomatitis virus glycoprotein (CEA-VSV-G, SEQ ID NO:28).

FrC and DOM coding sequences were obtained by PCR amplification from pRep-TeT.C plasmid as described in Rice et al. (*J. Immunol.* 169: 3908-13 (2002)). FcIgG was obtained from total RNA of human PBMC. VSV-G and HSP70 were obtained from p-FAST-VSV-G and from plasmid pY3111, respectively. LAMP1 was obtained by gene assembly. Amplifications were carried out using the following primers: FrC sense (5'-TATTCTAGATTCAACACCAATTCCATTTTCTTATTC-3' (SEQ ID NO:29) FrC antisense (5'-GCGGCCGCTAGAATCATTTGTCCATCCTTCATC-3' (SEQ ID NO:30), DOM sense (5'-TATTCTAGATTCAACACCAATTCCATTTTCTTATTC-3' (SEQ ID NO:31) DOM antisense (5-TTAGCGGCCGCTAGTTCTGTATCATATCGTAAAGGG-3' (SEQ ID NO:32), FcIgG sense (5'-TCTAGATAAAACTCACACATGCCCA-3' (SEQ ID NO:33) FcIgG antisense (5'-GCCGACTCATTTACCCGGAGACAGGGAG-3' (SEQ ID NO:34), LAMP sense (5-TCTAGATTTGATCCCCATTGCTGTGGGCGGTGCCCTG-3' (SEQ ID NO:35) LAMP antisense (5'-GGCGTGACTCCTCTTCCTGCCAATGAGGTAGGCAATGAG-3' (SEQ ID NO:36), VSV-G sense (5'-ATATCTAGATTTCACCATAGTTTTTCCACACAACC-3' (SEQ ID NO:37) VSV-G antisense (5'-GCGGCCGCCTTCCTTCCAAGTCGGTTCATCTCTATG-3' (SEQ ID NO:38), HSP70 sense (5'-GCTCTAGATATGGCTCGTGCGGTCGGGATCGACC-3' (SEQ ID NO:39)) and HSP70 antisense (5'GCCGCGGCCGCTCACTTGGCCTCCCGGCCGTCGTCG-3' (SEQ ID NO:40). The amplified DNA was introduced at the 3' end of the CEA coding sequence generating plasmids pV1J/CEA-FrC, pV1J/CEA-DOM, pV1J/CEA-FcIgG, pV1J/CEA-LAMP, pV1J/CEA-HSP70 and pV1J/CEA-VSV-G.

pV1J/CEA-DOMopt and pV1J/CEA-FcIgopt: The codon usage optimized cDNA of DOM and FcIgG were synthesized by oligonucleotide assembly (Geneart GmbH, Regensburg, Germany) and cloned in pCR-script vector (Stratagene, La Jolla, Calif.). To generate pV1J/CEA-DOMopt, $DOM_{opt}$ was amplified by PCR using the following primers: $Dom_{opt}$ sense (5'-GTTATCTAGAAGCACCCCCATCCC-3' (SEQ ID NO:41)) and $Dom_{opt}$ reverse (5'-TTAAGATCTCTAAGATCTGGTGTCGTATCTCAGGGG-3' (SEQ ID NO:42). The amplified product was then inserted into the XbaI/BglII sites of plasmid pV1J/CEAopt. To generate pV1J/CEA-FcIgGopt, $FcIgG_{opt}$ was amplified by PCR using the following primers: $FcIgG_{opt}$ sense (5'-TTATCTAGAAAGACCCACACCTGCCCCCCTTGC-3' (SEQ ID NO:43)) and as $FcIgG_{opt}$ reverse (5'-TATAGATCTTAGGGTACCTTACTTGCCGGGG-3' (SEQ ID NO:44)) the amplified product was inserted into XbaI/BglII sites of plasmid pV1J/CEAopt.

EXAMPLE 3

Adenovirus Vectors $Ad5/hCEA_{opt}$: Plasmid pCR-hCEAopt was digested with EcoRI. The resulting 2156 bp insert was purified and cloned into the EcoRI of the polyMRK-Ad5 shuttle plasmid.

Ad5/CEA: The shuttle plasmid pMRK-hCEA for generation of Ad5 vector was obtained by digesting plasmid pDelta1sp1B/hCEA with SspI and EcoRV. The 9.52 kb fragment was then ligated with a 1272 bp BglII/BamHI-restricted, Klenow-treated product from plasmid polyMRK. A PacI/StuI fragment from pMRK-hCEA and pMRK-hCEAopt containing the expression cassette for hCEA and E1 flanking Ad5 regions was recombined to ClaI linearized plasmid pAd5 in BJ5183 *E. coli* cells. The resulting plasmids were pAd5-hCEA and pAd5-hCEAopt, respectively. Both plasmids were cut with PacI to release the Ad ITRs and transfected in PerC-6 cells. Ad5 vectors amplification was carried out by serial passage. MRKAd5/hCEA and MRKAd5/hCEAopt were purified through standard CsCl gradient purification and extensively dialyzed against A105 buffer (5 mM Tris-Cl pH 8.0, 1 mM $MgCl_2$, 75 mM NaCl, 5% Sucrose, 0.005 Tween 20).

Ad5/hCEAopt-LTB: Plasmid pMRK-hCEAopt-LTB was constructed by cutting polyMRK-Ad5 shuttle plasmid with SwaI and by ligating the linearized vector with the 2300 bp DNA fragment derived from pV1J/hCEAopt-LTB that had been restricted with EcoRI, BglII and treated with Klenow. The pMRK-hCEAopt-LTB was linearized and recombined into the Ad genome as indicated above.

Ad5/CEA-DOMopt and Ad5/CEA-FcIgGopt: Plasmid pMRK-CEA-DOMopt and pMRK-CEA-FcIgGopt were constructed by cutting polyMRK-Ad5 shuttle plasmid with SwaI and by ligating the linearized vector with the 2.9 kb DNA fragment derived from pV1J/CEA-DOMopt or ligating the linearized vector with the 2700 bp DNA fragment derived from pV1J/CEA-FcIgG1opt that had been restricted with EcoRI, BglII and treated with Klenow. pMRK-CEA-FcIgGopt and pMRK-CEA-DOMopt were linearized and recombined into the Ad genome as indicated above.

EXAMPLE 4

Comparative Expression Efficiency of Various CEA-LT Fusion Constructs

The use of codon optimized cDNAs for genetic vaccination against viral diseases has been shown to elicit a greater immune response due, at least in part, to an increased expression of the target protein. To verify whether the LTB coding sequence would also enhance the immunogenic properties of the CEA cDNA designed to incorporate human-preferred (humanized) codons for each amino acid residue, plasmid pV1J/hCEAopt-LTB was also constructed. Finally, a fully codon optimized version of the CEA-LTB fusion was also constructed using a synthetic codon optimized cDNA of LTB to generate plasmid pV1J/hCEA-LTBopt.

To determine whether the LTB effect on CEA immunogenicity was not limited to plasmid DNA immunization, an Adenovirus type 5 vector encoding the CEAopt-LTB fusion flanked by the CMV/intron A promoter and the BGH polyadenylation signal was also constructed. The molecular mass of the CEA fusion proteins expressed by both plasmid and Ad vectors did not differ from that derived from the corresponding vectors encoding the full length form of CEA cDNA (data not shown).

To compare the efficiency of expression of the vectors encoding the CEA-LTA and CEA-LTB fusions and that of the cDNA of full length CEA, HeLa cells were transfected with plasmids pV1J/hCEA-LTA, and pV1J/hCEA-LTB. The CEA expression of these constructs was compared to that of the corresponding plasmid carrying the wt cDNA of CEA, pV1J/hCEA. Similarly, plasmid pV1J/hCEAopt-LTB expression efficiency was compared to that of pV1J/hCEAopt. Expression efficiency of these constructs were determined two days post transfection by monitoring the amount of CEA protein in cell extracts.

Figure 8A:
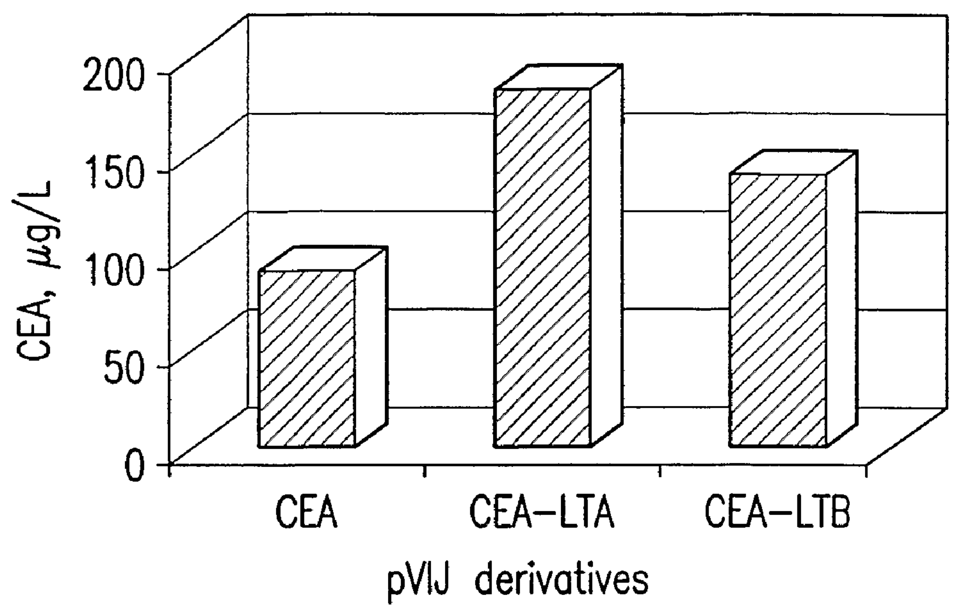
FIG. 8 shows a comparison of CEA expression efficiency in cells transfected with different CEA constructs. Panel A depicts the expression efficiencies of HeLa cells transfected with 3 μg of plasmids carrying the wild type sequences of hCEA, hCEA-LTA, and hCEA-LTB, in conjunction with 0.2 μg of plasmid pV1J/mEPO as tracer. Panel B shows results from a similar transfection experiment using pV1J/hCEAopt and pV1J/hCEAopt-LTB. Expression efficiency was determined three days post-transfection by measuring the amount of CEA protein present in cell extracts and by normalizing this value for EPO expression. Data shown relates to the average CEA expression values of two independent transfections.
Figure 8B:
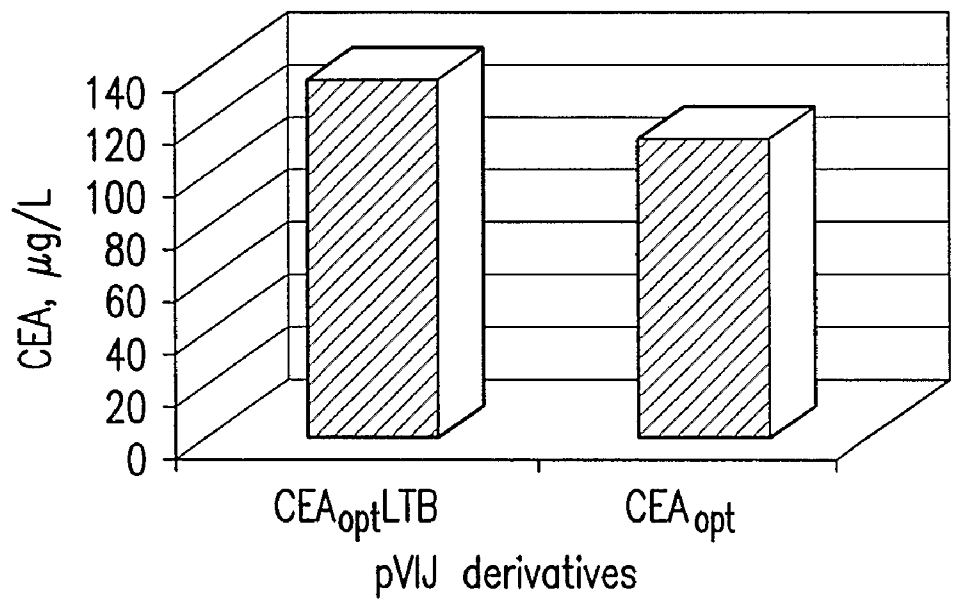
Figure 9:
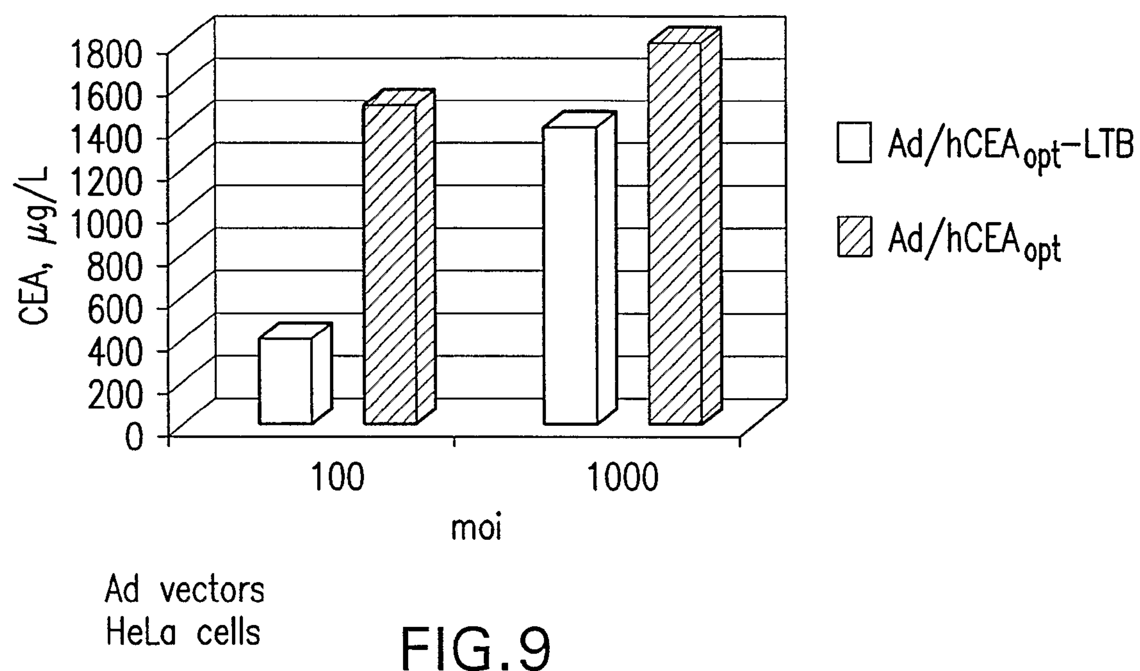
FIG. 9 shows a comparison of the expression efficiency of different Adenovirus recombinant vectors expressing CEA. HeLa cells were infected at an moi of 100 and 1000 with Ad/hCEAopt and Ad/hCEAopt-LTB. Expression efficiency was determined by measuring three days post infection the amount of CEA protein released in cell extracts. Data shown reflects the average CEA expression values of two independent infections.

Transfection of plasmids pV1J/hCEA-LTA and pV1J/hCEA-LTB yielded approximately two fold higher amounts of CEA protein (183 and 139 μg/l, respectively, FIG. 8A) detected in the culture supernatant as compared to plasmid pV1J/CEA (91 μg/l). Similarly, the expression efficiency of constructs pV1J/hCEAopt and pV1J/hCEAopt-LTB was also comparable (113 and 136 μg/l, respectively; FIG. 8B). Finally, the expression efficiency of the Ad/hCEAopt and Ad/hCEAopt-LTB was also compared by infecting HeLa cells at different moi. The CEA expression efficiency of these two vectors was comparable at moi 1000 (1790 and 1400 μg/l, respectively, FIG. 9) whereas at moi 100, vector Ad/hCEAopt-LTB yielded approximately four fold lower amounts of CEA protein detectable in the culture supernatant than Ad/hCEAopt (390 and 1500 μg/l, respectively).

Thus, these results indicate that the cDNA encoding the CEA-LTA and CEA-LTB fusion proteins are expressed with equivalent efficiency to that of the corresponding cDNA encoding the full length CEA protein. Additionally, the comparable CEA expression of these cDNAs is not influenced by the type of the gene transfer vehicle utilized for their delivery.

EXAMPLE 5

Detection of CEA Expression.

CEA expression by plasmid and Ad vectors was monitored by Western blot analysis and ELISA. Plasmids were transfected in HeLa cells with Lipofectamine 2000 (Life Technologies). Adenovirus infections of HeLa cells were performed in serum free medium for 30 min at 37° C., and then fresh medium was added. After 48 hr incubation, whole cell lysates were harvested. The CEA protein present in the cell lysates was detected by Western blot analysis using a rabbit polyclonal antiserum. The protein was detected as a 180-200 kDa band. The amount of expressed CEA was detected in the cell lysates using the Direct Elisa CEA Kit (DBC-Diagnostics Biochem Canada Inc).

Expression of the fusion proteins in transfected cells was examined by Western blot analysis using antibodies specific for CEA, VSV-G, FcIgG, tetanus toxin, or HSP70. HeLa cells were either transfected with the indicated plasmid or infected with the selected Ad vector. After 48 hr incubation, whole cell lysates and culture supernatant were harvested.

Figure 18B:
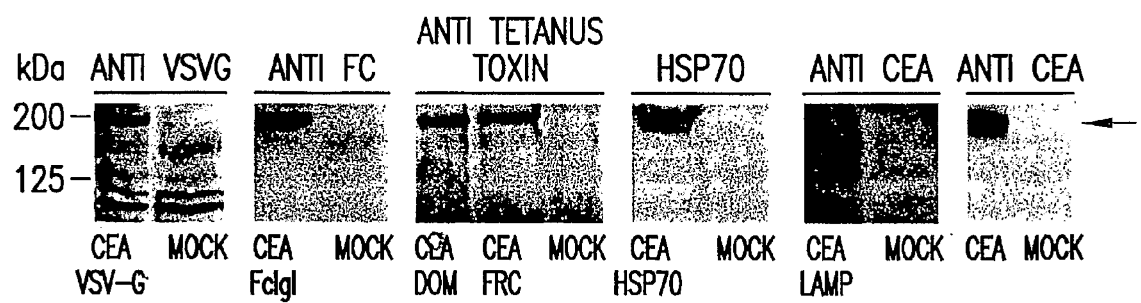

CEA expression in cell lysate or supernatant was also monitored using the Direct Elisa CEA Kit (DBC-Diagnostics Biochem Canada Inc). CEA protein was detected with the antibody specific for the fused polypeptide in transfected cell lysates, whereas no expression of the target antigen was observed in the mock transfected control samples (FIG. 18B). The molecular mass of the fusion proteins did not differ significantly from that of CEA. This apparent lack of difference in molecular mass between the various CEA polypeptides is probably due to the high degree of glycosylation of the tumor antigen.

Figure 19A:
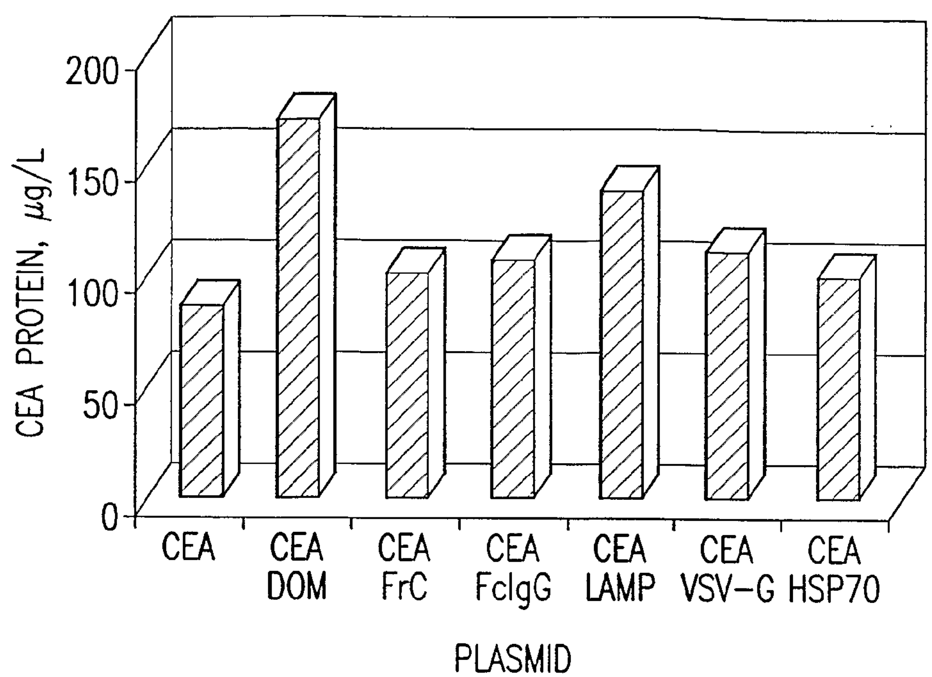
FIG. 19 shows a comparison of expression efficiency of the CEA fusion constructs. HeLa cells were transfected with the indicated plasmids and CEA derived protein present in cell lysates (A) and supernatants (B) was measured by ELISA as described in EXAMPLE 8. Results obtained are representative of two independent experiments.
Figure 19B:
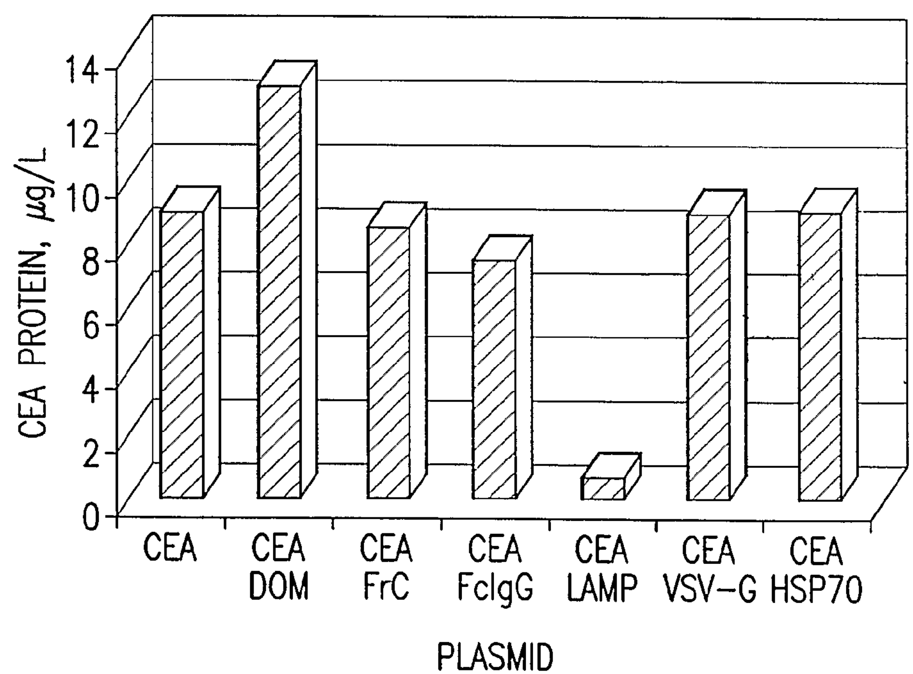

To compare the efficiency of expression of the vectors encoding the CEA-fusions to that of pV1J/CEA, HeLa cells were transfected with the different plasmids and CEA expression of these constructs was determined two days post transfection by ELISA. Plasmids pV1J/CEA-FrC, pV1J/CEA-DOM, pV1J/CEA-FcIgG, pV1J/CEA-LAMP, pV1J/CEA-VSV-G and pV1J/CEA-HSP70 expressed CEA with comparable efficiency as pV1J/CEA (FIG. 19A). Most of the fusion proteins were secreted and detected in the cell supernatant; however, CEA-LAMP was not released from the transfected cells, probably due to its re-routing to the lysosomal compartment. (FIG. 19B). Thus, these results indicate that the cDNA encoding the CEA-FrC, CEA-DOM, CEA-VSV-G, CEA-FcIgG, CEA-HSP70 and CEA-LAMP fusion proteins are expressed with equivalent efficiency to that of the cDNA encoding the full length CEA protein.

EXAMPLE 6

Peptides

Lyophilized hCEA peptides were purchased from Bio-Synthesis and resuspended in DMSO at 40 mg/ml. Pools of peptides 15 aa long overlapping by 11 residues were assembled as described (Facciabene et al. *J. Virol.* 78: 8663-72 (2004). Final concentrations were the following: pool A=1.2 mg/ml, pool B 0.89 mg/ml, pool C 0.89 mg/ml, pool D 0.8 mg/ml. Peptides were stored at −80° C. Immune response to DOM was monitored using the tetanus toxoid peptide p30 ($F_{947}$NNFTVSFWLRVPKVSASHLE$_{967}$ (SEQ ID NO:54)) (Rice et al. *J. Immunol.* 167: 1558-65 (2001)).

EXAMPLE 7

Mice Immunization and Tumor Challenge

All animal studies were approved by the IRBM institutional animal care and use committee. Female C57BL/6 mice (H-$2^b$) were purchased from Charles River (Lecco, Italy). HLA-A2.1 mice (HHD) were kindly provided by F. Lemmonier (Institute Pasteur, Paris, France). C57BL/DR4 mice were purchased from Taconic (Germantown, N.Y.). CEA.tg mice (H-$2^b$) were provided by J. Primus (Vanderbilt University) and kept in standard conditions (Clarke et al. *Cancer Res.* 58:1469-77 (1998)). Fifty micrograms of plasmid DNA were electroinjected in a 50 μl volume in mice quadriceps as previously described (Rizzuto et al. *Proc. Natl. Acad. Sci. U.S.A.* 96(11): 6417-22 (1999)). Ad injections were carried out in mice quadriceps in 50 μl volume. Humoral and cell mediated immune response were analyzed at the indicated time.

C57BL/6 mice were subjected to two DNA injections in quadriceps muscle followed by electrical stimulation as previously described (Rizzuto et al. supra). Injections were carried out at three-week intervals. CEA transgenic mice were subjected to either 5 weekly injections of plasmid DNA (50 μg/injection), 2 injections of Ad vectors ($1\times10^9$ viral particles/injection), or 5 weekly injections followed by a boost with Ad. Two weeks after the last injection, humoral and cell mediated immune response were analyzed. Mice were also challenged with a subcutaneous (s.c.) injection of $5\times10^5$ MC38-CEA cells (Clarke et al., supra). At weekly intervals, mice were examined for tumor growth.

EXAMPLE 8

Antibody Detection and Titration.

Sera for antibody titration were obtained by retro-orbital bleeding. ELISA plates (Nunc maxisorp) were coated with 100 ng/well of highly purified CEA protein (Fitzgerald), diluted in coating buffer (50 mM $NaHCO_3$, pH 9.4) and incubated O/N at 4° C. as previously described (Facciabene et al., supra). Plates were then blocked with PBS containing 5% BSA for 1 hr at 37° C. Mouse sera were diluted in PBS 5% BSA (dilution 1/50 to evaluate seroconversion rate; dilutions from 1:10 to 1:31,2150 to evaluate titer). Pre-immune sera were used as background. Diluted sera were incubated O/N at 4° C. Washes were carried out with PBS 1% BSA, 0.05% Tween 20. Secondary antibody (goat anti-mouse, IgG Peroxidase, Sigma) was diluted 1/2000 in PBS, 5% BSA and incubated 2-3 hr at RT on a shaker. After washing, plates were developed with 100 μl/well of TMB substrate (Pierce Biotechnology, Inc., Rockford, Ill.). Reaction was stopped with 25 μl/well of 1M $H_2SO_4$ solution and plates were read at 450 nm/620 nm. Anti-CEA serum titers were calculated as the reciprocal limiting dilution of serum producing an absorbance at least 3-fold greater than the absorbance of autologous pre-immune serum at the same dilution.

EXAMPLE 9

IFN-γ ELISPOT Assay

Assays were carried out using mouse splenocytes and CEA-specific peptides as previously described (Facciabene et al., supra). Ninety-six wells MAIP plates (Millipore Corp., Billerica, Mass.) were coated with 100 μl/well of purified rat anti-mouse IFN-γ (IgG1, clone R4-6A2, Pharmingen) diluted to 2.5 μ/ml in sterile PBS. After washing with PBS, blocking of plates was carried out with 200 μl/well of R10 medium for 2 hrs at 37° C.

Splenocytes were obtained by removing the spleen from the euthanized mice in a sterile manner and by spleen disruption by grating on a metal grid. Red blood cells were removed by osmotic lysis by adding 1 ml of 0.1×PBS to the cell pellet and vortexing for approximately 15 s. One ml of 2×PBS was then added and the volume was brought to 4 ml with 1×PBS. Cells were pelleted by centrifugation at 1200 rpm for 10 min at RT, and the pellet was resuspended in 1 ml R10 medium. Viable cells were counted using Türks staining.

Splenocytes were plated at $5\times10^5$ and $2.5\times10^5$ cells/well in duplicate and incubated for 20 h at 37° C. with 1 μg/ml suspension of each peptide. Concanavalin A (ConA) was used as positive internal control for each mouse at 5 μg/ml. After washing with PBS, 0.05% Tween 20, plates were incubated O/N at 4° C. with 50 μl/well of biotin-conjugated rat anti-mouse IFNγ (RatIgG1, clone XMG 1.2, PharMingen) diluted to 1:2500 in assay buffer. After extensive washing, plates were developed by adding 50 μl/well NBT/B-CIP (Pierce Biotechnology, Inc., Rockford, Ill.) until development of spots was clearly visible. The reaction was stopped by washing plates thoroughly with distilled water. Plates were air dried and spots were then counted using an automated ELISPOT reader.

EXAMPLE 10

Intracellular Cytokine Staining.

One to two million mouse splenocytes or PBMC in 1 ml RPMI 10% FCS were incubated with pool of peptides (5-6 μg/ml final concentration of each peptide) and brefeldin A (1 μg/ml; BD Pharmingen cat #555028/2300kk) at 37° C. and 5% $CO_2$ for 12-16 hours as previously described (Facciabene et al., supra). Cells were then washed with FACS buffer (PBS 1% FBS, 0.01% NaN3) and incubated with purified anti-mouse CD16/CD32 Fc block (BD Pharmingen cat # 553142) for 15 min at 4° C. Cells were then washed and stained with surface antibodies: CD4-PE conjugated anti-mouse (BD Pharmingen, cat.# 553049), PercP CD8 conjugated anti mouse (BD Pharmingen cat# 553036) and APC-conjugated anti-mouse CD3e (BD Pharmingen cat# 553066) for 30 minutes at room temperature in the dark. After the washing cells were fixed and permeabilized with Cytofix-Cytoperm Solution (BD Pharmingen cat #555028/2300kk) for 20 min at 4° C. in the dark. After washing with PermWash Solution (BD Pharmingen cat #555028/2300kk) cells were incubated with the IFNγ-FITC antibodies (BD Pharmingen). Cells were then washed, fixed with formaldehyde 1% in PBS and analyzed on a FACS-Calibur flow cytometer, using CellQuest software (Becton Dickinson, San Jose, Calif.).

EXAMPLE 11

Immunogenicity of CEA-LT Fusions

To examine the immune responses induced by the plasmids encoding the CEA-LTA and CEA-LTB fusions, groups of 9 C57BL/6 mice were immunized with two injections i.m. of 50 μg each of plasmids pV1J/hCEA, pV1J/hCEA-LTA and pV1J/hCEA-LTB. Additionally, to verify whether coexpression of the CEA-LTA and CEA-LTB fusion proteins could have an additive effect on the immunogenicity of the CEA protein, a group of mice was immunized by coinjecting 25 μg each of plasmids pV1J/hCEA-LTA and pV1J/hCEA-LTB. Immunizations were administered three weeks apart. The plasmid DNA was routinely electroinjected into mouse skeletal muscle in view of the enhanced transduction and immunogenicity connected with this particular procedure (Zucchelli et al. *J. Virol.* 74: 11598-11607 (2000); Widera et al. *J. Immunol.* 164: 4635-4640 (2000)).

The cellular immunity elicited by the different plasmids was measured by ELISPOT assay 2 weeks after the last injection. Antigen-specific IFNγ secretion from stimulated splenocytes was measured using four pools of 15mer peptides overlapping by 11 aa and encompassing the entire CEA glycoprotein. Pool A covers aa 1 to 147, pool B aa 137 to 237, pool C aa 317 to 507, and pool D aa 497 to 703. As a negative control, cytokine production was also measured upon stimulation of the splenocytes with DMSO at the same concentration utilized to solubilize the CEA peptides.

Figure 10A:
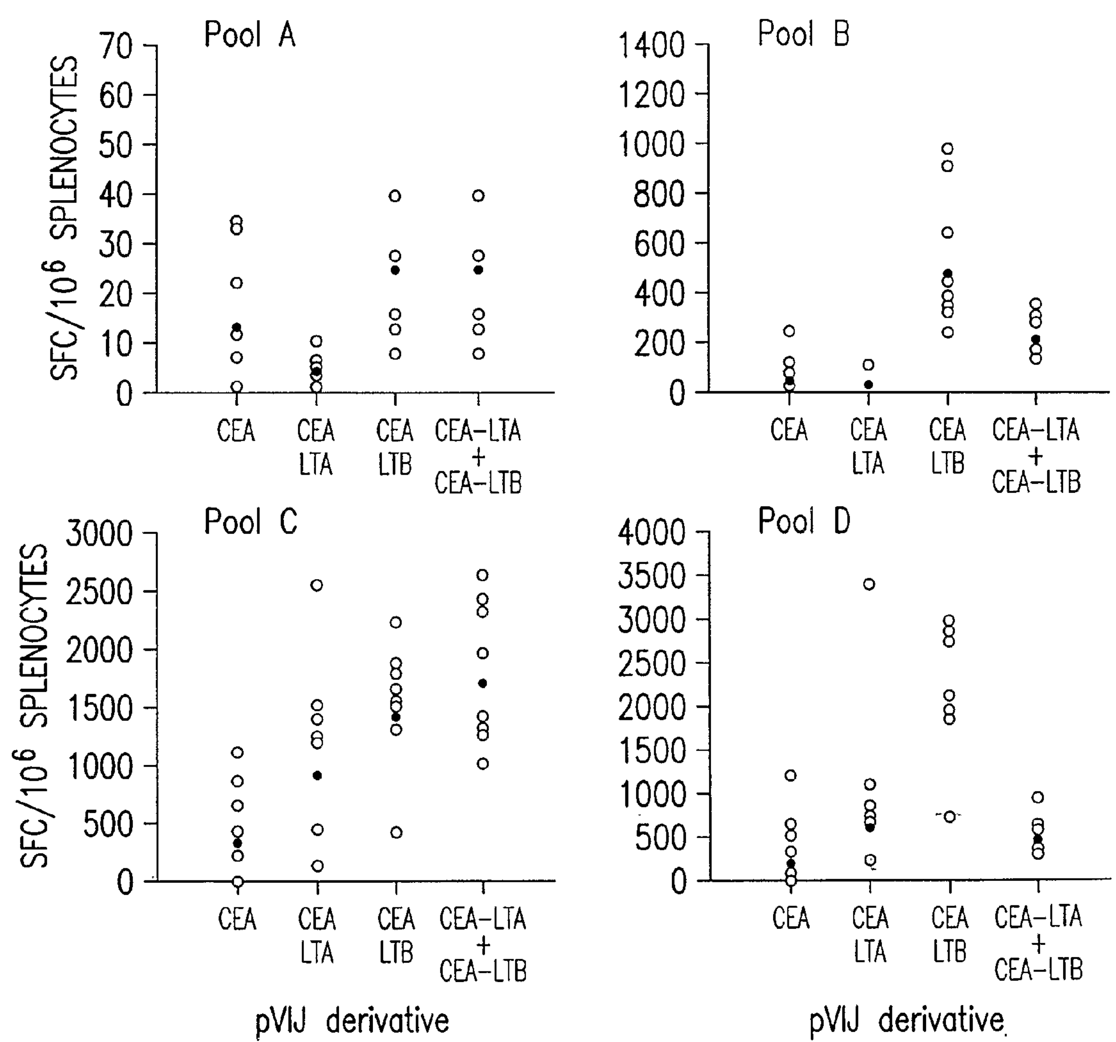
FIG. 10 shows an analysis of the cell mediated immune response elicited by different plasmid vectors encoding human CEA. Three groups of C57BL/6 mice were electroinjected intramuscularly with 50 μg of the indicated plasmid (CEA, CEA-LTA fusion or CEA-LTB fusion) at 0 and 3 weeks. A fourth group of mice was immunized with a mixture of 25 μg of pV1J/hCEA-LTA and 25 μg of pV1J/hCEA-LTB. Panel A. Two weeks post boost, the number of IFNγ-secreting T cells specific for CEA was determined by ELISPOT assay on splenocytes from individual mice (empty circles) using peptide pools that encompass the entire protein. Geometric mean values (filled diamonds) are also indicated. Panel B depicts results of IFNγ intracellular staining of pooled splenocytes from immunized mice using peptide pool D. The nonspecific IFNγ production (DMSO) is shown for each group.
Figures 1, 10B:
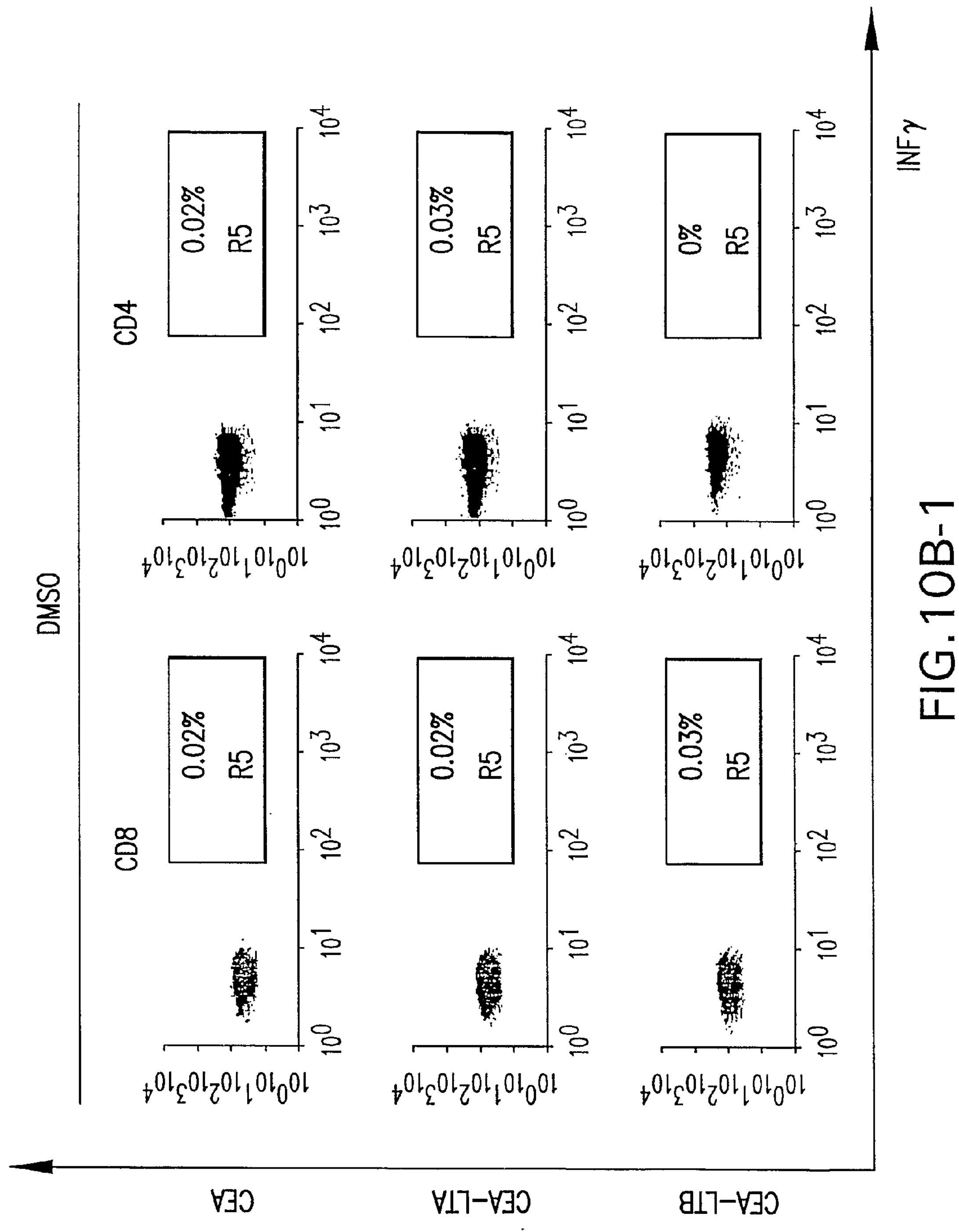
Figures 2, 10B:
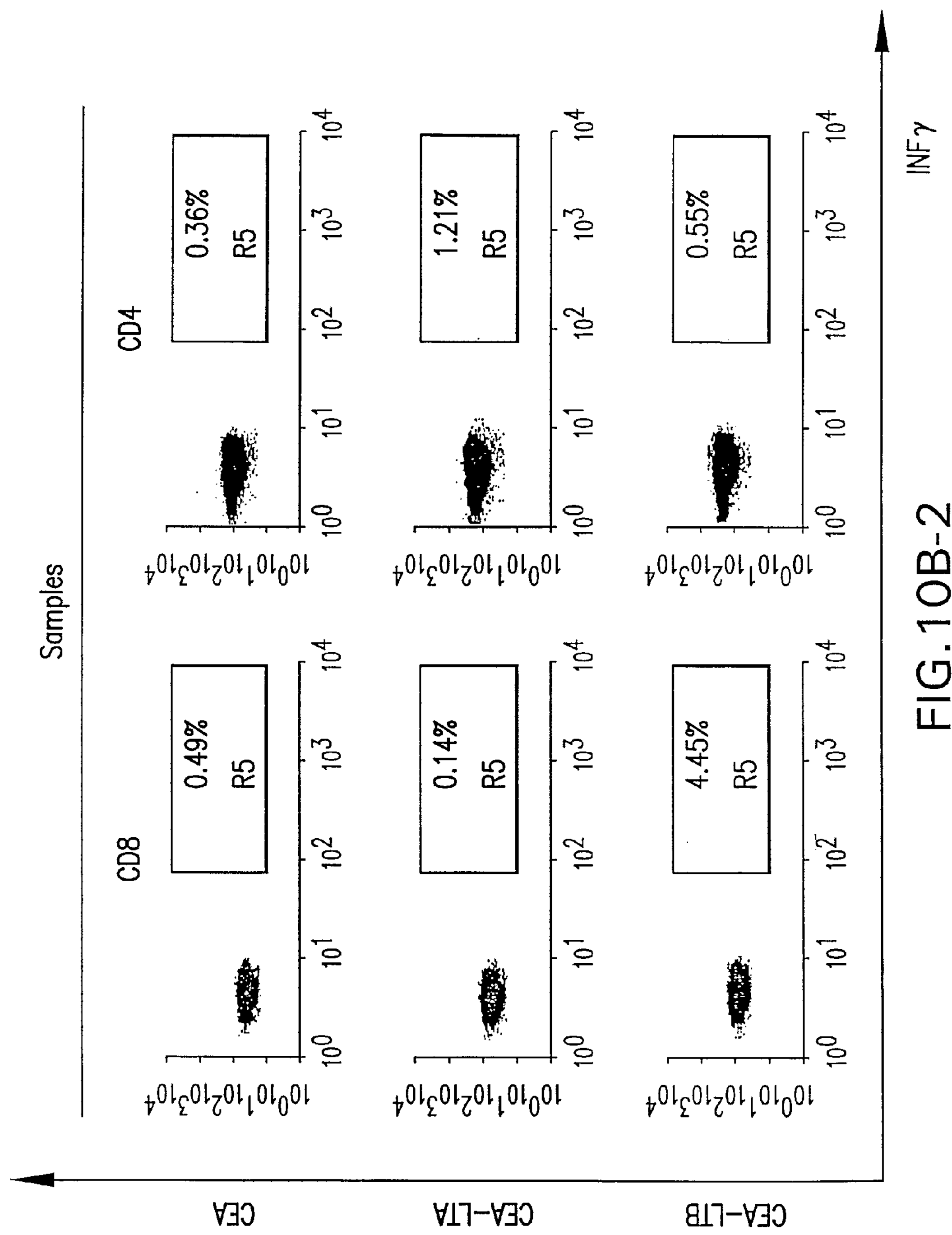
FIG. 2 shows the nucleotide (SEQ ID NO:7, Panel A) and amino acid sequence (SEQ ID NO:8, Panel B) of an exemplary hCEA-LTA fusion. The LTA nucleotide sequence is shown in bold.

The immune response elicited by DNA vaccination in C57BL/6 mice was primarily biased towards the C-terminal region of the protein since the SFC values detected with the peptide pool A were slightly above background with all constructs (FIG. 10). The pV1J/hCEA-LTB vaccination regimen was superior to that elicited by pV1J/hCEA as indicated by the higher geometric mean values of the SFC detected with peptide pools B, C and D (pV1J/hCEA-LTB: 482, 1436, and 2054 SFC/$10^6$ splenocytes, respectively; pV1J/hCEA: 45, 350, and 264 SFC/$10^6$ splenocytes, respectively). Similarly, plasmid pV1J/hCEA-LTA had also an enhancing effect on the CEA specific immune response when compared to pV1J/hCEA. However, the increase in immune response was only observed with peptide pools C and D (925 and 528 SFC/$10^6$ splenocytes, respectively), while the immune response measured with peptide pool B was low (15 SFC/$10^6$ splenocytes). Additionally, coinjection of plasmids pV1J/hCEA-LTA and pV1J/hCEA-LTB did not have a significant synergic effect on the immune response to CEA when compared to the immune response measured in the pV1J/hCEA-LTB treated group, but rather, it resulted in a decrease of the SFC values detected with peptides pool B and D (210 and 528 SFC/$10^6$ splenocytes, respectively).

To define the T-cell specificity elicited upon vaccination with the different CEA constructs, IFNγ intracellular staining was carried out on pooled splenocytes from injected mice using peptide pool D. A $CD8^+$-specific response was detected in mice injected with pV1J/hCEA-LTB (4.5%) superior to that detected with pV1J/hCEA-LTA and pV1J/hCEA (0.14% and 0.8%, respectively, FIG. 10B). In contrast, pV1J/CEA-LTA elicited a strong $CD4^+$-specific response (1.21%) greater than that observed with pV1J/hCEA-LTB and pV1J/hCEA (0.55% and 0.58%, respectively).

Figure 11:
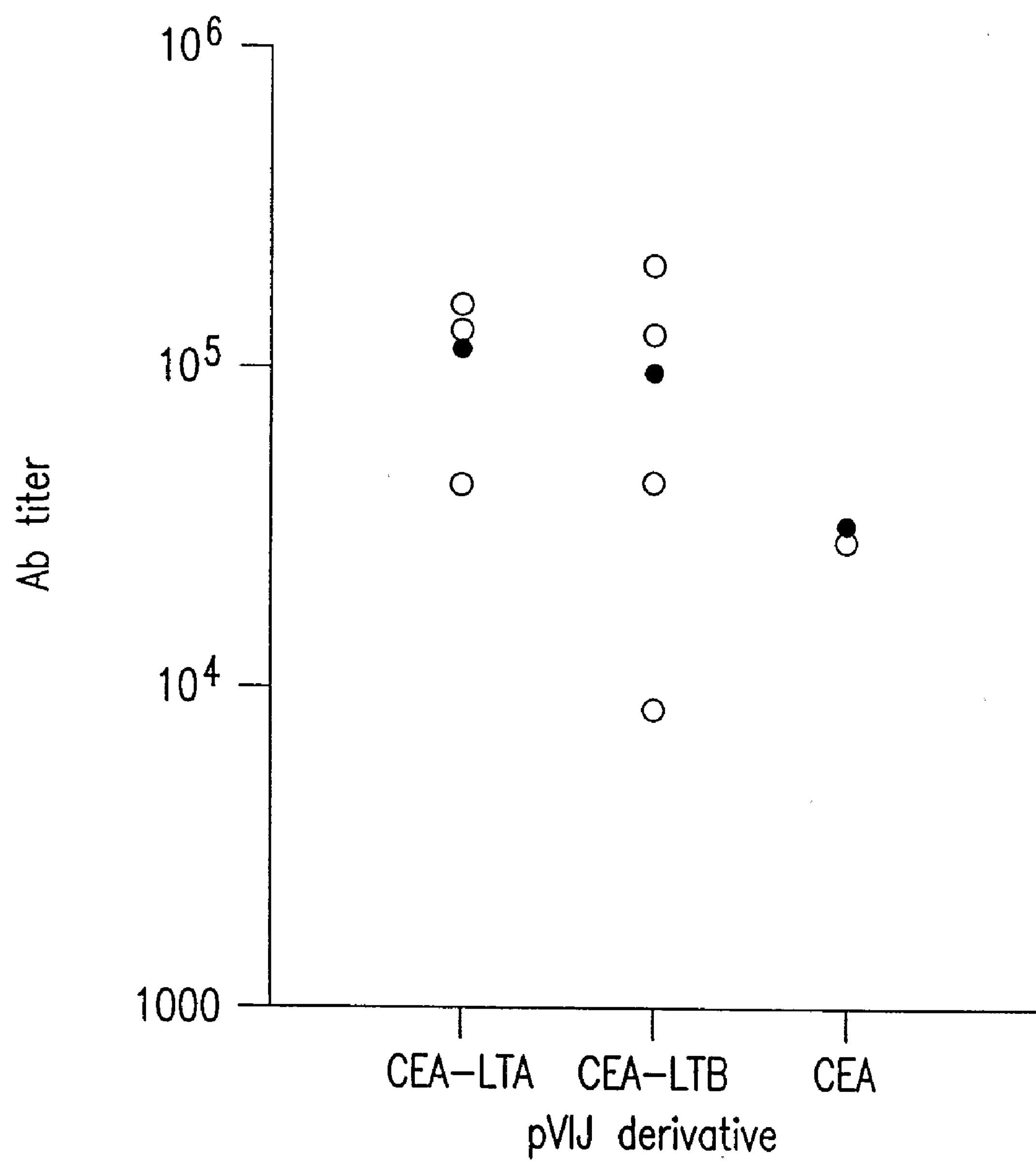
FIG. 11 shows antibody titers from mice immunized with plasmid DNA vectors encoding CEA. Individual titers against purified human CEA protein were measured by ELISA on serum from individual mice immunized with plasmids pV1J/hCEA, pV1J/hCEA-LTA and pV1J/hCEA-LTB. Average values are also shown (filled diamonds).

The induction of the humoral immune response to CEA was examined by measuring antigen specific antibodies (FIG. 11). Both plasmids pV1J/hCEA-LTA and pV1J/hCEA-LTB elicited a greater antibody response than pV1J/hCEA, confirming the adjuvant effect exerted by the LT subunits on the CEA specific immune response. Thus, these data demonstrate that fusion of the CEA coding sequence to the LTA or LTB cDNA results in an increase the CEA specific immune response. However, LTB appears to have a greater enhancing effect on the immune response with a prevalent induction of $CD8^+$T cells, whereas LTA elicits a predominant $CD4^+$ response.

EXAMPLE 12

Immunogenicity of CEA-LTB Fusions in Different Mouse Strains.

To determine whether the enhancing effect of the LT subunits on the CEA specific immune response was not limited to a single mouse genetic background, DNA based immunizations were carried out in BALB/c, C57/DR4 and HLA-A2.1 (HHD) mice. The BALB/c mice were chosen in view of their immunocompetence, being a mouse strain extremely reactive to immunization regimens of various sorts. The HHD transgenic mice express the human MHC class I genes. Similarly, C57/DR4 transgenic mice carry the human MHC class II genes. Thus, these two transgenic mouse strains may provide information as to the immunoreactivity of the CEA-LT fusions in the context of human MHC class I and II haplotypes.

Figure 12:
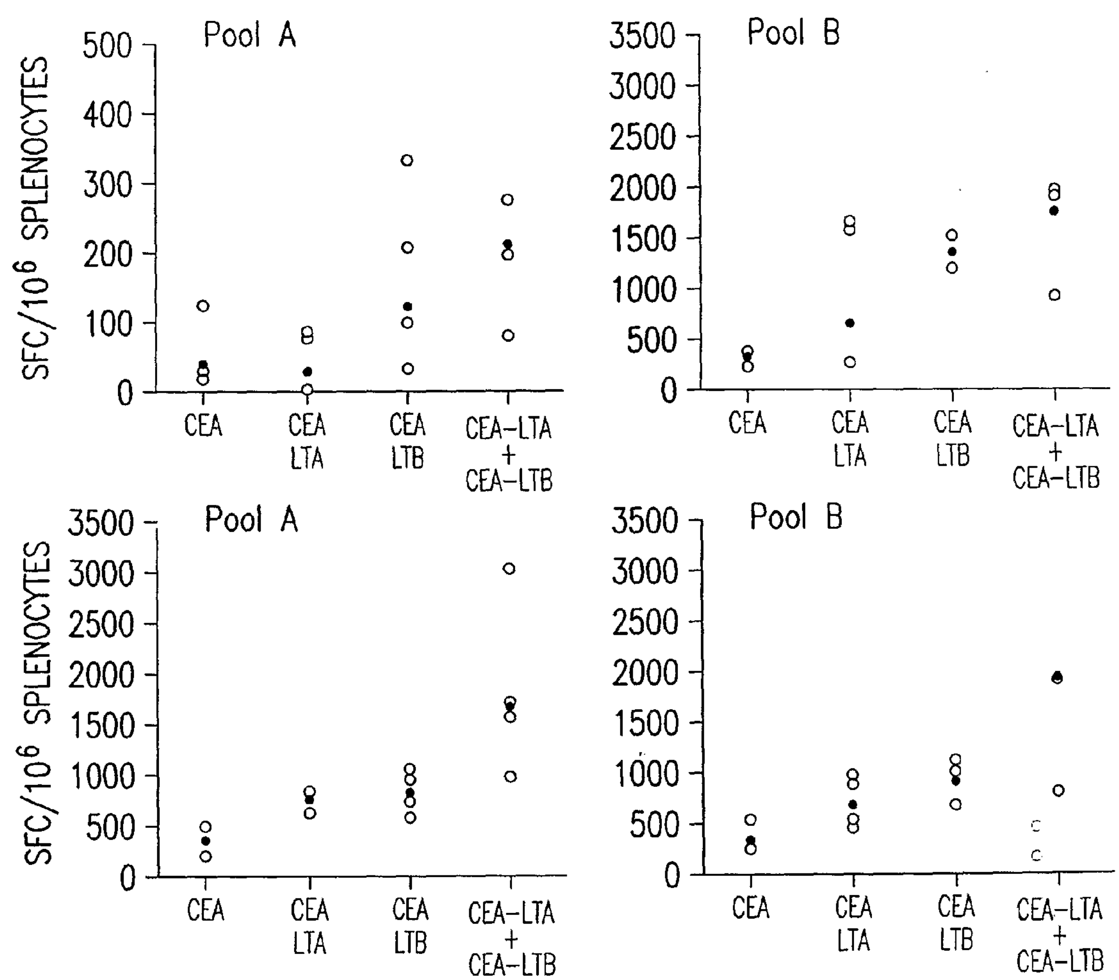
FIG. 12 shows an analysis of the cell mediated immune response elicited by different plasmid vectors encoding CEA. Groups of 4 BALB/c mice were electroinjected with the indicated plasmid as indicated above (FIG. 4). Two weeks after the last injection, the number of IFNγ secreting T cells specific for CEA was determined by ELISPOT assay on splenocytes from individual mice (empty circles) using peptide pools that encompass the entire protein. Average values (filled diamonds) are also indicated.

The CEA specific immune response in BALB/c mice was first assessed by ELISPOT assay. Enhancement of the antigen specific immune response upon immunization with plasmid pV1J/hCEA-LTB was detected with peptide pools A, B, C, D (pV1J/hCEA-LTB: 166, 1353, 796, 899 SFC/$10^6$ splenocytes, respectively; pV1J/hCEA: 57, 312, 327, 318, SFC/$10^6$ splenocytes respectively, FIG. 12). As observed in the C57BL/6 mice, the N-terminal region of the CEA protein appeared to be the least immunogenic as compared to other sections of the tumor antigen, pV1J/hCEA-LTA immunization also yielded an increase in the antigen specific immune response as compared to pV1J/hCEA. The increase in the immune response was detected with peptide pools B, C and D (936, 727, and 650 SFC/$10^6$ splenocytes, respectively). Additionally, coinjection of the two plasmids pV1J/hCEA-LTA and pV1J/hCEA-LTB yielded a significant additive effect that was detected mainly with peptide pools C and D (1783 and 2141 SFC/$10^6$ splenocytes, respectively).

Figure 13:
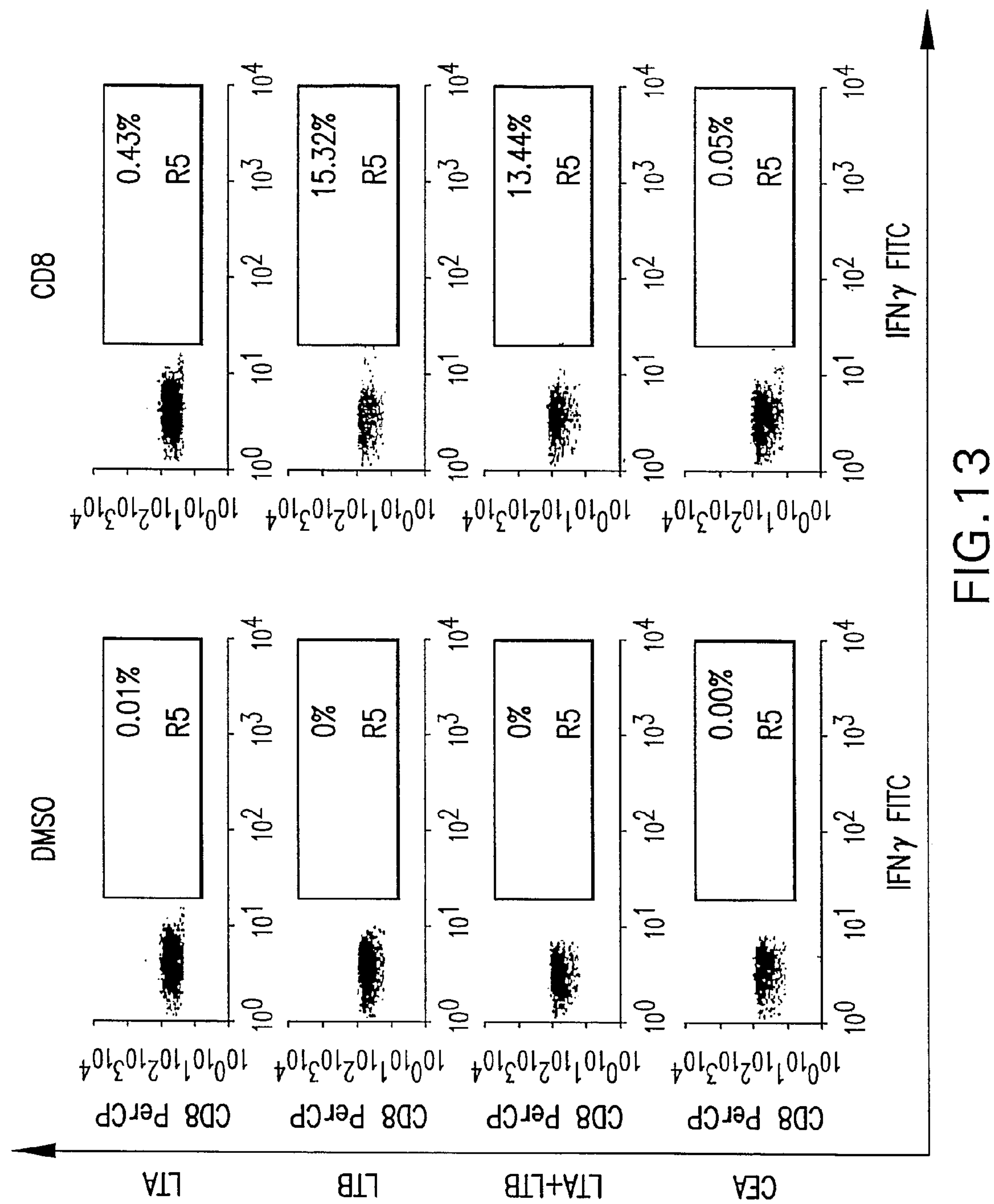
FIG. 13 shows an analysis of the CEA-specific $CD8^+$ T cell response elicited by different plasmid vectors encoding CEA. C57/DR4 mice were electroinjected with the indicated plasmid as described above (see FIG. 4). Two weeks after the last injection, IFNγ intracellular staining of pooled splenocytes from immunized mice was performed using peptide pool D. The nonspecific IFNγ production (DMSO) is shown for each group.

The CEA specific immune response in C57/DR4 mice was considerably enhanced by the immunization with pV1J/hCEA-LTB, and was detected only peptide pool D (FIG. 13). IFNγ intracellular staining performed on pooled PBMC from injected mice showed that the $CD8^+$ response to CEA was highest in mice immunized with pV1J/hCEA-LTB (15.32%), whereas was very weak in the pV1J/hCEA treated group (0.5%). pV1J/CEA-LTA immunization increased the antigen specific immune response only moderately (0.43%), and did not further enhance the CEA immunogenicity when coinjected with the construct encoding the CEA-LTB fusion (13.44%). Interestingly, no significant $CD4^+$ T cell response was detected in the immunized mice (data not shown).

Figure 14A:
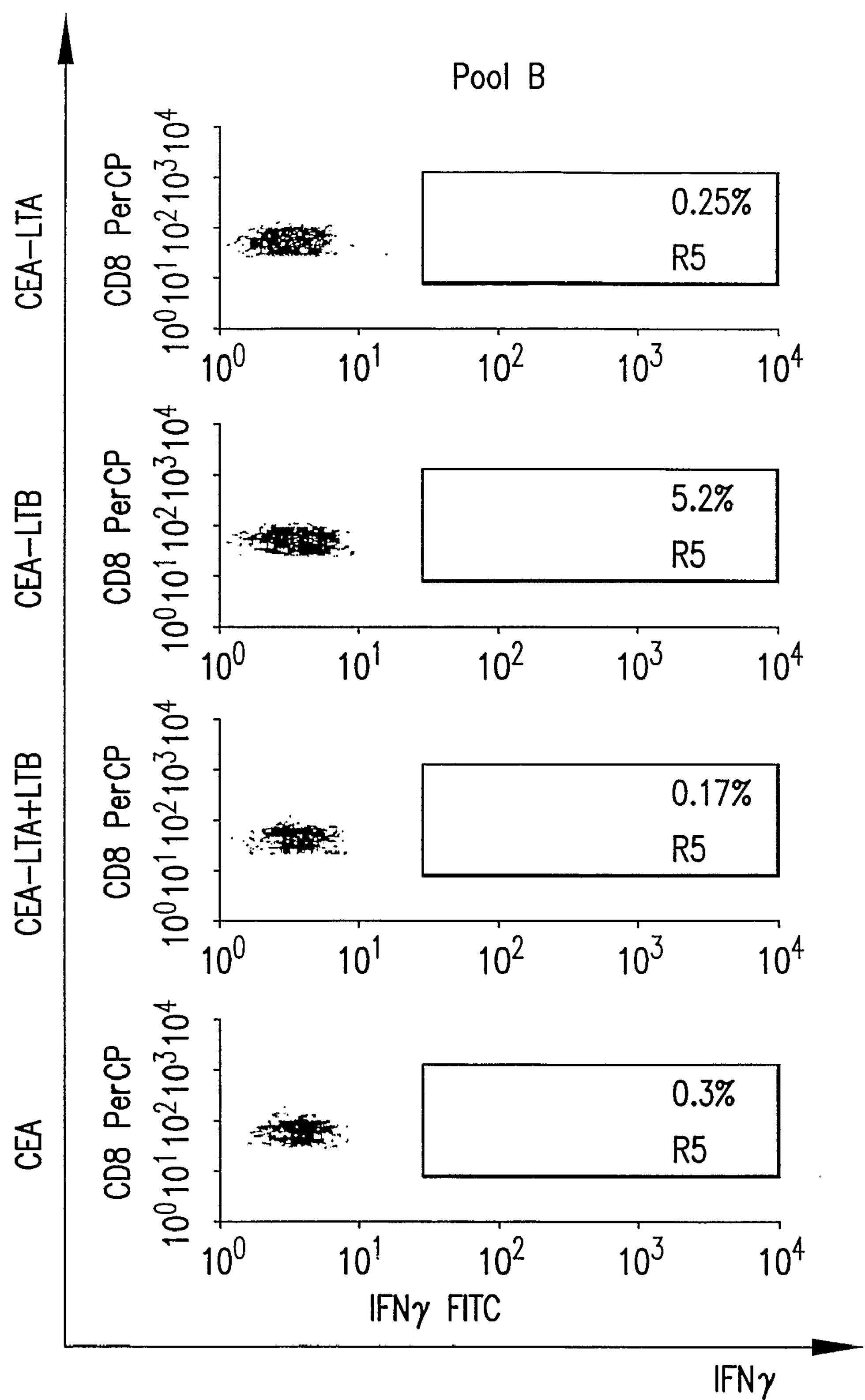
FIG. 14 shows an analysis of CEA-specific $CD8^+$ T cell response elicited by different plasmid vectors encoding CEA. HHD mice were electroinjected with the indicated plasmid as described above (see FIG. 4). Two weeks after the last injection, IFNγ intracellular staining of pooled splenocytes from immunized mice was performed using peptide pools B and D. The nonspecific IFNγ production (DMSO) is shown for each group.
Figure 14B:
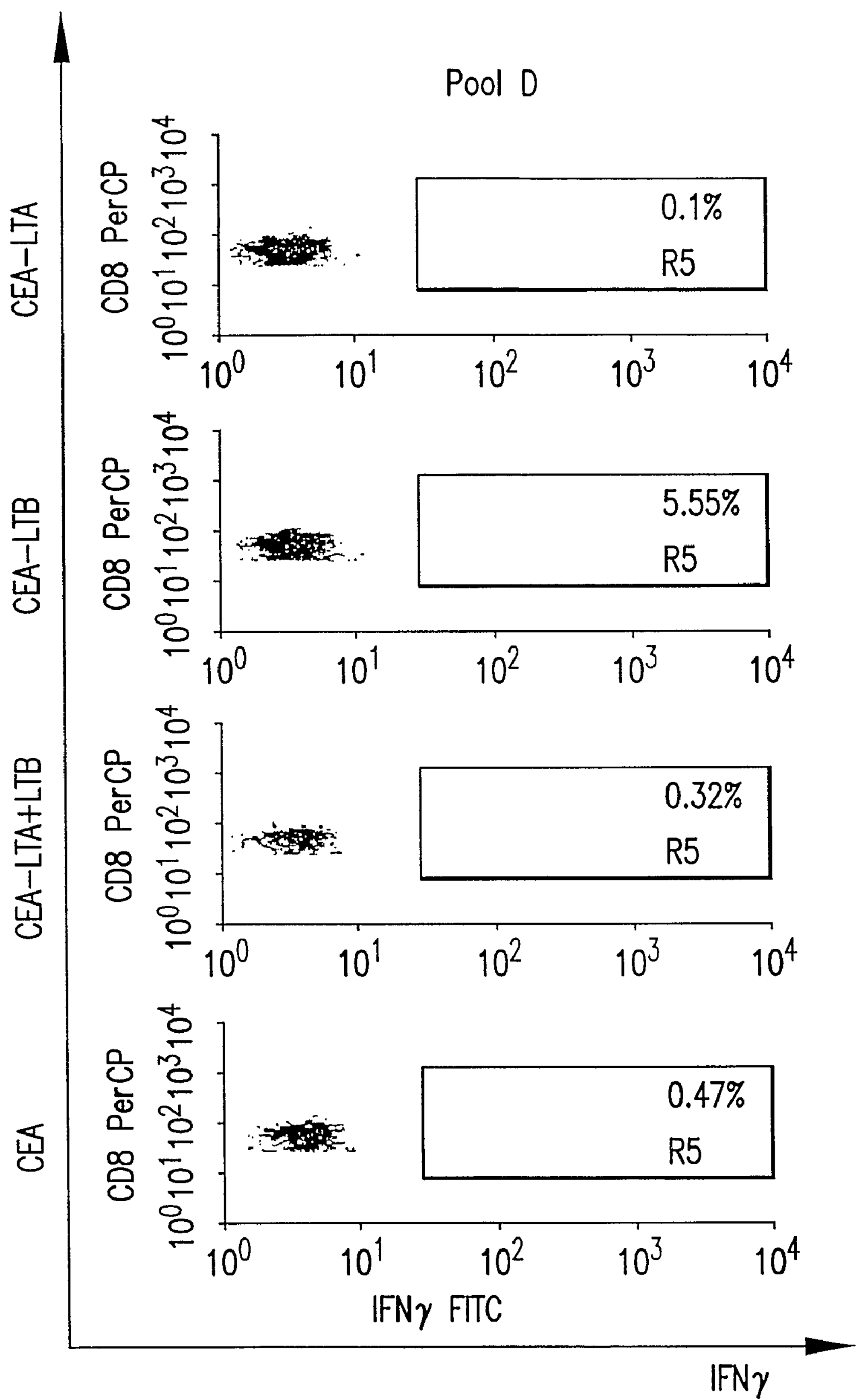
Figure 14C:
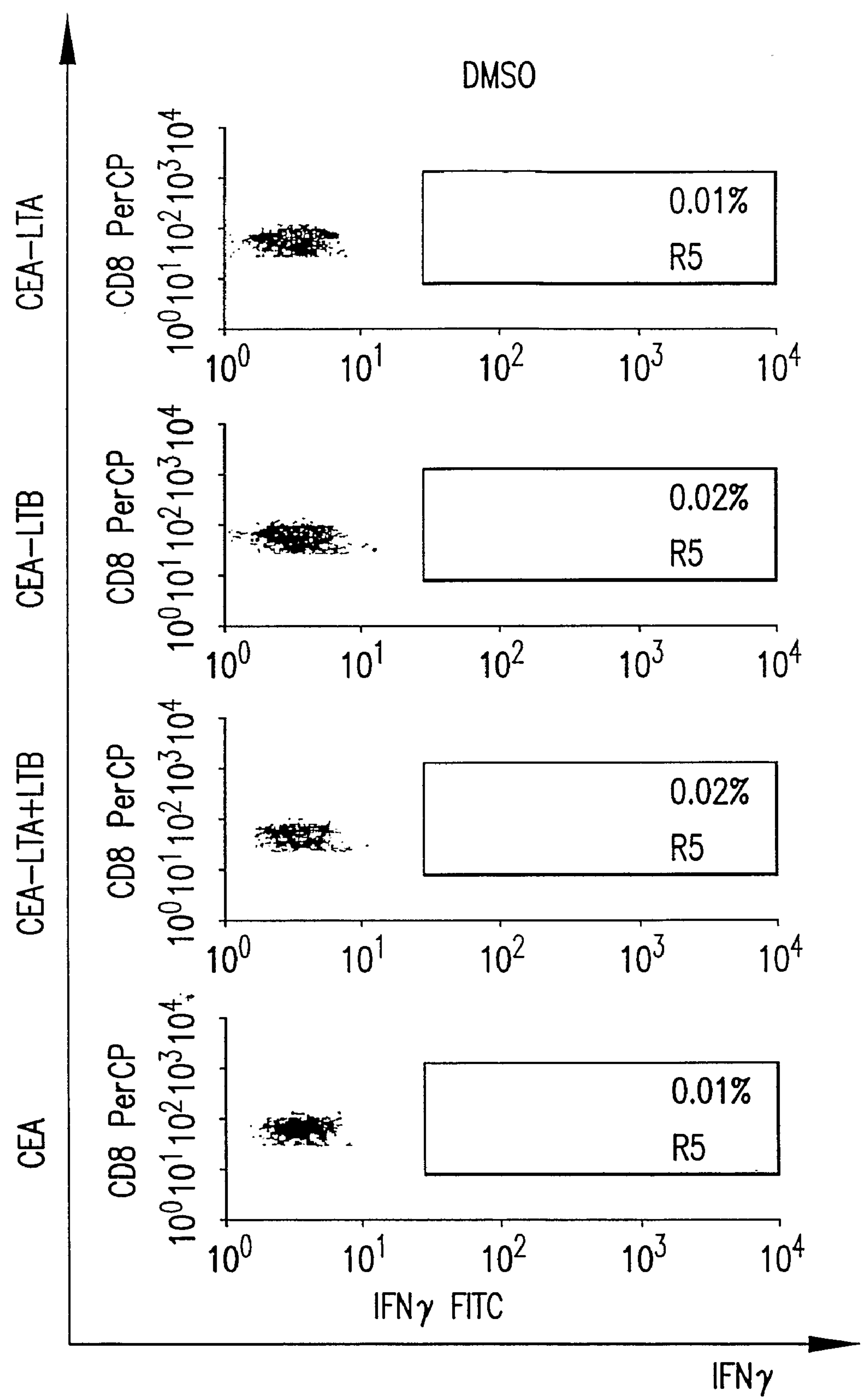

The immune response elicited by the different CEA encoding plasmids was assessed in HID mice by performing IFNγ intracellular staining on pooled PBMC. The immune response was only detected with peptide pools B and D, and as shown in FIG. 14, immunization with pV1J/hCEA-LTB resulted in more than 10 fold increase in the $CD8^+$ response to the target antigens. In contrast, no increase in the immune response was detected using pV1J/hCEA-LTA either alone or upon coinjection with pV1J/hCEA-LTB. No $CD4^+$ T cell response was detected in the immunized mice (data not shown).

Taken together, these data confirm that fusion of the LTB coding sequence to CEA results in a considerable increase in the antigen specific immune response. Interestingly, this response is predominantly $CD8^+$-specific and can be observed in different mouse strains, thus indicating that the enhancing effect exerted by the LT subunit is not genotype restricted.

EXAMPLE 13

Tolerance to Human CEA in Transgenic Mice.

To determine whether the enhanced immunogenic properties of the hCEA-LTB fusion would break tolerance more efficiently to human CEA, hCEA transgenic mice were immunized with vectors carrying either the fully codon optimized cDNA of hCEA or CEA-LTB. These transgenic mice carry the entire human CEA gene and flanking sequences and express the hCEA protein in the intestine, mainly in the cecum and colon. Thus, this mouse line is a useful model for studying the safety and efficacy of immunotherapy strategies directed against this tumour self antigen (Clarke et al., *Cancer Research* 58: 1469-1477 (1998)).

Figure 15B:
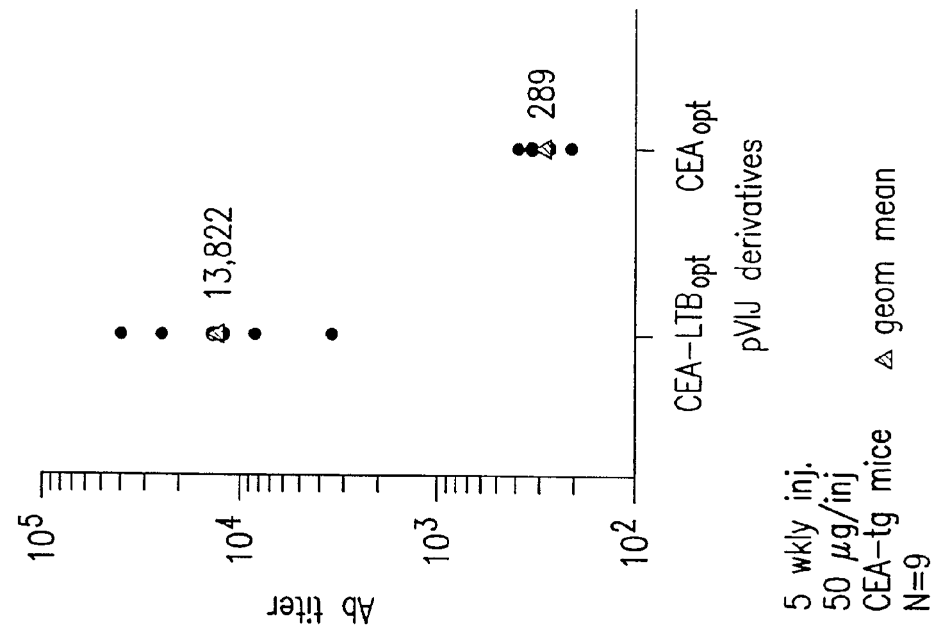
FIG. 15 shows the cell-mediated and humoral immune response of CEA transgenic mice (N=9) immunized with 5 weekly electroinjections of the indicated plasmids. A total amount of 50 μg of plasmid DNA was injected i.m. at each vaccination. Panel A. Two weeks after the last injection, the number of IFNγ secreting T cells specific for CEA was determined by intracellular staining on splenocytes from individual mice (circles) using peptide pool D. Geometric mean values (triangles) are also indicated. Panel B. Individual titers against purified human CEA protein were measured by ELISA on each serum from mice immunized with plasmids pV1J/hCEAopt and pV1J/hCEA-LTB. Geometric mean values are also shown (filled diamonds). These data indicate that the CEA-LTB fusion breaks tolerance to CEA in transgenic mice.
Figure 15A:
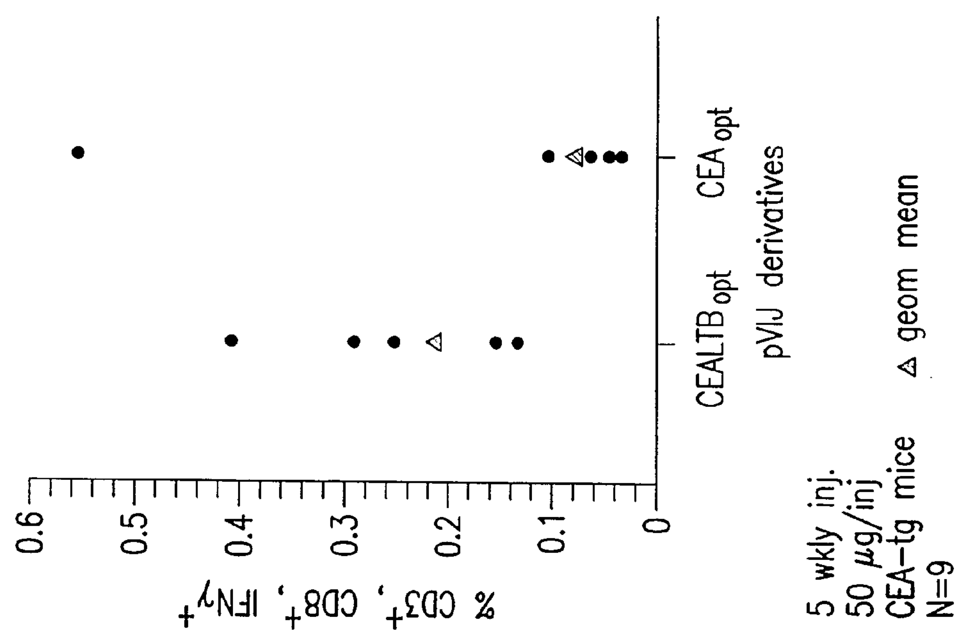

Immunization with pV1J/hCEA-LTBopt resulted in a significant increase in the CEA specific immune response measured by IFNγ intracellular staining on PBMC of the injected mice (FIG. 15A). The enhancement of the T cell response was detected with peptide pool D and was predominantly $CD8^+$. Additionally, also the CEA specific humoral response was increased in the CEA-LTB treated mice as shown by the 47 fold increase in the geometric mean values of the Ab titer as compared to the pV1J/hCEAopt treated group (FIG. 15B).

Figure 16:
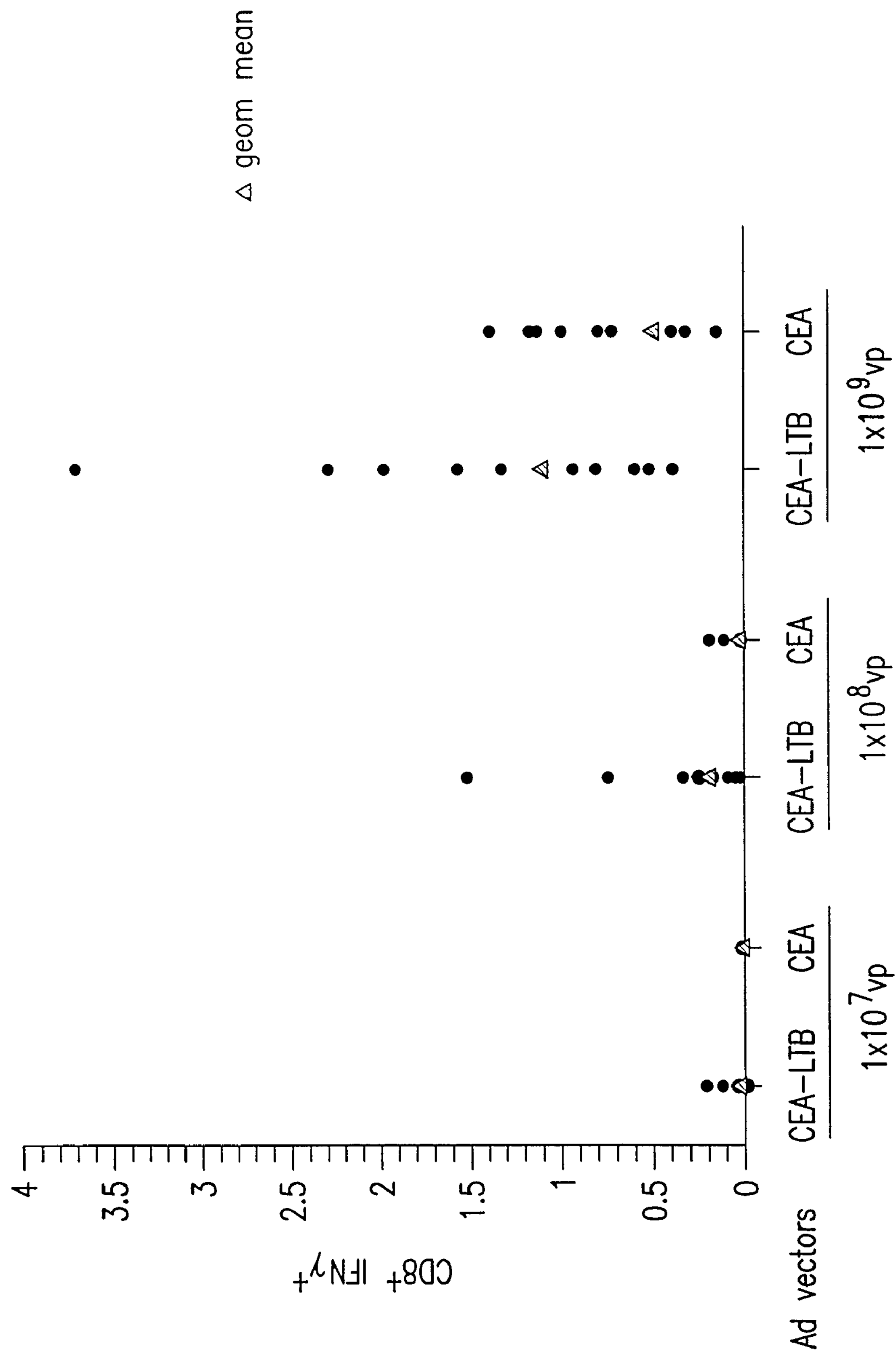
FIG. 16 shows an analysis of the CEA-specific $CD8^+$ T cell response elicited by different Adenovirus vectors encoding CEA. CEA transgenic mice were immunized with different doses of Ad/hCEAopt and Ad/CEAopt-LTB at 0 and 2 weeks. Two weeks after the last injection, IFNγ intracellular staining of PBMC from each immunized mouse was performed using peptide pool D (filled circles). Geometric mean values are also shown (filled diamonds). The nonspecific IFNγ production (DMSO) of each injected group was less or equal to 0.01%.

To determine whether the enhancing effect exerted by LTB on the CEA specific immune response could also be observed upon immunization with vectors other than plasmid DNA, groups of 12 CEA tg mice were immunized with Ad5/hCEAopt-LTB and Ad/hCEAopt at a dose of $1\times10^7$, $1\times10^8$, and $1\times10^9$ vp. Mice were subjected to two injections two weeks apart and the immune response was measured by IFNγ intracellular staining on PBMC two weeks after the last injection. The immune response was assessed using the peptide pool D. Ad/hCEAopt-LTB was more immunogenic than Ad/hCEAopt since significant immune responses to CEA could be detected with the $1\times10^8$ vp dose, whereas $1\times10^9$ vp of Ad/hCEAopt were necessary to break tolerance to the target antigen (FIG. 16). No $CD4^+$ response could be detected in any of the immunized mice (data not shown).

These data confirm that tolerance to this self antigen can be broken more efficiently due to the increased immunogenic properties of the CEA-LTB fusion. Furthermore, the enhancing effect of LTB on the immunogenic properties of CEA is also observable upon injection of plasmid carrying the fully codon optimized cDNA of the CEA-LTB fusion. Lastly, these results indicate that that enhanced immunogenicity of CEA-LTB is not limited to plasmid DNA immunization.

EXAMPLE 14

Tumor Growth Kinetics in CEA Transgenic Mice Immunized with CEA-LTB Fusions

Figure 17A:
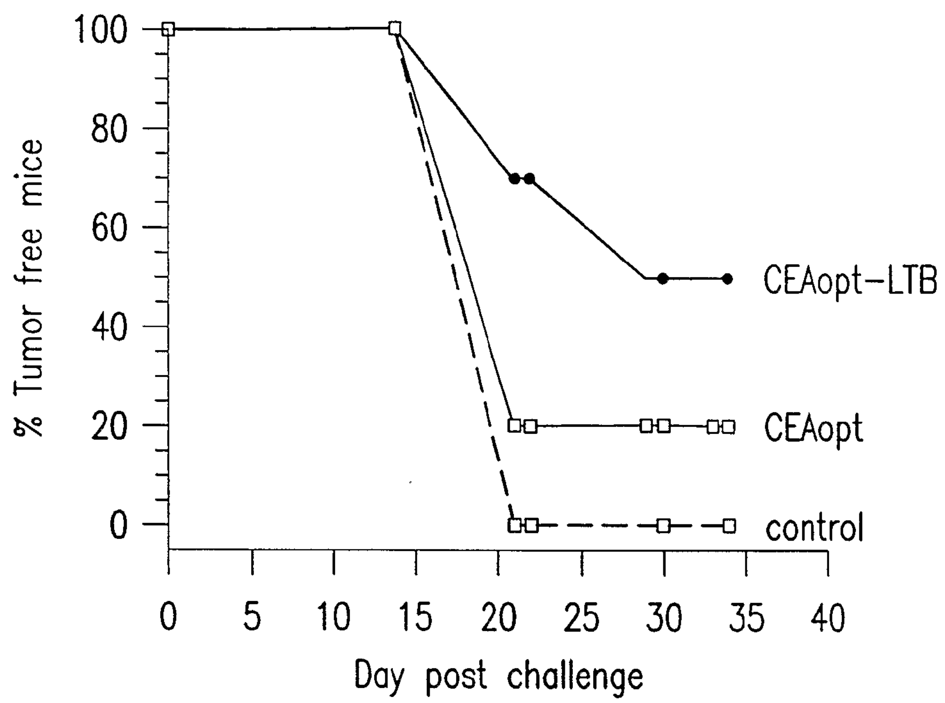
FIG. 17 shows the results of tumor protection studies of immunized CEA transgenic mice challenged with MC38-CEA cells. Groups of 10 CEA transgenic mice were immunized with 5 weekly electroinjections of the indicated plasmid DNA (50 μg/injection). Two weeks after the last DNA injection, mice were boosted with a single injection of $1\times10^{10}$ vp of the corresponding Ad vector. Fourteen days after the Adenovirus boost, mice were challenged with a subcutaneous injection of $5\times10^5$ MC38-CEA cells. Panel A shows the percentage of tumor free mice at the indicated timepoint. Panel B reports the average tumor volumes of each immunized group. These data demonstrate that immunization of CEA transgenic mice with CEA-LTB protects mice from tumor development FIG. 18. Panel A shows a schematic representation of representative CEA fusion proteins used in this study. Vectors expressing the CEA fusion proteins were derived from plasmid pV1Jns as described in EXAMPLE 2. The constructs comprise a CEA nucleotide sequence from nt 1 to nt 2037 with a net deletion of 64 aa corresponding to the GPI anchoring sequence and express CEA from aa 1 to aa 679. The sequence coordinates of each protein fused to CEA are also indicated. Panel B shows expression of pV1J-derived constructs in transfected cells. HeLa cells were transfected with plasmids pV1J/CEA-VSV-G, pV1J/CEA-FcIgG, pV1J/CEA-DOM, pV1J/CEA-HSP70, pV1J/CEA-LAMP, or pV1J/CEA and processed for Western blot analysis as described in EXAMPLE 5. The specificity of the antibody used for Western blot is indicated. The CEA protein is indicated (black arrow). The positions of molecular size standards (in kilodaltons) are also shown.
Figure 17B:
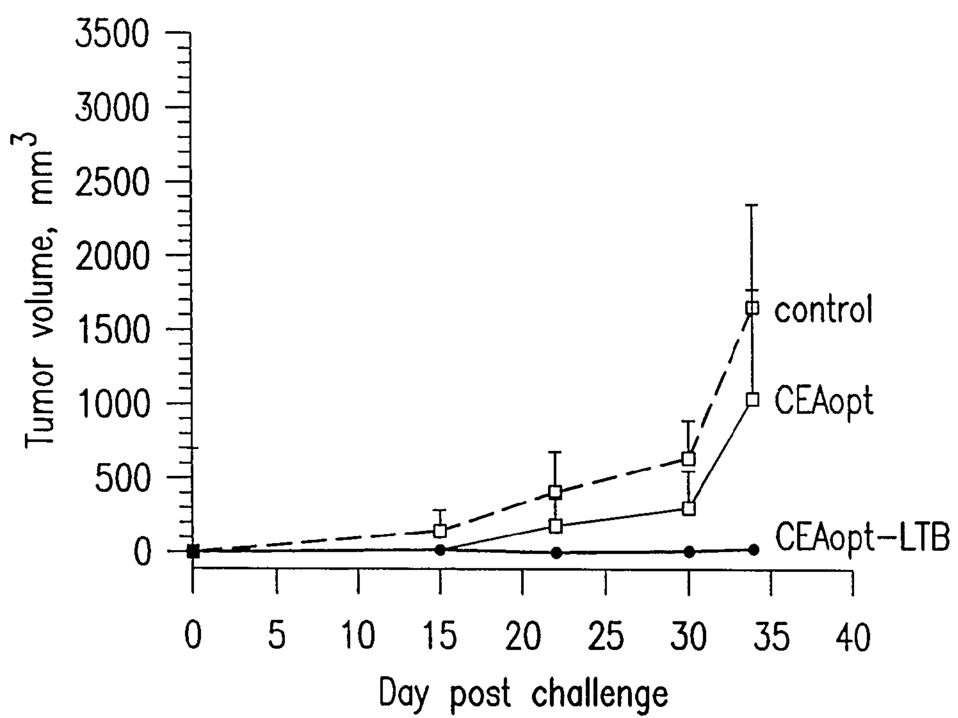

It was deemed appropriate to ascertain whether the increased immunogenicity of the CEA-LTB fusion would also lead to an enhanced therapeutic effect capable of interfering with tumor progression. For this purpose, groups of 10 CEA-tg mice were subjected to 5 weekly injections of plasmids pV1J/hCEAopt or pV1J/CEAopt-LTB followed by a final boost with $1\times10^{10}$ vp of the corresponding Ad vector. In view of recent reports that indicate that high levels of cellular immunity can be induced against viral and bacterial antigens by utilizing plasmid DNA prime-Ad boost modality, the same immunization protocol was employed in this study. Two weeks after the last immunization, the CEA tg mice were challenged with a subcutaneous injection of $5\times10^5$ MC38-CEA tumor cells. This syngenic cell line was derived from a chemically induced colon cancer and expresses CEA. Tumor development in mock treated mice was detected by 22 days post challenge as all the treated mice were no longer tumor free (FIG. 17A). Additionally, there was a concomitant increase in the average size of the tumor mass that reached significant volume by 34 days post challenge. Mice vaccinated with vectors encoding pV1J/hCEAopt showed a partial resistance to tumor development since 2 out of 10 treated mice remained tumor free at day 34 post challenge. The average size of the tumors of this group was smaller than that observed in the mock treated mice. Immunization with vectors encoding the CEAopt-LTB fusion resulted in a significant protective effect from tumor development. Five out of 10 treated mice remained tumor free at day 34 post challenge, and the average size of the tumor mass in this group was significantly smaller that that observed in the mock or pV1J/hCEAopt treated mice. Thus, these results indicate that the enhanced CEA-specific immune response associated with vectors encoding the CEA-LTB fusion correlates with a significant antitumor effect resulting in partial protection from tumor growth and reduced growth kinetics of the tumor mass.

EXAMPLE 15

CEA-DOM and CEA-FcIgG Fusions Enhance the Immunogenicity of the CEA Protein.

To examine the immune responses induced by the plasmids encoding CEA-FRC, CEA-DOM, CEA-VSV-G, CEA-FcIgG, CEA-HSP70 and CEA-LAMP fusions, groups of 9 C57BL/6 mice were immunized with two i.m. injections of 50 or 5 μg of each plasmid. The immunizations were three weeks apart. In view of the enhanced transduction and immunogenicity reported with electroporation (Zucchelli et al. *J. Virology* 74:11598 (2000), Widera et al., *J. Immunol.* 164: 4635

(2000)), plasmid DNAs were routinely electroporated (DNA-EP) into mouse skeletal muscle.

The immune response elicited by different plasmids was measured by IFNγ ELISPOT assay, 2 weeks after the last injection. Antigen-specific IFNγ secretion from stimulated splenocytes was measured using a pool of 15mer peptides overlapping by 11 aa and encompassing the C-terminal region of CEA (pool D, aa 497-703) (Zucchelli et al., supra). The analysis of the immune response to CEA was carried out with peptide pool D since the cellular immune response to CEA in C57BL/6 mice is primarily biased towards the C-terminal region of this protein (Zuccelli et al., supra). As a negative control, cytokine production was also measured upon stimulation of the splenocytes with DMSO at the same concentration utilized to solubilize the CEA peptides.

Figure 20A:
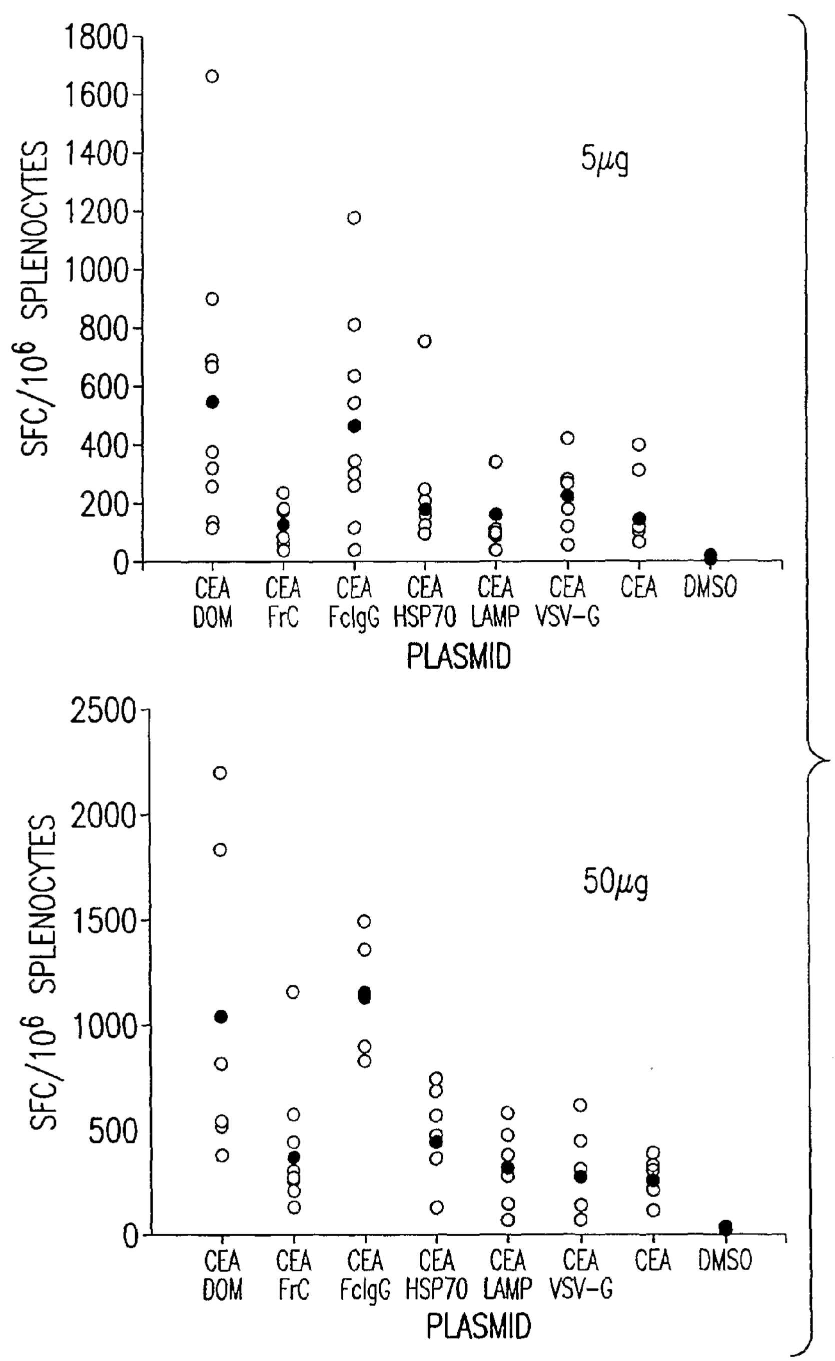
FIG. 20 shows a comparison of immunogenicity of different constructs encoding CEA fusion proteins. C57BL/6 mice were electroporated intramuscularly with a 5 or 50 μg/dose of the indicated plasmids. Injections were carried out at days 0 and 14. Panel A The number of IFNγ-secreting T cells in PBMC in each individual mouse was determined using a pool of peptides covering aa 497-703 (pool D) as described in EXAMPLES 6 and 15. Average number of IFNγ-secreting T cells are also shown (filled circles). SFC values of the pV1J/CEA-DOM, and pV1J/CEA-FcIgG are significantly different from those of pV1J/CEA. Panel B. Antibody titer was measured by ELISA using purified CEA as substrate. Average values of each cohort immunized with 50 μg dose of the indicated plasmid are shown. Titers that are significantly different from those of mice injected with pV1J/CEA are indicated with an asterisk.

Injection of pV1J/CEA-DOM or pV1J/CEA-Fc elicited a greater immune response to CEA as compared to pV1J/CEA. The greater immunogenicity of these two fusion proteins resulted in higher geometric mean values of spot forming cells (SFC) per $10^6$ splenocytes (FIG. 20A). Plasmids pV1J/CEA-DOM and pV1J/CEA-FcIgG had similar immunogenic properties and exerted a 3- to 4-fold increase in CEA-specific immune responses upon injection of 5 or 50 μg of plasmid DNA (pV1J/CEA-DOM: 590 and 1098 SFC/$10^6$ splenocytes, pV1J/CEA-FcIgG: 510 and 1160, pV1J/CEA: 146 and 264 SFC/$10^6$ splenocytes, respectively). No significant differences were noted between the SFC values elicited by the pV1J/CEA-FrC, pV1J/CEA-LAMP, pV1J/CEA-HSP70 and pV1J/CEA. No CEA specific immune responses were detected in negative control samples.

Figure 20B:
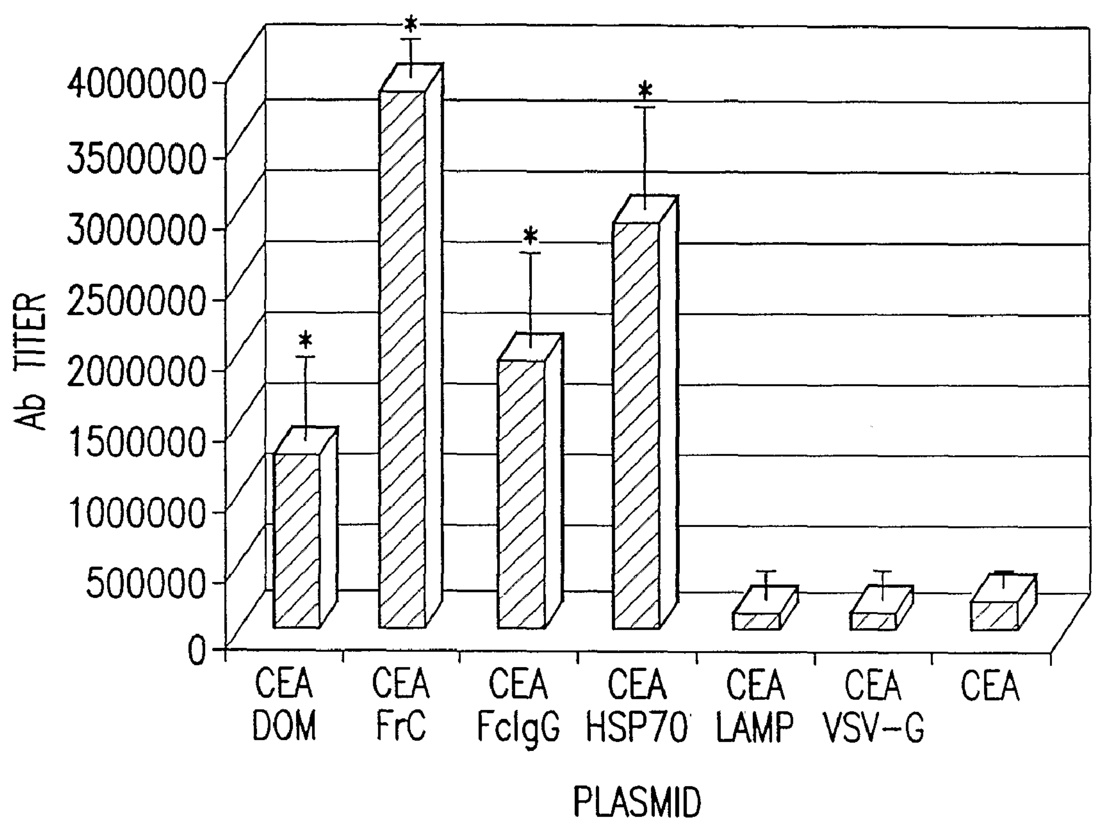

To determine the effect of the CEA-fusions on the humoral response to CEA, sera from immunized mice were tested in ELISA using purified CEA protein as substrate (FIG. 20B). An increase in CEA-specific antibody titer was observed upon injection of 50 μg of plasmids pV1J/CEA-DOM, pV1J/CEA-FcIgG, pV1J/CEA-FrC and pV1J/CEA-HSP70. On the contrary, injection of pV1J/CEA-LAMP and pV1J/CEA-VSV-G resulted in a CEA-specific antibody response similar to that observed upon immunization with pV1J/CEA. Taken together, these data demonstrate that fusion of the CEA coding sequence to the DOM or FcIgG cDNA results in an increase in the CEA-specific cell mediated and humoral immune response.

EXAMPLE 16

CEA-DOM and CEA-FcIgG Fusions Break Tolerance to Target Antigen in CEA Transgenic Mice.

Tolerance to the target antigen is one of the hurdles that a cancer vaccine must overcome to elicit an immune response and to exert an efficient antitumor effect. Thus, it was deemed appropriate to determine whether the enhanced immunogenic properties of CEA-DOM and CEA-FcIgG fusions would break tolerance to CEA more efficiently than the CEA protein. To this end, CEA transgenic mice were utilized to perform comparative immunization studies. These transgenic mice carry the entire human CEA gene and flanking sequences and express the CEA protein in the intestine, mainly in the cecum and colon. This mouse line is a useful model for studying the safety and efficacy of immunotherapy strategies directed against this tumor self antigen (Clarke et al., supra).

In view of the enhanced immunogenic properties of vectors carrying the codon usage optimized cDNA (cDNAopt) of CEA, both plasmid and Adenovirus vectors were engineered to carry the cDNAopt of the CEA-DOM (CEA-DOMopt) or CEA-FcIgG (CEA-FcIgGopt) fusions. As observed for CEA, CEA-DOMopt and CEA-FcIgGopt cDNAs were shown to be expressed with a greater efficiency of the corresponding wild type cDNA leading to an enhanced immune response to CEA (data not shown).

The immunogenicity of these two fusion proteins was compared to that of CEA by a series of immunization studies based on the use of plasmid DNA and Ad vectors administered either alone or in combination. Cohorts of CEA transgenic mice were immunized with the following varying regimens: i) 5 injections at weekly intervals of 50 μg of plasmid DNA (DNA/DNA), ii) 2 biweekly injections of Adenovirus in doses ranging from $1\times10^7$ to $1\times10^9$ viral particles (vp) of Adenovirus (Ad/Ad), or iii) 5 weekly injections of plasmid DNA followed by a final injection of $1\times10^9$ vp of Adenovirus (DNA/Ad). Immune responses were analyzed by intracellular IFNγ staining on PBMC or splenocytes of each immunized mouse using pool D peptides. Additionally, the induction of CEA-specific antibodies was monitored by ELISA.

Figure 21A:
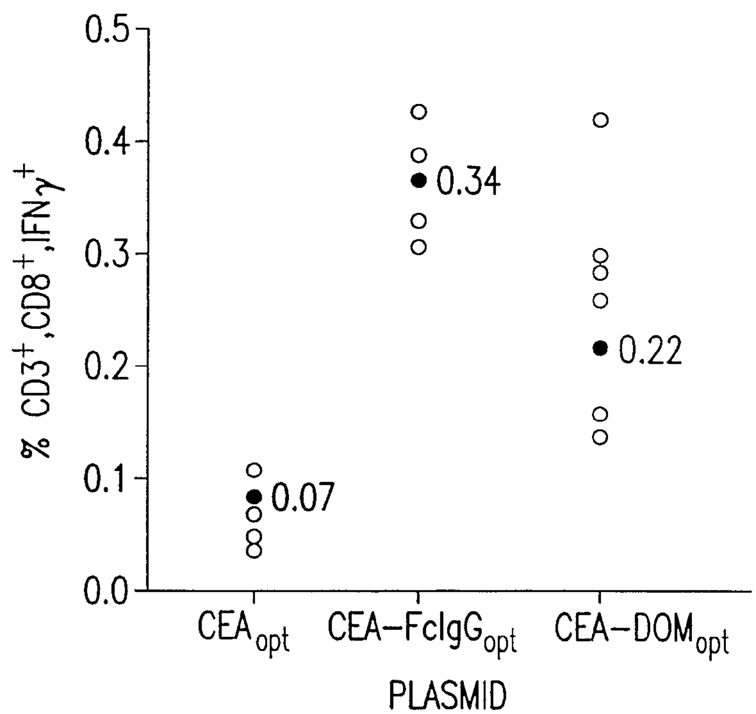
FIG. 21 shows the induction of CEA-specific immune responses in CEA transgenic mice. Groups of 12 CEA transgenic mice were immunized with plasmid DNA (50 μg/dose electroinjected in the quadriceps muscle) or Adenovirus vectors ($10^9$ vp/dose) carrying the codon usage optimized cDNA of CEA, CEA-DOM or CEA-FcIgG. CEA-specific $CD8^+$ T cells elicited by the DNA/DNA (A) and Ad/Ad (C) immunization regimen were measured by intracellular IFNγ staining on PBMC of each immunized mouse. The average values for each cohort are also shown (filled circle). The CEA-DOM and CEA-FcIgG cohorts immunized with DNA/DNA and Ad/Ad regimens were significantly different from the CEA vaccinated group. CEA-specific antibody titers of each individual mouse vaccinated with the DNA/DNA (B) or Ad/Ad (D) immunization regimen were measured by ELISA. Titers elicited by CEA-DOM and CEA-FcIgG vectors were significantly different from those elicited by CEA.
Figure 21B:
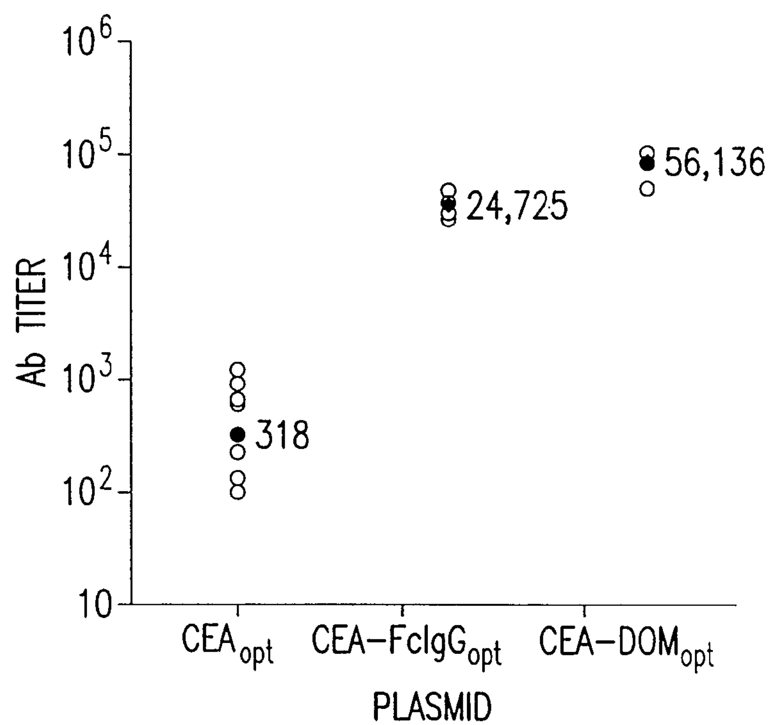

DNA/DNA immunization of the CEA transgenic mice revealed that the CEA-DOMopt and CEA-FcIgGopt vectors exerted a measurable $CD8^+$ T cell response to the target antigen (FIG. 21A). Thus, both constructs were able to break tolerance to CEA in these mice. The antigen specific response elicited by CEA-DOM and CEA-FcIgG fusion proteins was comparable as indicated by the average values of IFNγ intracellular staining (0.22 and 0.34%, respectively). Nonetheless, the immune response elicited by these two constructs was greater than that observed upon vaccination with pV1J/CEAopt (0.07%). Similarly, anti-CEA humoral response was also greater upon vaccination with the fusion proteins. CEA-specific antibody titer was detected in all mice immunized with pV1J/CEA-DOMopt and pV1J/CEA-FcIgGopt and the average of the antibody titer was 56,136 and 24,725, respectively. By contrast, the pV1J/CEAopt immunized group showed an at least a 77 fold lower average titer of CEA-specific antibody (318) (FIG. 21B).

Figure 21C:
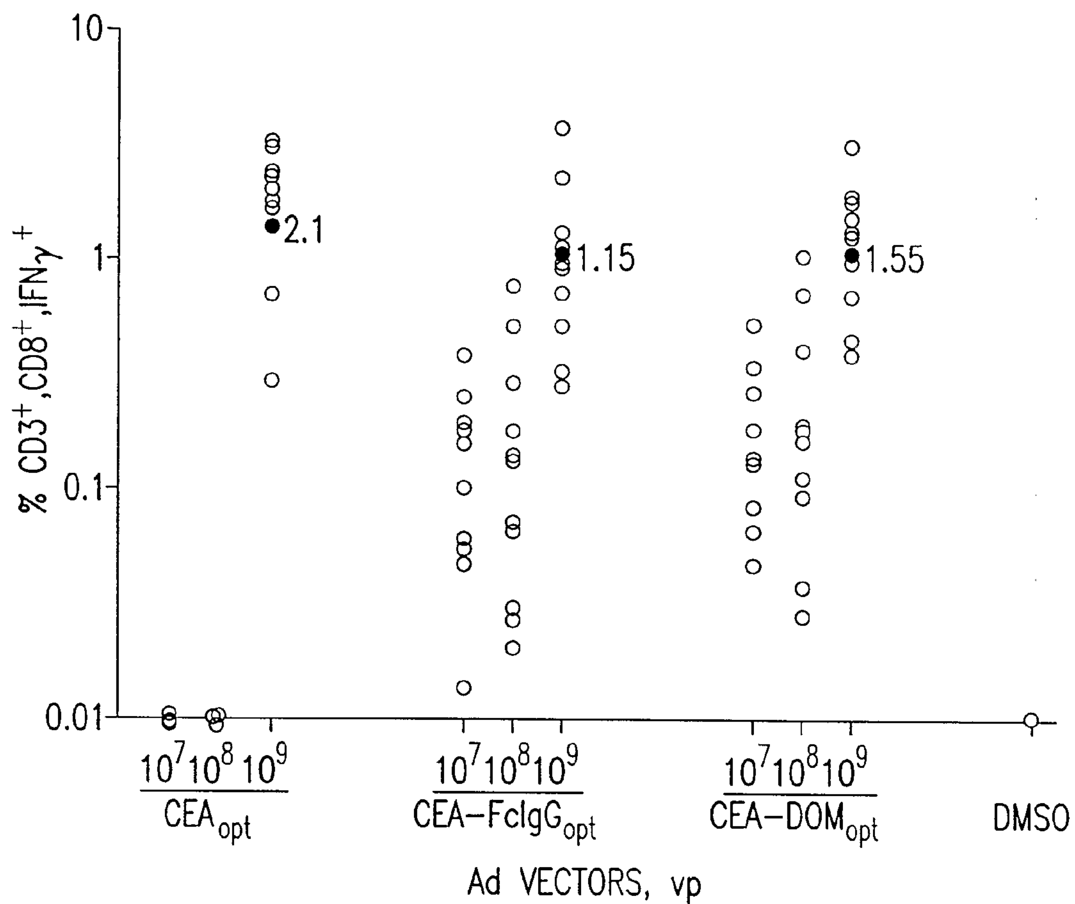
Figure 21D:
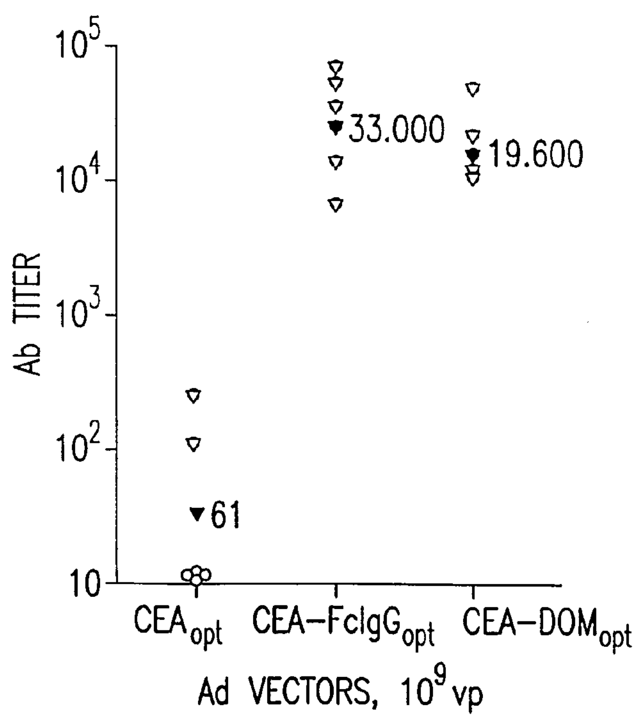
Figure 22A:
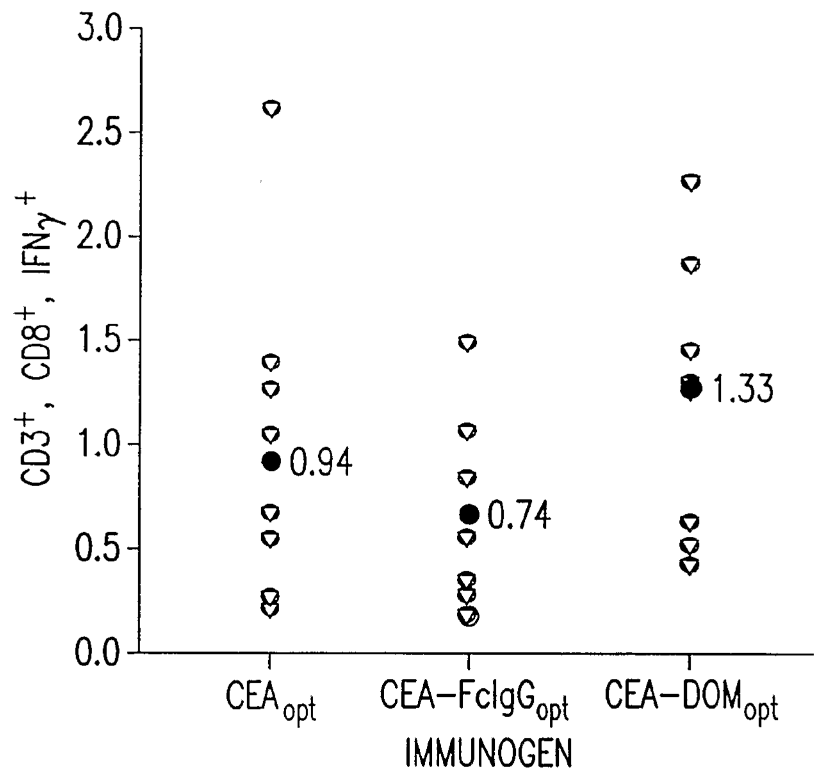
FIG. 22 shows the immunogenicity of the DNA/Ad regimen. Groups of 12 CEA transgenic mice were immunized with plasmid DNA (50 μg/dose) and Adenovirus vectors ($10^9$ vp/dose) carrying the codon usage optimized cDNA of CEA, CEA-DOM or CEA-FcIgG. CEA-specific $CD8^+$ T cells were measured by intracellular IFNγ staining on PBMC of each immunized mouse (A). The average values for each cohort are also shown (filled circle). The CEA-DOM and CEA-FcIgG cohorts were significantly different from the CEA vaccinated group. CEA-specific antibody titers of each individual mouse were measured by ELISA (B). Titers elicited by CEA-DOM and CEA-FcIgG vectors were significantly different from those elicited by CEA. Average values are shown (filled circles).
Figure 22B:
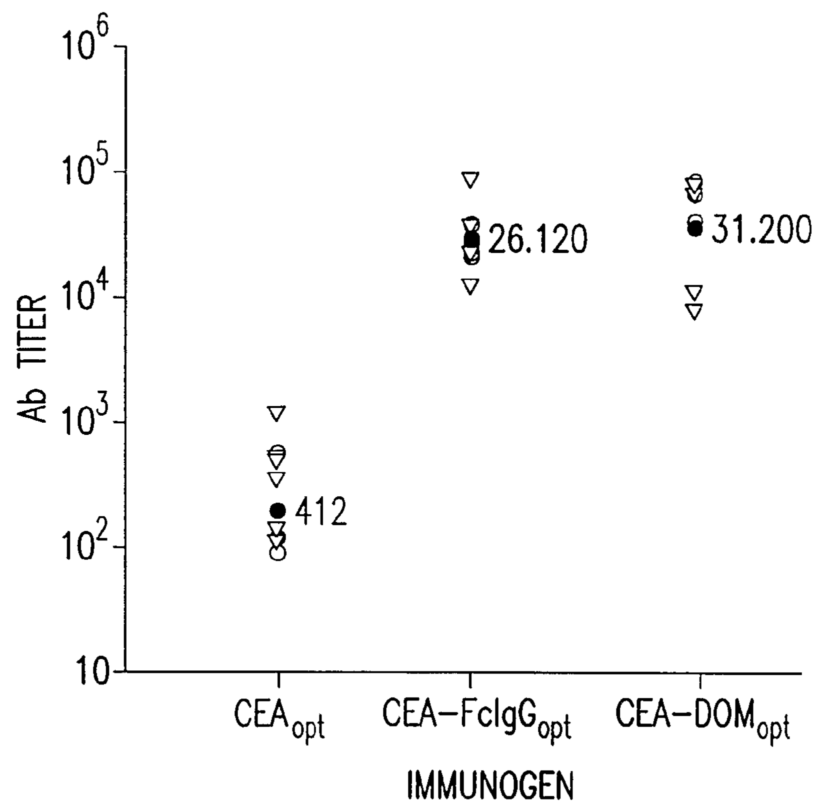

CEA transgenic mice treated with the Ad/Ad vaccination regimen also showed a better efficiency in breaking tolerance to CEA upon vaccination with CEA-DOMopt and CEA-FcIgGopt Ad vectors than with Ad-CEAopt. A CEA-specific $CD8^+$ T cell response could be observed in the vaccinated mice upon injection of a little as $10^7$ vp of Ad-CEA-DOM or Ad-CEA-FcIgG, the CEA-specific response was comparable between the two antigens, and increased upon injection of $10^9$ vp (1.55% and 1.15%, respectively). By contrast, $10^9$ vp of Ad-CEAopt were necessary to elicit significant $CD8^+$ T-cell precursor frequencies (2.1%) (FIG. 21C). CEA-specific antibodies were detected in all mice immunized with Ad-CEA-DOMopt and Ad-CEA-FcIgGopt. The averages of the antibody titer were 19,600 and 33,000, respectively. Injection of Ad-CEAopt resulted in a measurable CEA-specific response in only 2 of the treated mice, and the antibody titer was significantly lower (Zucchelli et al., supra) (FIG. 21D). Interestingly, the DNA/Ad immunization showed reduced differences in the $CD8^+$ T cell precursor frequencies elicited by CEA, CEA-DOM and CEA-FcIgG vectors (FIG. 22A). However, averages of CEA-specific antibody titers were greater upon vaccination with vectors expressing CEA-DOM and CEA-FcIgG than CEA (31,200, 26,120 and 412, respectively) (FIG. 22B).

Figure 23:
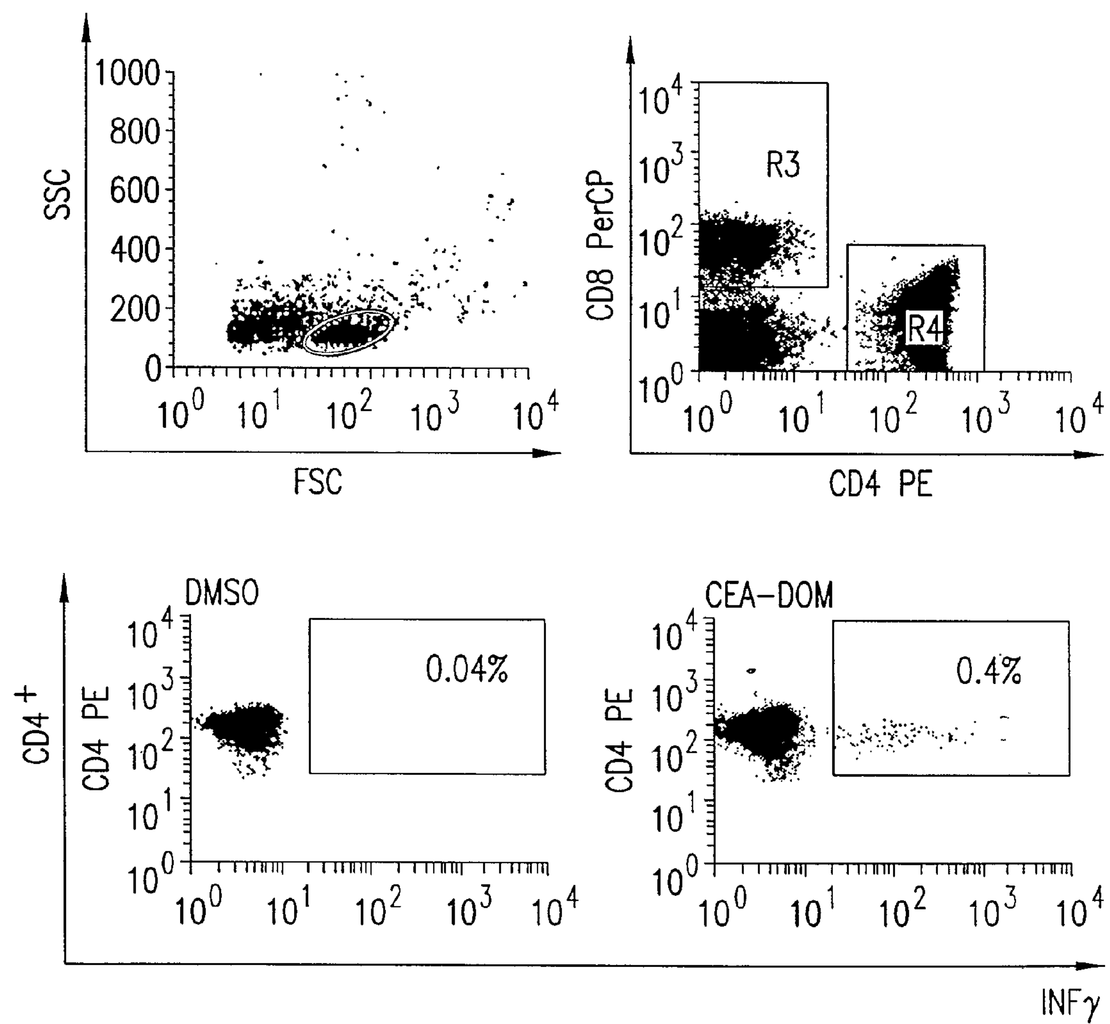
FIG. 23 shows the detection of $CD4^+$ T cell response to tetanus toxoid protein. CEA transgenic mice were immunized with pV1J/CEA-DOMopt as described in EXAMPLE 16. IFNγ intracellular staining on pooled PBMC from immunized mice was performed with peptide p30. Whole lymphocyte gating and gating for $CD8^+$ (R3) and $CD4^+$ T cells (R4) are shown.

Interestingly, regardless of the antigen, no obvious $CD4^+$ cell Th1 response to CEA was detected in any of the three vaccination regimens (data not shown). However, significant $CD4^+$ cell Th1 response against to the helper epitope, p30, present within DOM sequences (Rice et al., *J. Immunol.* 167: 1558-65 (2001)) were detected after DNA/DNA vaccination (0.4%) (FIG. 23).

Thus, these data demonstrate that the CEA-DOM and CEA-FcIgG fusion proteins can break tolerance to CEA in transgenic mice with greater efficacy than the CEA protein. The enhanced immunogenic properties of these fusion proteins can be observed upon immunization with DNA or Ad vectors. However, the greater ability of these two fusion proteins in eliciting $CD8^+$ T cells to CEA can be overcome, at least in part, by DNA/Ad vaccination regimen.

EXAMPLE 17

T-Cell Depletion Studies.

Immunized animals were depleted of $CD4^+$ T cells, $CD8^+$ T cells, NK cells, by i.p. injection of anti-CD4 (GK1.5 hybridoma), anti-CD8 (Lyt2.2 hybridoma), or anti Asialo GM1 (Wako Chemicals, Richmond, Va.) as described (Perricone et al., *J. Immunother.* 27(4):273-81 (2004); Yoon et al., *J. Ethnopharmacol.* 93 (2-3):247-53 (2004)). Antibodies (100 µl diluted ascitic fluid/dose) were injected on day-7 relative to the tumor challenge and then injected every week for 3 weeks after injection of $5\times10^5$ MC38-CEA cells. Depletion conditions were validated by flow cytometry analysis of peripheral blood using phycoerythrin-conjugated MAbs anti-CD4, anti-CD8, and anti-NK (PharMingen, San Diego, Calif.); 99% of the relevant cell subset was depleted, whereas all other subsets remained within normal levels.

EXAMPLE 18

DOM Immunization Exerts an Antitumor Effect in CEA Transgenic Mice.

Figure 24A:
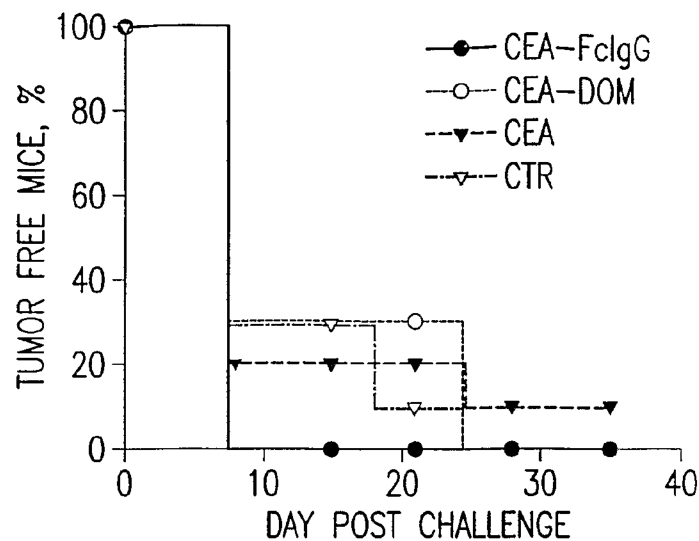
FIG. 24 shows the antitumor effect of vaccination with vectors carrying codon optimized cDNA of CEA, CEA-DOM or CEA-FcIgG. Groups of 10 CEA transgenic mice were immunized were with DNA/DNA (A), Ad/Ad (B) and DNA/Ad (C) vaccination regimens using plasmid DNA and Ad vectors carrying the codon usage optimized cDNAs of CEA, CEA-DOM or CEA-FcIgG, as described in EXAMPLE 18. Two weeks after the last injection, mice were challenged with sc inoculation of $5\times10^5$ MC38-CEA tumor cells. Percentage of tumor free mice in the vaccinated groups was determined at weekly intervals and compared to that of untreated controls. Mice vaccinated with CEA-DOM vectors (DNA/Ad modality) was significantly different from control mice (log rank test $p<0.05$).
Figure 24B:
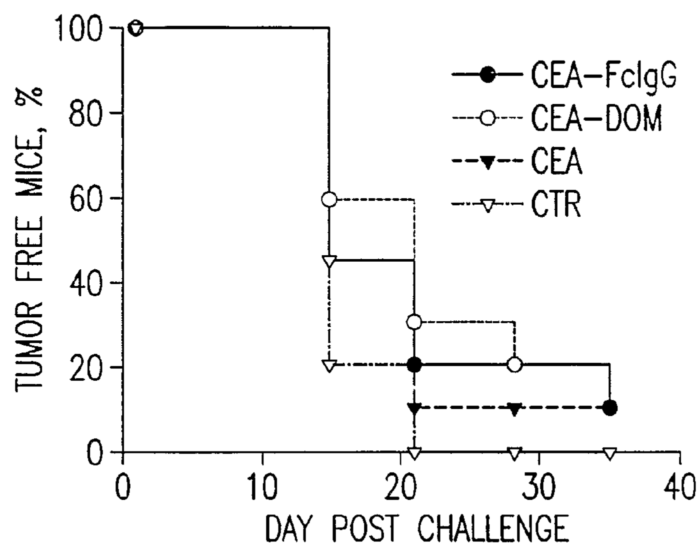
Figure 24C:
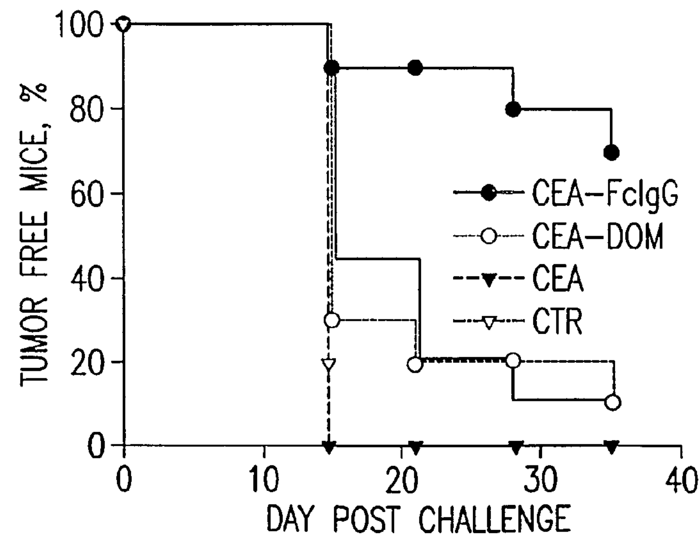

We next ascertained whether the increased immunogenicity of the CEA-DOM or CEA-FcIgG fusions would also lead to an enhanced therapeutic effect, capable of interfering with tumor progression. For this purpose, groups of 10 CEA transgenic mice were subjected to the DNA/DNA, Ad/Ad or DNA/Ad immunization regimens with the CEA-DOM, CEA-FcIgG, or CEA vectors. Two weeks after the last immunization, the CEA transgenic mice were challenged with a subcutaneous injection of $5\times10^5$ MC38-CEA cells, a syngenic tumor cell line that expresses CEA (Clarke et al., supra). Immunization with DNA/DNA or Ad/Ad modalities did not result in any significant antitumor effect, regardless of the protein expressed by the injected vectors (FIG. 24). In contrast, DNA-EP/Ad immunization with vectors encoding the CEA-DOM fusion protein resulted in a significant antitumor effect with 7 out of 10 treated mice remaining tumor free by day 34 post challenge. Thus, these results indicate that the enhanced CEA-specific immune response associated with the CEA-DOMopt cDNA, and the DNA/Ad vaccination regimen correlate with a significant antitumor effect in CEA transgenic mice.

EXAMPLE 19

The CEA-DOM Antitumor Effect is Dependent on $CD4^+$ T Cells, $CD8^+$ T Cells and NK Cells.

Figure 25:
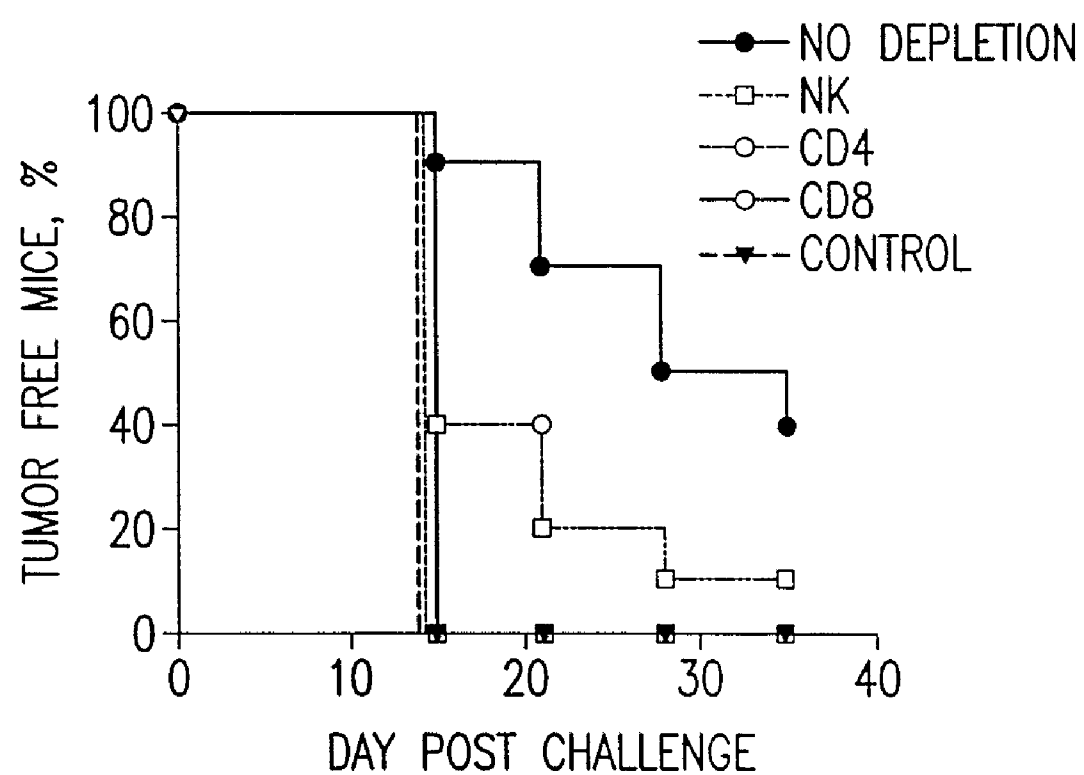
FIG. 25 shows the effect of CD4, CD8, or NK depletion on the induction of anti-tumor effect induced by CEA-DOM DNA/Ad immunization. CEA transgenic mice were immunized with repeated weekly injections of 50 μg of pV1J/CEA-DOMopt followed by a boost with $1\times10^9$ vp of Ad-CEA-DOMopt (EXAMPLE 19). One week after the last injection, mice were either not depleted, or were depleted of $CD4^+$ T cells, $CD8^+$ T cells, or NK cells. Two weeks after the last immunization, mice were challenged with sc inoculation of $5\times10^5$ MC38-CEA tumor cells. Percentage of tumor free mice in the vaccinated groups was determined at weekly intervals and compared to that of untreated controls. The data indicate that the percentage of tumor-free mice in the vaccinated group was significantly different from untreated controls and depleted cohorts.

The effector cells involved in the antitumor effect observed upon DNA-EP and Ad immunization with vectors encoding CEA-DOM fusion were characterized. After DNA/Ad immunization, but prior to tumor challenge, mice were depleted of $CD4^+$, $CD8^+$ T cells, or NK cells by MAbs. Antibodies were given during the course of tumor challenge to ensure continued depletion of the relevant NK and T cell subsets. The depletion of all three cell types was monitored by flow cytometry analysis using antibodies specific for cell surface markers (data not shown). Depletion of $CD4^+$, $CD8^+$ T cells, or NK cells had a negative effect on survival of the immunized mice resulting in the drastic reduction of tumor-free mice as compared to the vaccinated group (FIG. 25). Thus, these data indicate that NK, $CD4^+$ and $CD8^+$ T cells play an important role in the antitumor effect exerted by CEA-DOM vaccination.

EXAMPLE 20

Statistical Analysis.

Where indicated, results were analyzed by the log rank or two tailed Student t test. A p value<0.05 was considered significant.

What is claimed is:

1. A nucleic acid molecule encoding a carcinoembryonic antigen (CEA) fusion protein, wherein the CEA fusion protein comprises a human CEA protein comprising the amino acid sequence as set forth by SEQ ID NO: 20,wherein amino acids 679-702 are deleted, or variant thereof, fused to a subunit B of heat labile enterotoxin of *E. coil* (LTB); and wherein the fusion protein is capable of producing an immune response in a mammal.

2. The nucleic acid molecule of claim 1 wherein the LTB is truncated of its signal sequence.

3. A nucleic add molecule encoding a carcinoembryonic antigen (CEA) fusion protein, comprising a sequence of nucleotides as set forth in SEQ ID NO: 9, SEQ ID NO: 11, or SEQ ID NO:12, wherein the CEA fusion protein comprises a human CEA protein or variants thereof, fused to a subunit B of heat labile enterotoxin of *E. coli* (LTB); and wherein the fusion protein is capable of producing an immune response in a mammal.

4. The nucleic acid molecule of claim 3, wherein the sequence of nucleotides is as set forth in SEQ ID NO:12.

5. The nucleic acid molecule of claim 2, wherein the C-terminal end of the CEA protein is fused to the N-terminal end of LTB.

* * * * *